US006410712B1

(12) United States Patent
Olafsdottir et al.

(10) Patent No.: US 6,410,712 B1
(45) Date of Patent: Jun. 25, 2002

(54) HUMAN NARCOLEPSY GENE

(75) Inventors: Berglind Ran Olafsdottir, Reykjavik (IS); Jeffrey Gulcher, Chicago, IL (US)

(73) Assignee: deCODE genetics ehf., Reykjavik (IS)

( * ) Notice: Subject to any disclaimer, the term of this patent is extended or adjusted under 35 U.S.C. 154(b) by 0 days.

(21) Appl. No.: 09/426,290

(22) Filed: Oct. 25, 1999

(51) Int. Cl.[7] ........................ C07H 21/04; C12N 15/11; C12N 15/63; C12N 15/85

(52) U.S. Cl. .................. 536/23.5; 536/23.1; 435/320.1; 435/325

(58) Field of Search ............................ 435/6, 455, 325, 435/320.1; 514/44; 536/23.1, 23.5

(56) References Cited

FOREIGN PATENT DOCUMENTS

| EP | 0875566 A2 | 11/1998 |
|---|---|---|
| WO | WO 96/34877 | 11/1996 |

OTHER PUBLICATIONS

Verma et al., Nature, vol. 389, pp. 239–242, 1997.*

Orkin et al., in Report and Recommendations of the Panel to Assess the NIH Investment in Research on Gene Therapy, Dec. 7, 1995.*

Verma I.M., et al., "Gene–thereapy–promises, problems and prospects", *Nature*, vol. 389, pp. 239–242, (Sep. 1997).

Orkin S.H., et al., "Report and Recommendations of the Panel to Assess The NIH Investment in Research on Gene Therapy", pp. 1–41, (Dec. 1995).

Peyron, Christelle, et al., "A mutation in a case of early onset narcolepsy and a generalized absence of hypocretin peptides in human narcoleptic brains", *Nature Medicine*, vol. 6, No. 9, pp. 991–997 (Sep. 2000).

Pavitt, R., "Human DNA sequence from clone RP11–73M7" (May 7, 2000).

Aldrich, Michael S. and Reynolds, Paul, R., "Narcolepsy and the Hypocretin Receptor 2 Gene" *Neuron*, 625–626 (1999).

Sakurai, T., et al., "Structure and Function of Human Prepro–orexin Gene," *J. of Biol. Chem. 274*(25):1771–1776 (1999).

Lin, L., et al., "The Sleep Disorder Canine Narcolepsy is Caused by a Mutation in the Hypocretin (Orexin) Receptor 2 Gene," *Cell 98:*365–376 (1999).

Chemelli, R.M. et al., "Narcolepsy in orexin Knockout Mice: Molecular Genetics of Sleep Regulation," *Cell, 98*:437–451 (1999).

Siegel, J.M., "Narcolepsy: A Key Role for Hypocretins (Orexins)," *Cell 98*:409–412 (1999).

Sakurai, T., et al., "Orexins and Orexin Receptors: A Family of Hypothalamic Neuropeptides and G Protein–Coupled Receptors that Regulate Feeding Behavior," *Cell 92*:573–585 (1998).

De Lecea, L., et al., "The hypocretins: Hypothalamus–specific peptides with neuroexcitatory activity," *Proc. Natl. Acad. Sci USA 95*:322–327.

Mignot, E., et al., "Narcolepsy and immunity," *Adv. in Neuroimmunology 5*:23–37 (1995).

Mignot, E., "Genetic and familial aspects of narcolepsy," *Neuro, 50*(Suppl 1) :S16–S22 (1998).

Faraco, J., et al., "Genetic Studies in Narcolepsy, a Disorder Affecting REM Sleep," *Amer. Genet. Assoc. 90*:129–132 (1997).

Kadotani, H., et al., "Genetic Studies in the Sleep Disorder Narcolepsy," *Genome Res. 8*427–434 (1998).

Mayer, G., et al., "Segregation of HLA genes in multicase narcolepsy families," *J. Sleep Res. 7*:127–133 (1998).

* cited by examiner

*Primary Examiner*—Michael C. Wilson
(74) *Attorney, Agent, or Firm*—Hamilton, Brook, Smith & Reynolds, P.C.

(57) ABSTRACT

The gene for hypocretin (orexin) receptor 2 (HCRTR2), which is associated with narcolepsy, is disclosed. Also described are methods of diagnosis of narcolepsy, pharmaceutical compositions comprising nucleic acids comprising the HCRTR2 gene, as well as methods of therapy of narcolepsy.

3 Claims, 51 Drawing Sheets

```
LOCUS          __________   168,575 bp   DNA      PRI     20-OCT-1999
DEFINITION     Human hypocretin (orexin) receptor 2 (HCRTR2) gene, complete cds.
ACCESSION      __________
NID            __________
VERSION        __________
KEYWORDS       .
SOURCE         human.
  ORGANISM     Homo sapiens
               Eukaryota; Metazoa; Chordata; Craniata; Vertebrata; Mammalia;
               Eutheria; Primates; Catarrhini; Hominidae; Homo.
REFERENCE      1  (bases 1-168,575)
AUTHORS        __________
  TITLE        Direct Submission
 JOURNAL            Submitted (__________) deCode Genetics, Inc., Lynghals 1,
                    IS-110   Reykjavik, Iceland.
FEATURES            Location/Qualifiers
      source        1.. 168,575
                    /organism="Homo sapiens"
                    /db_xref="taxon : 9606"
                    /chromosome="6"
                    /map="6p11-q11"
                    /clone="BAC 403B19"
      gene          1..129,305
                    /partial
                    /gene="HCRTR2"
                    /note="OX2R"
                    /db_xref="LocusID:3062"
                    /db_xref="MIM:602393"
      exon          20,867..21,403
                    /gene="HCRTR2"
                    /number=2
      CDS           join(21,181..21,403, 95,252..95,430, 101,753..101,996, 110,324..110,439,
                    124,058..124,278, 127,009..127,130, 128,910..129,139)
                    /gene="HCRTR2"
                    /note="HCRTR2 exons defined by comparison to mRNA sequence (NM_001526)"
                          /product="HCRTR2/orexin 2 receptor"
                    /db_xref="LocusID:3062"
                    /db_xref="MIM:602393"
                    /protein_id="NP_001517.1"
                    /db_xref="PID:g4557639"
                    /db_xref="GI:4557639"
                    /translation="MSGTKLEDSPPCRNWSSASELNETQEPFLNPTDYDDEEFLRYLW
                    REYLHPKEYEWVLIAGYIIVFVVALIGNVLVCVAVWKNHHMRTVTNYFIVNLSLADVL
                    VTITCLPATLVVDITETWFFGQSLCKVIPYLQTVSVSVSVLTLSCIALDRWYAICHPL
                    MFKSTAKRARNSIVIIWIVSCIIMIPQAIVMECSTVFPGLANKTTLFTVCDERWGGEI
                    YPKMYHICFFLVTYMAPLCLMVLAYLQIFRKLWCRQIPGTSSVVQRKWKPLQPVSQPR
                    GPGQPTKSRMSAVAAEIKQIRARRKTARMLMVVLLVFAICYLPISILNVLKRVFGMFA
                    HTEDRETVYAWFTFSHWLVYANSAANPIIYNFLSGKFREEFKAAFSCCCLGVHHRQED
                    RLTRGRTSTESRKSLTTQISNFDNISKLSEQVVLTSISTLPAANGAGPLQNW"
      exon          95,252..95,430
                    /gene="HCRTR2"
                    /number=3
      exon          101,753..101,996
                    /gene="HCRTR2"
                    /number=4
```

FIG. 1A

```
exon            110,324..110,439
                /gene="HCRTR2"
                /number=5
exon            124,058..124,278
                /gene="HCRTR2"
                /number=6
exon            127,009..127,130
                /gene="HCRTR2"
                /number=7
exon            128,910..129,305
                /gene="HCRTR2"
                /number=8

BASE COUNT    55,308 a  29,672 c  29,838 g  53,757 t

CGACTTGATTTTATTTTTTGCATATGGATATCCAGTTTTCACAGCACTGCTTGTTACCCT
CAGCAAAGAACAGTTGTCTGTAAATTCATGGGTTTATGTCTAGGCTCTCTGTTCTGTTCT
ATTGGTCAACATATGGTCATATATCACTTAACTGCAGGGAAGGGATACATTCTGAGAAAT
GCATTATTACATGATTTCATCATTGTGCAAACACTATAGAGTGTAGTTACAGAAACCTAG
TATCTCTAGCTGTGTTCTTATGATTCAAATTTGCTTTGGTCATTTGAGATCCATACTGGT
GGAGTCTAATTATTCAAAACTAGGGAAAACAGACAAACAGAAAAAACTAAGACCAAGTTA
GCAGAAGAAAGACAATAACAAAGGTTAGATCAAAAATAAATAATATAGAGAATGAAAAAA
TTAGAAAAAGTGGACAAAACTACAATGTACTTTTTTGAAAAGACAAACAAAATTAACAAA
CCCTTACCTTGACTAAAAAAAGAGACTCAAATAAATAAAATTGGAAATGAGACAGGAGAC
ATTACAATTGATGTTAACAAAAAGATCATAAGGTACTATTATGAACAACTATACACCAAT
AAATTGGACAACCTAGAAAAAAAATGGATAAATTCCTAGAAATACACAGTCTATCAAACT
GAAACAAGAAGAAATAGAAAGCCTGAACATACCAGTAACAACCAAGGAGACTGAGTAAAT
AATCAAAAACCTCCCAAGAAGAAGAGTCTAGGACCAGAAGTCTTCACAAATGAATTCTAC
CAAACATTTAAAGTATTAATGCCAATCATTCATTCTTATACTCTTCCAAAAAGAAAGAGG
GAATATTTTCAAACTCATTTTATGAGGCCAGCATTATTCTGATACCAAAACTACGCAAAA
ATACTACAAGAACATAAAAACTACAAATGTGGGAATTATCATGTATACATATGCAAAAAT
CCTCAGTAAAATCCTAGCAAACTAAATTCAACAGTACATTAAAAAGATCATATAGCATGA
CCAGTGAAATTTCTCCTTAGGACGCAAGGATAAGTCAACATATAAAATTGAATGTGATAT
ACCACTTTAACAAAATGAAGGATAAAAATCATATGATCATCTGAATAGATGCAGAAAAAG
CATATAACAAACTTTGACGTTGTTGAGAAATTGAAAGCTTTTCTCTAAGATCAAGAACAA
AGCAAGGATGCCCATTCTTGCTTCTATTCAGCATAGTGCTTGAAGTCCTAGTCTGGACAA
TTGGGCAAAAATAAATAAATAAATAAATAGATAAATAAATAAATAAATATAAATAAATAA
ATAAAATCCACCAAATTGGAAAGGAAGAAGTGAAATTACCTCTGTTTGTAGATGAGCTGA
TCTCATGTGTAGACAACCTTAAAGATTCCACAAAAACAAACAAACACACAAACAAACAAA
ATAGCTAGAGCAAAGAAATGAATTCAGTACAGTTGCAGAATGCAAAATCAGTATACAAAA
AGTACTTGTAATTCTATATAATAGCAACAAACTATTTCATAAGGAAATTAAGGAAACAAT
CCCCATTACAATAGCATCATAAATAATAAATCTTAAGAACAAATTTAACCAAGGAGGTGA
AAGACTTGTGTACTGAAAACTATAAAATGCTGATAAAAAAATTAAAGAAGATACAATAAA
TGGAAGATATTCCATGCCATGGTTTGGAAGAATTAATATTGCTAAATGTACATACTACCC
AAAACAACCTGTAGAGTCAATGCAATCCCTATCAAAATACCAATATTTTTTTTTTTACAG
AAATGAAAACACAATCTTAACACTATTTAAACCAATTAAACAAACCTATGATTTCAATTT
GGTCAAATGTGTTAGAATGGATTTCCTTTTATTGTTTTGAACTTGTCTCTTCCAAATTTC
AAAGCCTGGTTCCTAATTTTTACTTGAAATACCAAATAACAAACCCACTTAATGAGCTCT
GAGCCAGTTTTAGTAGCCAAACTTGTATTTAAATAGTGTGTTACATATTTGCACAAAAAG
CCAACGGAGTCTAAATCAACACTAATTCACATCATTACTAGCAATCTAAAACATCAGATG
ATAATTTTGCTGTTGTCTTTCAGGCAAGATATTCAACCATTGGTATTAAATGTTTTATAT
GAATGTGCGGTGTTTTATTTCAGAAACACTTCTCTGAATTCCCAAGGCCTAAGAGCTATT
CATCATAGAGGTTTGTGGAGGCGGTAGTTAGACATTTTCTACATGCATAATGTTAATTCA
TTCAAACATTATAGAAAAAAAGTTTGTAAAGAAGTTAATTTTCAAGGTGACAAAAAAATC
AGATTGAATCATGTTTATTTTATTTCAATTTAAACTCGTTGGCTATCTTAGGAAATTCAC
ATTGTTTTTGAAGAATATATGAACAAAGTTTGATTCATCTTATCTATATAAGCATGAGAG
```

FIG.1B

AAATACCTAGATGAGAGTGAAAAATGACTAATTTTGTGACCATTGTTATATCATAGATTA
ACTTGTTCTCTTCTACTTCTAAGCTGTGTGATCTTGAAAAGTCATCTAAACTTCAGGTAC
CATCCTCACTTGCAAAATGAGGGGAAAAACCCCAGCACCTTTAATATGGTGTTATGTGGA
TGAAATAAGTTAATATATATTAAGTGCTTAGGTTTCATGCACTTTCTATATAGTATTAAT
AATATTATTGTTACATTATTATAGTTACATTATTATTTTTATTAATATTATTGGAACATG
AATGGAATTGTTGTGGCTCATTTTAAAGATGCTGCAATGGAGACCAAGAGAAATTAAGTA
TAATAATCCTAGTTAAGGTACAGCCATTTCTAATTACATTTTCCAACTGCTGCTTTTACT
CCTAGCACTCACACCAATTCTTCTCATAATCTAATAAATACTGAAATTTAAAACTTATAA
AGAACACATAATAATCTTATTTAATTATCACAACAATTTCTGTGGAGTTACTATTAATCC
AGAGATGAAGAATCTAAAACTCTAAATTATCAAGCAACTATTCCAGCTTTAAACAACAGT
AAAACTGGAATTAAAACTAGAGTTTCTTTATGAGGCCAGTATTACTCTTATACTAAAGCA
AGACAACTGTCTCTCTCTCACTCTCTCTTTCTCTCTCTCTGAGACACACACACACACACA
CAAGCACACACACACACACACACCAGATCAATATAACTTATGGATGTTGATGCAAAAATTTT
CAAAAAATTAATAGCAAATCGAATCCAGCAGTATTTTAAAGGACTATACACCATGGACAA
ATGGGGTTTATTCCTGGGATATAAAGTTGGCTAAACTTAATGAAAATCAACCAGTGCAAT
AAATAATAGTAATTAAAAAAACATAATTATCTCACTAGATGTACAAAAAATGACAAGATC
CAACATGTTTTCAATATAAAAGCATTCCACAGACTAGGAATAGAAGGGAACTTCCTCAAC
TTTACAAAGAACATCTACAACGAAACCACAGCTAACATCATATTTAATGGTGGAAGACTG
AAATCTCTGAATATTTTCCCCTAAGATCAGAAAAAGACAAAGAGGTCTACTAATTCTATT
CAACATTGGAAAGATAGTTCTAGTCAATTAATCATTAAAAAAAGGCATTTAGATTAGAAA
GGAAGTAAAATTACCTCTGGCAGATGACATAATCTTATACATGGAGAACTCCTAGAGATT
ACATACACACTCACAACTACCAGAGTTAATAAATGGGTTCTACAAAGTTGCAGGATACAA
TATCAATTCTCAAAAAACACTTGTATTTCTATACACTAGCAAATAACTCTGAAAATGAAA
ATAACAAAACAATTCCACTTGCAAGAGCATCAAAAAAGCATGAAAATCTTAGGAAGGAAT
TTACCAAGAATGTACAAGTTTTATGTACTGAAAAATAAAAAATGTCATTAAAAATAGTTA
AAGAGAATCTAAGCACATTGCAGTTTTCTGACTCCAGGCCCGGGCTCTTGGATGGCATCT
CTGGATCCACTCAGGACCAGGGAGAACTTGTTGCCCTGAAGGGAAGGACACAAGTCTGAC
TGGCTTTACCACCTGCTGATTGTAGAAGCCTAGGGCCTTCAGGGAACACAGGTGGTAGCC
AGATAGCAGTTACCATGGGCATTAGGCATGACCCAGTGCTATGTTGGCTTCTAGTTTGAC
CCAGCACAGCCCAAGGGTGGTAACCACATGGGTGCTTGTGTCACCCCTCCTTAAGTTCCA
GGCAGCCAGCAAAGAGAGAGTGACTCTGTTTGGGAGAAAGTAAGGGAAGAGAATAAAAGT
CTCTGTTGGTAATACAAGGAATTCTTCCAGATCTTATCCAAGACCTCTATGAATCTGCAA
CAGCCAAAGCATTATTAGTTTTCAGGTTTCCCCAGTGCAGATATGACTGCAATGATCAAA
AACTTAGATTATAACACTCAAGTCCCATTTGATACCTGAAAAGCTTTCCAAGAAAGATAG
GCACAAACAAGTTTGGACTGGGAGGACTACAATAAATACCTAACTTCTCAATGCCCAGAA
ACTGATGAACATCCACAAGCTTTAAGACCATCCAGGAGGTGGCTGGCAAGATGGCTGAAT
AGGAACAGCTCTGGTCTGCAGCTCCCAGTGAGATCAGTGCAGAAGGTGGTGGTTTCTGCA
TTTCCAACTGAGGTACCCAGCTCCTCTCATTGGGACTGGTTAGATAGTGAGTGCAGCCCA
CAGAGGGTGAGCCAAAGCTGGATGGGGTGTCACCTCACTGGGGAAGCACAAGGGGATGGG
GAACTCCCTCCCCTAGCCAACGGAATCTGTGAGGGACTGCCATGAGGGATGGTGCATTCT
GGTCCAGATACTATGCTTTTCCCATGTTCTTCACAACCCTCAGGCCAGGAGATTCCCTCG
GGTGCCTACACCACCAGGGCCTTGGGTTTCAAGTACAAAACTGGGTGGATCTTTGGGCAG
GCACCGAGCTAGCTGCAGGAGTTATTTTTCATACCCCAGTGGTGCCTGGAATGCCAGTGA
GACAGAACCATTCACTCTCCTGGAAAGGGAGCTGAAGCCAGGGAACCCAGTGGTCTAGCT
CGGTGGATCCCACTCCCATGGAGGCCAGTAAGCTAAGATCCACTGGCTTGAAATTCTCAC
TGCCAGTGCAGCAGTCTGAAGTCAACCTGGGATGCTTGAGCTTGGTGGAGAGAGGGACGT
CCACCATTACTGAGGTTTGAGTAAGCAGTTTTCCCCTCACAGTGTAAACAAAGCCACTGG
GAAGTTAAAGTAGGTGGAGCCCACGACAGTTCGGCAAAGCCACTATAGCCAGAATGCCTC
TCTAGATTCCTCCTGTCTGGGCAGGGCTTCTCTGAAAGAAAGGCAGCAGCTGCGGTCAGG
AGCTTATAGATCAAACTCCCATCTCCCTGGGACAGGGCACCTGGGGAAAGGGGCAGCTGT
GGGTGCAGCTTCAGCAGACTTAAATATTGCCGCAAGCTGACTCTGAAGACAGCAGGGGAT
CTCCCAGCACAGCGCTCGAGCTCTGCTAAGGGGCAGACTGCCTCCTCAAGTGGGTCTCTG
ACCCCTGTGTCTCCAGACTGGGAGACACCGCACAGCAAGGGTCGACAGACACCTCATACA
GGAGAGCTCCGGCTGGTATCTGGTGGGTGCCCCTCTGGGACAAAGCTTCGAGAGGAAGGA
GCAGGCAGCAATCTTTGCAGTACTGTAGCCTCTACTGGTGATACCCAGGCAAATAGGGTC
TGACGTTGACCTCCAGCAAACTCCAGCAGACCTTCAGCAGACGGGCCTGAGTGTAAGAAG
GAAAATTAACAAACAGAAAGGAATAGCATCAACATCAAAAAAACAAAAACAAAAACAAAA

FIG. 1C

ACAAAAACAAAAACAGCACATCCGCACAAAAACCCCATCTGAAGGTCACCAACACCAAAT
ACCAAAGGTAGATAAATCCACAAAGATGGGGAAAAACCAGCACAAAAAAGCTGAAAATTC
CAAAAAACAGAATACCTCTTCTCCTCCAAAGGATCACAATTCCTCACCAGCAAGGGGACA
AAACTGGACAGAGAATGAGTTTGATGAATTGACAGAAGTAGGCTTGAAAAGGTGGGTAAT
AAACTCCTCTGAGCTAAAGGAGCATGTTCTAACCCAATGCAAGGAAGCTAAGAACCTTGA
AAAATGGTTAGAGTAATTGCTAACTAGAATAACCAGTTTAGAGAAGAGCATAAATGACCT
GATGGAGCTGAAAACTATAGCACAAGAACTTCGTGCAGCATACACAGGTATCAATATCCA
AATCGATCAAGCAAAGAAAAGAATATCAGAGATTGAAGATCAACTTAATGAAATAAAGTG
TGAAGACCAGATTAGAGAAAAAAGAATAAAAAGGAATGAACAAAGTCTCCAAGAAATATG
GGAATATGTGAAAAGACTAAACCTACATTTGATTAGTGTACCTGAAAGTGACGGGGAGAA
AGGAATCAAGTTGGAAAACATTCTTCAGGATATTATCCAGGAGAACATCCACAACCTAGC
AAGACAGGCCAACATTTAAATTCAGGAAATACAGAGTACATCACAAAGATACTCCTCGAG
AAAAACAACCCCAAGACACATAATTGTCAGATGCACCAAGGTTGAAATACAGGAAAAAAG
TTAAGGGCAGCCAGAGAGAAAGGTCGGGTTACCCACAAAGGGAAGCCCATCAGACTAACA
GTGGATCTCCCTGCAGAAACCCTACAAGCCAGAAGAGAGTGAAGGCCAATATTCAACATG
CTTTAAGAAAAGAATTTTCAACCCACAATTTCATATCCAGCCAAACTATGCTTCATAGTG
AAGGAGAAATAAAATCCTTTACAGACAAGCAAATGCTGAGAAATTTTGTCACCACCAGGC
CTGCCTTACAAGAGCTCCCGAAGGAAGCACTAAATATGAAAAGGAAAAACCAGTATCAGC
CACTGCAAAAACATATGAAATTGTAAAGACCATCAACACTATGAAGAAACTGCATCAACT
AATGGGCAAAATAACCAGCTAGCATTATAATGACAGGATCAAATTCACACATAACGATAT
TAACCTTAAATGTAATAGGCTAACTGCCCCAATTAAGAGACACAGACTGGCAAATTGGAT
AGAGAGTCAAGACCCAACAGTGTGCTGTATTCAGGAGTCCAATTCATGTGCAAAGATACA
TATAGGCTCGAAATAAAGGGATGGAGGAATATTTACTAAGCAAATGGAAAGCAAAATAAA
GCGGAGGTTGCAATCCTAGTCTCTGATAAAATAGACTTCAAACCAACAAAGATCAAAAGA
GACAACAAAGGGCATTACATAATGATAAAGGGATCAATGCAACAAGAACAGCTAGCTATC
CTAAATATATATGCACCCAATTCAGGAGCACACAAATTCATCAAGCAAGTTCTTAGAGAC
CTATAGAGACTTAGACTCCCACGTAATAATAGTGGGAGACTTTAACACCCCACTGTCAAT
ATTAAACAGATCAATGAGACAGAAAATTAACAAGTACATTCAGGACTTGAACTCAGCTCT
GGACCAAGCAGGCCTAATAGACATCTATAGGACTCTCCACCCCAAATAAATAGAATATAC
ATTATTCTCAGCACCACATTGCACTTATTCTAAAATTGACCACATCATTGGAAGTAAAAG
ACTCCTCAGCAAATGCCAAAGAACTAAAATCATAACAAACAGTCTCTCAGACCACAGTGC
AATCAAATAAGAGCTCTGGAATAAGAAACTCACTCAAAACCGCACAACTACATGGAAACT
GAACAACCTGCTGCTGAATGACTACTGGGTAAATAATGAAATTAAGGCAGAAATAAATAA
GTTACTTGAAACCAATGAGAACAAAGACACAACATACCAGAATCTCTGGGACACAGCTAA
AGTAGTGTTTGGAGGGAAATTCATAGCACTAAATGCCCACACGAGAAAGTGGGAAAGATC
TAAAATCAACACCCTAACATCACAATGAAAAGAACTAGAGAAGCAAAGGCAAACAAATTC
AAAAGCTAGCAGAAGACAAGAAATAACTAAGATGAGAGCAGAACTAAGGAGAGAGAGACA
CGAAAAACCCTTCATAAATCAATGAATCCAAGAGCTGTTTTTTTGAAAAGATTAACAAA
ATAGATAGATCACTAGCCAGACTAATGAAGAAGAAAAGAGAGAAGAATTGTATAGACACA
ATAAAAAATGATAAAGGGGAGATCATCACTGATCCCACAGAAATACAAACTACCATCAGA
GAATACTATAGACACCTCTATGCAAATAAACTAGAAAACCTAGAAGAAATGGATAAATTC
CTGGACACATACACCTTCCCAAGACTAAACCAGGAAGAAGTCAAATCCCTGAACAGACCA
ATAACAAGTCCTGAAATTGAGGCAGTAATTAATAGCGTTCCAATGAAAAAAAGCCCAGGA
CCAGATGGATTCACAGCCAAATTCTACAAGAGGTACAAATCAGAGCTGGTACCATTCCTT
CTGAAACTATTCCAAACAACAGAAAAAGAAAGACTCCTCCCTAACTCATTTTATGAGGCT
GGCATCATCCTGATACCAAAACCTGGCAGAGACATACACACAAAAAAGAAAATTTCAGGC
TAATATATCCCTGATTAACACCGACGCAAAAATCCTCAATAAAATACTGGCAAACCAAAT
CCAGCAGCACATCAAAAAGCTTATCCACCACGATCAAGTTGGCTTCATACCTGGCATGCA
AGGCTTGTTCAACATACGAAAATCAATAAATGTAATTCATCACAAAAACAGAACCAATGA
CAAAAACCACATGATTATCTCAATAGATGCAGAAAAGGCCTTCAACAAAATTTAACAGCC
CTTCATGCTAAAAACTCTCAATAAGCTAGGTATCGATGCAATGTATTTTAAAACAATAAG
AGCTATTTATGACAAACCCATACCCAATATCATACTGAATGGGCAAAAGCTGGAAGCATT
CCCTTTAAAAACTGGCACAAGACAAGGATGCCCTCTCTCACCACTCCTATTCAACATAGT
GTTGGAAGTTCTGGCCAGGGCAATCAGGCAAGAGAAAGAAATAGAAGGTATTCAAATAGG
AAGAGAAGAAGTCAAATTGTCTCTGTTTGTGGATGACATCATTGTATATTTAGAAAACCC
CATTGTCTCAGCCCAAAATCTCCTTAAGCTGATAAGCAACTTCAGCAAAGTCTCAGGATA
CAAAATCAATGTGCAAAAATCACAAGCATTTCTATACACTAATAATAGACAAACAGAGAG

FIG. 1D

CCAAATCATGAGTGAACTCCCATTCAAAATACCTAGGAATACAACTTACAAGGGATGTGA
AGGACCTCTTCAAGGAGAACTACAAACCACTGCTAAGGAAATAAAAGAGGATACAAACAA
ATGCAAAAACATTCCATCCTCATGGATAGGAAGAATCAATATCATGACAATGGCCATACT
GCCCAAAATAATTTATAGACTCAATGCTATGTTCATCAAGCTACCACCGAATTTCTTCAC
AGAATTAGTAAAAAACTGGCCAGGCTCAGTGGCTCACGCTTGTAATCCAAGCACTTTGGG
AGGCCAAGGCAGGAGGATCAAGAGGTCAGGAGATTGAGACCATGGTGAAACCCCGTCTCT
ACTAAAAATACAAAAAATTAGCCGGGCGTGGTGGCAGGCGCCTGTAGTCCCAGCTACTTG
GAGAGGCTGAGGCAGGAGAATGGCGTGAACCCAGGAGACGGAGCTTGCAATGAGCCAAGA
TCCTGTCACTGCACTCCAGCCTGAGTGACAGAGCAAGACTCCGTCTCAAAAAACAAACAA
ACAAACAACAAAAAAAAAAAAAACTACCTTAAATTTCTTATGGAACTAAAAAAGAGCCCAT
ATAGCCAAAACAATCCTAAGCAAAAAGAACATAGCTGGAGGCATCATGCTACCTAACTTC
AAATTATGCTACAAGGCTACAGTAACCAAAACAGCATGGTATTGGTATGAAAACAGATAT
ATAGACCAATGGAACAGAACAGAGGCCTCAGAAATAACCCCAGACATCTACAACTCTCTG
ATTTTTGACAAACCTGACAAAAACAAGCAATGGGGAAAGGATTTCCTATTTAATAAATGT
TGTTGCGAAAACTGGCTAGCCATATGCAGAAAACTGAAACGGGACTCCTCCCTTACACCT
TATACAAAAATTAACTCAAGATGGATTAAAGACTTAAACGTAAGACCTAAAAACCATAAG
AACCCTAGAAGAAAACCTAGGAAATACCATTCAGGCCATAGGCATGGCAAACACTTCAT
GTCTAAAACATCAAAAGCAATGGCAAGAAAATCCCAAATTGACAAATGGGATCTAATTAA
ACTAAAGAGCTTCTGCACAGCAAAAGAAACTATCATCAGAGTGAACAGGCAACCTATAAA
ATGGGAGAAAATTTTTGCAATCTGTCCATCTGATAAAGGGCTAATATCCAGAATCTACAA
TGAACTCCAACAAATTTACAAGAAAAAAACAACCCCATCAAAAAGTGGGTGAAGGATGTG
AACAGACACCTCTCAAAAGAAGACATTTATGTGGCCAAGAAACATACAAAAAAAAGCTTA
TCATCACTGGTCATTGGAGAAATGCAAATAAAAACCACAGTGAGATACCATCTCACTCCA
GTTAGAATGGCGATCATTAAAAAGTCAGGAAACAACAGATGCTGGAGAGGATGTGGAGAA
ATAGGAACGCTTTTACACTGTTGGTGGGAGTGTAAATTAGTTCAACCATTGTGGAAGACA
GTGTGGTGATTCCTCAAGGATCTAGAACCAGAAATACCATTTGACCTAGCAATCCCATTA
CTGGGCATATACCCAAAGGATTATAAATCATTCTATGATAAACACACATGCACATGTATG
TTTATTGTGGCACTATTAACAATAGCAAAGACTTGGAACCAACCCAGATGTCCATCAATG
ATAGACTAGATTAAGAAAATGTGGCACATATACACCATGAAATACTATGCAGCCATAAAA
AAGGATGAGTTCATGTCCTTTGCAGTGACATGAATGAAGCTGGAAACCATCATTCTCAGC
AAACTATCACAAGATCAGAAAACCAAACACCACATATTCTCACTCATAAGTGGGAGTTGA
ACAATGAGAACACATGGACACAGGGAGGGGAACATCACACACCAGGGCCTGTCAGGCAGT
GGGGGGCTAGGGGAGGGATAACATTAGGAGAAATACATAATGTAGGTGACAGGTTGATGG
GTGCAGCAAACCACCGTGGCACATGTATACCTATGTAACAAACCTGCACGTTCTGCACAT
GTATCCCAGAACTTAAAGTATTAAAAAAAAAAGACCATTTATGAAAACATGACCTTACCA
AAGAACTATATAAGTCACTGGAGACCAATCCTGGAGTGACAGAAATATGTGACCTCTCAG
ATGGAGAATTCAAAATAGCTGTTGTGAGGAAATTCAACAAAATTCAAGATGACATGGCAA
AGGAATTCAGACTTCTATCAGATAAATTCAAAAAAGAAGATGAAATAATTTTTTTAAAAA
TTCATGCAGAAATTTTGGAGCTGAAAAATTCAATTGATATACAAAAGAATGCATCTTACC
AGCAGAATTGATCCTGCAGAAGAAAGAATTAGTAAATTTGAAAACACTCTATTTGAAAAT
ATACAGTCAGAGGAGACAAAAGAAGAAAATTAAAAACAATGAAGCATACCTACAGGATCT
AGAAAATAGCCTCAAAAGCATAAATCTAAGAGTTACTGGCCTTAAAAAGGAAGGAGAGAG
AGAGAGAGAGTGGGATAGGGGTAGAAAGTTTATTCAAAGGGATAACAATAGAGTATCAGT
ATTCAAATACAAGGTTATGGAACACCATTCAGATTTAACCCAAAGAAGACTACCTCAAGA
CATTTAATAACTGAACTCTCATTCAATGGGAAAAGTAAAGTCCTTTCAATAAAGGTGTTG
GGATAATTGGGTATGCAAAAAATGAATTTGGATACCTTTCTTGTGTCATATACATAAAAC
CCCAAAATAGATTAAAGACCTAAGTATAAGAGCTAAAACTATGAAACTCTTAGAAAGAAA
CACAGTAAATTTTTGTGACCTTTGATTAGGCAATGATTTCTTAAATATGATAAAATATGG
TAAAAGCAACAAAAGAAAACATGAATAAATTGGATCTTATCAAAATTTAAAACTTTTTTG
CATCGTAGAATACTATCAAGAGTATGAAAAGAAAACCTACAAAATAGGAGAACATGTTTG
GAAATCATGTATTTGTTAAGGGATTAGTATACAGAATATATATATATATATATATATATA
TATATATATATATATATATATACTCTTACACCTCAACTATAAAGAGACGAATAACCCAAT
CTAAAAAAATAGGCAATAAATAGCTATTAGTTCTCCAAAGTACATACACAAATGACCAAC
AAGTTCATCAAAAGATGCTCATCATCTTTACTCAGGAGGCAAATACAGATTAATATTACA
ATGATATTAGACATGGATTTGTCATATACAGACTTTATTAAGTTAGATTCCCTCTATGCC
TAATTTGTTGAGAGTTTTTATCATGAAGAGATGTTGCATTTTGTCAAATGCCTTTTCTGT
GTCTTTTGAGATGATCATATGGTTTTCGTCCTTTATTTTGCTGATATGATGTACCACATT

FIG. 1E

TATTGATTTGCATTTATTGAATCATCCTTCCACCCCTGGGATAAATCCCACTTGATCATG
GTGTATTATCTTTTTGATGTTTTTGGATTCACTTTGCTGATATTTTGTTGAGGATTTCT
GCATCTATAATCATTAAGGATATTGGCCTGTAGTTTTCTGTTTTTATGTTGTATTCTAGT
CTGATTTTGGTATCAGGGTAATGCTGTTCTTGTTGAGCGTGTCAGGAAGTCCAAAAGACT
TCTTCTTTAGTGTTTTGGAATAGTTTGAGAATTGTTAGTTTTTTTTTTTTATAAGTTTGG
TAGAATTCAGCAGTAAAGCCATCCAGTTCTGGGCTTTTCTTTGTTAAGAGACTTAAAACA
CACACAACGCACACACAAAATGAAATATCACTTTCCACCCATTATAATTTACAAAGTGGA
AAATAACTCGTGTTGATAAGAATGTGGAAACCTTGAAACCTTCATGCATTGCCAGTGGTA
ATGTGAAAGAATCTTGCCATTGTGGAAAACAATTTGTCAGTTCCTCAAACAGTTCAACAT
AGAGTTACTGTATGAAATAATTCAACTCCCAGGCATGCACCCAAGAGCATTGAAAACATA
AGTACACACAAAAACTTGTACAAGAACAGTCAGATCAGTATTATATATAATTGGCAAAAA
ATGGAAACAATCCAAATATTCATCAACTGCTGAATAGATAAAATGTGGCATATCCATATA
ATTAAATACTATTCAGCCACAAAAATAATAAAGTACGGATAGACACTAAAACATGGAAGA
ACCTTGAAAATATTAAGCTAAGTGAAAGACATAAGACACAAAACCCAACATTTAAAGGAA
ATTTCCAGAATTGTCAGATCCACTGAAGAAGAAACTTGAGTGTTTGCCAGCATGTGGGAG
GAGAGGAAAATCAGTAGTTATGAGGTTTCTGGAATTAGTAGTGCTGATGGTGACACAACA
TTGTGAATATACTATAAACCACTAAATGATACCTCTCAAAATGGTTAAAACATTACTGTT
GTGTTATGTGAATTTTACCTCAATTAGAAAAGAAAAAAATCTTATCAATAACAAAGAGAA
ATTTCCACACAAGGTGGGATCGCTTCCACAGTGCTACTCAATGCAGTTTAGCGATTGCAT
TTGTATTGGAGTAAAAGCATGTCACATTGCTTTTAACATTGGAGTCCAATACATAAACCT
CTTTCACCATAACTATATGGAGTTCATTGTATGTATATTTATTAAAATGGAATTAAGATG
AATTTCACAACACAATGGATCATTTTTTTTTCATGTGGAAAATCAGAACACATGCCTTA
ATGGTTACATGCCCCACCTGCTGCTCACCTAAAAGTAAATTTCCTCTAACTCAGACAAAT
ATGTTATTTTCAAGGAAAAGAAGCCCAGAGAACTGAGATCCAGAAGAAATAACATGTATT
GAAAGCACACAGAAGTATTTCAATGAACTCAAACCCAAGATTGTAGAAAACTCTCATGTG
CCCCTGGGACTGATGTTTGAAAATACACATATTTTGCTCCTACTCTTTCCTTCCCCAGAT
CCCACCCTTCAGAGCACCCGACGATAATGGATAGTTTCTAGCAGGGTGTCTGGAATGGGC
AAGTACCCCCAAAGTTATAGTTTGTACTGCAAGACTTGAACCCACTCTTTTTCTGCCCTC
TATTATTATTTTTGCATTTTAACCATTTATTATTTTGAAAAGAAAAGAGAATTTTTAGAA
TATGGAAAGAGGAAGTGAATTAATAAAATAGCACACCCTACATAGAGACTGCTAATCCAT
CTCCAGTCTAAAGATTTAGTAATAGGCAAGAATATACATATCCAGGAATTTCCTTGGTGT
TACATAAACAAAGGCGGCACATATGTATATTTTTCACAAAATATTCACTGTTTGAAGAAG
GAATTACTCCCTTCAATTGAGTTCAGGCCTGATCAACAAGTAGTGATTGGCCAACAGCTA
AATGCAAAGTGCATGCTAAGTCTGGGGATACAAAGATGAATGAGAAAACATTTATGCCCT
TAGGAGAAAAACAAATATCTTTATCTCAGAGAATAGAGAAGGAGATTGATTCTCTTTGGG
GGAGATGTCATCCTGAAGAGTATAACAAGTTCCCCTATAATTCTACTTTTCAGTACTGTT
TAAAATACAACTGGATTTTTTAAATATGTAAAATTTATATAATTTTACAAATGTCTTTG
TTAAGAATTAAAACTATCATTAGTAAAGGACACAGCTGGAAAATTGAAAACATTTTGGTT
CTCTACTGTGGAAACAGAATAGAGTAACAGCAAAAAGCGTATTTCTGGAATTGGACCCTG
ACAACTCTGCTTAAACACTCCACCACTTTCTAGCTATATGACCTTGGGTAAGTTACTTAA
CTTCTTTGTGTGTCAGTTTCTTCATTTGTAAAATTGGAATAATAGATGCTTTTTTTGAGA
CAGTGTCTCATTCTGTTGCCCAGGCTGGAGTGCAGTGGCGTGACCACAGCTCACTGCAGC
CTCAACCTCCTGAGTTCAAGTGATTCTCCAACTTGAGCCTCCCAGATAGCTAGGACCACA
GACACATGCCACCATGCCTGGGTAATTTTTTTTTTAAGTTTTTCATAGAAATAGTGTCTC
ACTAAGTTGCCCAACCTGGAAAATTGGAATAATAATTCATAAAATCTTCCTCCTAGATTT
GTGAAGATCAATTGAGTTAATGTATGTAACGTACTTGGCACAGAGCTTGGCCCATGTAAT
CTCTCAATGAGTGCTAACATTACTTGTCTCACAAAAAGTTACTTACTTCCGTCTGGCACC
AACTCCCTCTCTCACTTCCCACAATCTGGTTACCATTCATTCTTCAGTTCTCAGCTTAAA
CAATGTCTTTTCCATATGGTTTCATTGACGCCACTTTGGGAAAATAGATGTCTCTTCTGC
TTGCATTTTCAGACCTTTTTAGGTGTATACCTTAGGGCATTTGCTTTACTGACCAAAATT
ATTTGCCGGCTACTCTGTGCTTTTCATGACACACTGAATAAGACAGGAAGAGTGTTTATC
TATGCTCAACATAAGATAGGCATATAATGGAAGCTTCGTATATATTTGTTGAATAAAAAA
CATAAGGGGAAAATATCAGATCTAATAATGCAGGACAGGAGGCAAGATGGAACGGAGAGA
ACCTTGTCTGAGAAGAGACATAATTAAAACAGGGCATGGGAGGTAATAGAAAGATTGGAG
GAAAAAGAGACAGAGAGACAGAAATGTTTGTGGTAATTTGTGACAAGTAGCTTTGATTGT
TCATGGCCTAATCTTTTAGGGCATGAGGTTATTTCATTCTCTGTAGCCCACCGAGAGTGC
GTACAGTGACACATGTTATGTAAGTCCCCTTTTCCCTTTTTATAAATGTCTAGACCCCCT

FIG. 1F

GTGATTTGAGACTTTTCTAGAAGAATTTAGCTGAAGACCATATTGTTTTTAAATGTAGT
ATTTGGAGCCTAGAGGTGCCAGATAACTTCCTGCAAAGCTAATGCATTTATTTTGGGAAT
ATATAAGCTCAGTATCATCATTACCAACAGTGCTCAGACTTGATTTTATTTTCATTCCAA
CAGCAAAGGAAAGAAAGCAACTTCTTTCATGCTTCCATGCCACTCTGCATCTCTCTACCT
TCACAGAGTTTCTCAATAATGGCAACATTTCCAGTTCACCAATGGACTGAGAGATCATTG
AGGCTAGACTAGTCTTATTAATCCTTATACCCCAGCTCCTAGCCGAACTCCTGGACACAC
AATAGATACTCAGATACATTTACTGAAATGCATATAGAAAGTTACACCTGCAAAAAAGAT
GATCTCTCACCAGGAATAAGAAAATATAATCTGGGACAGCCCATATATGAGATCTCTAAA
CAACCTACCTATAACCACCAAGAAAAAAAAATACCTGAGTTTGAGATTTATTTTTCCGTC
TCATTTTTAATATATTCCAGTTAGTGAAAGAGCTAAAATAAATGACAAGAAAAATTTAAT
CTAGGTATTTAAACAGAATTATTCTGAATGTTGTGAGCTACATTTCTTTTTTACCTTTTA
TTTATACATAGTATTTGTATATACTTATACAATATATTTATTTTGTATATATAAATATAT
TGTATTTATTTATACATGTAAATGTATAATATATTTATTTATACATAGTATTTATATATA
CATAGTATTTGTATATATTTATAGGGTACATGTAATATTTTGTTACACGCATAGAATGTG
TAATGGTCAAGCCAGAATATTTAGAGTATCCATTACCTTAAGTATTTATTATTTCTCTGT
GCTAGGAGCATGTTAAGTCCTCTCTTTTAGCTATTTTGAAATGTACATTGATGTTAACTA
TCATTAACACAGAGTAATTGATATGTATAGCAAATAATATTTGCAGTAGGATATCACATG
TTTACTTATTTATTTATTTATTTATTTTTATTATACTTTAAGTTCTAGGGTACATGTGCA
CAACGTGCAGGTTTGTTACATATGTATGCATGCGCCATGTTGGTGTGCTGCACCCATTAA
CTCCTCATTTACATTAGGTATATCTCCTAATGCTATCCCTCCCCCCTCCCCCACCCCACG
ACAGGTTCCAGTGTGTGATGTTCCCCTTCCTGTGTCCAGGTGTTCTCATTGTTTAATTCC
CACCTATGAGTGAGAACATACGGTGTTTGGTTTTTTGTCCTTGCGATAGTTTGCTGAGAA
TCATGGTTTCCAGCTTCATCCATGTCTCTGCAAAGGACATGAACTCATCCTTTTTTTGGC
TGCATAGTATTCCATGGTGTATATGTGCCATATTTTCTTAATCCAGTCTATCATTGTTGG
ACATTTGGGTTGGTTCCAAGTCTTTGCTATTGTGAATAGTGCCGCAATAAACATATGTGT
GCATGTGTCTTTATAGCAGCATGATTTATAATCCTTTGTGTATATACCCAGTAATGGGAT
GGCTGGGTCAAATGGTATTTCTAGTTCTAGATCCTTGAGGAATTGCCACACTCTCTTCCA
CAATGATTGAACTAGTTTACACTCCCACCAACAGTGCAAAAGTGTTCCTATTTCTCCACA
TCCTCTCCAGCACCTGTTGTTTCCTGACTTTTTAATGATCGCCATTCTAACTGGAGTGAG
GCACTGGTCTGAAAATATCAATTCATTTAATTCTTTTAACAACCTTAAGGGGATATCATG
GTACAAATTTAGAGCTTTCTTTTGTGTTTGTAAAATGGATTGATTCCTTTTCCCTACATC
CAGCAGAAATATTTGAATTGAAGAGAAGAGTAATACCTAAGAACTAGAAATTCCTTTCTT
ATGTTTCAAAAGATATCAAAAGATCTAAGGAAGATATTCACATCAAAAATGAGTATTATA
ATATTTATTATCTATGGTGCACTTGCAAAAAAGAAAACAAGTAATAATCTGAAGATTTAA
GTGAATATTTTATGACATTGGAGTACCACATATTTAGAAGAAAGCACCAGAGAAATCATA
GATAGAAGGAAATGGAATATTTGTAGGATCAAGATAAATACAGCTTGTCATAAAATAAAG
CAGGTATCAGGATAAAATCTTGAAAATATTTTCATTTCTCGTTATTTATAACTTCAATTT
ACTGTGATGATTAATTGTAGGTGGAAGATTTACGAAGAGAAGACTGAAGTATAGACAAGT
TGAAGTGCCACAAAATGAAAGCTAATGACACTGACTACTTAGGAAATAGCAGACTGGGTC
CATATTTATAGATTGTCAATGACAAGGAATTTGCAGATGTTAATGAATATAGATCCGAAC
TTAAGTTGCAACAACCTTTCCCACTTTGAGATGAATAGTGCATGGAAGAGTAAAATGCAG
ATGTTAATAAATCAGAGGAAGACATCGTGCCAGAGTATAAAGTTGACAGATTTATGCCGA
TGAACTTGAACAAAGCCACAGAAGGCCTACTTGTCAAATTTACTGGTGACAACAGGTCTG
GAGAAATGGCTAATGTTTTGGATAATAGCATTAGAATTTAAGGTCTGTTTAAACTTCAAA
TTAACAGAATGAAATTAATATATGCACATATCAATTGGGTCTTTTGCTTATATATCATCT
CTTAATAGAGCCTTTTTGAACAATCATTTCTAATGTGACCTTTGGGATTTTCTACTCATC
ATCACCTCATCCTGTTTGGTTTGCATTATAGCATCTATCCCTTCCTAACGTTTTCCCTAT
GTATTTGTTAGTTTGTTTTTTTTTAATCTAACTTTACTAGAAAGTAAAATGCATGGAAAC
AGCAACCTGTTTAACTTTGTATCACTAAGAGTGGAAAAATAACCCTCAGGAAATATTTGG
TAAAATAATAAAATGCCCATTGATGCCCTTCTCTTAAAAAGAAATTTAATTAGTGCAGAT
TGGGGAAATACAACAATATTTCTCATAAAATGTGATATCTATACAATAACAGAAGTACTA
TGTCCCAAAAAGTATTCTATAAATAGAAGAAAGAACAGATGGTTTTGCTGCTGATTAATC
CATTTATCTTTCGTAAATCATCTAATTTCCCCAGGAACAGCTTCCTCATCTATTAAAGGG
GGTTAGTAATAGCTAAGCCCTCAGGGGTTTAAAAATGCATATGAAATAATTTTATAAACC
ATAAAGCACAAAACAAATATGAAAAATTATGATTGGAGGAGGGGGTGGGGTAGTTAACTA
AATCTCAGTGTAAACCACCAATGTCTTGTGTGTGTTGAAAAAATAATTACATATAAAAAC
TGGTTGCATCCAAAGAATAATGTACTTTTTGCACTGGCAAGACTCAAACCATATTATTGT

FIG. 1G

TACTTCCTCCCAGTTACATATTTTGCAAGATATTGACAATTGTCTAAAGGAAGACCAAAC
AGATGTAGGTGGAGCTACTGTCATTTGAACAACATTGAAAAGAAAAATACTAAAAAAGA
AACATGAGGGCATATAAAGGAGCGCTGGGGCTGTGATGTTTATTTTGAATCTGTGAAGCA
TTGTCATGTGGAAGATTTATTCTGTGTAGCACCAAGATGCAAACTAGGAATTAGAGGTAA
AAGTCTCAAAAAGACAAATCGTGGCTTGAGACCTTGGTTTAATGTAAGAAACAGTTTTCT
CACCCTTAGAGCACTCCCATAAGGATGGAAGTAGTGAATTGTGGTGGTCACATTCAAGCT
AGATGGGGACATGTCAGCAATGTTATCAGGAGGCTTCTACTCTGAAGCTGAAGTTCAGAC
AAGATTTCCAGGCTCTTCCCAAGTGCAAGATTGTAATTACTTAAATGCAATATTTTTACC
ATGTTTATTAAGAATAAAAGGATCATGAATTCACATTCTGACAAATGCTAGAATACTTAT
TATTAGAGACAAAACCAGTGCATGAGAGAATGGCAGGTGACATCAGCCCTGAATCAATGG
GAAGAAAGACCCAATGGGATGTGGTATTTACCAGAGAGAGCACTTCTGCTTAGATTGCTA
CATCCTACAGTGAATGTTTAATATCATTGAGTATATTGGTGGTCTGTCATGCTTGACAAC
ATTAACTATGATCATATTTATGACACTTGGCGTCCTTCAAGAATTTGTAGCTCTATTTCA
CATGACACTTAACTATCGCAAATACAAATTCCAGCTAAATAGACCCTTCAGTTTAAAAAC
AGTCTCATTCTCAAATTTTAAGGAGAAAGTGAAGACGGAGATGTCTTAAAGACTCGGCAA
GTACTAAGTTGGCAAATGTCAAATGTTAAAATAAGTTTATATTAAATGTTAAAGTGTTTG
CCTGGAATGACTTTTCCATTGTCCTGCTTGAGAAACACAGAGGCACCTCCTTATTGCTTT
TATATTTGCTTTACAAAGACAAATGTATCAACATGCTCTGTATTAATTGTATGTTGACAT
TTTTGTCATATCCACAGACTGATGCATGTCTGTGCATGGTTTATAATAAGTGCACGTAAA
AATAGAGAAAATAAGTAGAAAAAGAGAGAGATTTAACTCTCACCCCCCACCCCCCAAAAA
AACAGATTAAATTAGTTTTCATTACTTTTTTTTTTTTCTTCAGCTTCAGCTCTCCCTCAG
CGAGGGAGGAGGCTGTGGGCTGCGGACTGAGTGCTGGAATGAGGAGTAATTGAGCTTCAG
CTGAGCCGGACGTAGCTTTCTCCTCCTGGTGTCATTGCTGCAGCCTCCAGTGCCGGGTCC
CTAGTTCCTCAGCTGCCTATCTTCCCGGTGCAACATCGCCTGTAAAGACAGCAAAGCCAC
CGCAGAAGTTGCCCGGCAGAAGACTCCGGAGGCATTGGCTCAGTAACTTTTCACGTCATT
TTCTGCTCGGGAGCCCCTTCTAGCCTCTCCGCGCAGCCTTTCCCACCGCAAATCACCAGT
GCTCATGGGGCAGGCGGAGAGGAGCTTGCAGCATTGAGCGGAACCGGACTTGAGCCCGTG
ATGTCCGGCACCAAATTGGAGGACTCCCCCCCTTGTCGCAACTGGTCATCTGCTTCGGAG
CTGAATGAAACTCAAGAGCCCTTTTTAAACCCCACCGACTATGACGACGAGGAATTCCTG
CGGTACCTGTGGAGGGAATACCTGCACCCGAAAGAATATGAGTGGGTCCTGATCGCCGGG
TACATCATCGTGTTCGTCGTGGCTCTCATTGGGAACGTCCTGGGTGAGTCTCCTCCCGGG
CAGCCCTCCTAGGGGCTATCACCCCCTCTCCGCCCCGGGCTGAGAAGGCTCTAAAGAGAC
CCCTCCCTCCCCCGGGAAGCAAACAAAGAGGTCGCTGCTCTCGGATGGGGTTTTCTAATA
AAATAATAATAATAATAGAAAGTTTTCTGATTTTCCGAACCGGGACCGAGCCCTGGAAAG
GTTATTCCCTGTTTTGCAGGAATAACGGGGAAACCGCGTTTCTTTTTCGAGCACCTAGAT
TACAAGCGCAGGGAGAGGGGCCGCGGCAGGGATCTCCAGGTGGATTTTGTTGAGTGTGTG
TGTGTGTGGGTGGGTAGGTGGGGGAGTCAGTCATCCCTTTGTGTAACGTGGCTGGGTGTT
TCAGGGGGGTTGGGACGAGACAGAGCTTGCAGAATACAAAGCTACATCCCTAAGGAGCAA
GCTCTCTGTGGCTGTGGAAGTCACAAAGCATTTGTGAGCTAGGTGGCATTGCCCTTTGGC
GAGGAGGTTTAGTCTCCAGTCAAGAGGTGGTAATGAACCAGCAGGGAGTGGAGACGGAGG
CAAAGCAGGGAAGTGCACTCACTCATAGAAGCTGAATTAAACAGGATCCATGCCTGGAGC
AAGAAGGAGGGGCATCGGAGAAAAGTACCACAGAGATCTCAATCATCCATCCATCCATTC
ATTCTTACATCCATTCAGCCAAATATTTTTTTTTTTCAGTCTGCTTGTTGCCAGGCTCAG
GAATTATTCATGTCAACTGTTTGTTGTTGTTTTGTTTTGTTTTGTTTTCTCCAAAGATGA
GACTAAGCTTAATGCTAGGCTATTTGTCCCGGTCTAGGTCTGTATGCAAACACGGGTTTC
CTCGACCCCTCATCCCCCTCCCCCTAAACAATTTCTGAGGGTTGGGGAGGGGGTGAGATG
GCAACATGGTGAGTGCGATGATGGAATGTATTAGGGCAGTTGGGGAATATACCTCCAGAA
AAGGGGCTTTGGAAGGGAGGGATAACTTGAAATAAATTGTGAATGGAAGGAGAGTGTACC
TTGATGAATGAAGAGTAGAAGGCTGGGAGACTTTTCACATGCAGAGGGCAGTGTGGAGGA
AGTCTCTGCTGAAAATGACAGGAGATGGAGGAGGCTAGGAGTTGCTCTTGATTTTCATTT
ATAAAAGAAGAAGAAGGTGAGTGAGGTGAGATAGGCTGGGAGGCTTTGCAGTCAAAAGCA
AAGAACTTGTAGCTGCAATGGGGACTGACAAGGAAATTATCAGGCTTTCAGACTAACCTG
ATTTTTGCCTTCTCTCCCAAGTGTGTTGGTCTGGGTAGAAATCATCCCGAGTAGTCTCTC
ACCAACTCAGCAGGCAGAATAGATGATAGTATGTGAATGACAGGAGTTCTCCAGAGTGTT
GGTAGAATGTTATTTGAGGAGACAAGAAACCTCTGAGAACTTTAGTACATTTTTAAATAT
TATTTTTAGACTGTTTTCCTTTGGTTGATTTAAAAGTAAAAATAAAGGAAATCTTTTTGG
GATACTAACAAAATGAAACAAAAGTGGAAATACACAAGATTAGGATTCTTGTTATAAGCA

FIG. 1H

TAATTCTGTTGATAATAATCCTAATCTTGCTTTCCTTCTTCTTGTTACCCATCCTTAGGA
TTACATCTCTTAAGACACATGGCTACCAGCATAGCAACATTTTACTGCATTATGCCAACA
CTTATTGATAAGTGAATAATCAAAATTGAACATATATTGAGTACCTACTGTGTGCCAGAG
CCCTTCATGTACATTCTCTCCCTTAAATATCAAAATAACCCACATTAGCCAGAAGAAGAA
ACAAGACTTAGAGAAATAAAATGACGTATTAAGGGACATAATTTAAATTCAGTTCCATTT
TTTCTGACCTCAGATCCAGAATTCTCCATTGTTATTCCACTCTAGAGCTAAAAAGCATAT
AGAGAATAGATTCTCTGCTCCTGATTGTCTGCAAGTTTATTAGATGTGTTCCTGTTCTCC
TCTGCATCAACGCCCACTGCCAATAAAGTACAATGAGGGATTAATGGCACTGTCATTCTC
TTCACCAAAAACCTTTCCAGAGAAGCAGTAATTTTTTTATGAATAGCTATCAATAGTAAC
TATTTGCCTTCCTTATTTTAATTTTCGGCTGAATCTTTGTGGTAAAATGTGCTCTTCTTT
GTTGTTATTGCATTTTTACCTTGCATAGACCTTGTAGTGAATAGTCTCCATATCCTAATT
GCATAGTTTAGGGATACATGTTTGCTAGCCTGGGGAGTTTTAGTTTCAAGAAGGAAACAC
CTCTACAGTAAGGCTACTTGTTTCATAATGTCAAGGAAGATAGCACTGTCCACAGCCCCA
AGTGCTGAAATGGCCAATTCCATTCAGCCTAAAAAGAAAGATTTACTCAAAGCACTCTGC
CTTAAAGAAACTGACAGCTATTTTCCTCAGGACTGAATAACACTGAAATCCTCTCTGGTT
GAACTGAAATGCATTCTTTTCTGACATACTGCCTGAAAGTTGATGAGGTTTAGGTTTGAC
ATTTAAACAAACGAGTAGTGTCGTTACTCACAGACAACTTCCTGCTCTTTGATGTCACTG
TCAAATTTGCAAAATGAATTAGATTGAGAATTGCTTCTTTGCCCCTCTGGTATAAGTAAT
TTTGCACATAGAGTGGTAGGACAGGATGTCACATGATTTATGCAAAATAAAGATGCAATA
TTAAGTATGAAGGTAAAATACCACAGTGTAGGCAGCAGATGTAATCACTGAGCCTTCAGG
TCCAGTCACCATTTGTACTTTCATATAACTGCTTGGAAAATCTCAACCTTTTTGGGCTTA
CAAATATAATGCCATCAGTTAGAAGTCATCTTCTCCACAATGTCCTTTCATGAAGTGATG
TAATAGGATATGCTGTGGGTAGCATAACAAAGTCTTGATTGTCCTCATCTCTTTTTCTTC
TCCCCATAGTCCCTCTTTATCACTATGCCACCTCTCCACTCTCATATACTCCTCCCAAAG
ATGGAAAGCAGTTTCCTGGGGGAGTAAAGTTTTAAATAGAATGTTATGAGTATTTACATT
CAATGAAAAGCTGTAAGCATGTTTAATGTGAAATTTTAAGTTCTAAGGAAGGAGCATAGG
GTAAGGTTCTTTTTGGAAGGAGTATCTTTTCAGTATCTTCAGAATAATGCCACCTATAAC
CTATTCCTAACTATGTCTTCTACTACAGCTAAGTAGATGTATCAACTTATTCAATTGGTA
TATTGTGAGCATTATCATTTTTTTAAATTAGTGTGTATATCAGGGGAGCCTCTGGGGAAA
TGTAAAGAAATGTGACTGATGTTAATTTTTACTCCTGATTCCTTGAATGACAATTGTAGG
GAGAAATGTGTTCTAGTCAGTTTAAACATTAAGTACCTAGGGAAAATGATCAATTTTCTG
CTTCTCATATCTGCATTCAAAGATATCATATGTTTCATCTGGTATGCTTCTGTCATATCT
GTTGTTGTCTCCATATGGAAAATAGGAAAACATCAGTCTAGCTATGCTTCTTGCTTCTTG
TGTGCCATTAGCAAGTTATTGAACTATCCAAGTCAATTTTTTTATAATTACAAATTAAAG
ATCGATAATGACTGCATTATAGAAATAGTATCAGGATATAATGTACGTATACCCTCTATA
AAGACATATAAAGGGACACAGGCATATACATATTTTTCTTGACACATAGACACTAATTAA
TGTCAATTTTTATCCCTTAATTTTCATGACTGAACTTTTTGTGATGTGGTGTATAGCCAG
CTTCTGCCTTCATGGGCCAGTCTGTATCTCTGTAGCTCTTTATGGCCTCTGCCCCAGCCT
TTTCCTTAATTGCATATTTTCCTAAAAGGTGTGAATAAAATGGTGTTGGCACACATTACT
CTCCTTTTCCACACTAGCTCCACCCACCCATCTCCTTCATACTGATTGCTTAACATTGCC
TTCTTGCCTTTAAATGAAAGCCATTCCTAACTATTGGAATAGTTTGCTTTCTCTCTCAAC
TTAAATTTGCCTGTGCTGGGTCCCATTCATTTAGAGTTTTTGAGTTGTTAATAGGTTGTT
GATAGGCAGGTCTATCACTACTAGTGTTTTAAATAACACACACATTGGTAATATGTTGAT
TTAACTCATACATTGTTAAAATACATTGTGAAGTATTCATAGTTAAAATAAATTATCCAT
TAAGTAATTTACCTAATAACAGTTTACCCAAGTTAGGTGTGTGGAATGGGGAAATATTTG
TAATAAGTTTGCTTCCTACAGAGTTAGTCTTGTGTCAGATATGTAAGTGGTAGAATTGCA
AGTTCATGTTACTCCTAAGCCTAGAGACATTTATTTTCTGCTTCTCCGAATGCCCATTTT
AGTTTCATGGGTGTTTGTAAACCCATCCTTACCTACACAGGAAGCAAAAAGGGGTTATTT
CTAAACCCTTTTTAGATATAGAAATAATACATCACTCATCTCGGCCAAGACTCAATAGAA
TCATGAATAGTGACTGTAAAAGGTAATATTAACTATTAGGCTTTAAACCTATTGTGCATT
TTAGTTTTAAAATGCAAACATGCTAATCTGAATAAGAATTAATCTGATGCCTCTACATTT
TTGCTAAAATCATAACTGTTTAGTCTTACTTAGTAAAATAAATTATATCTTTGACTTAAA
ATCCCAATGATAACTTTTAAGATGGCTATTTCATAGATAACAGCAACATTTATCATGGAC
AGACAATAATGAGAATAACATGTGCAACTGATAATTTAAATGCAATGAGTTATTTCTGTA
TTTGAAAAAATATATTTGGGAAATGGGATAATTAAAAAATACCAGTTTTCAAGAGACCAA
ATCTAAAACTCAAACATAAACACAATGCTCCAGTTTTTAGAAAACTGTCTTGATTGTAGT
AGTGCCTACATACTAAATTGTATCATATGATTTATATTAATTTTCCTTATTTTGTATTTT

FIG. 1I

AGATTATATTTGAAAATTTTCATGTACTGCAGCTATGTTAGCATCTCAAAGTCTCCATAT
TCTCACTCCGCTCCGAAACATCCACTGCTGATGTTATTTAACTAGTGAAAGAAGATCCTT
CCATGTTTCTTCTTATAGCATTCTGACATCTTCTCCACCCTAAGGAATGCTGGCTTTATT
AAGTATGTTTCAGTCAATGACATGTGATTGGTGAAGCTGACGGTATTTGTCTTCAGTTCC
TTTTTTCCCTGCAAAGGAAATTTGTTGAATATTTATTGGGTACTATATGCCAGGTACTAT
ATGTCAGGCTCCACTTACATATACTCTATTGATGCCTTACAACAAACTTATAATGAGAAG
ATTAATAGGTTTTACAAATAAGAAAAATGAATTCAAAGAGCAATGCTAACTTACTCAAAA
GTTTAGTCAGGCAGTAAATAGCAGCACTAGGTTTCAAATATGGATTTAACAAATTCCATG
GTCCATGCTTATTCCATTACTTCATCCTGCCTCTTTCCTTAGCTTCTAACCCTGACTGGA
GATGCATAGGCAAAAAGAGGAAGGAAGAGATACTTAGATGTGCCCTCTAGACAATTTACA
GAGTTGTTTGGGCATGTTGCCATGCTGTTTTTCTGATAGACTACAGTTCTTCAGCTCTGA
GGATGAGCTCATTTGATAAGCCAATCAAGGTCGGGCTAGGGTTACTTTACAAGAGAAAAT
TTCAAGGTAAAATAGGTGCTGCCAAAAATGCTTTTACCTGTTCAGGGGGTTGACTCACTG
GAAAAAAAATGTTAGATAATTGTGGCCAAGGATTATTTTGTTATTGAAAGTGCTATTTTT
AGACACAATTTGAGCCTGAGAGCCTAAACACTTAACACTTCACATAATCTACAGATATTT
GTTTATTTTTCTTTTTGTCATGCATTGCCAAATAAATAGTATTTATTTAAACAAATCATG
TTGCTATTGATTTTATTAAATAGATGAACTTTTTTTAATTTTTTTTTTTTGAGATGGAGT
CTTGCTCTGTCACCCAGACTGGGGTGCAGTGGCACAATCTCGTCTCACTGCTGCCTCCAC
CTCCTGGCTTCAAGCTATTTTCCTGCCTCAGCCTCCCCAGTAGCTGGGATTACAGGCACA
TGCCACCATGCCCAGCTATTTTTTTTTTTTTTTGTATTTTTAGTAGAGATGGGTTTCACC
ATCTTGGCTAGGCTGGTCTTGAACTCTTGCCCTTGTTATCTACCCACCTCAGCCTCCCAA
AATGCTGGGATTGCAGGCATGAGCCACTGTGCCTGACGTGAACAGGTCAATTTCTATATC
ACCGGACAGTGTTCCTGGATCAGAATAATATATTATATGTATGAAGAATCATTACCTATT
ACATCAGACATGAAATGACCTTTAGATACTGACTTTGAAAGAGTTTGAGATGCTATTGGA
TGAAACACATGACCCATATGACCAGTCTTTTGAATTGCTGACTCTGAGTATAAAATGTTT
TCATTTCACCTTTGTTCACAATGAGAAGTGATCTCTTAACCAAGTAAATGAATTAAATCG
ATATTTAAAATAACATTAAATTTCTTGCCAGAAAAACTGTTCTTTCATAAACAAAAAACA
AATTGCTCAAAATAAATGACTATATCTTTATTTCTAAAAAATGTTTAGAGATTATTATTA
TTGGGTCTTTACAAGTAATTTGCCTTCAATACTAAACACATGAGAACAATGTTTAATATT
TATATAGTATTTTACTCTTCAGAAGATATTTGTCCATATTCTCTCTCAGTTATTCTTCAC
AACAACATTATGAGGTAGGTCTTTTTTAATGAAAAAAAACTCAAGTGCTTGAAGTGATTT
AAAATCACTGTGGAAGAAAAGCATGGGCATACAGAAAAGCCAAGTGGTTGTGTGTCAGCT
TGGGAAAAGCTTGCAAATTTCCTGTATTTCAAGAGGCCAGGATGAGGTGTGTAATTATCT
TTTACTGGTCTTCAGCTATCCTGTCTTTGATATGTGATTGTGTCAAAACTATGAGGAAAA
ACTCACATTAACAAACTTCATAAACTTGTTAAACATAAAATAATAATTTCGATGTTTTAA
TTTACAGTAAGAGTTTATTCTTACAAGTCCTTAAATACCCAAAGTTCTTTCAGTTATCAT
AGTCTTTTTCAGTAGACAGAAATCCATGTGGACTGTTATTGTTCTGAATAGCTAGGCTAT
GCCATAGTAGCAAACAAACCCTGAATTTTCATTGGCTTAGTATCACGAAAGTTTATTTCT
TGCTCATTTAACATCTGAGGTGGGTTGGAGAGTCTCCTTCATCCAATGACTCACAGTTCA
GGCAGCCTCCACATTTTGTGCACTATCCCTAAAAGGTGGACTCTGTGGTAATCAGTTTCC
AATATGGCTTCCAATGACCGCCCCCGGGCCCCGGCCCCACTTCCTGATAGTCACATCATC
GTGTAGTCCCTTTGCATATTATGCCAGAATTGGTCTGGGTGACCAACAGCTCATAGCAGC
AGTGAAACGATGTCACTTTCAAGATTACATAACAGGAGCTTACAGCTTCTGGCTCAAGTA
CCCACTTTCTCTCTAGCTCTTGGATCTCTTCTTCTGGAGGAAGTAAGCTGCCTTGTGGTG
AGCAGCTGTTGGCTGGAGTTAAAATCTCCAGCCAGCAGCCAGAGAGGAAATACGGTCTGT
TAACAACCTCATGTGTGAGCTTGGAAGCAAATCCTTCAGACCAGGTTGAGTCTTGAGGTG
ACTACAACAGCCACTACCCCAACCCACCCCCAGCTTCAGTGCAACTTAGTAACAGACACT
GAGTCAGAACTATTCAGCTAAGCTTCTTGCAGATTCCTGACCATTCAGAAGCTATGTCAT
AATAAATTTTTGTTGTTTGACTTCAGTTTCGGGATAAGTTGTTGCACAGCCTCTAAAGTT
GTGAACTAGAAGAAGTATACTGGCTCTTAACCACCTTTGCCAAAAATTAACACTTGTCAG
TCATGGTCATATTCATTTGGTCCAAATCAATCATATCGTATCAACCTAACTACAAAGGGG
ATTGGGAGATGGTGATGTCTCTGTCACAGAATCTATATAATAGTTAAAAGTATTTTTAAC
TTGCATAGACTCAGAACAAGATAATTTGGAGGAATTCAATGCTTAATGGCATACCACTAA
GATAAGCTGATAGATATATCGTTGCGATTTGGGTCTCTGACAATAGAGGCAATTGATAAT
ATTAAGAGACTATGTGCCAATTATTGTGCTTGGATTGAGGGTACAAAGGTAATAGAATCC
AAGGAACCTGCACTCTTTTTGAAAGATAGACACATAAACACATACTTTTAAAATAACGTG
GTAAGTGCTACTATGACAGATGGTTGCACAGAATGTAGTGGAAGTATTTGAGAAGGACAC

FIG. 1J

TTAGCTCTGCTGGGGGATTAGAGAGAGATACAGGAGGAGATGACACCTAAACTGAGTTTT
AATAGATGAATTCAAGTTACCCAGGTGAAGAAAATTGGGTAAGGATGTTCTAAGCAGAGG
AAACAACATAAGCAAAATCAAAGAGGCGTGAAATAGAATGAGCTATGAAGAAAGTGTTAG
GCAATTGGGTAAGTCCAATGTAAGTGCAGATGAGGAGAGTCTGGAAATGAGGCTGAAGCA
GTAAATAAGGATTGGCCATAAAAGACCTTGTGTACAATTCTTAAGATCTAGGCTTTGACA
CTGTTGTTTAGGGGGAGCTGTTAAAGGATTTTAAATTAGAGTACCATCATTGGTTTGCAT
TTTCCATGAGAGCATTTTGAGGAAAATGCAGAGAATAAATACATGAGGGGAAAGACTAGT
GAAGGTTTTCACACTGGGGTTTGCATCCTGTTTTGGCAATAAGCTTGTTTTAATGAAAAC
AAACAAACAAACTGACAATAAAGAACATAATCCAAATTCTCCAGATAATTACTTCCAGGA
GGCTTTCTACGTGCTGCATACAAAACAAAGAAAGAAAAACATAAAGTGAGAAAACGAAGG
AAAAACAAGGAAAGAAGAGAAAGAAAGAATACATATTGGAAAAACTGTTGCTGTTTTTGT
TTTGCTGAATATTTAAATTTGAGAAGCAATTTCTCTTTTTCTTTTTACTTTTTTTTTGA
GATAAAGTCTCACTCTGTTGCCCAGGCTGGAGTGCAGTGGCGCCATTTCAGCTCACTGCA
ACCTCCGCCTTCCAGGTCCCAGTGATTCTCCTGCCTCAGCCTCCCCAGTAGCTGGGACTT
CAGACATGCACCATCACGAGCAGCTAATTTTTTGAATTCTTAGTAGAGATGGGATTTCAC
CGTGTTGCTCAGACTGATCTTTAACTCCTGAGCACAGGCAATCCGCCCACCTTGGCCTCC
CAAAGTGCTAGGATTACAGGCGAGAGCCACTGCACCCAGGCGCAGGTTTTCTTTATGATG
TTTTAATTATATCTTTCTTGGAACATATATGTATGAATCTTGCATGCCATAGGTCTATTA
ATATTTTCCAATATTCTACATGGTTTTTTACTAAAATCATTTTTATGATTAGTTACTGAC
TGAGGTTTCAATGCATCACTGTACTCCTAGCTATCTCTCATTTTAGCTTTTACATCACAT
TTTGGCCTCACACTGAAACACAAAATATTAAAAATTTGAGATCTAATAAACAATTTTCAC
ATTTTCCAACTAAATCCCCACTTCTTTCTAAATTTTCTACAACTTTCTAAACATTCTCAC
TTGAAAATTTATTTTAAATGACATGTATTTTATTCAAACAATCAATGAAGATGCTACATT
GACCCCAAGTGAGCCCTTAGGGAATTTCCGTGAATATTTCCCTACAGGTTGGCATGGTAA
CACACTTCACAATTTCTAAATCTGTGGATAGTTTAGAAGCTTTTATTTGCTGTTCCTAGT
TCACAATGGAAATACAACAATGATTAAAAATTATAATATCCTTTTGTAGATTCTTAGCTT
TTATTCCTACTCAGTGACTCTAAAATGAATTTATAAGGCCCATGGTTTATAACCATGTGA
GGCCTTGATTTTGTCACTACATTGCTAGAAATGGGGTCAGAAGGCCACCAGCTTTAATAA
TTTAATTCATCAATTCGGAATGAATTTGATGAGTCAACCACTTTGGTAGAGAACCATATT
GCTCATAAATACTGTTTTGAAGGCAATTCGTCTTTCATAAAATGTGAAGATTGTGCTGAT
CTTTCTGGGCAGGGTTATGGAGGTGTGATTAAATGCTTAAGAAACCATTTTGTTATTATA
TTAAACCGAATCAACTTTTTATTATTAAAAATAGATAAAAACTTAGCATCCTCAATTATA
ATACTTTATACAAAAGTTTCCCAATTTTATATAGACTGAAGATAAAAATACATTAACAAA
TCTTACCAGCTGGTTCAGGAAAATAACTTCATAATTATTGAGACATTTATGTGTTTGGGC
TTGATTTATACTTTGGACACAGGAAAACCTAGAGAGATCTGGTTCTTTGAAATCATCAGA
GATGGTGATGGTGACTCAGAGATTCCTGAAAATCAGTAAGATTACCCTAGTTTATAGACG
TATGTGTTATTTTTTCCCCCAGGCATAATGAACTTTATAACTTGTCATTGACAAGAAGCC
AAATCATCTTAGAGAAAAGGGGGAGAATAAAAATTTAAGAACTTAAAAACACATAAATAA
AAACATGTACATACCTCACACATGTGTACACACACAGTTTGGGGATTGGATGATATGAAT
AATATAATTAATACACCCTAATTTTTCATGCAGGATTAAGAAAGTATCTTCCAAACATTA
AAAATGCTGAAAACTGGACATAAGGCCTTGAGTTTCCCAAATTCAGGACATATTTTCAAC
TATCCCCTGAGTAAATGAACTATAACATTTACAGAAGTAAAAATGATAAATACACTAAAG
ATGAATAAGTCCTTGAATTAACAGCCAAACAAGAAGGCGCATCCTTTGGATGATTGATCA
CTGTAGCATGATTTCTTTTCCTTGAATAGACAATATTCCTTGACAATCTTTCTGTAAACA
GAATACAATGTTTCCCTAAGCAATATATGCGTGCTCTAGAGTTTTCACAATTTCTGATCC
TCCTATGACTGGCTCCTGCTCAGCTCACACTGCACTTTCATGGAAGTTCTCTTAGAATGC
CAGCTTTGAATCACTGCTCCCTCATGTGCTGTGTGTGATAGCATCCCATTTTAGTTTTGT
CATAGAATTGATTACCATTTCAAATTGAATTGTTAATTTATTGTTCATTTTTCTGTTGTC
TCCCTTAAGTAAAAGGTAAGCTGCATGAGAATAGTTTCATTTTTTTTCCTGTTTGCCAAT
GTATCCTCAGTGCCGAGAACAGGTTCAGGAATACAGAATTTTTAGTTAGCAAATGAATTA
AAGTGTAAGACTTCCAGCAGGAGGAATTTTTTACATATAAGTACATTTTTTAAATTAAGC
ATTGCAGGCTTTAAATTTCTTCTATATAAATATTTAAAATAAAGCTTCAATAATTTGAAT
TGCTTTTGTGATTATTTTGTTTTATACCTTGAGTAACTTATACATCAACTATTTTGTAGT
TATTCTAGTAATGATTATGAAAGACCATTTGAAAATCTTTCCCCAGCACTGAGATCTCCT
TGACATGACTAAGTGATTTATACTATGCAATTATATTGCTCTTCTCAAGAAAAGCAAAAT
GAAATTTACAAATTTGGTAGCTTTTGTTCTTTTGTTTTCTCAAGTAAGATACACCAAGA
TTTCTTTAAATGATACGCTATATTTCTGCAATAACTGAGAAGAACATGTAATGTGCAAAA

FIG. 1K

CTCTTAAACTCTTTTTGTTTCAAAATAATTCTTGGTTGTTTTTATAAAAGTCTAAGCAAA
TACTTAATGAACTGTGTCCCAAATGAGGTGAAACAGCTGTGACAGAATGTTACTATGACT
CTGTACTTTCTATAATAAAAAGGGACAGACATATCCTCACCTGAGCCTTGGGATGTTTCA
GGCATGCCCATAGAGCCTAAGCTTTAGGAATCCTCTGTCATTCTTTTCCATTGCCAGTGA
CTTGTGCCAATTCTAGGGTTCTGGACTGTGCAAACAATGGAAAAAATAATAACACTTTCA
GGTGGCGCACAAAACCAATGTTCATAGTAGATGGATAGTTCTAGACACTTTATTTAATAG
AGAATAGGAGAAACACTAATCCCATCTAATTCTGCCTTCAAACTCCTAAAATATTCATCA
TTATGAATTAAAAAAAAAAATCAAAGTGTAACCTCACCCAGAGAAAGAAGACATTGGGGC
CAGGTCTGGTGGCTCATGCCTGTAATCCCAGCACTTTGGGATGCTGAGGCGGGTGGATCA
TGAGTTCAAGAGATCGAGACCATCCTGGCCAACATGGTAAAACCCCATCTCTACTAAAAA
ACAAACAACAAAAAAATTAGCTGGGCTTGGTGGCATGCGCCTGTAGTCCCAGCTACTTGG
GAAGCTGAGGCAGGAGAATCACTTCAACCCGGGAGACGGAGGTTGCAGTGAGCCAAGATG
AAGCCACTGCACTCTGGCCTGGTGACAGAGTGAGACTCCGTCTCAAAAAAAAAAAAAAAA
AAAAAAAAAAAAAAAAAAAAAAGGAAAACGAAAAGAAAAGAAAGCAGATATTGGTAATTCT
AGCAGATCCTGGAACAACTGAACCAAATTTATTAATATGTATTATTACTGAAAATCAGTA
ATGAACAAAATTTACAGAATGGGCTTCTTGGAGTTGTTACATTTCCCTTATTACATAACT
CTTCAATAAAAGTGTTTGTCATACCTATTTTAGTTAATTCTACAACAACTAGTGTGATAG
GGCTATTATTTGATCTTTTTTTTTTTTTTTTTTTTTACAGGTAGTGACATTCAGTATTA
GACAGCTGCTATTGTGTTAGTTGTCTGAATACCTTTACATATTATCAACTGGCCTTTTCA
TTCCTGAGTTGTGAGTAAATGCTCTGTCTCCCAGACTGGAGTGCAGTGGCGCAATCTCGC
CTCAGTGCAAGCTCCGCCTCCCGGGTTCACACCATTCTCCAGCCTCAGCCTCCCGAGTAG
CTGGGACTACAGGCGCACGCCACCATGCCCGGCTAATTTTTTTTTCTTGTATTTTTAGTA
GAGACAGGTTTTCACCATGTTAGCCAGGATGGTCTTGATCTCCTGACCTCGTGATCCACC
CGCCTCAGCCTCCCAAAGTGCTGGGATTACAGGCATGAGCCACCACACCCGGCCATAAAT
GCAGTCTTGTGTTCCCCACTTCCATTCCTCCTTTGACAGTACAGCTATGCTAGTCTGCGT
AGCAAATTGAAAAAATATGACCTGTGGGATTTAAACAAAACACAGTGTCATACACATTTT
CTGGTAAACTTAACCAAAAGGGACTTGGGTTCCATAACTAATCACCAATGCCTCAGTGAT
CTGTAACTCCTTGTAGGTACCTGATCACAGTTACTAAAGGGAAAGAGGAGCGAGGAATAC
AAGAGCAAAGTCAAGCCAGACATAGATTTTATCTCTTTGTAAACAGGAGTTCAGAAGACC
GCTCTGAATGCTGAGTTAGCATCAGCAATAATAGAAATATATGCAGATTGTTGATTTGAA
GTCATGCAAAGATATCTTTTTCATCCAAATGGAGGCAAAAGCATCATAGAGCACCAGAGG
GCTAAATCCAACTGTAGCAGCAAAAGGTACACAGAAAAATAAAGCATCCTGAACCAACGC
ACTGACTTTCTAGGGCTTATCTAATTTGGAGCTATTTCCTTTTCTTATTTCATTCAGCAA
ATATTTATTGAACACCCACAATGTGTAATCTGTTCTATTACATTCTGTGGAGGAAATACA
GAAGTGAATGAGGCATGGTTCTTACCTACAAGGAATTTCTAATCTTGTGGGGGAGACTAA
CATGTAAACAATAAACTATAGTATGAGGATTACTGAAGAGGCATATGCTAAGTCTCAGAA
CATTGAAATATAAGAGTTGGGTTTGACATGGGGAAAGAAATACCTTCTTCACTGAGGAGG
TAGCATTTTGAGTTATTGTTGACATGTGAATACGATTTTGAAAAGTTCCAAAGAATGAAA
AATTCCACCTACATTGGTGAAGTACTAAGATTAAATGCATGATAGCTTGAAGACACAAAA
ATAATTATTTATAAACCATTCCAAAAATCATTCAGGGAATTCCAATAATACACAAGTTTT
TAAACACATTTCTGGGTAATTTTGAGTAATAAGGTCTTAATCTCCTCTACTGCTTTCAAT
TGTTTTTGTGGCCTTCTTTATTTTGTGGGTATCTGGCCCAGTCTTGTCTGTAGTGTATTA
TGGTGGATTGGATTAAACATGTTTTGCAATCTCTGGAGTGATTTTAAAATGACTTGTGTT
ATATCAGAGTTTCCTAAAGGGAGATTAATTTGGCTTAATGGTAAGAACGGATTAAAGTTA
TGAGATACCAGACACTGGGAAAACAGTTAGAAGCCTGTTGAGACTCTTCAGGGCAGTTGT
TGTGAGAATGAAGTTAAGACAATGGGATAGAATATGAAAAAAAATGAAACAAACATGAGA
GGCAGTCTGAAGATGGAAGTTGGCAACTCATCAAATGTGAGAAATTTATAGGAACAGAAA
AGAACCTGCTGATTAATATAAATTTTCTGCCAAAGAAAGTACAGTGGCTCTCCTCAGCAA
ACTAACATGGGAACATAAAACTAAACACTGCATGTTCTCACTTATAAGCAGAGCTGAACA
ATGGGAACACATGGACACAGGGAGTGGGACATCACACACTGGGGCCTGTTGTCGGGACTA
TGGGAGGGAGACCATCAGGATAAATAGCTAAAGCATGTGGGACTTAATACCTAGGTGATG
GGTTGATAGGTGTAGCAAACTATGATGACACACGTTTACCTATGTAACAAACCTGCACGT
CCTGCACATGTATCCCAGAACTTAAAATAAAATTAAATTATTAAAAAAAGAAAAAGACAG
TGCTTGTCTTATTCGTTTTTTTCTTAAAATGGGAAATATGTAATATATATCAACTGTAGT
GTATAGAAGGGTCATGATGAATTGGACAAAGATACGTGGAGTTTGAATTGCTAGAGGAGT
ACCCACGTGCAGTTGTCCAGCAGAAATCAGGGCTTGTTCCCCAACATGCTATTCACAATC
AGTCTACTACTCTCAGGTATTTGTTTTTCTGTGTGGCTATGCAAGCAATAGATACAGTTT

FIG. 1L

ATGTGAAAATGTTTTAGAAAATGTCTTCTGGAATAATTAAAAGCATACAAGGGAATGTAA
ATCTCTTAATGTGACAAGACCTTTTTGCCACAATAAACAAATTCATTAGTTCAAAAAATA
TTTATTGTGTGCCTATTGCAGCAAACAAAACAGACGAAGCTCCTTCTTGTAGGGAACTTA
TACTCTAGTGATATTTAGTATATATTTTGACAATTGAACCAACAGGATTTGCTGACGGAT
TGCCTTATGGGTATAAGAGAAAGAGAGGAGTCCACACTTTCATGCCAGGTAGGTTGATGG
AGGTGCCATTTACTGAGATACAGGGCCGTAGAGGAGGAGTGTGTTTGCAGCAGGGAAGGA
GAAGACTCAAAATTTGGTTTTGATCATACTAAATTTGATATAGTACAGGTAAGTGTATGG
TGGCCATTAGAACATGAAGGTAAGAGTTTAGATAAGGAGACAGGTATGGTGAAATACATC
CAATATTTATAACCAATATTATCTTTTGTGTCTGTACCTTTTTATACATTCCCCATATAT
ATCAAAGACTATAGAAGGGACTGGATAGTGAATAAGTGATTATACATAAATTCTTTTTTA
CAGATTATTTTGCTCTTGATTTCTCCTATGTAAATCATCACAGCTACATTTTTTAAAATC
TTAAAAAGGATTACTTTGAACAATGCATTTAAACATCCAGAAAACAAAAACAGGAGTGCA
TGGTAAAAATTCTGATTTCAGAACGTATGCCTGACTTATCAAGTCAGAATTTCAGGGAGT
GAAGACCCTGGAATCTACACTTTAAATAGAGCCTCAGTTCACCAAGTATGAGAAGTCCTG
TAACAGGGAAAAGTAACCTCCTGTTATATTTGATGGAGGCCAATTGACAAGCCAAGTAGT
TTTCCATTTGACAAAAATTCTATTGTACCAATGAAGAGCTATCAGAGGGGAGTAGATTAA
AACACCTCCCTTGAAATGGAATTTGGCAAGAAAGCAAGAAATTACAGCAAAAAGACCAAT
AAGAGGAATTAGGGGCAATGAAGGAAGGAGCAAAGATGTGGGAACCCAAAAAGTTTTCCT
AGTAACAACTTTGAAATTATATTTTTAGTATATTAAATTTAAAGTAGAGTTATTAGTGCA
TACATTGGTGTAATTTATTATTATATTAAGCCAACAATATACTTTTAAACTTATACAACT
TTGCAAAAAAGTACAAATCAGAAGTCTGGGCTAAGTAGAATGCATAATAGAATCAGTAGT
GCAAAATATTGTTCTATATTTTCTAGCTTATGATTTTCTATATAAAGTCAGTCTTTCAGG
ATTAAAATGAATGTCACTTCTTTTTACCATGTGTCCTTTAAATTATTAAAATCTATACAC
ATATTGCTATACATAGTAAATATAGTTAGTCAATTATGTCATGGAAAGAATTGAAGGGTT
GTTATAAATTTAAAGGTGTTTCACTATACAAAAACATTGTGAAATACTGGTGCTGATTTA
GTTCTAGTATCTCTGATATATTAAATCATAAATGTCAGGAGTTATTGGTCACAAAATAAA
CACCAGAATTATATGACAGTCTAAAAACAAAAACAAAAAACTTCAGCAACAATATTGAAG
ATATGGAAGTGCCAGAAGAATAAGGATTAAGACAATGAATAAAAATCTCTTCCAAGGACT
GGTCTACACTAAGAGTTTAGAAATGCATTTTTTTTTCACAGAAATATCCTTAATCCTCTA
TATAGAAATGAGAAGAAAACATAAGACTTTAGCAAGCTCCATCTAATCCATTTGCAGACA
TATGGTTACCTATCTTTTCTTCAATATATTGGAGTTTGCAAATATTCTACCTTCAAAGAA
TAGGTGTTACCAAAACATTGTCTGCAAGATTTCTAAGATTTGAAATATATTTGCTATAGT
AGGTTAGAGATGAGACATTTTTACTTTAAATTGCAATAATTCAGACTTAAAATATAAAAT
GTGTAAGTCTAAATTTTTTTTTCTATTCATTGCAAATATATCTTATATATACATAAAATCC
TGTGTATACTCATATGAACTTTAAGGAAATATCAGAGGCATCAGTAATAGATAACTTGCA
TCTCTTTTACATTCAGTTCAAGCTACTCAAATTTTAATCTTTTGTTTTCATTCCAACAAA
AAAAATTAGGATCTGCCTTGGCTTTTGCTAAGAAAGTAATTATTGGCTGGACATGGTGGC
TCACATCTGTAATCCCAGTACTTTGGGAAGCTGAGGTGGACAGATTGCTTGAGCTCAGGA
GTTCAAGACTATCCTGGGTAACATGGTGAGAACCTTTCTCTAAACACACACACACACGCGCA
CGCGCGCACACACACACACACACACACACACACACACACAAATTAGCTGGGAATGATTACACGC
CTGTGGTCCCAGATACTTGGGAGGCTGAGGTGGAAAATCACCTGAGCCCAGGAAGTCGA
GGCTACAGTGAGCCGTGATTCCACCACTGCACTGCAGCCTGGGTGACAAAAAGAAAGTCA
TTATCTTCAACACTGTGCATACACACTTTTCTGCATCTAGATCCCAAATTTTTGTTTTGT
ATTTACATAGAACATTGATAAGTAAGGTAAGTATTAATTGATAAAACATTTCAAACTCAT
TTTTCACTAAATCCAATGGCCTTCCTCTTTTGCATGAAGTCTCTAAGAATCATGTTAATC
TACATACTCAATCTACGTAACAACTGGATATATCCTGTAGTTGTTGCCCATTTTTCTGCT
AAATGTTATCTTTAGCACTAAGCATGAGTATGAGGAAACAGTATCTGTGCTCAGATTCCA
GAAATGAAGAAAATGTACTGGAGGTCTTTTGGATAATGGCTACAAGGTCACAGGGACTGA
CTCCTTTGGAAGCTCAGCGATAACCATTTTCAGAGAGAATATGTCAACATCTTTCAGTCT
AGAACTTGATGTTCTGCTGAGATCTAATCTGGGGGTGTCCTACTATTGAATAGGTATAAA
CTAAATAAAAATAGTGAGAGAACATTCATGTGTTCACTCATTCATTCCTTCATCAAACAA
ATATTGAAAGTCTATTAATTGGCAAGCACTCTTCTGACATTAGAAGGAGCAAAGATAAAA
AAGATATTATCATTAACCTCAAGGACATGACAGCATCATGGGAAGGCCAGAAATGCAATA
TGTTAAAGTAAAACACAGTGTAGTGTTTACTACTAAAGAGATATAAACAGAGTACTGTGG
TCTAAAATCATATATATAACATTTGCTTAATGGATGAGAAGGAAACTTTAACTTCAGGAG
GCAGAGCATTAAGAAAGTGAATGACAGGAGGGTCAAAAGAAAAAGCCGACAGTGTTGCAG
AGGCAGGGCATAAAGGAGCTAAACCTTTGCTACCTTCAGTTTTTATTATCCACAGAACGA

FIG. 1M

CAAAGAAACAACAACAACAACAAAACTTTGGATTTGAGGGTTTTTTGTTTTTCTTTTTTT
TTTTTTTCCTCTCATTCCAAGCATCAAACCTTGGGATTTATTTACCTTCTAGCAAACCAA
AATTTATGGGGGCATTCCTATGGTCCTCACCTCACCCCATTTTTCTGTTTTACCTATGAA
ACTTGATCAAAATACTGTCTCCACATTTCTCATAAAATACATTAGTTTAATTTTCTACTA
TTACTTTCTTTTAGTTGATTTAAAAAAAGGTCATTTATGACCTATTTAGGTTAGCATCAT
TAATTTTATCAATGTAAGAATATGGTAGTACAGTGTGAATTCCATTAATGGATATGTTGA
TACCATGGGTTTCTCTGACCTTTCCTCTTCCGCTCCTCCCTGATGATTGGTTCTGAGCTT
ATTATCATGTCAGCAATGAAACAGAAAAGGGAGAAAAATCTCAAGTAGGTTGTCTGTCTC
TTTAACACTGAATAAAGATTTTTTTTTCTCTAACAGACTTAAAAATAGTGCCCTAAAAAT
GTTTTGTTTCATTTGTCTGAATTCCCATTCTTTCCCGTGATCATAGATAGTTGAGCTAAA
AAAAGAAAAAACAAAAAACAAAAATAAACATTGTGTCCTACATTTGTATTAACTTTCTTA
GGAATGAGAAGTAGAATCTTAAAAACCTTAGAATGGGAGTTTCCAAGCTAGCTTGCAGGC
TTGAGTTTTATTGATAATACCTTTAGGATGCATGTATTATTAGAAACATCAGTTATTTAC
AAGTTCACCTATTTAAAAGTCTAATAGGAAAAAATATTTCATGTTGCTAAGTATGTGACT
TCCCTTTAAAAGATAATAATGCTTTCCCTTTAAACAACAATAGTAAAAGAAGTAGAGTTC
CTTTTAAACACATACTTTTATATTATAACCCATTCTGTTTAAAAAATAGCAGGCATATAA
TCTAGAAATGCAAATAATTTAGTGAAATTTTTAAAATTATTCTACATATAATTAAATATG
GATATTCGTTTTCAAATATCAAATAATAAAATATGTCTGAGATGCTGACTAATCCTTAAT
TATAGGTGTGATTTCTACTTCACCATCAATACTATGGTACTCCAAATCTTAACATGAGTC
TGATTTTCTAATAAACATGATGAAAAAAGTTATGGAAAAATTTTGAGATTTACTTTGGGA
GGTTCTATTGTGTTCTGTTCAGCTTCATAATATTCAGTTTCTATGAGTTTGGTATTTAAT
TATGTGTGTTTGTCATTCAGTAGGCTGGAAGTATGACCATTGGGAGATCAAAACGATAAG
ACATTAATGACAGTGCTTTATCACTGAATCTAGTACTTTTTTTAATGAAAGAGATGTTGG
CCTCTTGTATTGTTATAAAACAACACAATTTTATGGCTTTAAATTAAAGTACAATCATAA
CAGAAGACAAAATTAGATTAAAAAACAAACATGGAGTGACTCATATAAAATATTTAGAAA
CCAATAATACAGATAGAGACACATTAGTTCCTCTAGACATTGTGTTTTCCAGTAAAATGA
TCACCAAACTTACCAGGAAAATGATAATTATCAGATTATTTACTTTCAGAATTAAAGGCA
GGAAGAGAAAAAAATGAATGAAGAGGAAACACAGTAACCATATAGGACAATAAGAGTGAA
TGAAGATAAAATGAAAAATCAATAAGATATCGACTTTCTTAAAAGACAAATATCACAATA
GGAAACACCTCAGAAAGGGAAATCTCAAGAAAATAATAAACTGAAAGAAGAAAACATATC
AAAACAACTTGAGGACTGACAAAGTTTTAAAATGTATTTAGATAAAGATACCATGAGGAA
AGTGATCAAGGTGTTCTAGGTAATCACTGAAGATAAAACTAAAAATAGCTTAAATTAAAA
TCAGATAGAGAGAAGGTAACTGAAACAGGCATAGAAAGAAAGTAAGAAGGAATACAATCC
TGAACATCTTAACAATGTCTCAAATGTCAGGAATTGATCCAGTTTTTGGCTGCACAACAG
AGTGGCTATAGTTAACAATAATTCACTGTATATTTCAAAATAACTCAAAGAGTAGAATCG
GAATGTTGCTAACACAAAGAAATGATAAATTCTTGAGGAAATGGATATCCCAATTACCCT
GATTTGATCTTTACACATTGTATGCTTATATAAAAACAGTATTCATGGCCGGGCGTGGTG
GCTCACACCTGTAATCCCTGCACTTTGGGAGGTCGAGGTGGGCGGATCACAAGATCAGGA
GATTGAGACCATCCTGTGAATGGTGAAACCCCGTCTCTACTAAAAATACAAAAAATTAGC
CGGGTGTGGTGGTGGGCGCCTGTAGTCCCAGCTACTGGGGAGGCTGAGGTGGGAGAATGG
CATGAACCCAGGAGGCAGAGCTTGCTTGCAGTGAGCTGTGATTGCACCACTGCACTCCAG
CCTGGGCGACAGAGCGAGACTTCGTCTCAATAAAACAACAACAACAACAACAACAAAAAC
AAAAACAGTATTCATAATAATTAAAATAAATTATTTTTAAAATAAAATAAAATATCAGTA
ATTTAAATTTTTCCTATAGCATAGAGATCTGTAATTAATACTTGTCGATCATTGTTGTTT
CTGTCTTCCCAACAACTACACTCCTGTTTCTTCACATTCCCCCTTCTTCTAACAGCACTA
CATCTTTCTTTAGGAAACTATCCTTTTGCCATTTCATGTATATGGTGGGGTGGGGGAGTT
ATCAATCACAGTACCCCAGCAGATGGGACCAGAGGCAAAAATGCCTGACCTTCTCCCATC
CCCCAACCACAGCAGCAAATGAATTATAATTTGATGCACAAGGAAGTATCGGAGCTTTTG
TGTTGGGTTTTACATATCACCTGTGGGAGATAAATGAACTTTTCCCCACCTAACCTTTAG
CCACTTGGGATGATTAGACATAGAGGTGCCTAAGATCTTTCCCTTTGCCACATTAAAAAC
AAATCATCTATGGCACGAGCATACAAGACCAGCTTTCAGAGACACAAAATGATGGAGAGA
ACCATGATACTAGTTTTAGACCTAGTCACTGAGACTTTCTCTGCTCCTTCCCAGTTACCT
GAGCTTTATTTTGTTTACATTTATCAGATTTGAATGGCTGTACTTCAAAGTACTGATTAA
AATAGGAACCAACCTATATGATTCAGGTGGTGAGAAGGAAGAAAAAGAGAGAAAATGAGG
TTAACAAAAGAGAATAAAGAAAAAGAAAGAAGGAAAACAAGAAACTCTGACTACCTCTCC
TCTTTGACATAGTTTACACTTCTGACAGATTGTTCTTCTCTAAATTTATGTAGAGATTAG
AGTGAGGATGATGTATGCACTGTAGCATGGGTGGTCTTCCAGGAAGCCTTGACTGAATGA

FIG. 1N

GGCAAGGAGTATGTTGCTCCCTCAGTAACCTCAAATTTACCTGCAAGCCTGATAAAAATC
TAACACTAACACTAAACCCAATCTTATCTACAGCCCTAACTGCACCCTAATATTAACAAC
CCTACCTCTGTACTTCAAAACTAAAACTAATTCTGATTTTACTCCCATCTGCCCCTTTTA
CCCTAAAACCAACTGTAAAACTAAATTTAACTCTAAACGTAATCCTAAAACTAAGAATTA
ACTAACAATTTTATCTCTATACCCAACTGTTAACCCCAAGCCTAACTCTAATCCTATCTC
TAACCTAACATTAACCACAAACCTACTTCTAACTCTAATCCTAACCATAACCTCAAATCT
AACTCTGATTCCAATTGTAATCTAAACACCAACCCACCCCTACCCTTTTATCCCAAATCC
ATCTGAAACCCTCATCAGAACACAAATTCCAATTCTACTTCCCACCCTGACTCTGACTCT
AAACATAGGCCCAAATATAACTCTAACTCGAAGTCAAAAACTTAACAAACCTTATCTTGA
AACTCAACCTTTACACTAACCCCAATTCTATCTGTAATCCTAACCCTAATATTATCATCA
AACCTATGTCTAACACGACCTCCAACCCAAAACCAAAACTAACCTCAGACCTAACTCTAC
ATCTAATTATAACCCAAACCCCAGGCTGCTACTTACCATAACCCTGAAACTAAGCTTGAT
CCTTTCTCTTTTTTTTGAGATGGAGTCTCGCTCTGTCTCCCAGGTTGAAGTGCAGTGGCG
TGATCTCGGCTCACTGCAAGCTCTGCCTCTCAGGTTCATGCCATTCTCCTGCCTCAGCCT
CCCGAGTAGCTGGGACTACAGGTGCCCGCCACCATGCCTGGCTAATTTGTTGTATTTTTG
GCAGAGATGGGGTTTCACCCTGTTAGCAAGGATGGTCTCAATCCCCTGACCTTGTGATCT
GCCTGCCTCGGCCTCCCAAAGTGCTGGGATTACAGGCATGAGCCACCACGCCCAGCCGAC
CCTTTCTCTTAACCTACACTAACACTAACTGTAAACCTAGCTGTAACTCTAATTGTAAAC
CTAACCTGATTACTCACTACAAAGGTCCCTCTAATTCTAACAAGAAACTCAATCCTATCT
CAATTCCACCCAACCCCAAAAGTAAATCTAAACTTAAACATAACTCAAAATGTATCTCAA
ACCTTAACCTTCACGAAACTACATGTAGCACTAATGTAACCCTAAGCCCAATCCTATCAG
TAACACTAATGCTAAAACAAACCCCAATCTGTATCTCTACCCCATCACTGACACTACCCA
AATCCCAATATTTAATGCTAATCATTAAGTCTCAAACTAACTCCAAACTTATCTTTAACT
ATATCTCCAACCCTAACCCTAACATTAACCCCAAACTTATCATTAATCATACATCTAGCT
CTAAACCTAACCCCAACTTTAACTCTTACCCTAGCTCTAAAATTAACCCCAACACTATCT
CAAACTGTAATCCTAATGCTAACGTTCAGGCTACTTTTAACCCTCACCCTACACAAAATC
CTGCACCTAAACTCAACCCTAACTTTAAACCTACCTCTAATCCAAACACTAAATTTAAAT
CTGGATCACGACTTGGGCATACTAGCACCCACTAGTGTTCTGGGTGTCATTTCTTTGCTT
CACTCTCATCCAGCTTTCTTTACTAATTTTGGATAATGAATCAGAAAATAGTGGTGTGGA
ATCAGGGTCTTTGAATTATTGTATTATCCAGAGTTTGTCCTGCTGCAAATGATAAAACAC
TGAAAATTAGCTTAACAAGGAAAAAAATAAAAATGTGTGTGCAGGGGAGAAGTAGGAGAG
TTATTGGCTCAAGGAACAGAAGAATTCAGTACTGAGTTTCACAAATACCTGGATTCCCTA
GTCCCCATACTGCCATCAGGATCCAATCTGTCACTCACTCCAATCTCTTCCTCCTCCCTG
TTGGATTCATTGTTAGGTTTCCTGTGGCAAGATGAAATGGCCTCAGGCCTGTAACACAAT
AGGATCAATTACAACAGAAGATAGTATTTCTGTTTTCCTGGTTGCTCAAGCCTAAATTCC
AAGATTAGTTTATATCAAACCTAGTTAGTTTTGCTCATGTAAGGGATTACTGCAACTGGG
TACACTAATATGAAGAGTGGGAGAGTTGGTTAAGGGGGTTCTCTGAAAGGAGAATTAGGT
TACTGTTAATGGGAGAATGAGAAATGGGTATTGTAATGACAAAAACACACACGACTACCA
CAAATGTTGAGGAAGAATTTTCCTTTATGATCATCTAGCCCAACTTTTTAATTTCTAATT
TTGTGGTTTTGACCAGTTTTTTGTTTTTTTTTTAATGCAGCATGTCATAAAGTTGGGAA
TACTTCACATTTTGTCTTTGAAAATTTGGAGAGTACTTAAAAAGATTTACAAAGGGGAGG
ATTGAATTATTTTAGGAATGTAAATGGTGGTCTTCTGTCTCAGGCAATGTAGATGCTTGC
TAGAAAACAGCTGACTCATGACTGTTTTCTTTCTAATTCATTAATATGAATTATTTCAAA
CTGCAAAGTTATCTCCTTTCTTCTCCTAATCTATCCACTTAGAGTATACATGTTCAAATT
AATGTATTGAACTAATTTTTCTAGTAATACATTCTATGCATTACAAAAATAGCAGTGGGA
AGGTGAAAACAAAATGCAGTTATGCATTTATCTCTAAATGTGTTCAACATCTCTTATGCG
TACTTCAAAATAATTACATTTGTTTAATTTTGAAAAAAATATTAACAAGAAGTTGTAATT
TGGGGAAAATTTAAAGCTGGCGAAAAAGGCTTCATCATAATTGACAATATGGGAAAATAC
TGTATTAAAATCCTAGGTTTCTCCCTTGTTTGCATGAAGGAAATGAAAAATATATAAGGG
AAGGATTTAATCAGTCAGGCAAAAATCTAAATTCATCACAGGTTTATTCACTGCATACTA
TCAATGTGCCCAGTACCTGAATGAATATATTAAAGAAATCCACCTCTTGTACAATGAATG
TAAATGAGCAGAGTGTGGTGATTAAAGGTTGGTATTTGGTGCTGGGTAGACCCAGCTTTG
CCACTTACTGCCCAAGTAAATATTGCCATCCATCAGATATCTCCACCTATCAGACCCACC
CTGTTGTAATAACAAGATTAAAATCTGTATCACTAAAACTTTAAAAGAATTTATAGCCGA
ATCTAGAAATCTTTCACTATAATTTATCTTTCCTTAAAATGTCGTTTTTTTTTCAATTTT
ACTATATATGTTTTTGTACTTGTTTGCTGTCTTGTGTGTGTGTGTGTGTGTGTGTGTGTG
TGTGTGTGTTTTTGAAACGGAGTCTTGCTCTGTCGCCTAGGCTGGAGTGCAATGGTGGGA

FIG. 1O

TCTTGGCTCACTGCAACTCCCGCCTCCTGGGTTCACGTGATTCTCCTGCCTCAGCCTCCT
GAGCAACTGGGAGTACAGGCGCACACCACCACACCCAGCTAATTTTTGTATTTTTAGTA
GAGATGGGGTTTCACTATGTTGGCCAGACTGGTGTTTTTGAAAAGACTTTTTCCTGATT
CAGAAGGTGGGACTCACAATTGTAATTCTGCTAATGGTTGTCTTTCAGTCTATCAATTGC
TTCATAAATGCATCCACTGTTCCTTCTTCTTCTGCCCTGCTTATAATTTTCCATGAGTCC
ATATATCTTTTTACACTGTCTTTAGTCTTATTCACTAAATTAAAAACTAATTTTTGATAT
TTGGTATTCATGACAAGACAATTAGTAGAATTTTGATGCTTCTTGTCTGCAATTACAGAA
TCAATATATTTTCTATATTATTGTATATTCTCTAAATCTTATTTTGTATAATAGCTTTCA
GCATGTTCTTTAATTCTGTTTAGATATTTAGAAAGTATTTGTTGTTATTCTGTAATTTAT
TTCAATATTCAATTATAGTTTAATATTTTGTTATCTAGTGTTGTCTTGATTTTGATATAC
GTACTGATTTTGTAGATCCAAATTCCTCTTTCCTATCAGAGAATGCAATTTTTTACTTGG
ATAAATAAGAATCATATCTCCTCTGCTTGCTACCGTATTGCATACATTCATGGGTAGAGA
AAGAGTTAAGCTGATGAGAGTAGGAATTAAGGTAGACCTGTTTGGTAGGTTCTCCCAGAT
TTCAGAGGACAGACATCTTTTTTTCCCTGCCTTGGTCATTTAAACTTTTTGGATTTTGGA
TTAAGTGTAGGCAGGGAAAATGTATCAGATATTTTTATTTTTCTTTGGTGCCATTTGTCC
TTCTCTGCTTTAGGCAGAGAAGCATATGTAGTCCAAGAATGTGCTTTTCTATCCAGCTAC
ATCAATAATAACAATTAGTAAAATTCTACTTAAACTTAGACCTTTGCTGTTCTCTTTTCT
CTGCTTGTGTTAAGTCATGCTCATGATTCTGGCAGTTTTCCACAGTACCATGTACAGAAA
GCTTGAATAAGGTACATCTAGAATACTCATATATGTTCACTTCAAAAACACATTTTTGTG
GAATTCTAAATGCAAATCTCAATAGTGCAATTCTAATTTACAATGAGAAAAAACTAAGGG
ATTTTTTCTGGTGATTCTTTTTGCTCATTTATAAATATGTTTTTAAATGGTAAGCAAATA
TATAAATTAAGCTTTTCCTTACGTAGCTACATTGATTTACTAGTGGTGGAAAAGGTTAAG
CAAAACTAATTTTCATGAGTGTAAATGAATTAGTAAGTGACATATGCAATGCTTAAGGGG
AATTTGCATAAATCTATGACTGATACTCAACCTCTTGCTTAGCGAGAAGATAATTAAAAT
ATTTTATACTTCAAGAAGACCTAGTTTTCCAAATTATTTACATCCACAAACTCAGATTTT
ATAGCAAGTAAGAAAAGTTAAGTCAGAAGCATATACTATTAACAGCTACTTACATTGCTC
AAATTTAATATACGATTGCTGCTTTTGTTGGTTTTGAAATGTTTCTTGACCATGGATCTG
AATAATGAAGTTATTCAAGAAGCAACTTTAAGAATGTTATATTCTTAGAAAGAAGCTATA
GATACAATAATATTAAAAAATTAAATGTAAGTTCCTGCACTCACAGTAGAGGTAAGTTCA
AGGTTATAAGAGAGCTTATAGATTCTGAGATTTGGAAAGAAGAGAATAGAAAAAACTTTT
CAGATTAAATAATGTGTTAATTGTGCTTCTAAAACAGCTTTGGTGATCTTAATAAAATAA
ATATTGTTTTTATTTCCATTTTTGCTTTTCAGACAAGAAATGCTACTTGATGGCTGCATA
TATTTGTTTTGTCTCTTTTCACCACCTACTCTTGCTAAATACTCTCAACCCACTCATGAA
ATTAAAGCACATTGGAAAACATTTATCAACTACCTGTAAATACAACCTATGCTCTCTTTT
GTGGAGGTGATAGACATTCATCAATGGAATAGTTGATCTAAATCCTAGTCTTCATTATCT
TGTTTTATACATTCTTGTCTTAATCAGTTTGGGCTGCTCTAACACAATACCATAGACTAG
GTGGCTGATGAACAACAGAAATTTGTTTCCGACTGTTTTGGAGACTGGGAAGTCCAAGAT
CGAATTTTATGTCTGGTGAGGGCCTGTTTCCTAATTAATAAACATCTGTTGTCTCATATG
TCCTCACATGATAGAAGGGGCAAAGGAGCTCTCTGATGTCTCTTTTTTAGAATATTAATC
TCGTTCATGAAGGCTCTGCTCTCATGACCTATTCCTTCCCAAAGGGCCCACTTCCAAAGA
CCATCATATTAGGGATTAGGTTTCAACAAATGAAGCCAGGGGGAGGTTGGTAAACATTCA
ATCTATAGCAATGCCTATCTCCAGGAGCTGCCTGTGGAAACACTTTTATCTGATATGGTA
GTTTAAAGCATGGCAGGGATAAGTGGTATGAGGAAAACTCTCCCTGCCACCCAACGCACA
CATCCCACTTAAGCTTCAGCAGCTCCAATTTTATCTGTGTAATATTTGGTTCCACATCAA
AGTTGTTTTGAATATACTTCCATTACCTTAAAAAATGTAAAAACACTGCTTTAAAAAGCC
AAGCCTATTCCCTTTTCATTATTCAGAGTTCTTCCAGTTTTACCGTTACATCAAATTAGA
ACTACATAATTAGGAACCCCTCTCTAAATTTGCCTCTATACAGAGAAAAACTGTGCCTGA
AACTTTATTAAAACTCAATAAAGGAAATATGTATGAATGTATATATATAATTTCTCTGAA
GGACAGAATTTGTACTTCGTTCCATACATAAAAACTCATTTGACAAATAACAAGCATAGC
TCCAAGCTCAAAGAATAGCTTAATTTTTCCTGATTAGTTTATATCTCTCTTATTAATCAA
TGACATTTAATATTACAACCATAGCTTGGGGTTTTAGTTTATTTGCTTTCTATCTTTTTT
ATACTGTCGGCCTACCTGTGCCCAACTATGTTATAGTCAGGGGTTGGTAAAATAAAGACA
AAACAAATCCTGTCTTCCTGGAGATCACCTTCACTGGGGGTTGAGAAACAATAAGAACAA
GTAGTAAGTAAAATATGTACATTAAAATTTTAGATGAAGTTAAGTGCTATGGAAAAAAGT
AAAATGGAAGAGGTGTTATGGAGTACCTGTTCGGGTATGGGTTCAATTTACAAGTGGATG
GTCACCTTCTCACTGATAAGGTGACATTTGAGCAAAAGTCTTCAGCAGGAAGGGAGAATG
CCATGCAGTTATCCTAGGAAAGAACATTTCCAATATAAGTAACAGCCAGTGCAAAAGCCC

FIG. 1P

TGATGTAGATGCATACCTTAGGTATACGAGTAACAGTAAGAAATTAGTGGCACGAAAGAC
AGATGTACTTGGAAACCAAAAAGAATCTCTGGTAAGAAATTGTAAGTCATTGTAAGGACT
TAAGGTTTTTTTTTTTCCTCTCCAAATGAGATGGAGATCCATTAGAAGGGTTTGCGTAGA
GAAATAATATGATCTGACTTATATTTAACAGGACTACTCTTTTGCTGAATTGAAAATTGT
CTCTAAGGGTGTATATCAGATCTTATATTGATCTTACCCTTCTCTGTTCAATATTTAACA
CACAAGCCTGTTAAATAGTCCATTCCCAACTTCTGTGACTTCTTGCTTGAGAGCCTTTCT
ATCCCCTCTCATAAGGGCTGTGAGGGCCTAATCTGCTTACCTATCCAGCAGGCTGGGAAT
GACACAGAGCACTCACCAGGAGCACTCTCAACCTATGACTCATGGAAGTTGGTAGATGAA
TACCCCAGCTCTCATATTCCTTGGGTGGAAGAGCTCTGAGATGTGTGTTCTACACCATTA
CCCAGAGGGCACCCTCTGGATTAGGCTCAAGTTGCTGACAGTAGTATCTTGCTGACTAAC
ATAATTTTTATTAATTTTCTCCCCATTTGACCTTATTTCTCCATTTTTCTAATAGTGTTC
ATTGGTATCACTTCCAAAATAAATTACCTTTACTTGAATATTTTTCTTAGAATCTTCTAT
ACAAACCTGAGCTAATACTGGGGCAAAGAGTGGAAGCAGGGAAATATTTTGTAGGTGTTG
TGGTGATGTAGGACAGAGCCTGATAGCTTGGATCAAGGTGGTAGCAAAGGAGATTGTAGA
AGCTATCACACTCTTTATATATTTTGAAGACACAGCCAAGAGGTTTGGTGGAAAAATGGA
TTGTGAGAAGTAATAAAAAGAGTGGGAGAGAAAGTCAAGGATGTCACCAAAGTTGTCCTA
AGCAAGTGGAAACTTAGATTTGGGAGAATCAAAAATCCTAAAATATCCAAATCCTCTCCC
CTGCCTTCCCCTCCCCTCCCCTCCCCTTCCCTTTGGAGATAGGGTCTTGCTCTGTTTCAC
AGGCTGTAGTCTAGTTTCGCGATCTCGACTCACTGCAGCTTCGACCCCCTGGGCTGAAGT
AATTCTTCTACTTTAGCCTCCCAGGCAGCTGGGACTACAGGATTGCACTAATGTGCCCAG
CTGATTTTTTTTAGTTTTTTTTATTTTTAGTGGAGATGAGGTCTCGCTATGTTGCCTGAG
CTCAAGCAATCCACCCTCCTCAGACTCCCAAAGTTCTGGGATTACAGGTGTGAAACACTG
TGCCTGGCCCAACATTTTATTTTCAAATATTTAAGTTTTGAATGTCTATTCGATAACCAA
GTAAAGAAGTCAACTAGAATATATGAGAATGGAGTTTTCTAGAGAAGTCTGGGTTGAGGA
TGTACTTTTGGGAAATGGAGCACATACTTGGTATCTAAAGCTGTGAGCCGAGATGAGATC
ACTAGGTAGGTAAATATAGATAAATTAGAGAAAATATCTAATAATTGAGACATGGAGTAC
TATCATAAATTTTGAAAAGACAAGAAAATGTGAGAGATCGAGAAGAATGGCTGGGGAAGA
AGGAATCTAAGGTAGTGAAGAGATTGAAATGTGTCAAGGAGAGAAGAGAGTAATTAGCTC
AAATGCTACTGATAAGTAAAGTGAAATGTAGAATGAAAGTCAACCATAAAATTTGGCATT
ATGGGGATCATTAATGACCTTAAAGAAAGTGCTTTTAGTGTAGTAATAGAAAGATGCAGA
AAGTAAGTAGAGTGAATTCAAATTCAACAGAGAATAGACAGAGAGGAATTGAAGACATTT
ATACTGACAATTCCTTCCAAGACTTCTGCTATTAAAAAAAATAAAAAAAGAAGGAGAAAT
GGCAAGTGTTTGGAGGCCAATTTATACTCAAGAATAATTTCTTGAGTTGGTTTTTTGTGT
TTGTTTGTTTTTGATTGGTTAGTGTGTTTATTTTTTAGACGGGATTGGAGAAATACTTTC
ATTTGTGTTTTTACCCATGTTTTCAGCCTTGCCCTGGCTGCCTGGTATAACGCAACTCTA
TTTGTTATTCTGCTATTATAGTTTCCCTAGCTTGAATTTTTTTACACCCTTATTATAATT
GTAGCGTTGCATGCCTATTTCAAAACATCTCATGTACCCCATAAATATATACATCTACTA
TGTACCCACAAAAATTAGAAATAAAAAAATTTAAAAATTATGATTTTTTAAAATTTGTTA
AATAATGTTTACTGACTCTTTTATTTGTTGAAATCATTCATTTTTTGGAATATCAGGTCC
AATTAAATATTTAATCAGACTTTGAGAAGGATTTAATAAGACCAATAAATAACCAAGTAT
TAGTTGAAGGAAATTTCAGATATTTTGGTAGCAGAAGGAACTGAGTTATGGCTCAAGAGT
TTTTTAATAAGTGTGAGTGGAGTTATACAAACTACTCATTAAAATCTTTATTTGAATTTG
TAATATCTGAAACCATTTTCATATTGAAGAATCACTTAAAATAGTCATAAAATGTAAAAT
TGCAAGACAATTAAAAACAAAAATATGATTTCACGACTGTGATAGTACCTGAGAAATTTC
TTCATCTCCTTAGTAAGAGAAGTATTACACCTATTTATAGTTATTTTATGAAACTAGCTA
AGATGAATTATGTAGAAAAGATACAGATTTTCAAACAGAAACTAGAATTAATGGAAGCTA
TGTGAGACTATAAAGAGTTTAATAGTTATTTTGATTTTTTTTTATGAGTGCAAGGAGTAT
AGCGAAAAATAGCATCTACCTATAAGGATTTGCAAAGCCAGTAATCTTTCTAAAAATATC
AGCAAACCCAGAATTAAGGCTTATGTTCTTAGCTCATTGTAACTAGATCAAAAATAAAGA
AGGCCAAATAAAGGTATGTGACATTTGTTGAAAACCTGAAGTGTCCTATATGCAGAAATA
TTTTTATCATTTAATTAATTTCAGAAACTTCTTAACATGACATGATCCTCTTGAAAAGAT
CACATCAAAAAAGGCAAAATAATTGCATAATTATTGTAGAATAATTTTTGTGTGAGTATT
TTTGACTTAGTGTAAGTTTCCAAGTTCAGGATTTATCATGCAGTGAAAAAAAATACACTT
GTCTAGAAGACAGGAGACTTCATTATATTCCTCTCTTTACAATTAATTAACGTAAGACCA
TTTAAAATATGCCTAATTTTCCAGGCATTGGTTTGCTTTGCTATAAAATGGGAGGATAGA
AAATAACTTTCAAAATATCTTATAAATCTAAGAATCTTTGCATCTTATAAATCTAAGAAT
CTTTGGAAATTCATAGATTATTGAGATGGAGTCTCGTTGCTATGCATTGTAGCAAAGTTG

FIG. 1Q

GAAATAAATTCTAAATTTTATTTCATTTATATTGATCAATAAATTGTTACATTTCACTAA
TACAATAAGGAAAATTTATTTTACCTGAGTGTATGTCTAGCTTGTGAAATAAAAATGCTC
AATTATGAAAGCATTTATTGCCATTTTGAATGAAAAATGTAATATGTAGAACAGAATTTT
TTTTGCCTTGAACTCAGTTAAATGTAGAAATTGATAAGGACTTGCATTTTCATGAACTTA
ATAATTATCTGTCTTTTCAATGGTCTCCATATCAAGTCTGAGAAATATGGATGTGATTTA
TTTTAAACCTCACCATTTGAAGTAAATCTAAAGATTCCATTAGGTTATGAGCATATAGGA
TACAAGGACCATATTGACAGTTTTGTGGGATTGTATTAGGATAAAAGGGTAGGAACAATG
GGGAGAAAATTATAGCTTACAATAGGGAAGAACCAAAAATTGTTGCAAAATGATGGAACA
GGCTGAAAGAATGATATAACCTCCTAAACACTTCAAATGTTTAAGCAGTTCATTGTACCA
GGGCCATTGTAGCAAATATTTTCTGTCTTGGGTGGAAGGTCAGTCAAGGTGACTGATAAA
GTTTCTTCTAACGATAAAATAGCACAACTCACTTTTTTTCTAACCTCTAAGAGTATATTA
ATATCAAAAGAAGGCAAGCAACAAACTACTTCTGAATGTTAATATATATCTGCATTCATT
TTAAAAGTCTGCTACAACTACAGATAGAGGAACAGTTTGTAGTATCCGTGATCCTAGAAC
AAATTTAGCTTTTAATATCTTGTCAACTTTTTTGTTTTAGTATCTCTTCCTTGGAACTAG
CTGAGCTTTAATGGCATCATCATGTGATATGACTTGAGATTTATATTTGGAAGAGCTTTG
AAAAATCACGGATTGTTACCCTAATGAGGTGTTATTCAGTCTTTTAAACAAGAGCAATTT
CTTTACAAAAAGGAGCAGAATTCTTAATTGTATCTGTAAACCTCCATTTAAGAATGAATT
ACTTGGCTGGGCATGGTGGCTCACACCTGTAATCCCAGCACTTCGGGAGGCAGAGGCTGG
TGGATCACTTGAGGTCAGGAGTTTCAGACCAGCCTGGCCCAACACGGTGAAAAACAGTCT
CTACGAAAAATAAAAAAAAAAAAAAAAAAAAAAAAATAGCCAGGTGTGGTGGTGTGTGCCT
GTAATGCCAGCTACTCGGGAGGCTGAGGTGAGAGAATCACTTGAACCTGGGAGGTGGAGG
TTGCAGTGAGCCAAGATTACACCATTGCACTCCAGTCTGGGTGACAGAGCGAGACTCCAC
CTCAAAAAATAAAAAATAAAAAAAAAAAGAATGAATTGCTCATAAATGTGCCTCACTGAT
GATTAAATTTAATCCTGCAAGATTATGTCTTTTGATGGAAATGAGAGGGTTTATACAAAG
TTTTATTCGTGATGTTATCTATGTCATCTATTGATTTCTGCTCTGATTCATGTGGATGAA
GTTACACCTCACACTTTAAGCTGGTGTCAGTCTTCCCATTTTCTGCTGTGATGTGTACTC
AAGATCTCCAGATTACATCTGTAATGTAATGCAGCCATGATTGTTTATAGGTACATTTAG
ATGAATTCAATGATGAGTTATGTTGTAATAAGTGTCAGATTTAGATGAACCATACAAATA
AAAGAACCATGCATTAAAATGACAAATGTGTAAAAGCATTATTTGGGCCTTAAGTCAAGG
CCCAAATGTGGATACTGGTACTGAGACATCTTTCAGAAAGGAGGTATGAAGTACTGAAAA
ATATTTACAAAATGAAGACTACTTTTATCTTACTTATCATGATTCTTTTATTACATATGC
ATTTTCTAAGATAACTATAGTGCATTAGTTTGTACTATGTTAATATAATAATAGGGTAAA
TCAAACAATGTTTTCTAAATCCATTAAAATAGAGTTCCCTAAGGGAGTTAAAACAATTAC
GTTCTACTGTATATTATTGGCATGCTTCAGGAGACATGATTTAATCTCTAGACTATCAGA
ATTCAAGAACTAGTGAGTCATATAACAAAGGAGGCTTAATCATGCCATTTAAGTGTCATG
GAAAAAGGTTTATTGGTCAGGAAAAATTAATTAGAAAAAAGTTATAAAATACTTCACTAA
GAAAATAAAATGTCAGGAAGCCCACTTAGACAATGAGTGAAAATGAAACAAATTCAAGTT
TTTACAATATTTGGTTTCTATAGGATTGCTTCATTGTTTTGGTTTTTGTTTTTCCCCATA
AGCTGATCTCAGAAACTTTTCCTCTACATGAAGAGGCTGTCATTTTTTCATGGTGTGTGT
TTGTTCACATGCCACACAGACAATCAATTATGAAGAAAGGAGAGACTCGTAGGAGGCAGG
GCCAGGCTGTTCACACTTTTAAACTAGGTAGCCACAAATGAGGCTTAGTTACAAAAACTT
GAAAACTGGATTCTTCCCAATGTATTATACATCCCCAAAGAAATGATGAAGTTCCTTACT
CTCTTCTCTTTGTTTTTGTAAATCTTACCACTTCAAGTGTTGGCAATACTTACTTTAAAG
TAGGTTTTCATATTGGCTTAGATTTTTTTTTCATTAACTTGCAATTTGTGGTTGGGAAAT
GATCTGCTTTTTGTTTCAGGTTGTTTAATGTTTTCCAATGTAATATTCTTCTTGCACTCC
AGTGAGTTTATTTACAAAACATTTAATGTCATTTGCGTCTTCGAAGAACAATGTATTCGG
TTAGAACAAAAGTGAGCTCCTGCATAGAGCTTATGATGGTTTATAATTGGTAAATTATTA
CCTTGGTCAAGTTTGTAAACTAATAAAGGGAGTAGAAAACTTTTAGATAAAAAAAACTAC
CTCATTCAAAGGGACCGTTCACCCACAAAATGCCTTTTTGTTTATCTTTTGGAATGACAC
CATTGGAAACTCAGTATGGCCACTTTTATGGTAATAATAAAAGTCATATATAAAAAGGAT
TATTAGAAATGTGTTATTTCTTAGGCAGGTATGCTTATTTAAAGTATGTATGCATACATA
CTTTAAACTACTAAATACAAATAAATTAGTAGTACAGTCATTAGGATTGCTCTTAGTTTG
TTAGTGTTGGAATAGACTTTTGGATTTTCTTCCTAGCTTAGATTGATACAATGTGATGGG
GACTTGCTCTCCAAACACAGGAATAGGTGGCCTGCAGACACACTCTGTGATGCTGTAATT
CTAATCCTCACTGAATATATCAGGGGTGGACATCTGGCCTGGGGCAATTCAGATACTTTT
TCTTAAAATTTATACTACAAATTCAAAAGTGGTAACTCATCTCTGCCATCACTTATAGTA
GAATAAGACCCACTGTTGCAGTGGGGAATTGAGAAACCCAGTCCACAGGGAGAACAAACA

FIG. 1R

TGGAGAATAAAATAAGTAAATTAGAACAGGAAAAATGCCAAAACACACAGACATGACCCT
GATAGTTTTCCATTTCCTGATCACTGTCCCTTCCTGTGGCTGGATAAGGAACTGTCTCTA
GGCTCTGTAAGACATATTTGCATCCTTACGACAAATTTCTACTCCTTTTCATAAACTAGA
CTTGGGTTCTTTAACTTGCAACAGCAACAACAATAAACGATTTTGTTGGGTACAATCTGA
TTTTATTAACTTCTGGATTTAAAAGCCCTTCTAAATGTTGATTGGCATTGTTTTTACTTC
CTAAGAGTACGCTCATGCACCACATAGTGATGTTTTGGTCAACGACAGACTGCATTTACG
ACTGTGGTCCCATAAGATTATAATACCATGCTTTTCTGTACTTTTCTATGTTTAGATATG
TTCAGATACACAAATGCTTATCATTGTGTTATAATTGCCTACAGTGTTCAGTACAGTTAC
ATGCTGTACAGGTTTATAGCCTAGGAGCAATTGGCTATACCCTATAGCCTAGGTGTGTAG
TAGGCTATACCATTAGATTTGTGTAAGCATACCCTATGATGTTTGCACAATGATGAAATC
ACCTAAGGATGCATTTCTCAGCATATATCCCAGTCATTAAGCAAAGACTGACTCTATTAT
TAGGTCTATTTTATTCTATAGCATTTGATCATGAGATATGTGAAAATAAATATAATTTTT
AGAAGTACAATAACTTTCAAATCCTGAATGTTCTGTACTTTCCATCTCACAAGCATTTTG
CAAAGCATCAAATGGTATAAGCCAGATTACTGTTAAGGCAACTTGGAATTAATATGCTGC
TCAGTTCTGGAAAAGGCATATTCTGTAAATATAGATGAGAGAATATAGACTTTTTCCCTC
TCTTCTTACAATCCACATTCTATTCAGTATTTCATTTACTTGAGGGGTTATATGCTACTT
ATCTTTATCTGTTGTGGAGTGAGGACACATTCCAAATGCCTTGGTATTATTAAAAGCCCT
TCATGATGTGGCCCCATCTTTTATGACTTTTCCTTTTCAACTGTGCCCTCTAGCCTTATT
TGATTTCTCTCAAATTCTTAAACACAGCATGCTTCACTGACCTTTAAGCCTTTGCACATA
CAGTGTTGATGTGGAGCTTCCTGACCAACTCCTAATTCTCCTTCAGGCCTCAATTTAAAC
ATCACTTCCTCTGGGAAGCTTTCTATTATTCCCAAGGTACTGGGATATGTTCTTGCACAG
CATGCTGGGCTAATGTCACAATGGCTACCTTGTTTTATTGTTAGTATTTGATCAGCGACA
CCTTGCCAGGGAGCCCCTGAGTATTGTCTGAGCAGAAACTATGGCTATCTTGTCCCCTGT
TTAGCACAGGGCTTCTCTAAAAGTGGGCTTCTCTAAAAGTAAGTGCTCAAGAACAACAAC
AAAAAGTGTTACATTAATAAACACACACACATACATACAAAGAAATACCTGTCTTTCTCC
ATATCTCAAGATCATGCTGAAAAGCCAGCATTCATGAACAAATTCCTGTGCGAAGATTGA
GAATGAAAGATGAATAAGAGGTATCTTTAGAACCCAATTATGGCTGCCGTTGTTCCCTGA
GTGTGAGGCTTGCTGTTAGAGTGACAGAAGGAATTTTGACTACTCAAGACCATACAAATT
TGGAAATGACTCCAAAGTAAACATGGTTAGATAACTACACATTCCATTCCCCCTTTTTTA
TTTCTATAGAATCCCAACTTTGTTCAAGTAGTAACATGCCCAGCTTCAGAAATGAGTCAT
GATTTTTCTAAAGCAACAATATCAATCTTCTTTCCCTTCCCCAGTGATTGGTATGGAAGT
GGACATTTCAGCAAGTTTTAGCCAATAACGTGAATTCTGTTTTGAAGCATCTAAGAAAGA
TTTTGCTTTCTGCTGTAAATCAAAAGCAGAAACAGGAGAAGATTCTTTTGGGCCTCTTTC
CCTCTTCCTGGCGTGGAAGTAGTTGTGAGAGCATATGATACCCAAAGTTTCGGTAGACAT
TTTATAATTATGTGATGAATAACCTAAGGATAATTAAACATATAAAAGAATGGAGAAAGA
CTGAGTCTGTTTTACTCCACAAGATGCTGAACCAACCCTGAGACATAATTTATCTGGATT
CTTAAATAACTAGTGTCTTTGTGGTTTAAGCTGTTCTTTGTAAACAAACATATCATAAGT
GATTAAGTGATGTTATCTTCCTTTAAGGCAATCAAAATGCATCTGACAAATGGCCATCTA
ATTTAAAATTCCAACTATGTAGACATCTCAAACAAAGTCAGTATCTCAAAAAATATACTA
CAAAAATTCTCATGTGTCCATTGGGGATAACTTCCAATGCTCTTTCATTGGTATTGTAGC
TATGGCATTTGATTTCCAATTGTATGTGGATCAGGTAGTTGCAGGGTGACTCTCAAGGGC
GAGAAGAAAGTAAGAGTACATGAAAAAAAAGAGGAAGAGAGAGAGCAGACAAGAAGGAAG
AACAAGACAAAGTCAAACCCTAGGTAGAAATAAGAAGGAGCTAGTACAGAAAGCAAATGC
CTAAGGTGTTGGAGAACATAGAAAGGTAGAGTGGAATGAAAAAGAAAAAAACACTAAATA
GCAGCACATAGAATCTTGGGGTTTCAGGGATATTGTTTATGAAAGGTTAGAATAGGCAAC
AATCTACCTTGTGGCATCTTCTTAAAATTATCAACATATAAAACAAACAATAATTATTTA
AATTACCTGTCATATGGGTCTTGTCATTTATTTATAATTTAAGGAGAATTAAAACTGAAC
TAGTTGCTGGGGAGTGACATCAGCAAGATGGAGATATAGAAATCTTCAGGACCTCCTTCC
GTCCATGGAACCACTGACTCAAAAATGACAAATGGAAAAAATTTACTTTCTGAGAAATCA
AGAAGCCAGTTAAGAGGCTCCTGTATCTCAGATGAGTGCAAAGCCAGCTGCAACAGAGCC
AGCAGAAAATTTGTTGTACTCACTCTTCATGGTCACTTCTGGCATAGCACAGTGCAATCT
AGAAGAAATTCTCGGCTCCTGACTACTTTCTTGGAAAAGAAAGAGAAAAATGTACCATAT
GTCTAATATTCTGATGGGGATGGGGTGTGGGCTGCTCAAAGGACTAGCTTCCGTCATGCC
TAAATACAAGTGCTAATTGGGAAGTCCACAATGTTGGGGGCTGCAGAAAACAAGGGCAAC
AGTTTGGACTAGCATGCACTCATTTGCCGCAGTTCCTCCTCTCACTTCATAGAATGAGTA
GAAGAACCCCTTAACTCTCAAGGTTTTTTTCCTGGGGAGAGAAAGAGTCAAAGCAATTATA
CAATATTATGGCTTTGTGGGAGTGATGTATCCAAAAAAAAAAAAAAATGAGTTTTTACCAC

FIG. 1S

ACCAATCTCAGAGTGCAGATGGAACCTAGCATATTCTAGATGCCTGGGGGCCATTGAGAA
CAAAAGAGAGCTAGGCAACTTTCAGCAGCTCCAGAAGAACTGTGGTACCACAGATAGACA
CCAAAGGGAGGAAGAGATTACAAGCTCCTGAAAAAAGAAATGAGCAATTCATTCTAATTG
AGAATTTACACACACTGGTACAGATAAGATGAATTTGCAAAAAAAGAATAGAGGCCCCAG
AATTTCTAGCTGGGTTTTTTGGTGAAGGCCTTTCTCTGTATCAAGCTAGTCCCTAAAGAC
TGGGTGAGGTGGTTTTTGTTTGTTTTACATTTTTATTTTAAAAGATGGGGATCTCACTTT
GTCACCCAGACTTGAGTGCAGTGATGCAATCATAACTCACTGCAGCCTCAAACTCCAAGG
GTCAAGTGATCTTTCCACCTCAGCCTCCTGAGTAGCTGAGACTAGAGACACATGCCACTG
TGCTTGATTAATTTTTATTTTTTTATTTTTTTTCGTAGAGATGTGGTCTCACTTTGTTGT
TCAGGCTGGACTTGAACTATTGACTTCAAGGGATCCTCCTGACTCAGCCTCCCAAATCAT
TGGGATTACAGGCATGAGCCACCATGCCTGACCTGTTTTGTTTTGTTTTAAAAAACTCAG
AAAAATTTCAAAATAGCAATTATAAAGACAATGAGCTTAGAAAACCAATTAATGGACAAA
ATGTAACTATAAGTAAAGAGATACATGTAAAAAGAATCAAACAAAATTTGCAGTGGAAGA
ATATGATAACCAAATTGAATATTACATTAGAGGAGTTTAATACTAGATTTGAACAAGCAG
AAGAAAGAATCAGGGAACTTGAAGATGGGTCATTTGTAATTATTCAGTCAGAGAAACAAA
AAGAAGACTAAAAAAGAGTGAAGAAACCCTAAGGACATCATCAAGTAGACCAATATGTGT
TATCAGAGTTTTAGAAGAAAAAGACAGAAAAATAGGCATAAAGCATCATTGACAAAATAA
TGACCCAAAACCTCCCAATTATGAAAGACAATAGATATTCTGAATCCAGAGCACAATGGC
CTGCAACTAAGATGAACCCAGAAAAGTCTATACTTCAGCACATTATAATCTAATTATCAA
AAGCCAAGGACAAAGAAGGAATTTTGAAAGCAGAAAGAAAATAGTGACTCATCAGATACA
CAAGGGCTGTCATGAGAATATCAGCAGATTTCTCAGCAGAAAACTTGCAAAACAGAAATA
AGTGGGATTACATATTCAAAGAGCTGAAAAAAAGTCTGCCAACAAAAAATCCTTTATCCA
GAAGAATTTTCTTCAAAATGAAGGAGAATAAAGGATATTCCAGATAAACAAAAGCCAAGG
GAATCCATCACAATTAAACCTGCCTTACAAGAAATGCTAAATGAAGTTGTTCAAGTTGAA
ATAAAAGAACGCTGAACAGCAACACAAAAGCATATAAAAGTATAAAGCTCATTGGTCAAA
GATAGATATAAAGGAAAAACAACGGGATATTATAATGGTGGTGGGTAACTTACTCTTCAT
CCTGGTATAGAAGTTAAAAAAAACCACAAGTATTAAAATAACTGTAACTATAAAATTATT
AATGAATACACAATGTAAAAATATGTAATTTGTGATACTGATAACATACCATGTGTGGAG
GGGAGAAGTCAAAGTGTAGAGTTTTAAATAAGACTGAGGTTAGGTTTTTATCACCTTAAA
ATAGATTGTTATAATATGTTTGATTTAAGCCCCATGGCAACTACAAAGAAAATACCTACA
GGTAATAAACAAAAGAAAATGAGAAAGAAATGAAAGTGTGTCTCAGTCCATTTTTATTTT
GCTATAACTAAACATCTGAGACTAGGTCATTTATAGAGAAAATAAATTTATTTCCTGCAG
TTCTGGAGGCTGTGAAGTTCAAGACTGAGTTGCTGCCTCTGTTGAGGGGCCTTCTTATTG
CATCATAACATGGCAGAAGGCATCACATGACAAAAAAGCAACAGCAAGAGCCAAACTGGC
TTTTATCATAGGCCTAGTTTGTGACACCTTACATAGTCCTATGAAAACCCATTAAGCCAT
TAGCCCATTAATCCATTAATTCATGAATAGATTAATACATCCATGTGGGGAAAGCCCTCA
TGACTCAAACCTTTCTCAAAAAACCCATCTCTTAATACTGTTACATTAGTATTAAGTTTT
AACATGAGTTTCAGAGTCTAGAAATATTCACACCATAGCCTTTCACCCATGACCTCCCAT
AATTTATGTCCTTATCATATGCAAATACCTTCATTCCATTCCCGTAGCCCCGAAGTCTTA
ACCTGTTCTAGCACCAACTCTAAAATACGAAGTCAAGAGTCTCATCTGAGACTCAAGGCA
TGATCCATCCTTGGGCAGGTTCCCTTTCAGTTGTGAAATCAAAACAAGTCATATAATTCT
AAAATACAGTGCTGGTACAGGAATAAGACAGACATTCCCTTGTCGAAAGGGAAAATAAAC
TAGAAGAAGGGGTTAATGGTCCCCAAGCAAGTCTTTAACACAGCAGGGCACATATTAAAT
TGTAAAGCTAAAGAATACTCTTTTTTGGGTCCATGTTAAGCATTCTCTGCACAATGTGGG
GAACACATTGAGCCACTCTGCCCCTATGGCTTTGCTGTGCTCAGAACACACTTCAGCTTT
CTCAGATTGGAATTGCTCATTGGTGCCTGCAGCTTTCCCAGGTGGGCACTGCACACTGCT
GGTGTTTCTATAATTCTAGGATCTCAAAGGCAGCTCTGGCTCTCACCCCGTATTTTTACT
CAACATTGCTGTAGTGGGGCTCTCAGCCATGGCTCTGTCCCTGTGACAAGTCTCTGCCTG
GGTCCCCATGCTTTTAGATACATCCTCTGAAGTCTAGGTGAAGGCCATAGTGGCCCTACA
ACTCTTGCATTCTGTATCCCTGCAGAATTAGCACCAGGTGGACACTGCCAAGGCTTATGG
CTTTTGCTTTCTGGAGCAGTGAGGTAAGCTACACTTGGAGCCTCTTGAGCCAGTTGGAGT
GGCTGAGGAATGATGCGCTCACATGAAGGGAGCAGAGGAGTCCTGAGCAGCCCTGGGCAG
CAAGCTGTGGAGAGTACCCTGGGCCTGTCCCCTGAAACTATTCTACCCTCCTTGGCCCCT
GGGCTTTTCATGAGAGGGGGCAGTCTTAAAAATATGCAAAATACTTTTCAAACATTCTCC
TCATTGTCTTAATGAATAACATCTGACTCCCTTCTATCAGTGCTAATCTCTTTAGCAAGC
AGTTTTGCTGTTTACATGGCTAAGCAAGCTGCAAACTTTTCAAATCATTTTGCTGTGATT
CCCTTTAATTATACATCTGTCTTTAAGTCATGTTTTTGCTCCTGAATTGGCCAAAAGTAA

FIG. 1T

CCACACAGCCAAAAGTAGCCAAACAGCATCATGAATGCTTTGCTCCTTAAAAATTTCTTC
TATAAGATATTTTACTTTATTATTGTCAAGTCTGGCCTTCTACACAGCCCTAGAGTATGG
ACACAGTTCCAGTAAGCTTTTTGCTACTTTATACCAAGTATGACCTTTATTCCAGGTTCT
GATACCTTGTTCCCCCTTTCTGTCTGAAACCTCATAACGGCCTTCATTGTCTATATGTTT
ACTAGTATTTTGGCCATAATCACTTAAATAATTTATAAAATGATTCAGACTTTCCCTAGT
CTTCTCATCCTCTGATCCTTCACCAGAAGCACCCTTAACACTCTATTTACAGCAATATAA
GATTTTTTTTGCCTGCTCCTCCAAACCCTTCCAGCCTTTGTCCATTACCCATTTCCAAAG
CCACTTGCACATTTTTAGGTTGAGCATCAGCCTCACTTCTTGTTACCAAAGCCTGTATTA
GGGTTCTCCAGAGAGACAAAACCAATGGGATATACAGAAGGGGATTTGTTAGGGAAATTG
GCTCACACAGTTATGGAGACTGAAAAGACCAAGGTCAAGGGGACGTATCTGGTGAGAACC
TTCTCATTGTATCATAACATGGCAGATGGCATCACATGCTAAAAGAGCAAGAACAATAGC
CAAACTGGATTTTATAACAGACCCACTCTTGACGACTATCCTATTCCTGTGATAAGCCAT
TAATCTGTGAATCCATGAGTAAATTAATCTATTCATGAGGGCTCTGCCTCTATTGTCCCT
TAAAGGCCCCACTTCTTAATACTGTTACATTGGGGATGAAGTTTCAATATGGGTTTCAGA
GGAGACAAACATTCAAACCATAGTGATGTCACTACAAAAAAATTAATGAAACACAAAGGA
GTACAGTAAGAGAGCAAAATACAGATAAAAGTGCTATATGATATATAGAAAACAATAAAA
TGGCAATAGTAGGAGTTTATCTGTCAGTAGTTACTTTAGCCATAAATGAACTAAACTCAA
ACAAAAGACAAAGATTAGCTGACTGGATTTAAAAAATACTATATGCTGTCTACAAGAAGT
ACAAGGAGCCCACTCCAAATTTGTAGACACACATAGGATAAAATTAAAAGGATGGAAGAA
AGTATTCCATGTGAATGGTAACCAGATGAGAGCAGGGCTCATTATACTTATATCGGACAA
ATAAATTGTAAGTCAATAATTGTCACAAGGAACAAAGAAGGACAATATGTAATATTAAAA
GAGTCAATTCACCAGAAAGATATAACAATTTTAAACATATATGTATTCAATCTTAGGGCT
TTAAAATATATAAACAAATATTAATGGAACTGAAGGGAGAAAGACAGCAATACAACAATA
GTAGGAGATTTTAATTCTCAGCTTTCTTTTTCTAGAGACAGAGTCTCACTCTGTCACTCA
GGCTGGAGGGCAATGGTACAATCTCAGCTCACTGCAATCTCCACTTCCCAGACTCAAGTG
ATTCTCCCACTTCAGCCTGCTGAGTAGCTGGGACTGCAGACATGCAACACCATACCCAGC
TAATTTTTTAACTTTTTGTACAGATGAAGTCTCGTATATTGCCCAGCTGGTCTTAAACTC
TTGGGCTCAAGTGATCCTTCACCTGGGCCTCCCAAAGTGCTGGGATTATAGGCATGAGCC
ACCGTGCTCAGGACCCAACTTTCAAAAATTGATAGAACATCCAGACAGAAGATCAATGAG
AAGCGGATTGAACAACGTAGACCAAATAAGCCTAACAAACATATGCAGAAAATTCCATCT
AACAGCACCAGAATATGCATTCTTCTAATGCACACACACATATTATCCAGAATAGATCAT
ATGCTGTGTCACAAAACATGTTTTAACAAATTTAAAAATACAGAAATCATATCAAATATC
TTTTCTGAACACAGTGGAATGAAACTATAAATCAATTATAAAAGGAAACTGGCAATTTCA
CCAATATGTGTACATTAAACAATAAATTCTTGAACAGTCCATGAGTCAAAGAAGAAATTA
TAAGGGATATTTGAAATGTTTCAAGATAAATGAAAATGTCTCAAGATGAAATAAAAAGAC
AACATATCCAAATTTATGGAATGCAACAAAAGTGGCAAGAGTTAAGTTTATAGTGGTAAG
TGACTACATTATAAAAGAAAAAAGATTTTAAGTAAACAACCTAACTTTACACCTCAGAAG
TGGAAGAAGGAGAAAATACTAAGCCTAATGTTAGCAAAGAAAGGAAATAATAAAAATTAG
AAAAAATAAATTAAATAGAAAGTAGAAAATTACTATAATAATTAATGAAACTAACAGCTG
CTTTTTAAAGATCAATAAAATTTACAAACCTTTGGCTAGAATAACTAAGAAAAAAGAGAG
AAGACTCATAAATAATATTGTAAATAAAAAAGGAGCTATTGCAATCAAAGAGGCAGGAAC
AATAAAGATTTTCAGGCTATTCTGTATAATTATACACTAACAAATTGGATAACCTAGAAG
AAATGTATAAATTCTCAGAAATACACAACCTACCAAGACTGAATCAAGAAGAAATACAGA
ATCTGAACAGATCTGTAACTAGTAAGGAGATTAAATCAATGATCAGAAACTTCCCAAAAA
AGAAAATCCCAGGATCAGAAAACTTCACTGGAGAATTCTGCCAACATTTAATAGAAAAAA
AAATGCCAATTCTTCTCAAACTTTTGCAAAAAATTGAAGAGGACGAAGCATTTCAAACTC
ATTTTATGAGTCCAGCATTTTCCTGATACCAAAATGAGATAAAGATATTACAACGAACAC
ACACACTTTCAAACAAGCTACAGGCCACTATCTCTGATGAATGTAAATGCAAAAGTTGTC
AATAAAAAATAGCAAACTGAATTCAACAGTGCATTAAAAGGATCACACACTGTGACCAAG
TTGAATTTATCTCTGGAATGATGAATGGTTTAACATATGAATATCAATCAATGTGATACA
CTATATTAACAGAACAAGGGATAAGATCACATGATAATCTCTATAAATGCTGAACAATCA
TTTGACAAAGTTTAATACCCTTTCGTAATAAAAATACTCAACAAACTATGAATAGAAGGC
ATGTACCTCAACACAATAATAAAGGTCACATATCAAAAGCTAACAGATAACATCATACTC
AATGGTAAAAACTGAAAGCTTTTCCTCCAAGATCAGGAACTAGGTAAGAATGTCCATTCT
TGCCATTTCTCATCAACGTATTACTAGAAGTCTTTGCTAGAACAATTATGCAAGAATAAG
AAATAAAAAGCACTGAAATCAGCAAGGAAGAGGGAAAATTATCTCTATTCCCAGATATAA
TAATCTTATATGTAGAAAATTCTAAAAATCACACAAGGAAACTGTTGCAACTAGTAAGTT

FIG. 1U

CATCAAAATTGCAGAACATAAAATCGAAATGCAAAAATCAGTTATGTTTCTATACAATAG
CAGCAAACTCTCTGAAAAAGACATTACAATCCCACTTACAATATTATCAAAAATGACTAA
AATGTTTAGTAATAAGCTTAACCAAGGAGGCTAACGACTTATACACTGAAAACCATAAAA
GCATTACCAAAAAATAATTTTAAAAGACACAAATAAATAGAAAGATAATTCTGTTTTCAT
GGGTTAGAAAACTCGATATTGTTAAAATGTGCACACTGCTGAAAGCAATTTATAGATCCT
ATACAATCTTACCAAAATTATGATGTCATTTTTTTCAGAAATAGAAAAAAAATCTGAGAA
CCATGGATACTTAGAAAATCTGGAGAAAGAAGAGCAAAGTAGAGGGTCTCATGCTTCCTG
ACTTCAAAACATATTCCAAAGCCATTGTAATAGAAACAGTTTAGCACTGGCATAAAGACA
GATATATGAACTTACAAACCAGCATAGCGAGCCCAGAAATAAGCCCACACATACATTGTA
AAATAATATACAAAGCACAAAGACTATGGACAGGATAGTCTCTTCAACAATTGTGTTGGG
AAAACTAGATAGCCATATTCAAAGGACTGAAATTAGACCCTACTCAAAAAATCAAGTCAA
AATGAATTAAAAATTAAAGATCTGGCCGGGCGTGGTGGCTCACGCCTGTAATCCCAGCA
CTTTGGGAGGCCAAGGGGGTCAGATCACGAGGTCAGGAGATCGAGACCATCCTGGCTAAC
ACAGTGAAACCCCGTCTCTACTAAAAATACAAAAAATTAGCCGGGCGTGGTGGTGGGCGC
CTGTAGTCCCAACTACTCAGGAGGCTGAGGCAGGAGAATGGCGTGAACCTCAGAGGCAGA
GCTTGCAGTGAGGTGAGATCACGCCACTGCACTCCAGCCTGGGGGACAGAGCAAGACTCC
ATCTCAAAAAAAAAAAAAAAAATACAAGATCTGAAACTATGAAACTCATAGAGAAAAACAG
GAGAAAAGTTTTATACCATTGGTTTTGGCAATAATTTCTTGTATACGACACCAAAGAACA
GGCAGTAAAAGCAACAAAAAATAGATAAGTGGAACTACATAAAATTAAAAACTGATGCAC
AGAAAATAAATAAAAAGAAAAAACAGAGTGTAAAAGCAAACCATGAAATGGGAGAGAATA
TTTGCAAACCATATATCTGATAATGGGTTAGTATTCAAAATATATAAGGAACACCTACAA
CTCAATAGCAAAAAACTAACCCAATTAAAAATGGACAATGGACCTGATGGATATCTCTCC
AAAGAAGATGTAAAAACAGCCAACAGATACATGAAGAGTGCTTAACATCATTAGTAATTA
GGGAAATGCAAACCAAACCACATGAGCTATCATCTTACACCTGGTAGGATGACCATTATG
AAACAAAAGAAAGAGAATTAAAAAAAAAAAGTGTTGAAAGGGATGTGGAGAAACTAGAA
CCTTTGTACAGCCACTGTGAAAAAATGTTTGGAAGTTCCTCAAAAAAATTAAAAATAAAA
CTATACGATCCAGTAATCCCACTTTTAGATACTTTTCCAAAATATTTGAAAACAGGAACT
CAAAGAGATATTTGCACTCTCATGTTTATTGTAGCCTTATTTACAATAGTCAAGAGGTGG
AAACAAATGAAATATATAATGACAGATGAGTCAATAAAATGTGGCATGTACATATCATGG
AATATTATTCAGCATTACAAAAGAAGAAAATCTTATAATATGCTGCAACATAGACAAACC
TTGAGGACCTTATACTAAATAAAATAAACCAGTCACAGAATGACAAATACTGCATGAATA
TACTTCTATGAAGTATCTAAAGTAGTCAGTCATAGAAGCAGGAAGCAGAACGGCAGCTGC
CAGGTCCTGGGAGTAAGAGTAAGAGGAAAGTTGCATTTCAGTGGGTATAGAGTTTAAAGC
ATGCAAGATGAAAAAGCTCTAAAGATCTGATGTACAATAATATGCATATAATGAACAATA
TTGTACTGTTCACTTAAATATGTGTTAGGTCCATGTTATGTGATTTTTACCACATTTTTT
TGAAAGCAAGTTGCTAAAGAATTTGCCAAATGGAATTATAGTGACACGAGTTCAAATAAA
ATTAAAAAACGAGAAACAGTAGAGTTTACTTAATTTGTTAATATATCCATATTATCATTT
TAGGGAATTTTTACTAAAGCAGAGTATATAAACTATCTTTTTTTGTTCTAATGATCCATT
TGTTTTAGTTTGTTTCCCATTTTTATGTAGCTAGACTGCCAGTTAATCTCCTAAAATTAT
TGGCACCATATTTCCCATTTTTTCTGGCTTTTTATTAGTAACTGGGATCCTTGCAGCTG
TATCTATGTGATGCCAAACAATTAGGTTGATCAATTCTGTGACAACAAGCCATCTGGTTA
CTTTAGTGAATAGGCCCTTACTTACCTTTCATAAGTTGATTCTATTCTCCTTTGTGCCTT
CTCTTTAAATTACCATTATCCTGTAACCATAAATTAAAAATACAGCATCGCTTTTAAAAC
ATCCTGAAGTAATTTTTAACACTACAAAAGAGAAGAAATTTCCTTTGTTTGGTGTTCTTT
GACCCTAATTAGCATTTAGGAACAAACTACACTTGCAAAATTATTTTCGATTGGTAGAGG
GAAGAAAAGGGTCTTTTTATTACTATGTATTTGTAATTACTTTTGTCACTTATGTTATTC
TTGTGTCTAAATTCAACTCTAGATTTATTCTCTGTTGATATTTTTTATCACTTGAGAATA
TTTTAGTTTTTCAACCTCTATATGGCGGGCTATCACTCCAAATTTAGGTTAAACTGTAGG
TTGATTTAAAAATCTGGCTATGATGCAGAAAAATTCGGGCAACTTACCTAGAAAAAAAAA
AGTAGTTATATTTCAGTACTTCTTTTACCTAATCAGCCATTTTAAAATAATTTTGTTCAT
TATCAATATGGAGGAAATTATTTATATGCAGGGAAGTTATTTATATGCAGAGCTGTTAAT
GGCAGCAATCTGCATGACAAATTTCTACTTAATAAGCAATGAAATAGTTGGATAAATGTG
TATTTCTACATGGGTGAATTTCCCAAAATTCACACTTCAAAGACAGTTGCTGACATTTTT
TCAATGAGAGATTTTATTAGATAATGAGTCATCTTAGAGTTATCTTGTAAGTATTCTTTA
GTCTTAATTTAAATTTAAATGAAAGTCAATTCAAAGTGTTGTATTTTCTTAAATAAATTT
TGTTTTATAAACATTAGAAATTAAATAGGACTACCATATGGTCTAGCAATCACACTTCTG
GGTATATATCCAAAGAAAATCAGTTCAGTATGTCAAAGAGATGTTTCGTATTCATTGCAG

FIG. 1V

CTTTATTCACAATAGCCAAGATATAGAATCAATCTAAGTGCCCATCAATGGATAAACGTA
GAAAACATGGGCTGGGTGCGGTGGCTCACGCCTGTAATCGCAGCACTTTGGGAGGCCGAG
GCGGGCAGATCACGAGATCAGGAGATCCAGACCATCCTGGCTAACACGGTGAAACCCCAT
CTCCACTAAAAAAAAATACAAAAAAAATTAGCCGGGCATGGTGGTGGGCGCCTGTAGTCC
CAGCTACCCGGGAGGCTGAGGCAGGAGAATGGCGTGAACCCGGGAGGCGGAGCTTGCAGT
GAGCCGAGGTTGTGCCACTGAACTCCAGCCTGGGCTACAGAACGAGACTCCGTCTCAGTT
AAAAAAAAAAAAAGGAAAGAAAACGTGGTATATATACACAATGGAATACTATTTAGCCTT
TTAAAAGAAGGAAACCCTGTCATTTGCAACAACATGGATGAACCTGAAAAACATGTTAAG
AGGAACAAGTCAGGCACAAATACTTAATGATCTCGCTTATATGTGAAATCTAAAAAAGTT
GACTTCATGGAAATATAGAGTAGAATGGTGATTATCGGGTGCTGGGAGTTGGGGTAAGAT
GTGGTTGGGGAAACGGTCAAAGAATAAAAAATTTCAGTTAAAGAGGAAGAATACATTCAA
GAGATCTATTGTACATGTTGAATATAGTTAGTAACAATATTTTGTATCCTCAAATTGCTA
AGAGAGTAGATTTTAAGTGTTTTTGACACAAAAACTGATAATTATGTGAGGTAATACATT
TTTTAATTAGCTCCCTTTAGCCATTCCACAATGTATACATCTTTTAAAACATCATGTTGT
ACATGACAAATATATACAATTTTTATTTGTCAACTTAAAAAATATTAAAGATTTAATGTA
GATAAATGAAAGAAAATTAGGAATTAAGGTACAAAAATTATTTATAGTGTTTATTATTGG
TCTATGTTTACATAGTATTTCTTTGTCTCCATTAGTGTGTTATACAAATACCCAACTAGA
AACATGACTTTACAAATGGTGTATCTGATCTTTTATGTCCCTAGTTATTATTTTAGCCCT
GTCTTTTTTTTTAATAAAACATATTCTGCTTTTTCTTGTCCTCATCCTTCTATGAGTTGA
ATTAGTGACTCTACTCCAAAGTAATGGTGTTGCTTTCTCAGACCATATGGTGATACAAAG
GCATATGAGTTATCATAAGCATGGTCTGTGTAGGCAAAGCATGTAACTCCACAAATGCTT
CTTGAGAGATTCTAATATAATCTGTGCCAGACCTGCACAAGGCATAGAGAATAAAAATTT
GCACCCCACACAGTCACTCCTCATTCATTCATTCAACAATAATCAAGTACCTGGTAATGC
TAATGCAGTGTACTATAATTCCATATACATAAACTAATATTTTTAAGATACATGAAGGTT
ATGTTATAACTAATAGTCAATGTATTTTTAAAATTACTGTAATCAAATTGTAATTGTAAT
TAAGTATTTTCTTAATCAACAGAAACTAAAAGTATAATTTCCATCAACTCCTTTTAAGTA
TAAATGTAATTAAATGCCTGGCACATTCTTCACATTATATAAGGATCTTTATACTTAAGA
CATTTGGGAAACCCTACTTAGGCTTATCATTGACAAAACATTTTCAAAATCTTTTCATTT
GGTCCTCACCACAATACTGTTAAAAAGACAGCCTAAGCTGTTTTGTGCTTCCTCCCTAGT
TGGGCATCCCTGTGCAATGAGAGGGACAAACAAGGTGGTTTTAAGGTCAGAAACATCCAA
TTGCAGCATCATTGGGAAATTTGTAAGAGCAGCTTTTATAAAATGTCACCAACTCATGTA
TCTTTAAAAGATGTGCTGAATCTTATGCCTTGAGATTTTTCTTAGTTTCCTTATTTTCTA
TTCCCCTCCCACTTTCTCTTTGTCCCTTGGTGGCTTCATTAATCCCATATTACAATACAA
AGTAAATAATAGTGCTCTGAAGTGCTTCCTATTTGTTCAGGATGAAGTCTGAAAAATGAA
ACTGCAATTTTTTTTCTTTTGAGACAAAGTCTCACTCTGTTGCCCAGGCTGGAGTGCAAT
GGTACCATTTCAGCTCACTGCAACCTCCGACTCCCAAGTTCAAGTGATTCTCCTGCCTCA
TCCTCCCCAGTACCTGGGATTACAGGCATGCACCACCACGCCTGGCTAATTTTTGTATTT
TTAGTAGAGATGGGGTTTCACCATGTTGGCCAGGGTGGTCTCGAGCTCCTAACCTCAGAT
GATCTGCACACCTTGGCCTCCCAAAGTGCTGGGATTACAGGTGTGAGCCACTGAGCCCTG
CCAAAAACTGCAATTTTATCTTAGGGGACAGGTAAGCATAAAAACATCCAAAATCATGTA
TTTATGTTTAGGCTCTGCTTGTAGAGTGATACCAAATTCCAGGTGTTTTTTTTTTTTTTT
TTTTTTTTTGAGACAGAGTCTGGCTCTGTCGCCCAGGCCTGGAGTGCAGTGGTGAGATCT
CGGCTCACTGAAAGCTCCGCCTCCCGGGTTCACACCATTCTCCTGCCTCAGCCTCCCGAG
TAGCTGGGACTACAGGTGCCCGCCACCACGCCCGGCTAATTGTGATTCTTTACATTATCA
AAGAATTCATGAAAACAGGATATGAAGATTAGTGAAGGATTCTTTTCATTAGCAAAGTAA
CTTTTCTTATTTCAAATTTAACACATCTATTTATAAAAGTTATAGAATTTAAATTTTAAA
ATATGAATGAAGAAAAACAAAATCAGCATAACATAGTAATACATATAATTGATATGTACT
ATTCTGTTACTTGGATTCATTACTTAACCCTTGCAGTATTCTATGATTTTTTTTTAATCC
ATGTGTTACAGTTAGGGCTTAGAAAGATTTAAGCACCTAGCCAAAATTATGCATTATGTT
AAGTGGTTGATATCCACTTATTGACAAATATGTATTGATTGAGAATTAGTCATGGAGATA
TCAATGGGTTATTTTGATTACTTTTTCCATTACTCCCAAGTGGTCAGGATTAGTTTTAGA
TTATTTAAGTAGGTTGGCTGAGTTCACAAAAGCTATTACTATGGGGACCTTAATTGAAAT
CTAACTCTATCCAATTCTATTTCTTTTCCCTATCCCTCGAATGGGTGTATGTGTGTGTGT
GTGTGTTTGCACACATAAAAACCTGTTCTAATTTTATGCAACATGGAAAGCATTAATGTT
TAACATGTATGTTTGAACAGGGAATTTTGTACTGCATTAAAGATTATTCCTGTGTATTAC
ATACAATCAAATATTTGACTATTGACTGTCTTAGTATGTTCATCTAATTGTTTCCTATTC
CCATGAAAACTGTATCAGTCTGAGAACAGCTACTATATGATATGCATCACTAGTCTCCCC

FIG. 1W

ATGGTGCATAATACTTGATATAAATTAGATGCTGTTGGTTATACTTGGCGGGGGAAAGG
GGACACTAAAAAGGAAGAGTCAATTTCTACTGTGAACAAAGCAAAAAGCAAAAGGAGAGA
TAAATGGAATTAAATTAAAAATGAAATTGAGAGTGTAGATAAATCTATGTAATGAAGATG
CTAGTAACATAGGAAGAGAAATAAGATAGGGTATAACAGTGATTATTTTTCCTAATAAGT
AGTGTCATGGCAGTTGGAAGACAAGAGATTATCCAAGCACTGGTTATAGTCTGAAAGATG
AGGTGGTAGCTTACTTGTTTGGGCCTCAGGCATTGCAGTACAAACAGACAGTGAGGGAGG
AGTCAATTAAGACTTATACAAATGCAGAAGTCATGGTTGAGGTAGTGAGAGGATTTCCAG
GACAGTGATGAATAACAGAACCTCAGCAGAAGGAGCATGTGGACCCAAAGCATCATACGA
ATAATGATAGGACCAAGGGAAAAGAAGTCAAGCGGAATGGGGATAGACAAAAGTTTTGAA
ATTTATGTGTAAGAGTTGAATGAAGAAAGTTATTAATAAGACTTACACAACAAAGAATTT
CTACATAGAAGTTGAAAAGACAGCAACAGAGTTTAGAGTTTAGGAAAAAAAATTAAATAT
TAAATTTTAATATGTAATATTGTAGGATTTGAATACCTTAAAGCTGAAATTCAGTTTTTG
ATGCTGCTTCTTAGCATCTTTGTCTTGACATGTATATCAAAATGTAAGAATGTCTGTATC
TTACAATCTGTGATTCTTGAGAAGTCAATGCCATATTATTCACTACATTCATTCTTTCTT
ATTGGAACCATAATACTTTCTTCAATAATAATGTCAGTAGACATTCTAAATAAATAAAAA
ATATCCAATAACATGCCCCAATGTTTCACAGGTATCACACCAATAGCCCCTGAGATATTG
TCACATTCCATTTATCTGCAGAAGTCTTATTCAACTTTCTGTATTAAGTACCAAGAAATT
TCTTAGGCAATTAGTAAGTTCACTTGTATTCTTAAAACTTCACAGAATGAAAAATTAAAA
ATTTTAATCTCTTTTTCTAGAACAATTGTTTTACAAAGACTTTTCAAGGTTTTTTAATCC
TATTTTTTGACAAAATAACATATTTAATGAAAGTAAACATGTAGAAATGACTTAACCAA
AACTAGCTATTGACAACTTTTCAGCACTTTTTTTGGGTGAATTCAGGAACAAACTTTGT
ATTCATTTTATTAATCCACTAAGTAGGGTTGCTTCACTTCCTTGGTTACTGTGCATGTGG
ACGAGGCTGATTTTCATGGTGGGATGTTAAAAGGAGGGATTTTTGCAAATCAAACCACAG
AACCATCACCTCACACTTGTTAGGATAACAAACATTAGCAAAACCAAAGATGACAAATGC
TAGCAAGGATGTGGAGAAATTGGAACTCCTGTATATGCTGACAGAAATATAAAATGATGC
AGCCACTATAAAAATTTTTTGTTTTTGAGAATGTGTCTTGCTATGTTGTCCAAGCTGGCA
TCAAACTCCAAGACTCAAGTGATCCTTTCACCTCAGCCTCCTGAAGAGCTGGAACTATAG
GCATGAACCACTGTGCTGGCTTGGAATATTTTTATTTTCCTCAAAAAATCAAAAATAGAA
TCACCATATGAGCCAGCAATTCCATTTTTGGGTATATATCCAAAATAATTTAAATCAAAA
TGTTGAAGAGATATCTGCACTCTCACATTCATTGCAGTAGTCTTCACAAAACAACCTAAA
TGTCCATCCATGGATTAATGGGTAAAGAAAATATGGTCTACACATACAATGGAATATTAT
TCAGCCTTAAAAAAGAAGGGTATCTTTCTGAATGCAACATCATAGATGAACCTGCAGGAC
GTTATGCTAGGTGGAATAAGCCAGGTATAGAAGGACAATTATTGCATGATTCTACTTACA
TTAGGTATTTGAAATAGTCAAACTCATGGAAACAGAGACTAGAATGGTAGTTGCCAGGGG
CTGGGAGGAGGCAGAAATGAGGAACTGCTGTCCAATGAGTATGTAGTTTGAATTATGAAA
AAATGAATAGGTTCTAGAGATCTGCTGTACAACATTGTGCCTACAGTTAATGATGCAGTA
TTATGCACTTAAACATTTATCAAGAGAGGAGATGCCATGTTGAGTGCTCTTTTCACAATG
AAAGTACAGTAAAATGAAATGAAATATACAGCAGGCTTTACACACACCGCTTCACAGGCA
AAAACTACTTGGGAAACAAAATGGAAGGTCCCCAGAGTCGTGAGGGAAGTAAGGTATGGT
ACAGGGTCAAAATGGCTGTACCTGGAGCTCTCTGACTGGTCAGGCACCAACCAGCAATAC
TCTCATGCCTTAATTATAGTTTACTGCTGAGATAATTGAGAATGAGAGCTCATATTTACT
AACCAGGATATGAATAGACTGAGAACTTTAAATAACTTTCCTTTAATTCCATAAAAATCT
CCATTCTGTTTTAAAGTCTTTAGTACAGATTTTAGATGTAATAAACTGCTAAGATTTGAG
CAACAACTATAAGCATAATAAATGGTTTGCTTTATGGGCAGTTTTACACTAATGCCTCTA
ATAATAATAACAGTAGCAATAACAAAAATGACAGGATTCTTAGGACTTCATTACTCAGAG
CATAATCCCTAGAAAGCAGCAGTCATTATCTAACCCAGAAACTCCCAAGAGTTTGCTTAA
CACTTTAAAATGTATAATCTAAATTAAAGAAAATATGAGTAAATGGTATTGTTTCCCCTG
AATTGAAGTAATATGGGATGTGTTGAAAGAATACATCAAGACATTTTTCACTGTCACCTA
GCCTGATGACTGACATAGATTAATTACTACATAAATTTCCTCTTCCATTTAATACTGATA
AACAGATTTATGGGACTTAAACCACAGTACACAGTTTTGTATTTTGTACGAAATGGATAA
TCACATTTTAAAACATGTGTAAGGCATATTTGCAAACTTGAAACGTCGTCTTCCATAAAT
ATATGCTGAATGAATGAATTAATGAATAAAAATTGAGGCAAAAACTCAGGTGTGGCTCAG
TCATCTGAATGTTATTATCCAATGAAACAGGTCAAAGATTTTTTTTTTTTTTTACGGTTC
ATTTCTAGCCAATAAGACCAAGGTTCATTCACTTCACCTCTGTATAGAATCCTTTGTTGG
GGGCTGCGAGGAGGCAGTAAGAAGTATCACATCTAATCTTTTCCATAATTAGCCAAGTTA
GTTGGTACTTCCCATAACTCTGATACCCATAGGCCCTTGCTATTTCTAGACTTGAGTGTC
ATTCAGAAATATGGTTTAGGCGAGCACTAGGAAAGATACACAGTTTTTCTAAAACACATT

FIG. 1X

ATCCAATCAATATTCTACTTATAAAAGTCAACTACACACACTTCAGTCATGAGGTAAAAA
AATGAAATTTATACATAACACTCACTTATGTTTATCACTCACTTATATTTATAATAATAG
ACATACAGGTATTCTATTAAAGGAACTTTTTAATGTTTGACCAGAAAAAATTTCAATATC
CCTTTTTATTAAGTTTAAGTTACTGTAATGAAATTAAACATGTGAAGGGAGACTAATACT
CTCTTTTAAGAGAAGTAAGAATGAAATATCCATATAAAATACACTGCATTATTCTCTTTG
TTTCAATGGCAAATAGAATCAAAAGGAATAACCCACTTTATTTAACGGAATATCTGAAAG
TGTTCCACTTATTTATTTCTAATTTTAACTATGGAAAGTACTTGCATTTTTTTTTAGGAA
AGAAAGCCAAGATTTTATAAAGTAAAAATCTGCTTTGTGTGCCTTTCCAAATTAGAAGAG
AAATGTATCATCTTAATACAGCAGATTCAGTTATTATAAAGACCTACTCCATCCAAAAAA
TTGAGTGAAATAAAAAGAAATTGACTTACTTGTTAAAGAGAAAAGATTGCCAAGGCTTGC
AGACTTGTGAGGTGGTTAAATAACAAACTAAAGACTAGCGAATATGAGCTATTTTGTTTG
ACGTGCCTTCCATTTAATAAATGCTGTATCAATCTAGCTGTTTCTCTATTTTTAATCATA
CATTTTGTTGTTGCTCTAAATTTAATCTTACCTTATACATTGTATAATAGATGTCCCTTA
AATACATCAAATTTAACGTGTTCCAAAGAAAACTCATAATCTCCTCATCTCCATCCACCT
CACTCCTCCTGCTGTGATCAGTCTCTCCGTTTTTGTTCATTGTCCATCATCTTCTACAGA
ACAGATGTGTCCTAACCCACTTTCCTAAACACATTTTTGTATACAAAATAATTTCCTTTT
TTTAATTTCAGAACTCTATTCTGACAAACATTTGGCTTCAACCTGTAATTAAAAACTTAA
CAATACTTAATAGTTGCCTCAAAGAGCATCCCCTCTTTGTCAATGTGAGACTATTTACAT
TAATTTACATGTAATTCAGTTTCATACTCATTCACTGGGGTGTGAATATTAGTCAAACGG
GCAATTAATTAATACAATCTTTATATATTCACTTATTAAAATGCACCACACAATTCCTAA
TTTATTGAGAGTTCTCACTAAATCTATGGGATGTAAATTTTGAAACAGCTGCAGCTGTTT
ATGCCATTGCTCTTGTTGTCCAATAGAGCCAAGTGGACATTCTTTTTTGTTGTTGTTCTT
TCCTTGAATAGAGTCGAAATTATGAATCTAACTTTCTCCGACATGTTGTCTAAAAGGATA
TCATCTTACCTTACTCAGTGTGAGCCCTAAAACTAGGAAATGTTTATCAATCTCTGATTG
CAGATCAAGTTTAACTATCAAATACAGATTAACTTTTCAGCAAAAATTTGTTAAATATTC
AGAGATAGAAATCTTGATGTTGGATGACAAAGATCACTTGTGAAGAACTTTATTAAGTTT
TATTTGGTTGAAAAATCTATAATTTTTAGTGAACAACTATCATCCATTATGTTCCAAGCT
TTGTGACAACTGTTTTTATGTCCATTAAAACAGTCCTATAAAATAGGTACAAGTATCTCA
ATCTTATACATGTCAAAACTAAAGCACAGAGATGCTAAATAACTTGACTAAACAAGATAT
TGAAGGTGAAGTCTGAGATAGATTTTTAACTCCGAAGTGCATAAACTTTACCTCTATATT
ATCTGTCTTCAAAAAGAATGATTTTAAAGATTAGGCTTTTTTATTTCAGAAGAAAATATT
TTTACACAATTCTAGATTCTTAACAGTAATTTGAAGGAATGAATGTCTGATGATTCAAGA
AAAGTGAGGTACATTTTAAAGGAAAAGTGACAGACAAAAAATGGATTTTTGAAAAATGAA
TAAAGCTGCTTTTTTTTTTTTGATGGTGTCTTGCTCTGTTGCTCACGCTGGAGTGCAATG
GTGCAATCTCAGCTCACTGCAATCTCCGCCTCTCGGATTCTAGTGATTCTCCTGCCTCGG
CATCCCGAGTAGCTGGGATTACAGGCGCCCACCACCAGACTCAGCTAATTTTCTGTATTT
TTTAGTAAACATGGGGTTTTACCATGTTGGCCAGGCTGGTCTCAAACTCCTGACCTCAGG
TGATCCACCCACCTCGGCTTCCCAAAGTGCTGGGATTACCGGCATGAGCCACCACGCATG
GCCAAAGCTGGTTTTTAAAAGGGATCATTGTACATTATTATCAAATTTCATTTGAACGTC
AAAAATTCTGAGGCAAGAAGGAAATTGAGCCCAGGAGTTTGAGACCAGCCTGGACAAAAT
GGCAAGACCCCATCTTTACAAAAACAAAAATAAAATAACACTAGCCAGGCATGGTGGTGC
ACACCTATAGTTGTAGCTACTTGGGAAGCTGAGGTGGAAGGATTACTTGAGTACAGAGAA
GAGGTTACAATGAGGGAGGATCGTGCCACTGCACTCTAGCCTGGGCAAAAGAGCAAGACC
CTGTCTCTAAAGAATAACAAATAAATAAATAAAGTCTGGACAAGCCTAAAATCAGTAATA
TTTGGGGAATATGCAAATAGTCTTTGCTTTATTTACTCAATTATTGAAACTATATTCAAA
AATAGGAAGTAAAACATGATTTAATATTATTTAGTAAGTTAAACATGTTATAATAATTTG
GAAATCCATGTATGTTAGTTAAATATACATTACTATAAAATGTAAATCAGTGTGGTTTGT
AGCAGAGACCTGGATTTTTTATCTTTGTAGTGTACCTACACCATCACAGAAAGGTTTGCC
ATCAGTCTCTAGATTAGGTGCAAATTCATTTAATGTGATCCATCCTATTATCTAAAAGGT
CATTCTGTTGTTTTCAGCCTTCATCTAAGACACTCTCAGATACTATTTCAGGAATTTATG
ACAGCAAAATGATATAAGGTGACAAAGTAGAAATAGGTGCTATGCTGCTTTACCTATATT
GAGTTATTTTCTTCTCTCCAGGATCAGATATTAATGATAAATTCTCTAACATCAAAAAAT
AAAACCTAGGTCATATAAATTTTACACAATCAATGTCAGTCACTCAGCAACCATTGAGAA
TCTACTATGTTTAGAATGGAACACCTGACTTATAGAAAAAAAGGTAAAAGATTGGTTTTG
TAAAATGACACATACAATTTAAGAAAAAATAGGCTATCTATATTAGATAGTTAAAAGAAG
ATTTTAAAATACGATAAGAAGAGAGGGGAGAAATGGCTAGATTAATTTGAGGATTACCTA
GTGTTAAAATAAGTCCAGATTTAAATCAAGTTTATTAATTCTGAAAAAGATCACATCCTA

FIG. 1Y

AAGAAGGCATCAAATTGACCCATAAATGTGGATAAAACTTCTGTAAGATAATGAAAGCCC
TAGAGAGTAATGTTCAACTCCATTTTCTAATTGGCAACAAATGTATAATATGGGTACACC
AGAATATCTAACTCAAAAAGTGGGAAAAAAACTCAAAAAGTACGAAATGTTGGCAAAAA
TGCAGACAGCTAGGACACTCATACCAGCTGGTAAGTGTAAAAACTAGTACTGCACCAAGC
ACTTTAGAAAACTTAACGGCAGTTATGTAGTAATGGTGATCATATGCATACTCTATGATA
GCAATTTCACTGTTAGATATATAACTAACAGAAATTTGCACATATGTGTCAGAAGACGTA
CATAAGAATGTTAGTAACAGCCCTGTTTACAATAGCCCTGAATTAGAATGAACCAAAATT
TCCATCAATTGTAGAGTATTTCAATGATAATATAATCACACACTGGAATGAAAATGATGG
AACTACTACTAAACATACAACCTGGATCTTACAAACATAATCATAAGTGAAAGAAATTAG
ACACAAAATAACACATAAATGTTGATTCCACATAGATAAAGTTAAAAACAGATAACAATT
AATCTATGGTGTTACAAATCAGTATACGGATTTCCTTTTGTTGGCAGGGGGGATGTTGTT
GGAGAGGAAATAGGAAGAGAGCTTCTGGGGTGCCGGTCATATTGTACTTCTCAGTCTGAA
TAGTAGTTACAAGGGTATGTACACTCTGCTGTAATTTGTCCAGTGATACATGATGGTTTG
TACATTTTTATACATGTGTGATAATTCAATAAAAATATCTGAAAAGCTACAACAGCAGTG
GCAACAACAAAGCCCATTAACCACAAGAAATAATCATGTAAATTGTTTTCTTCAAATAAA
TGTGTTGTAAATAACTTCTCTCACTCTTTGGCATATATTTTTGTCCTCTTTTGATATACC
CTAATTTTAGGTTTGTTTAATTTTTCAAACATGTCCTTTATGTTTAATACATTTGAGGAA
ATCTGCTTAAGAAATGCTTATCTACTCCAACATCTTATCAATGGGAATTTTATTTTTTTA
ACTGTCAAATTTAGATCTATAAGTAACCTGGAATTTATGTTTGTATATGATGTGATGTAG
AAATCAAATTTTTATTTTTTCTATGTAGATATCAATTTATTCAGTATCATTTGTAGAAAA
GATACTTCTTTGATAATGCAGTACATGGCACTTTTGTCATATGTCAAGAGTCCTTATATA
CGTAGGTGTGGATCTCAACTATTTTTGTTTGTTTTGTTTTTGTTTTGGATCTCAATTTTT
ATTCTATTCCCTTGATCTACATTTATATCCTTGTACCAGTACTATACTGTTTTGTTTACT
GACACTTTGTATTAATATTTGATAGCTAATGTAAATCCTTCAAATTTGTTTTTCCATAAT
ATAATACTGACTAATTTTGGCCCATTATATTTTTATATAAATTTTGAAATCAGCTTGCCA
GTCTTTACCAAAGGAAAGCTAGCATTTTAATTTGGAATGCATTGAATCCATATATCAATT
TTAGAGAAAACTCACAGCCTTACAATACTTATTCTTCGATTCCATGAGTAGGGTATATCC
CCCTATCCATTTAGGTTATTTTTCATATTCCTCATATTTTACAGTGCAGAAATCATGTGT
TTCTCATTATTTTTTTCCTAGATGTTGAACATTTATTATTCTATTGTCAATAGTATCATC
TATTTAAATTGCATTTTCTAGTTGTTTTTATTTAATAGAAACATAATTGATTTTGCATAT
ATACATTATATTTTATATATCAATTTCATGTGCTCTTATGTTACATATTGTTTTATATTC
AGCAAGTGTTACTAAGGTATTTATTAAGATTAGTAGTTTATCTGGAGATTCTTTCACACT
TAATAAGTATGCCCTCTGTGGATAATGATAGGTTTTATTTAATCCTTTCCAAACTTCATT
ATTTTATTTATTTTTATTGCTTTATTACCCTTGCTCCAGCACAATGCTAAATAGAAATTA
CCATAAAAGACTTTGTGCACTTACTCCTGATCACTGAGGGAAAGACTATTTATGTGAATT
AGTATTTGTAGATATTAACTTTTGAGAATTTAGCTGTCAATCCCAATATGACAACTTGGA
GGTGATGCATTTTTTTCTTCCTGCTTTAAGATTTTTCCTTTCGTCACTGGTTTTTCAGCA
GTTTTATGATAATATAAGTGGGTGTGATTTTCTCTTATATTTATCCTGGTTGAAATTTAT
AGCACTTCTTATATCTACAAATATATACCTTTAATTCGTTTTGAAAAATTCTTAGATAAT
GTATTTGCCTTGCCAATATCTTTTTAAAGATTGCTTTTGTCTCATGCTACTTCTATACAC
ACATATTGAGAATCCAATCACAGGTATAATAGAATTTTCACCATGTGTTATGCACACTCT
TCTGCATTTTCCTTTTTTCCTCTCTGTTCTTTAGCTTGGATATTTTCTATTAGTTTGTAT
AATCCTATTAGATGGTTTTATCTAATCTTTCTTTCTGTTAAATCTCTTTGTTGTGTTTCC
AGTTCACATATTTTTAAGTTCTATAATTTCCTTGGACTATTTTTCTATTTTTTATATTCT
TTATAATATATCTACTTTCTTGACATTATTAATTCAATCATTTTAAAATTTCTGAAATAT
TTTATGAAAAATTGTAGAAATTATTTTATGTTCTAGATAATATTATCTTCTTTCACAGAG
AATTTGCTTTTGCTTTGGCCAGCAGCTAGTGTTGGGACAGAAAACCACTATCCCGTCAGT
CACTGGAGGCTTTGGAAGCTGGGCTTCATTCTTTAGGAGAGCTTGTCTACTTCAGATTTA
TCCCTATCAGAGTTCATAACTTGGAGTTACAGCTGAAAGCCAGGGTTGTTTACCTACTTG
ATAGGCCTTGAACTCCAATTATCATCTTATTTTTGGTTAGGTACTAAATTTCCGGCTCAG
CATCTCATATTATCAGCTTTGTTCTCTGTTTCTCTTCTCCTGTTCTTAGCTAGAGTTTGC
AAATTGCCAAAAACTTTGAGAAGAAAAGAGGCTAAATGCCAGAGCATCTCCCTCTTGCAT
TTTCTCCAGGATATTGGCCTTTGATGTCCCTTCTGCCTTAGTAGCTTTCCAATGTCTTAA
AGAAATGTGTAACACTTCTGGTTGTTTTAGGTGGGAAGTTTGTTCTGCAGTAAGCTTATC
TGCCGTTACCAGAAATAGAAACTATTTTGTAATAGTAAAACAAATGTATACTTTCGTACT
ACAATATTTAGTACTTCAGAGAACAATTGGCACTTTCTGGATATTCTCAACCAGGAGTAT
GTGGTTGAAACTGCACAGTTTTCTGGAGATGATTTAGGTTCTTCCCTTCTTACTCTAATT

FIG. 1Z

CTGTCACTGGTTGATCTTATCCACTCCACAAGCTTTAATCACAATTTCTATTCTGATGAA
TCCCAAATATTTACATGTAAAGAAATTATATCCCCTGGAGTATAGAACCATAAATCTAAA
TGCCAACTGGGTATTGACACTAGGATAACTCACAGGTGCTTCAAAATTACATATACAAAG
TTGAATTTCTCATCTTCTATCTACTCTTACAAAGCTACCTCATTATCCTTTATCCCCTAG
CTCAGTGAGCATCCCCAGCTGTCAAGCAATATACCTGCTAATCATCCTCAGTTCTTCTTA
CTCTCTCATCCTCATATCTAATCCCTCACTAAGGCCTGATATTTCAACCTCGTTATTATT
TTTGGCATTCACCTTTTTCCATTTTTTGGTTACCAACTTGCTTTCTTGGAATTTTAAAAC
TGTCAGTATTAATCTCTCTGCTTGCAACATAAAGACATATATTTTCCACATATTCCGCCT
AAGTAATCTTTGAAAAATAGTAGTAAGATATTGCCATTCTGTTGCTTAAAATCTGTCAGT
AATTTTGTAATTTTCCAATTCTCCATAGTCTGTAGGACAATATCCAAATGTTTTAACTGA
ATACACACACACAGAAACACACACACACGCTCACACACATTTTATGATTCATACTTTGAG
TTTAATTGAAAGATAGAACATCTATAAGATGAAAACAGTTGTAGTCAGAGATTCTGGTAT
GCAAAGTAGGAGAGAGAGCCAAGAACTAGAGGTATAACTTTGAATTATAATATTGGGTTG
GTCTTCTATAGATGAGACATAAAGTTGTGAGAGTCAATAAGAACAACTAAAGAAAGATAA
TGAAAGAACAAAAGACAAGTGGATTAAAGACAGATATGCGGTGAAAGAGAAAAGCATTTC
TACAGAAAAGACCCCCAAAATAAGTTCATTGCAGGTAGTAAGATGAACAGAAGTCAAATG
TCTTGGGGAGGATCGGATTGGTTGCTTGTGTATGTTAATTAATGCAAAAGGGTCAAAGAG
AAGGACTGACTTTATGGCCCTGTAGAACTCTGAGAACAGGGTCAAAATCCAGATGCATTT
CTAAGACATCACACTGGGAACGGGGACTTGTAATGAGTTATCTACAAAGTGTAAAAAGAT
GTGGGTAACCAAAAGGTTGTCATTTCCTCCAAAACAAATTTTCCTGGAGTGAAACTGTAA
CTACCAGGTATAGTCATTAATAGAACTGCAGACACTAAGACTATGGAACCTTCCGTCTTC
CTAACCTTCTCCTCAGGCCAGCCTTAAAGGCCTGTGAAGATCTATTAATAACACTGCTGT
TTTGTTCTCTGGCAGCTCTTGGTGCCAGAAGGCTTGGTGCCAATTTGTGGTTGAGCCCCT
CCTTGGGAGAAATCATGCCATTCAGAGACAGCTGATAAGTCAAGCCTATTTTCCCACTTT
CTTCACTGTATTTTTCCTGTCTGAAGAACTTGTTTATGGATTTGATTTCTGTAGAGATAA
TAATCACAGGATTCAGTGGTATAGCATTCCTCTATGCATTTTCTCCCTGCACATTTGTGT
GTGTGAAGATACTCTTTCTAAATCCCTTTCAAGACAAATTATTAATTGTGATATATTAAT
TATTCTCCACTGTACCTAACGGTTATCAACACTACAGAGGCACCATTGGTTGACAAAAGT
GAGAGCTTTTCTCAACATTAACATAATGAGCAACTCGCAATGAGAAAATATTTGTCCAAT
TAGAGACTTTTATATTTTCTTTTCTTGAGGAAATAAAACCCGAAACACATTTAAGATACA
TTGCTGTTTGTGCATAGGCGGTAAATTTTTTTTTTTTTTTTTTTTTGAGACGGAGTCT
CACTCTGTCGCCCAGGCTGGAGCACAGTGGCACGATCTCGGCTCACTGCAACCCCCGCCT
CCCGGGTTCAAGCGATTCTCCCGCCTTAGCCTCCGGAGTAGCTGGGATTACAGGCGCATA
CCACCATGCCCAGCTAATTTTTGTATTTTTGTAGAGATGGGGTTTCGCCATGTTGGCCAG
GCCGGTCTTGAACACCTGACCGCGGGTGATCCCCCCGCCTCGTTCTCCCAAAGTGCCGGG
ATTACAGGTGTGAGCCACCGCGCCCGGCCAGTAAATAGTTTTGAAGTTTTATTTAATCCC
AGCACTTTGGGAGGCCGAGGCAGGGGGATCACGAGGTCAGAAGATCTAGACCATCCTGGC
TAACACCGTGAAACCCCGTCTCTACTAAAAATACAAAAAAATTAGCCAGGCGCGGTGGCG
GGCGCCTGTAGTTCCAGCTACTCAGGAGGCTGAGGCAGGAGAATGGCGTGAACCCGGGAG
GCGGAGCTTGCAGTGAGCCGAGATAGTGCCACTGCAGTTCGGCCTGGACGAAAGAGCGAG
ACTCCAGCTCAAAAAAAAAAAAAAAAAAAAAAAAAAAAAGAGTTTATTCATATTCATATT
AGATAACCATTTGGGTGGCACATTTCACAACACAGATGCACTTCTTAAGAGTCCTCCATC
CGTCAGCGTTGTAAAAAAGGAAGTGGCACGTTTGCATGTAGTTCTTCTGAGACGGAGATT
TAGGGACAACTTTGCCAAGGTGTGTAGGTGGAGAATGGGAGATTGAGACAGGCATATTGG
CTCAGGAAGACAAGGGAGTAAAACTAGCAATAGAAAGGAGGGCCAATGCCGTAACAGTGT
GATGGAGTGAAAACAAGAAAAAGGAAAATGCCTCAGGATTTGGTGGAGAGTTTGTTTTAC
CTTTTTAAGATAATACTCCTGGTCAGCTTCCCAGGTTCTTAAGTCTGGATACTGTAATGA
TTTTGGATGACTGCATTCCATGACCTGTTTCAAGGTAGGTTTTTTGAAAATAGGAGTTAA
ATATAGGCTTTCTTCCCTATGTATTCAGTTGCGTTTTTTTCTTTTTCATTTAGAAATGTT
GTTTTATTTCACGTTCTCTTATTTATATTTAATTGAGATGGTGTTGGCCATTTTATCCTT
CTTTTTTTTTGTTTTCTTTTCTTTTTTTATTTTATTATTATTATACTTTAAGTTTTATAG
TACATGTGCACAATGTGCAGGTTAGTTACATATGTATACATGTGCCATGCTGGTGTGCTG
CACCCATTAACTCGTCATTTAGCATTATGTATATCTCCCAATGCTATCCCTCCCCCTCCC
CCCACCCCACAACAGTCCCCAGAGTGTGATGTTCCCCTTCCTGTGTCCATGTGTTCTCAT
TGTTCAATTCCCACCTATGAGTGAGAATATGCGGTGTTTGGTTTTTTGTTCTTGCGATAG
TTTACTGACATTTTATCCTTCTTTAAACATTATTTTCTATCTAGAAAATCCAACTTCAAA
TAAATATACTCAGTTCTACATTATAAAAAGTATTACAATGAATTTAATGCTTAAAACTCA

FIG. 1AA

TTCCGGAAGTGACGATGGAAGCAGGTTCAAATGCTTTCACTGACACTTTGTGGCAAAGTG
TGGAACTACAGTATATTTTTCCAAGTTGTTTCCTGATATATTTTTTATGTACATAACAAT
CAATAAATTGTTATGCTATTTATTTATGTACTTATATGTAAATTAAACAACCAAGAAATC
GCAAAGTGTTTTATTAAGATGATATCTAAACTGAAATATCACAACTTACTACAAATAATA
CTTTGTTTCAAAAATAATTTGAATTGCATATAAAAATCACAGTTGCTGTGATTAACATTG
CATTGATATATTGGAACTAAGGTTTTTGGAAAAATTGTGTTTTCTTTCAATCTTTTAAAA
AATACCATATTTATAAAATGAGTCATTAAGATTATCCCTAGGCATTTTCATTCTGTATTG
AAGGTTTTTGAGGGACATCATTATTAGTTCAAAGTGTGTTTCACATTTTGTAGTCTGTCT
TACTATGGCAACTAATTTTTTTTTTTTTTTTTTTTTTTGTGAGAGGGAGCCTCACTCTG
TCGCCCAGGCTGGAGTGCAGTGGTGAAATCTCGGCTCACTGCAGCCTCCACCTCCCGGGT
TCAAGCGATTCTCCTGCCTCAGCCTCCTGAGTAGCTGGGATTACAGGCTCCCACCACCAA
GCCCAGCTAATTTTTGTATTTTTTAGTAGAGACAGGATTTCACTATGTTGGCCAGTCTGG
TCTCGAACTCCTGATCTCAGGGGATCCACCCACCTCGGCCTCCCAAAGTGCTGGGATTAC
AGGCATGAGCCACCACTCCCAGTCGGCAACTAATTTTTAAAATTGTGGTAAAATATACAT
AATATACAATTCAACAACTTAATCAGTTTTAAGTGTATAGTTCAATGACATTAAGTATAT
TCACCTTATAGTGCAACCATCGTCACTATCCACCTCCAGAACATTTAAAATTTTTTAAAA
CTGAAACTCTTCACTCATGGAACAATAATGCCTCCTTCCCCTCTTCTCCTAGCCCCTGGG
CAAAAAAAAAATCTACTTTCTATCTGTCTGATATGATTGCTCTGAGTACCTCATATAAGT
GGAATCATGTAATCATTGTCCCTCTCTGTTTTTACCTTATTTTAATATAATCAAAACTAA
ATAAATAAGCAAATTCTTAAAATAAAATTGATATATTTAGTACAGATCCTTTTGAGACAC
TCAGTGGTCCACTAATTATGTACCATATCCAATCACATCACAATATCATAAATTTTATAG
TCAATTATTAGTTGGCATTTCAAGGCCCAAGTATATGTTTAATAAGAGACACAATCTTAC
ATATGCAGTTTACATGTTTTTAATCTAGTCTTAGCACCAGCATATCACCTTAGTTTACAT
TTGTCTAAGTGCAAGTATTGGTTTTGGAATGTAATTTTGCTCATATACAATCTGTAAGAT
ACTAAAACAAAAGCTAGTTTATTATAAGTGAAATAATGGCAAAGGCCATTTTAAAAATAT
TGTATTATTTTCCCATTTGAAAATCAGTTTAGTCTTTAGCCCACAAAATAACAGGAAAAT
AACTTAAATCATAAAAACTATATCTGAATATTATTTAACATATTTTATAAAGATATCCTT
CTTTGGATCATGGCTGCAGATGTTTTCATGCAGCTTGAGCCACTTTCCATGTCTTACGGA
GAATGTGCAGGAGCTATATATCATCAGATTCTTTCAGAGAAAGAACCGGTAAGACAAATG
ACAGTCTGAAAGATAAAGGAAAAAAATAATTGATATCTTCTTGGCACCTCTGCATTTCAA
AAATACTATTTCAATAAAGTCCATGTTAGAGGTGGAATTCAAGAATTCACTGAATCTGCA
TTCTTGCCTTCTGCTATCCTCTTTTGCCCTCATTTGCTCAATTATTCCTCACTCCTGGTT
AATGAAGGCAGGCTTTTAAATACAGACTAACCATAAATTGACTTTAATATTGGTGTTTAA
TGGTTATTCACAGAACTGATTTAAAATGTGGTATCAAGTTCAGGTCCTGGGATTTACCAA
AGTTCATCAGAGGACACAGTACATGGCGAATTGAGAACCATAGCCTACTTTATGTCTAAG
AGAATATTGACAAACAGCTAAGTTCTCTGTGAGCTCTCAGATTTCACTCAAAAGAAATGA
AGAAAGTAAATTCTCTGTTTAGACTTTGTGCCTTTTTTCTCCTTTTAAAGAATTTGCTCA
TCGGAAAATATACCATACCAATGGCAGCAACATACTATAAGTTTATGAGCAAATCAATTC
CATCCATAGTTACTGCAGAATGTATTATAGGCAGTATTTTTGTTGGGAGAAAAGCAGCAG
AAACTTAGCAAAGTAAGGGAAAGAGAAAAAGCAGCTTATAATGATAAAGAGCCTTTGTGC
CCGTAGAGAGATAAGAAAAAATACAAAAGAAATCCATAATGATCCACAATAATTTTAGAA
TGCAATTTATGGCCATGAAGGGTACAACATGTGATTGGGTATCAAAGAAGAAAGAAGTCA
TGTTAATTTAGGCTAATTAAAAGATATTTTGTGAAGCAGAAAGTTTTTTATTTTGTTGGT
TGACCAGTTGATTTTGGACAGTTTTGGATACTATTTAATTGGTTAAAAAGCTATTGAAAT
GGAGTATCAACCATTTCCAGACAGAGGAATGGCATGAGTGATGGTCTGGGCACGGAATAT
GTTTGACACACAGTGAAATATCAGATTCACTCTGATGCTCTGTGTATTTTACGGGAAACA
TTATAAGGGATAAAGGGCAAAAATTCAACAGAAACCCAGTTACTATTGGCCATCTGAGAA
TTTTGTACTGTCCAGGAGAAAAGAGAGCTCTCATTGAAATGGAAGAGTTAATACAACAAG
ACATTGTGCTTGTCTGTACTCCTATATATTTTATCCATTAAAGGAATTAATGGATTTTAT
CCATTTTATGACATTTATTATTTTATGACACTTATCCATTAATGACATTAATGGATAAAA
CATATAGGAGTACAGACAGGCACAACGCATGGGGAAACTATTAGGAGGTCACTGCAATAC
TCTAGCTAATGGTTACAACAATCTGACATTGGGTATTTGCAATAGGAATAGAAAGAATAT
AATAGAGGAAAGAGATATTTTGGAGATTTCAAGCATAATTAATGGGAGAAAATGGAAGCT
TATACTTCAGAGAAGCACAAAGTCCAGTGATAAGTTTAAGTTGTATAAATTTAGTGTGCT
CTCAGGAGAAGGTGATGTTTACTTTGTACTTTTACAACCTTGCACGGGTGAGTGGGTTAC
TGAATAAACAAATAAATGTTTGTGTAACACAAATTTAGAGAATGTGCAGTTGTAGATATA
TATGTAGTTCTGAATAGTCCATTTAAAGACAGATACTAGGTTTTCTTCCAGGGTTTCTAG

FIG. 1AB

AGTTTCGGGTCTTACATTTAAGTCTTTAATCCATCTTCAGTTGCTATTTGTATATGGTGA
GAGATATGGGTTTAGTTTTGTTCTTCCGCATATGGCTAATCCAATTTTCCCAGCACCATT
TATTGAGTAAGGCGTCCTTCCCCAGTGTCTCTTTTTGTTGAGTTTGTTGAAGATAAATTG
CCTGTAGGTATGTGGTTTTATTTCTGGGTTTTCTATTATGTTCTATTGATCTATATGTCT
ATTTTTATACTATTAATAGTATCATGCTGTTTGGGTTACTATAGGCTTATAGCATAATTT
GAAGTCAGTTAATACGATACCCACAGCTTTGTTCATTTTGCTTAAGATTCATTTGACTAT
TTGGGCATAGCCACAGTCTTTAAATATTTGAATGGACATAATGTGAAAACCACACTTAAG
ATATGTTTAAACGGCACAGTAATATTATCTAACACAAACTCAAAATTCAAATGTATCCAG
TTGTCCCAATAGCTTTCTTTATAAATATCTTTTTTTCTTTTTATTTCTTCTTAGGATTGA
AAGGTAAATATCCTAGCATCTACACAAGGGAACCGATGTGTGTGTGTATATATATATATA
TGTATATATATATACACACACACACACATAGGAATACATACATGTATATATACCAGTATA
CACATAGAATACATAGGAAGATTTTTATATATATATATATATATATATATATATATATATA
TATATATATATATATATATCTTCCCCAAAAGTGTGCCTTGGCTTTTAAAAAAGCTTACAA
GATCTCAAACTGTCTTAATAGACTGACAGTAACCAAATCAATCATCCTTCTCATTGTTGC
TCTGAGTAGATTGCACCTGGAGAAATGATTGCAGGTATGGATAGCTCACTTAGAGCTATT
ACTGATAATCTGAAGTGTGTTCAGAATAAAATAACCAGGGTGATGGGGAATGAAAAGCCC
ATAAGTTTCACATGATGGATTCTGATTATCTTTAGGCTGGAGAAGCATAGGCTAGGGAAG
TGGGCATAGCTGTTGTTGTTAAATACTTGAATGAATGCCTTTTTGATTTGAATTGTGTTT
CTCCAAAAATATATGATTAAGTCCTAATGATCATTACTCAGAATGTGACCTTATTTGGAA
ATGGGGTCATTGCAGATGTAATTTGATATGGTAAAGTCATATTGCAGTAGGGTGGGCCTT
TAATCCAATATGACTGGGATCCTTATGAGATGATGGCCATGTGAAGATAGAAACACAGTA
GAATGTCATGCACTGACAAAGGCAGAAATTGGAGTTATACTGCACAAGCTAAAGAGCACC
AAAGATTGCCTGAAAACCACAAGAAAATAGGAAGAGACTAAGAAGAACTTTACTACAGCT
TTCAGAGACAGGACAGCCCTGCTGACACCTTGATTTGAGAGTTCTAGCTCCAGAACTGTG
AGACAATAAGTTTGTATTGTTTTAAGACACCAGGCTTATGGTACTTTTTTACAGCAGCCT
TAGAAAACAAATACAATGTACATATATAGGTAAAGCTTATTCATTCAGTTCCAAGAAATA
ATTAGGATCTTGTAAGCAGAAACGAAGGGAAAACAGAACATGAACAAGAACTTGCTAGTA
ATTAAAGCCACTGCAAAATGAACTCAAGGGCTCCAGCAGGTTTTAAATTACCTGGTATTA
TAAATGTTCAAGCAGGATGAATCAGAGATGGTGCAGAGGTGATTATTCATGCATCAGATG
GAAGGTTAGACTGAATAATCTCCAAGTGAAAAAATTATATGATCCTATCTTAAAGCCCTG
TCAAATAGAGGTTGGTAGCTTCCTTTTCATTTTCTGCTTCAATCAAGAGGATATATGGAT
GATATAGCTTGGTGGATAACACTTAAATTGAAGACCTAGTACTTAGTTTTACTTTTACTT
ACTCTAGTACTTAATTTTTCTTAGGTAGGCCCCTTAACTTCTCTCTCCTTATTTTCCCAC
CTGTTAAACAGAGATATTAATGCTATTCACTTCCTAGTGTTATTATGATGAAACTAGTTA
ATAATTTAAAAAATGCTTAGAACAAGGCACAGCACATAGTAATGACTAAAGAAAGAAGTG
CTTTTGAACATATATTTGCTCTACTATTGTCTAGATTGTCTAGATATAATGCATTAAGTC
TTCCCACCAGTGCCATTGCTCGTGTCCAAAATACAGAGTTAAAAGATTAGAAATAATTGC
ATGTTTTCTAAGAGTCCTGCGCATTTTCCTAGATCCAATATTGTACTATTTGGACAATTT
ATTGACCAAGTACCAGAAATATAATATTTTTGCCAATTTTCTCATAACAAACTGTGATAA
TGTGTATGTCAACTGCTAGGGTGGGTTTGTGTGTGTGTGAATATGTGTGTGTGTGTGTTT
CAAGTGTTTATAGAAAATAAATCACTCAATGGCATAATTTTCAAATAATAAAGACTACAG
TTACCCTGATTAAGGTTCACCTGAGTTTTGGATATTACCACGTGAGAGTTAGAGGACAAT
GTGAAGTTTTCAAAATTAAATCCTCTGAAATCCAGGTATCTTGTTAAATTGACATCTGTT
GGTAGCTGACAGCCAATTTCAGCTTCAGGAACTAGTAAGAACATTTTCCAGCTTATGAAA
CTATTAATAAATGTTACATAATTGTCCAAAGAAATCCTCATTCAGTGATTCAAATTTAAC
AAAATTAGGTTTTATTTATTCGCTATGTAAAGATACTAATCCCTGCATTATTTGGGTGCA
TGGGTGACAGCTCTGACAGGTTTGTGATGCCCCAGACAAATTCAGTAACTTTCAGTGAAG
CAAACCCATGAATAGATGTGATGGCAGCGTGTACACCTATATAATTCCAGAGCTAGTGAT
TATGTAACTTTTATATACGTCAGACCGAAGGAAGACAGAGAATGGAGGAACTGGGTGTTC
TTTCAGTAAAGAGCAACTGAATGAGACAGTACATCTTTTGAACTGGGGATATACTACAAG
GCAATGAGGGAGGCTGGCTATGAAAGTATTGAAAAATATGTTTGATTGCTGGGTGATGTT
TAGAGGCCCTAAGGTAATAGAAAGGAGACAAAATTGAGAGTCTGGAACTTATATGTACTT
TATTACAGTACTCTCATTTTCACCAAAGAAGGCAACCCATGTGGTGAAAAGACCACAAGC
ATTGGAGCTAAAGCCAAGTTATAGCTGTAGTTTTATATTTTGTGAGCCCATATGTCCTCA
GACAAGTTTCGTGAGTTAATTTCCTTTGTCTCAGCTTCCTCTTTTATAAAATGTGGGTGA
TATCATTGTCCCTTAAGATTGTTGTCAGCATTAAACAACATAAGTATATGAACCATCTAG
CTCGGTATTTGGCAATGGTAGGAGCTGAATAATTGTTAGCTCTTACCTTAAAAAATTATT

FIG. 1AC

TGTTAAAAGTTCCAAATGCAGCGTTCAGGAGAAGATATGGGTCAAGGTCATGGATGAGGC
AAACACTACAATTCAATAAAAATTGTTAGTTCTTAATTTATCTTAACTCAGCAACCGTTT
CTTGAGACTCTACTACATATTGAGTACTGAGGGAATAGAAAGATGAATCAAAGACCATTT
TAAAACATCTGGCATTTGCAATTCAAAATCAAGTAAAAATAAATACAGCCTTATGATTTA
TTGAGAAATGTCATGCAAGGTAAATGAACTGATTTTAAGCATGTACTTAGCATTCACACA
GATTGACAGATTCAGTGAAAACACGGCACAGCCTTCAATTATTTTTCTTTTTAAATACAT
ATTTGTGGACTTTATAGAAATACTGACAGTGTTTCCTCACCAATACCTATTTTCTTTGTT
GAGTGACTATTCCTTTTTCTTTTCAAATTAGTTTGTGTGGCAGTGTGGAAGAACCACCAC
ATGAGGACGGTAACCAACTACTTCATAGTCAATCTTTCTCTGGCTGATGTGCTCGTGACC
ATCACCTGCCTTCCAGCCACACTGGTCGTGGATATCACTGAGACCTGGTTTTTTGGACAG
TCCCTTTGCAAAGTGATTCCTTATCTACAGGTAATTGTTTTAATGCTTTTTTGAAGCTA
CTAAAAAGAATGTTCAGCCATAGCGATGGCCCTTATGGTAAATTAACTAGTGAGTTGAGA
AATATATTTGCCTAAGGCATTGACAAACTGAAGGAAAATAATACTTGAGAATTTCTGGAG
AAATAAGTTAAGTTCTGGGTAAAAATTAAGCAATGAACTGCCAAATCATCATTAGATGCT
GCACAAACATTTTTGCACAACTTTTTTGATTACTAATTTGATTCCAAAAGTTTGATTTTG
CACAAACTTTTTTTATTCCAAATTTGATCCCAAAAGTTTGATTTTGCGCAAACTTTTTTG
ATTCCTAATTTCCCCATTGTTAAATAAGAAACTTGAACCAATTAATGATTTAACCAATTA
ATGATCTCCCCAAACCAATTATTGATCTTTCTCTTGAACCAATTAATGATCTGCCAGTCC
AAGTCATTGAGCATATTTGTTTTTACAAGTGATTTTATTTTATACTGAAGAATTAAGACC
TACTTGGTCAAATCAGTGCCATGAACAGGTTTTAGTGTAGATTCTAATTCAAACTACCGG
ATTTGGAATCTCCGTTCTGCCATTCACCAATTGTATGCTATCAAGCCAAATAGTTGTAAT
TCACTTATTTAAAAGAATAATTTAAATGAGATCTACCTCATATGGTTGCTGTGACCATTT
ACTTACATAATTCATATAAATAAGTTGGCACAGTGATTACCCTCTGGAAGAGATGATCTT
ATAAAAACAGTATATTCTCAATAAACATCAATTATCAGCATCAGAATCATCATTACTAGG
TGTTTTTCTTTCCTTAAGAGTGAAAACAGCTTCTTTTTCTATTTAATTGCCATTTCAGTA
ATTAAGAATGAATACTTTCAGAGATTAGTGTTCTGATTGTTATTATAGCTCTAAAATTTT
TGAAACAAAAGATTCATCAGATAATGTTCACATTCACTCATCCATCCTAAAAGATGGATT
TCCCTTAGGAATTGGACAGCAAATGAAATGGTGACCACTCTCTGCTTGTCTTCCCATAGC
TTTCCTGCACCCTCAGTTTTTACGCCATGCAGTCTCCCAGATGGTGCCTATAATATTTTA
AGAAAACAGAAAATAAGCTCCCAGTAACAAAAAAATTAGGGAGGGGTCACAAATAGCCTAT
TACTAGACATTATGCCGATTAGGCTTTTGGAATGAAATGTTGCAAAGAGATATTTAGTTC
AATAGTTCCTCAATTACCTCTTATAAAAAGAAGTGAAAAATTTTTAAGGTTAAACATTGT
TTATAGAATAGTAAGTGGAAAATACTATAGAAGTTATAAGCTCCATGCATATATTATGTT
TAATTATAAAGCTAGTTTGGATCAGCCTGCTGAAAATCATGAATGGATTACAAAACGAAC
AGTAGCACATTTTTTTTGTGTGTGAGGAAAAACTACATGGGACAATAGAGAAAAATATTCT
CATAGAGGAAAAGTTAGTAAGAAATGAATGGCTCTGGTGGTGTTTGCATAGAGGCACTAG
GAAAGTAATACATTTCAGATAATTCTAATATTTCATTATCTCTGTGGTACTTCCAGAAAG
CCTTTTACCTCTCTTGGTTTCAATAACTACCCAGGAGAATATTTTGAGGATTCTCTTAAG
TTTTGGGATGGCTGCAGTTGCCCAGAATCTTCAACTGACTGGTAACATTTCATGTTCTCT
CTGTGAAACAGAAGATTCCCTGGTGGGAAGTGAAGTGATAAGGGCAGGTGCAGTCATGTG
CTAATGCACAGCGATAGCTTTCTGCAGAGCAGGCATCTCAGAGTTTCCTGTGAGTATTTG
CATTAGAGGACAGAATGGAAGCAGTGTAACCAGTGAGTGATGCAGAGCATGGGTATCTCT
TATAATCACTTACAGTCCTCTTTCACACAGCAGAACTATTTAACAAGTCCTACAGTTCAA
GGAATATCCTCATCTCTGGAAGGATTCTGTCTGCCTCTCTGCACACAGTGTCCAATCTAA
TCAATTCCTTAGCTGCTCCTCTTCTCCATAGAGCAAGGGAAAAAACTACTGGGTAACCAC
ATGATGCAAAAGACTAGATCCATTTGTTACCCCATCTAACATTACTTCTTGATGGAAAGG
TGTAAATGCACCAAGAGATTGGTGCACAGGTAAAACTAGTATCTCCAAATTCTTCATATT
TATTGCCTCATTTTTCATAGAATGTTCCCAAATGCAATGAACAGTGCCAATGGGCAATAA
ACATATAATTTAAATTTGAGCAGATTTTCTCCCTAGTTGTGACATTCTGTAACTAATGAC
TTATATCCCTGATATGATATTTATGTCTTACTGAATATTTAAAAACATGTTACATCATGC
CCAGCCACATTTTAAAGTTATTTGGTTGCATTTTAGATTACTTGGACGTTTATTAATTTG
CTATAATTTATATGTTCTTTTTCTTCTAAATACAATACAGCCTTTAGATTTATGAGTGAT
ATGCTGTAACGCATTGGCAAATGCACAAAAATCTCAAAAGTCTCACAAATGTTATAAAGC
TTAGCTGAATAATTAAAATGACTCTTTTGTATCTTTAATAATTGCATAACTCCAAGACCA
TTAACATGTATTCAGCTATTTGCTGAACAATTATCATGTATTTCACTTCTCTTCCAACAA
TGACAAGAGCATTGGTTACTTTTTCAGAGTGATTTTTTTTAACTGCAGAAGACGCCCTAC
ACAGAAAATGCCAGAAAAAAAAAGAAGCCAAGTGAGATGTGGGAGGTGGGCAGTGGGTGGT

FIG. 1AD

CAAACAAGCTCCCTCTCTTTCAGTCATACTTTGAAACCTTTCTACCTATTAGTGCTTATC
ATCCAAATCTGTGATTTGGCAAAATTTTCATTTCTCCTTATAGTGAATCTTTAAGATACC
TTTGCCGTATCTATTTGCTAGTATAAAACAGTGGACTTCTCTACTAAAGGAAATCCCCAA
ACATTATCCTGTGCGAAGGGTGCCCATAGTATAGGTCAAAGACCAAGTACCTGAAGGCAG
AAGAAAGTTCCCATTATCTCACTCCACTTCATTCTCAACATTCATAATCCACACTAGATT
CATTTCTCAAATGACTTACTATTCAACAAACTTGAGCTAATATCAGAATCCAAATGAAAA
AGACACCCAGAAGTGCACTCTTAGAAGTTAAAAGCAACAACAAAACTTTCACTTATAATT
ACTTATGATAAAATGCAATTTTACATCACCTCCAAGAAAATCTTATACATTGCACATAAT
TGTATATTAATGTGTTAATTGCACAAGCAAATATAGTAGGTCAAACAATGAATATTAGCT
CACTGATTGTCAAGGGTTCATTCAATGGATTGGTTCATTCTACTGTTAGATACATCACAC
TAGCATATTCCTCCCTTTTCTGTGTGATGAAGGGCAGTGCTCCCTGGGTCACTATTGGCA
CTGGATGTCAGTCTTCCAAGTGAACTGATATGAATTGATTATTATGACCTAATGGCATTA
GGAAACACTAGAAATGACATTGATATTTGAACCATGCTACATCTATCCCATTTATCCATG
TTGATTAAATTAATGGATTATAAATTACTAAGGCTTGATGAACACTTTGTACTTCTAATT
GCTAGAGAGGATTGATATATCTCTAGCCCAGAAGCTATGAAAAGGCGACTGTGCGAATCT
ATACAACCATAGTTCTATTCCCAGGTTAGCAATGGTATTGAGGGGCCCTAGGTGCTTAAC
TTATTTGCAGAGAAGGAATGGAGGTTGTAGAGAATAAGGTGATACTGGTTTGAGAAAGAG
AGTTGAAGGTACCCTCAGGTAGCACTAAGAAATTTCTAGGAGTCACTAATCAACTTAAGC
CCATTCTCATAGAGTCCAGCCCCTTAAAATTACACTTAAAATGAAATTAGCCTCCAATAA
TTTAGCAAAGGTTAGGCTTTCACTTGTAATTTCTATGAATATTCTTCTCTGAAAAGCAAT
CTGTTCCAATTAAAATATAGAACTTCAGACTCAAGAATGAAAGATAAAACTAATAGTATC
ATCATCATTATTATTATTATAATCATAAGAAATAGTAAACACACAGCACTTATATGCCAG
CCCTGGAATAGACATTTTCATCTCAACTAACTGTCCATACAATTCCATGGTTAGGTACTA
TTAATCATCCACATTTTACAGATGAGAAAACTGAGGAATGGAGAGGTTAAATAATCTCCT
TAAGATCACTCCATATGTCAGATGGGATTCATGCCCAGAAAACCTGGTTGCAGACTCGAT
TCCAGCTATACTCTTCTGCCTCTCCCATAGAGAAACAAAAGAATCATACTTGATAAGAAT
CTTATCCTGTTGATTTACTTCATTTAGCACACACACACACACACACACACACACGCAACA
CACAACACACAACACACACATTAGGCCTAAAGCTGTAAAGTGAGTGACTCAATAGTGTGC
AGCTAGCTGATCAGAGAGAGAGAACAGATAGTTCATCCTGACAGCCCAGAGACTTTCTGC
ACTGTTGCACTGGATCTTAGATCTCTTTCACTCATTTGTACCTATAATCAACATATCAAC
AAGAAAGGTCCTCATGTAAAAGACAGAGATAACTACCCTTTCCACATATTATGAGATCAA
TATAACCAGGACAGAAAAATAGAAGAAGATGACTGGACTATATCTACTGCCTTCAATTAA
GGCTCACCACTATTAATGGATTAACAAATATTTGTTTTAAAGACACATGCAAGTATACGT
TCACTGCAGCACTATTCACAATAACAAAAACGTGGAATCAACCTAAATGCCCATCAATGA
TAGACTGGATAAAGATAATGTGGTACATATACACCATGGAATACTATGCAACCATAAAAA
AGAATGAGATCATGTCCTTTGCAGCAACATGAAAGGTGCTGGAGGCCATTATCCTTAGCA
AACAAATGCAGGAACAGAAAAGCAAATACTACATGTTCTCATTTATAAATGGGAGCTAAA
TGATGAGAACACATGGACACATAAAGGGGAACAACACGCACTGGGGCCTTTCAGAGGGTA
GAGGGTGGGAGAAGGGAGAGGATCAGGAAAAATAACCAGTGGATACTTGGATTAATACCT
GGGTGATGAAATAATCTGTACAGCAAACACCCATGACAGACATTTATCTATATAACAAAC
CTGCTCATGTACCCCTGAAATTAAAATAGAAGTTAAAAACAAAATATTTCTTAAATGCAT
AATGGATATCAAATGTTGTATCAGATATTGGGGACACAGTTGTGAAAAAAACAGAAGCAG
TCCCTCCTACCCACAGAGCTTTGTTCCAATAGAGAAAACAGATGATAAATAAGCAAATTAA
GCAAATAATTTACTACATTATACATGCTGAAAGAAAAATAAATAACAATCTGTAAAAAAA
AATGTAAAAGAAATCAGAAGTCTTTTTAAAGGGAGAGGGGATTCTGAGAGTGATATCAGA
ATCAATATTTCATCCAGTATAAGAGAGCACATTGAACATAATTACATTAACTAATAATGT
GGATATATGAATTTTTAAAATTTTTTGTTGTTGTTATTTCCTTAAAGTGTCAAGTTAAAG
AATGATTTGTGGCATTGTTAATTATATACAAATTTTGACTGGGTGAACTTACCTAGTTTT
TGGAATCACATTGACTAGGCTAGCAGTGAGCAAACTGTCATAAGGAGATTCGCATACAAA
ATTCTCTTTTAATATGACTCGTAACTTTCCTTGGGTGCTACATGTTGAAAATGCACTGAT
GTACAAATAGCCCTTATTATTTGAAAATATGAAATAAGCTACCCATAATTTAAAAATGTT
AATTAAATATAATTTCAATCAAATTTCTATGTGGTAATTTAGAAGAAAGACATATTATTC
TTTATAATTGAGGCTTTTCCAGTTTGGACTAAACATATGTGTTTTTTTTTTTCTATATGA
GGGTATGATTTCTTCCAATCAATGGAAAAATTACAGGACAAAATAATTACAGTAATTATT
TAAAGAATGCCATATTATAAATTAAGACATTTGGAGTAAAAAAAGATTGCAAAGTTTTCA
TCATACCTTTTCATGTTTAACAATAAATTTACATTTAAAAGTATATTTCTAATATTTCAT
TTTTGTGATATAATTTCTTTTTAAATAGAAAGCACTTGCATGGATTGTTTATTTTTGGCA

FIG. 1AE

GCTTTGAATTTGCTTATATGTTGTGACTACCTTTCTCATATAGTAAATATATTAAGAGTA
ATTCTTTTAACAGCTGGTGCTTCTCTATTACTATGATCTTTCTTTTCTCTAGACCGTGTC
GGTGTCTGTGTCTGTCCTCACACTGAGCTGTATCGCCTTGGATCGGTGGTATGCAATCTG
TCACCCTTTGATGTTTAAGAGCACAGCAAAGCGGGCCCGTAACAGCATTGTCATCATCTG
GATTGTCTCCTGCATTATAATGATTCCTCAGGCCATCGTCATGGAGTGCAGCACCGTGTT
CCCAGGCTTAGCCAATAAAACCACCCTCTTTACGGTGTGTGATGAGCGCTGGGGTGGTAA
GTACCTTATGGCCCATCAACTGACATTTATATTACAGCAGCAAATTGAAAATTGGATTAG
CATAGCCATTGTAAAGCTGGGCTTATATATTTTATTGACATTTGTGAATACAGTTTTGCA
AGAGCATGAAAACCAACTTGAATTTCAAAACAATTTCACAGAATAACTCTACCTATCTGA
ATCCTTTGGAAATGTTATCTATTATTTTCTCATTTTCATATCTTTTGGATAGGAAATGAA
AGGAGATTATTCTACAATTCAGATTTGATTATTTTAGTTTTTCTTAAACTCTTTAAACAA
AAAGCAATATGGAATACAAATCCGATTATGTATTCTGGAATGATCCACGATTTATAAGAT
GGTTCAACACTGTGTTGTCTAGTGTCAGGGTCCCTAATGGGCTTCAAATACAACTGAATT
TTTTCATTTTAAGACCATGTCCTGGATCACATGGTCCTGGGAACATGGCCAGAGTCAGCA
TGTGGTTCTCTAAGTCAAATAATCCAAATTTGTTTTCTCTATTCATAATACATTATTGCT
ACTCGCATAATTATTATCCAGTTTAAGAATTATATTAATTATGAATCAATCTGGTTTCCC
ATCTGACAAGTATGATGTGAAATTTAAGCAATCAGGTTTGAAGGCTTTATGTTTCTTTGG
TTAGAAATTCTTAGAGTCAGTCTGAGGTTTTTGTGTAACAGTGAGAATACTGCTATCAAC
ACCTGGTGCTAGCACAAATCTGGGCACAGGAAAGAATGACAGAAAATAAAATAACCCTGC
ATTTCAGCATAGCATGCACTGATTCCAATATATCATATGAAATATATATTTAAAAAAAAA
CCAATCTGACCTCTTCTAGGTAAGTATACTAAAAATGGCTGATATTTAGAGAATTCATAT
GTTAACATTGTTTTTTATTAGAAAGATGTATCAAAACAAGCAGTGCACACCAGGGACTGA
TTAAGGATAATATTCTTAAATATTGTAATCTTTGAATTTCTGTTATTTCCTACCTTGGTG
TTTGTACTAGAACACCGAAAGGAAAAAAAGCCAATCACTGATATATTAGGCATATACTAC
AGGATATATCTACAGCAAGATAATATTTAAGAGAGGCTGGGATTATTTCATATATTGTTG
CAAGACCTATAATAACTAAAATTTTATAATTTGCTTTATCTATTACCCCAAATATCAAAT
ATCTGTCTTTTATTGGGATTTACTTTTCCTTTTTAACATTCCAACTTTTTTTTGCTGTAT
TTTTCTCTGTATCATTTTCAGTTTTTTCCAATTTTCCAAATTAATAGTGCAGACAAAAAA
AAAATCAATGGAAATTTCCAAAATGGTAGGAATATTTATGAAGTGTCTTATGTCCCATTC
ATTTAATGCTCAAACACCACCTTGAGAACTTAGTATATGTCAGGCATTGTGCCCACCTGG
AGAGAAACAGACTCTGCTTACGGGAGCACACTCTATATAATAAGGCTCAAAGGCCAATAA
ACAAATTTTTATAGGGTAATCAGTATTTTAATATATTTATATACAAAATGCTGAGAACAC
AAATGAGAGAACAAACTCAGTTCTGGCCATTTGAACAAAAGTTTACAGAGGAACTGCTAA
CATTCCAGCAGAACATTAAAGATAAGCAAAAATTCTCCAGACTGAGAAGAGGGAAAAGGA
TGTCCAGAAAGCAAGAAAATCCACATCATGGATACTACATTACAAAGCAGAAAGAGTGAA
TCAGCACTTGTAGTTTCTGGAACATAGGGGCAGGTAGTGTAAATAATTGAATTTTGAAAC
AAGATGGGTTGCGGACTGACTGTGACATGTCTCTTATACGATCCTTTTACACTGGTTTAT
ATTTAGAAAGCCTAAAAAGGTCTTTCTCAGAATCCTGTATTAAACTCGAGACTAAATTTA
ACCCTAGAAAGATTATATTATTTTTTCAAGATTATGAAGCAAATAGGTACATTTAAATCT
AAAGCTTCCAACTTGTAAGTTGGGATTCCTTAAGTTTTATAGGGATTGCTATTAGATAAA
ATATAAAAATATTTTTCAATATGTGTCAGCAGTATTTTCTCTAATATTCCGGCAATTAGT
TTCACTTATATGTTTATGGGTTGCTTTTATAAGCTTTTCTTTTTTTAATGTTTCCCTGAA
TAATCAAGTAACAGTAACCTCCATTAACAAAAAGATTGCAAAGTCATGGATTCCTGTTCA
GTTATTATGATTATGTAAATAGACGTATGATTTTTAAATTACCTCTGAGTGGTAAATATA
AATACATAAAGCTCATTTCTACTCTGATATTTTATTACATAACTCTAGCATGGACATTTT
CATTAAAAAAAGGAAACAATTGTTGAATATGTAAAAACCTAAACTTAGCCTTCAGAAGTC
ATTTAAGAAAACTATTTGAAGGTGATTTTATAATAGCCTATAATTAAATGCTTGTAAAGA
CTAAAATTAAGTATTATTGGACTGAATTGATTAGCTACAAAATCCAACTTAGTAAAAGCT
ATACAGTCATTTAAATATTAAATGAAATTGCTAAGAATATTTTTAAGAAAAAATAATTCA
AGGCAGATTTTTATCTTTCTTATTAGATATTTATTATGATGATTTCTACATAGCATGTAA
AATCATTGTTCATGTAAACTATTTATAAGTCCATGTTCGACTTATAATGTTAAACCTTTG
TATATGTGTGATTGTCACAACTTTTTAAAAAACCATAGGAAAGTATATTTTACAGTGTCA
TCTCTCTAAATTCAAATATTTTTAAAGGCCAACTGTCATTTAGCCTGATTTTTAAAACTA
TTGTAAAATATCTTCTATTTGAGATTAATTCATAATCTGTGTTTCTTATCTTTATTCTAA
GTTAAATCAATAATGTAGTTATAAAAGTAGAGAGTAGAATCATAATTATCCTACAACCAA
TGTGGCAGTGGAAAAAAATTTGGAAAAGCAATTTGGTCAGTTGATACATATCTATCAAAT
AACTTTTGGAAAAGTTCTGTAAATGCTGTTTTACTCATGGTGCAAAATAACTGAGAACTC

FIG. 1AF

TGTCTAACTAAAAAATTTACCAGCAATATGTAATTATATATGGATAAATGATTTCTAAAA
CTAATTATATTCATTATTGCCTATTACTTCTTCATAAAAAGAACCATAAGCCATGATTTC
TGGCAGACACACACAACACTCAAGAACATATAAATAATGTAAATACTTATTTTAATAACC
TTTAAAATATACATTTGTATGTGTTCACTGTTTGCTTCAGTCACATCATTTCATACTTCT
AAAATTATTAAATTAACCCACAATTTCTTGCTTGCTTGGTTTGTAAATGCATAATTCTAC
AGGAAAGATCCTACAGAAAGAAATTCTTTGCTGGGTGTGGTGGCTCAAGCCTGTAATCCC
AGCACTTTGGGAGGCCGAGATGGGCGGATCATGAGGTCAGGAGTTGGAGACCAGCCTGGC
CAACATGGTGAAACCCCGTCTCTACTGAAAACACAAAAATTAGCTGGGCATGGTGGTGGG
CGCCTGTAATTCCAGCTACTCGGGAAGCTGAGGCAGGACAATCGCTTGAAACCGAAAGGC
GGAGGTTGCAGTGAGCCGAGATCATGGCACTGCACTCCAGCCTGGGCAAAAGAGCAAGAC
ACCATCTTCAAAAAGAGAGAAAATAACTCTTTTTGTACACTCAATCAAAGTTATATTTTC
TTCACTATTCATTCATCCAGTGTTTAATTAGCATGTACCCTTGGTCAATTGTTCTGGACA
CTGGAGATTAGTAGCATCTCTCTTTTTGAATATTACTGACAAATTGTTCTTTGGTAGGCT
AAAAAAAAAAAATGGAACCATTTTTACAGTCAAAGTAATTATGGCATCTGGCCTATTATG
AGGTTTGAAAGCATATAAATATGTGTATAAGTCTATTAATGGGAAGATTTATTAAACATA
TTTATTAGGGAGAAGATAGTAAAACATATTAAAGATTCAGGTAAACTTAATGAACCCCTA
AACTTTGAAAAGACATTCCATGTTGAATATTGGGAAATTATATTTAATTTACTTGTTCAT
TCAATTCCTGATAAGTGTACCATGAAAGAGGAATGTTTCTAGTTTCTAGATAATTAAGAT
AACATGCTGGCTGAATAATGAACCTTAAGTCATCTGAGAGAAATTAAGTTTTGCCTGTCA
AATATACAATATAACTCTTTAATCTCTGATTTCAAAGACTAAAGATCCACATTTGTTCCT
TATTAGTTAGTTTCATATATATATATATATAAAATTTATTTAGATTGTGCTTATTCATCAGT
TGAGTAAAAACAGTAATTTTTAATGATTATCAATATTTAAAACTTTTTTAAATTAAAGTA
ATGCTTATGTGAAACAAATTTTGTGTAGTTATATTCTAGGTTATATACAAATGTCTTAAA
TACATTGAAGACATTGCTTATGAAGTACAGAAAGACTTCAAAGATATTTTCATCACACAT
AATTTAAAATTTCAATGGCATATCTGAGTTTTTAATCAGCTTAGACTATCATGTTTCCCT
AGTTATCTATTATAATCTCCTTATTCAAACAATCTATCCTACCCTGGAAGGATAATTTTG
CTTGATCTTTTTTCCATATCAGTGTTCATTATAATAATTTGCATTTAGCAGTCAATTACA
TATTTTTTCTAATTATTCATAAATATACCAACCACATAGGAGCTTTTGCTACCATCTATT
CAAAACGCCAAACTGTTATCACAGTGATGCTATCCATAGCTGCAGTGGAAAAAATTTACC
TCTCAAATCTACTTTCCTCTATCCACTCAATTGGTCTTATGCAGACAACAGGGCTTCGCA
GGTATGTAAGCTTCAAAGTTATATAGATTTTGTCATGAGGAAAGCTCATGTGACACCTCT
TCAAAACAAATAAAAGTTCAAAGCCTCTTAGGTGCCTGGGAAGTGCTGAGATCACTTTCA
GATTCCTTTGAAATTGGCCCGCCATATGCTGTGTAGGCTGTGGCACTTCAAAGGGAAAGA
CTGTTATTTCTCAAGTCAGAATGCTTGAATGTTATCACTTTTTATGTAACTGGCCTGCTT
TACAGGATCAACTTGAAAGAAAGTTGGAAACTGATGAGGTAGGTGAGTGCTACCTGGGCC
AGAGAGTAGCTAAAAATGACACCTCAAATTGGTCTCTTAGACCTGCCAACACATGCATCC
TACTGACCCTGCTGAAGACTGCAGCGGATAAAGACATCTAAACCAAAAGAGAAGATGGGT
TTAGAAGCATGAATATGGAGAAAATTAGACTCAAACTCAACTGCATCTGAAAGACAGCCT
ATGGAAATAAGATTGTGGAGGATATTAAACTCATAAATATGTTAAAATATATCCAGCAAG
AATCAAATGCATGATTGCTCAATAAATATTATCTATTATTATGACAATCATCATGCTTAT
TATTGATTAATCCTGACTGTAAACTGCTCTTATCACAAATCTGATCACATAACCAAGCTT
TCATGCTTCTACATCCCCTTTATGAAGTAATGAAAAGAATAAAATACATAGAGGTAATAG
CATTATTCCTCAACAATACTATGGGATAAACCCCCTTGTCAATAGAAAAGTCAAAACAAA
GTATGTAAATTTTAGAAGAAAAACAAAACAGCTCTGTTGTGTTAGCATTCAATTAGAATT
ATAATGAGTTAATTACATTTAATATCTATGGAATCTATGCAAGATATATTGCTTCCTCTT
TTACATTGCAGTAAAAGTAGGTAGACCATTGTGATATATTCGAATACAAGTACAAAAATA
TCTTCTAAAATCTACAGGGAACTCAAACAAATCAGGAAGAAAAAAATGCAAACAATCTTAT
CAAAAGTTGGCTAAGAACATGAATAGACAATTCTCAAAAGAAGGTATACAAATAGCCAAC
AAGCATATGAAAAAAATGTTCAGTATCACTAAGAATCAGGGAAATGCAAATCAAAACCACA
ATGCAATACCACTTTTTTTTTTATTTTTTATTTTATTTTTTGATGGAGCCTCGCACTGTC
GCCCAGGCTGGAGTGCAGTGGCATGATCTCAGCTCTCTGCGACCTCCACCTCCCAAGTTC
AAACGATACTCCTGCCTTGGTCTCCCAAAGTACTGGGATTACAGACGTGAGCCTGTAATT
GGTGTCTGGCCAATACCACCTTACTCTTACAAGGATGGCCATAATCAAAAAGCCAAAAAA
TTAAGGACATTGGAATGAATGTGGTGGAGAGGGAACACTTTTACACTGCTGGTGGGAATG
TAAGCTAGTACGACAACTATGGAAAACAGTGTGGAGATTCCTTAAAGAACTAAAAGTAGA
TCTACTATTTGATCCATCAATCTCCCTACTCTGGTAGCTACCCAGAGGAAAATAAGCCAT
TATACTAAAAAGATACCTGCACATGCATGTTTACAGCAGCACAATTCGCAAATGGAAAAA

FIG. 1AG

TATAGAACCAGCCCAAATGCCCATCAATCAATGAGGGAATAAAAATATGTGGTATGTATA
TAGCATAGAATACTACTTAGCCATAAAAAGGAACGAAATAATGGCATTCCCAGCAACCTG
GAGGGATTTGGAGACCATTATTCTAAGTGAAGTAATTCAGGAATGGAAAACCAAACAACA
TATGTTCTCACTCATAAGTGGGAGGATGCAAAGGCATAAGAATGATAAAATGGACTTCAG
GTACTCAGGGGAAAGTGAGGGAGAGGGGGTGAAGGATAAAAGACCACAGATTGGGTAAAG
TGTACACTGCATGGGTGATAGATGCACCAAAATCTCAGAAATCACCACTGAAGATTCATG
TAACCAAACACCAACTGTTTCCCCAAAACCTATCGGAATAAAAAATTAAAAAAATACATA
CATACAAAAATTCAGATTCCCGACATAATATATAAATATATATTATATGTTATATATAAT
ATTATATATAAATATATAATGTATTATAGTTATATATAATATTATATATAAATATATAAT
GTATTATATGTTATATATAATATTACATATAAATATCTATTAATATATATTATTTATATT
ATATCTAAATATATAATATATAACTTATTATTATATATTATAATATAACTTATATATTAT
ATATAATATATATAATATAATATAACTTATTATATATTATATATTTATATATAAATAAAA
TATGTACTATATTAATATATGAATATATCTAATATTAATATACAATATATAAATTTATAA
ATATATAATGATTATATATTATATAATATATAAAATATATATTATGTAGGGAATCTGAAT
TTATTTATGTATTTATGTACATATATAAGGTAGGGAATATATATATATGTATTAGGTAGG
GAATATATATATATATATATATATCTTCTAGAGCATTTACAAAGTTAGTAATCAATATAA
TTTAGAAAAGCTAAAATATTAAACCACAATGCCATGAAGTGATTAATCGACTTATTCGTA
AGTGTCTAATCTGTGATGTGTATCATTTGTGTACATAGGATTAATTATAAATAAAAAATT
ACTACAGTCCTAGAGGTGTTTATGCTTAATAAGTGAGAAAATATTCATATTGGATTGGAG
AAAATAAATGTTATAAAGCCTTAAAATTCTCATTTTTATTAAAAGTATATACATGTATTT
TTAATAAAAGCATACACACACCACAGACATACTATGCTTAAAGAGGAATTTTGTATATGT
TCCAATAAGTCAACAAAAATAATCATTGTCAAATTTGTATTGTATTTAGTTTTCAAAATT
TTTTTCACATTTGTATTTGGAGATACAACTGAGAATAGCCTCCCATTTCTCAGGGAACTT
ACATTCTAATAAGGAACAACCAACTGAGTTTATATTTTCTTCCCATTTTAACCAAAGCAT
TAGTTTTTAGGTTTTCATTGATTCATGTCCCTTTTTGTAAATAAAAGTTTAGAACAACCC
AAATTAATTTTGTTAATTAGCCAGATGTAATCAAGTCAAATAAAGGGCCTTTTAATAACT
GAACACTTGACTTTGGGTAGCACAAATTAAGAAATAGCTAATGCTTATTTTTCTGAGTAC
ATTAAGTGAAATTACGACTTCACATTTGGCATGTGTATACCCATATACTGAGTAAAATAA
GTTGTTAAATATTATGAATTATTTTTCCCCTTTGCATACATAATATGACAATGAAATCAT
ATAAAAGGTAAATATGCACTTTGAAGAAAAGCATTGACATGTATCTTTTTTAAAAGTCCA
TCAATTGTAACGTAAGGTTTTGTTGTTTTGACTTTCATCCTAGGTGAAATTTATCCCAAG
ATGTACCACATCTGTTTCTTTCTGGTGACATACATGGCACCACTGTGTCTCATGGTGTTG
GCTTATCTGCAAATATTTCGCAAACTCTGGTGTCGACAGGTATATAGTTTCAAATATTTT
GCGTGCATTATTCCTCCACACATAATTTGTTATTTGTTATTCCTTCCAAATATTTTGTCT
GTGCTTTTTTTTTAGGATGCACTTATAAACAAAATTTAAGAATGCATTGAACCAATATAA
CATGTTCATAAAAGTATTATATTGTGTGTTCTTTTAAAGTAATGAGAACCCAGACATAGA
AATATGTCTAGGCATTTTTAGAGTAATATTCAGGAAATGTATTTTATAAACTGATTAAGT
ACTTTACATTTTAAATAAAATTTAACATCTGTGATTAATTGTCTTTTGTCTAGGAATAAC
ACTAATTTCGCTTTCTATGAGAAATAGCAAATAAAAATTCCTTTAGAGATTTTTGAGACT
CTAAGTCTGAAAGGTTATATTTGTAATCAGATTTATTTAAAACATTGGAACATATAGGTT
AAATCTCCAACTTCAAAGATCTTATTTTTAGAATATTATAAGAATCAGGCAGAATGTAT
AATTTTAAAAACTGTATATAATGCTGATTTGGGGTTACTACACTTTGTTAGATAATTCTG
CTGTATCAGTGAATGTTTGTATTCATTCACTCAGTTATTCATTCCTGAAATACATATCAT
GAACTTTTCACATACATGTCTCACACAAAAGCTAAAAATTCTACTTTTTGCCATTGAGGA
ATTCATAGTCTAGAGGAGGGGCATCATCAGATGCAGGGCGAAAATTACTTTAAATATAAG
CACAGAGAATCAGAGCAAAATGTACTAAAACCATATCTAATACAGGAAAGGTAACATTTA
ACTTAAACCTTGATGATTTGAAGGATATTACCAACAAACACATTTAGTGGTTTGTAAGAT
AGAGACAAAAAGGATATGGCTCAGTCTCTCCCATTTTGTAAAATGTATCTTAAAATGCCA
CAATTCTTAGAGATGTATTTCTCTCGTTCTCTAAACTTACTGCCGATACTTACTTTATCA
GGCTTGTGGAAGGACATGCCATTAGTCTGTTTTCTCTGACACATTTTATCCAACTGAAAA
GATTTACTGGAGTCACCTTAATTCATTAAAAAGATTTCACAAACACTTTATTTGGTCTTT
GAGGATGTGTCTTTGTTTTTTTAATCAACACTTGTTATTCAAAGCATTTTTCAAGATCAT
CTTTCACTGACTGGATATGAGCAACACTCATTTTTTTTAACACTATATGGCTCATAATTT
CAATATTTTCTCTTTTCCTCTGCTATTACAAAGAAGTCATTTCTTTTATGACCTTACAAG
TGAAACCAGTAGCAACATTTATTAACATTTTGTTTCCCATCATTTTTTACTATAAAAACT
AATGTGGACCACTATAAAATATGAGTGGTGATTTTCTAGATGTTGGTGACAGTTTTCTCA
GCACTCTCCACCTCCCTATGAAGCCAATGCTTATATTTTAGGGTGTTTGTTACTGCAGCA

FIG. 1AH

TCCTGCTTCCTAGTACCTATTATTGTATCTGTCAGGTTTTGCTAGGTTATTATTCTTCTA
TTAAAAAATGTGGTTTGCAACAACAGTTCTGTTTCACTCCTATTACAGGTCAGTGGGGAG
GGCTGGCTGGGGCACTGTGCTCCATTTGTTTTCTCATTCCAGAACCTAGTCTGAAGAAAT
GGCACTTTCTGGGACATGGCATTCTGAGACTGAGAGAAAAAGAAAACTGGAAGAAAAGTA
TATTTTCTTTTAATGTCTTTTATGAACCGGCATGTGTTACATCTCACTTTTCATTGGCTA
AAACAAGTCACGTGGTTAAACTTGATCATGAAGAGGGGACACATTCTTCTCTGACAGAAA
GACATCACACATCACAGGGTAATGGGGAGCTTCCTACAAGCTGGGGATGAATGATCTGGA
ATGATACACTATACAGAAGTCAAAAACACAAGGGCCAGACTGCATGAATTTAAATCCTGA
CTCCACCAAGTAGTAGTGACATGAATTTTGTAAATGGCTTAAATTTTTGTGACTCCCTTT
ATTAACTTTAAAATGGGGTTGTATAGCATCTTCCTCATAGGTTTGGTACATGCATTCAGG
TGTGTCCAAGGGAGAGAACACCGTCGTGGGTTCTCAGTTTCTATTTCTATTTGGGCCAGT
AAAACCCCTTCCTATCCCTCTTTTCTGCTTATTACTAGAGACAGAAACTAAAAACCAGGG
CTTCAGGCTGCTAAAAGCCTAAAACAAAACAAAACAAAACTACAACAACAAAATAAGGTG
GGTTGGACAAGCTTGCTTAGATGAATTAACTCAAGTGCCTAAATATAGACAGTGCTCATT
AAACAAAATATCTTAATGGATGTTGTTTAATAATGGCCTCTCAACTAATTGTACTTACAT
TTAAATAGCAAGCATGTGTTGAATTGGTATATGTGACTATTTTTTAAAAAATGCACATTG
AAATACCAGTATGGTGCTTCTTATTTGTCTGGTTCTTCTACTCTACTAAGATAAAGATAG
TCTCGCTGTCATCTTTGTATCCCTATAAATAGCACGTGCTCAGCACACATCAGTTGCTTT
TTTCATAAGAACAAAGTGAGTAGAATAGGAGAAAGTGCTGGGAAAGTTTAGAGAGGACAT
AGAGAATCTATTGCCCAGTTACTCCGATAAACATTTGTAGAAATGGATTAGAATCTGAAA
AATTTCTTGAAGGGGAAAAAGCAATTAATGAGCATGTAGGAATAAAGATATTTTAGATTT
AGATTCAGATTTTGTTGGGGAATGTTCAGTGTTAAGATTATCCCCTATTTCCTTATTTTT
ACTAGTTAGTGTGCATTGTATAAAAGGTATGCTTATAATTTCTTATTCATTTATTTACAA
ATTGACATACCTTTAAAACTCTTTCAAGGTTGCAATGTATCTGTCTTGTTACTTTTACAT
GGTAAAACTTTACCATGATACCATGGTTACCCTAAAGTTTACATGGTACCATCAGAGAAA
ATGTTTTAAAAAGTTTGTTAAATGAATGAGTGACACCAAAATCCAAACATTTTAATTTTC
CACCATTTAAGCATATAGTTTGACATTTCCCAAACTCTAAAATAAATTTTAAAATAAATT
GCATCACAGATTCATAAATAATCCACATTCTTTTCATGAATTATCCTCATTAGTACAAGC
CACATGATTCAGAAGATTTGCAGTAAAATGCTTGGGCTGTGAAACTAAAGTCATTTACAA
AACAGATTGGAATGGAAAATACCAAGTTCAGCTGAACTCACTTTAGCAGCCACAATAAAG
TGAATTAACCCCAAATGCGTGATTACATAGAATTCTGCTTGAGCAACTCTCAATTTCCAA
CTGTTAGTGTCTATAAACAAAGTTGTAAGGCATTATGCGTGCCATAGGCTACATCAAGTG
AGCCATCAAATGAAGAGCTTGTCCTATTTGCTTAAAATTACAGAGATGCATGAAATCTGT
TATGTACTTTTGAATTAGTAAGTGTAAGATTATTAGTGAGCAAATTGTGTGTCCTTGTCT
GACTTTCTCAAGAAGTTTAAGCCTCATTAAAAGAATTAGCTAATGCATTGCTGTGAACTA
CTTAAATTCTCTCTCTCTCTGTTTTTTTTTTTTTTTTTGGCAATTCGACTCAGAGTACTC
AGGAAATTCTACAGATTATTTGCTAAAACTTATTTTTTTAAAGAACTTAGCTTGCTTGAC
TCTTTCATTTATCTGTCAGCATTTTTTCTAGTTCAGACCCTTCATATAATTCAACACTAA
ATCTTAATCGTCATGTGCTTGTGTTAATTTATTTCACATTTATTAAGCACGTACTCTGTG
TCAGCTATGGTGTGAGGTACTGAGGATGGACTGTAATAGATATTTGGGTCTGAAACTATA
GTTCAGCTTCTCAGGGCCTTTGAAAGACCTTCTTGTTCCCAGCTCTTATCACAAAGTTTT
CTGCTGCTCTTTATTCAGCACTCTTCTAAGGGAACTTAAGATAAATAATATTTGATGATG
ACAAATCAGTCTAGTGTGAGAAAATAGGCAGCAAACAAATTACAATTGCAGGGGCAGAAT
CAGGAAGGCAGTAACTCGAGTCCATACAAAAAAAAAATAAGGAGCACCAGTAAAGGTAACT
ACATAGGTAAATACTGTAGACAGAATAAACATATTTATCTTCTGTTATCTGATGTAAAGA
ACAACTGCATAAAATAATAGCTATAAAATTGTGAAGATTCACCTTATAATGTATACAGAT
GTAGTTCAAAAAAGGAGGAGGAAATGGAGCTGTATTGGAGCAAATTTGTTTTATACTATT
GAAATTACATTGGCATAATCTAAGCAGCTTGTTTAGATTAAGTTGCTAATTTTAATTCCT
GGTGTAACCACTAAGAAAATAATTTTTTGAAGAATGTAGAAATATAGGTAAAGTAACAAA
AGAATTAAAATAGTATACAGAAAATATTTAACACAAAATAAAGCAGTAGTGAGGAAATAG
AGGAAGACAAGAGATACAATATATATAAGTCACAAATAGTAAAATGGCAGATATATATTA
TATTTTCTTAATAATTAGATTAAATGTAAATGGATACAATACTTCAATCAAAGGGCATAG
ATTGACATAATAGATAAAAACCAACCAATAATTTAAAAAAACCCATGATCCAACTTTATG
CTGTCTACAAGAGACATACCTTGTATTCAGATATACAAATAGGTTAAATGTAAAATAACA
GAAGAAGTACTAAAATAATCACAAAAAGGGAGTTAATGTGGTTATACTAAAATTAGACAA
AATAAATTTTAACAAAATATTACTATACATAGAGAGGGACATTTCATAATGATGATGGAG
TTGATCCATCAGGAAGATATAAAAGTTGTAAACATACATGCATTTAGCCACTGAAACCCA

FIG. 1AI

AAATATACCAAGCAAAAAGTAGTAGAATTAAGGAGACAAGTAGGCAGCTAGACAATTATA
GTTGAAAATGTTAATACTCACTTGCAGTAATGGATAGAAAACACAGGCAGGGTGCGGTGG
CTCACCCCTGTAATCCCAGCACTTTGGGAGGCTGAGGCGGGTGGATCACGAGGTCAGAAG
ATTGAGACCATCCTAGCTAACATGGTGAAACCTCGTCTCTACTAAAGATACAAAAAATTA
GCCGGGTGAGGTGGGGGCACCTGTAGTCCTAGCTGCTCAGGAGGCTGAGGCAGGAGAAT
GGCGTGAACCCGGGGGGTGGAGCCTGCAGTGAACAGAGATCGTGCCACTGCACTCCAGCC
TGGGCAACAGCAAGACTCCGTCTCAAAAAAAAAAAAAAAAAAGAAATAAAGAAAAAACAG
GCAGAATAGCAACAAGGAAATAAAAGATTTAAACAAACTATGAAACCACTGGGCTTAACA
GATATTTTAGAACACTCCACCAAAAACAGAAGAATGCATATTTATCCCATTTGCACATAA
AACATTTTCCAGGTTTTCTGACTAAAGTCAGAAACAAGACAAGTATGTCTGCTACAACCA
TTTTCATTCAATGTTGAACAGAACTGATTCTTTTCAGGGCAAACAGGCAAGAGATAATAT
TAACAATAATAAAAAATAAAAGGCATGACGATCACAAAATAAGAGGTAAACTATTTCTAC
TTGTAGGTTATGTGATATTTTATATAGAAAATCCTAACGAATTATTTTGCAAAAAAATAC
ATTAGAACAAATAAATGAGTTCAGCTAGTTTTCAGGATGAAAGATTAATATATATACAAA
AATCAATTTCATTTTTATACATTAGCAAATAAAAATTTAAAATGAAATTAACAAAAAATA
ATTTAAATAGCATCAAAATTAATCAAATACCTAGAAGTAGATTTAATAAAAGAAGCTTAA
TAAGAGACTTCATCCAGGCTTGATTGCTTATGCCTGTAATCTCAACACTTTTGGGAGACT
GAGGCGGGAGGATCACATGAGGCCAGGAGATCAAGACCAGCATAGTCAACGTGGTGAAAC
CATGTTTCTACTAAAAACACAAAAATGAGCCAGGCATGGTGGTGCAGTGCAAGACTATAA
TCCCAGCTACTCAGGAAGCTGAGGCATGAGAATCATTTGAGCCTCAGAGGTGGAGGCTGC
AGTGAGCTAAGACTGCACCACTGCACTCCAGCCTGTGTGGCAGAGTTAGACTCTTGTCAA
AACAAAAAAAATTCTTCAGCATAAACATGTATATTTAGGGAATGTCCAGAAATTATAGAG
ACATGGATTCCATGCAGCAGTTATAATTCCCTAAAAAGAGAATTATGAATTCACTGTATT
GCTGAGGATTCTAACATAACCACCAAAGATCCAGGGAGAAAATTACCCTATTTTTGTATT
TAAAAAGATGCATTTATTAAATGATGTGGTACTAGTCTCTATATAGGCAACAAAAATAAT
GAAAAGGAAATAGCTCTGGATTATTAAAAATAAATAGTCTGTTAATCAAATCAATTAAAT
AGATAATGTTCCTTCAACATTTTCAAGTCCTATACATGAATATCATTTACAATCATAATT
ATTAGCAACTTCAATGAGTAGGCCACAGTTATACAAGTTTCTTGAGTCAGTTTGGAACTA
TTTCCATTCAAGCAACATATAGTCCATTTCTGTAACATTTTGTTCTCCATCATTATATTC
AGTCTCAGAAAGGTTACCAACACAGTCCTTGAATCACATGTAGTACAGGTTAAGCATCTC
TAATCCCAAAACCTAAAATTCTAGCTGCTCTAAAATCCCAAACTTTTGAGAGCTAACATG
ATGCCAGAAGTGGAAAAGTCCCCTGCTATCTCATGTGACAGGTCGTGTCAAAAGTCAACA
AAAACTTTGTTTCATGCCCAAAATTATTAAAAATGTTATATAAATTTGTTTAAAGACTAT
TTGTATTGGGTGTTTATAAAATGTAAGTAAGTTTTGGGTTTAGACTTAAGTCACATCTAC
AAGATATCTTTTTATGTATATGAAAATAATCCAAAATCCAAAAAAACTCACATCTGAAAC
ACTTTTGGTCTCAAGAATTTCAGATAAGGGATATTCAATCGGTACACAACATATACACCT
ACAATTACAAAATATCATTGAAAAAACTTAAAGAAGGACTACCTAAATTAAAAGATATTC
TGTGTTTATGGATTGGAAGATTCAATCTTGTTAAAATAGAAATAATCTTCAAATTAATCC
ATGAATTCAATACAATTCCTATGAAAATCCCAGATGGCTTTGTATTTTGGACACAAATTG
ACAAACTGATCCTAATATTAATGTGGAAATGCAAGGGATAGAGAAGAGCCAAAATAATCC
TGAAAAAGAAATGGAAAACTTACTTCCTAATGTCAAATCTTAACAAAAAGCCACAGTAAC
TAAGACGGTGTGGTACTTCCATACAGTTAGTCATATAGATCAGTGGAATAGAATTCATGG
TCCAGAAATAAACTCATATTTATGATTAATTGAGTATTGATAAAGGTTTTAACACAGTTC
AATGGCAAAAATCATAGTCCTGACAACAAATGGTGTTAAGACAATTGTATATCCACAAGC
AAAAGGATGGAGTTGAACCTCACCTCACACCACATTCAAAACTTAACTCAAAATGAATCA
TAGATTTATATGTAAGAGCTAATCTCTTAGAAGAAAACACAGAAGAAAATCATCATGACC
TTGGCTTAACCAATAGGTTCTAAATATAACACCAAAACCAAAAGCAACAAATGACAATGT
AGATACATTAGACATTATCAAAACAAAAACTTTTGTGCTTCAAACTGCACCATTAAAAAC
GTTAAAAGTCAGCCCATATAAATGCAGAAAATATTTGCAAATCATATATGTGTTAAGGAA
TTTGTATCCAGAATATACAAAGAACTCTTATGAATTAATAATTTAAAAAAATTACAAGTA
GGCAAAGACTTGAATAAACAATTCTGCAAAGAAGATATACAAATGGTCAATAAGCACATA
AGAAGGTGCTTAACATCATTACTCATTAGAGAAATATTAATCAAAATCATGAGATACCTA
TTCACACTCAACAGGATAGATTTGTTTTAAAAGGCTGTAATCATTATTGGTAAGGATGTG
GAGTAATTGGAATCCTTCTACATTGTTGGTGGGAATGCAAAACGATGTAACTGCTTTGGA
AAACAGTTTGGTAGTTCCTTAAAATCTTAGAGAATTACCACATTACCCACTAATTCAATC
TCTAGTTATAGACCCAGAGAACTGAAGACATGTTTACACAAAAACTTACACATGAATGTT
CATAACAGCATATAATTCATAGTAGCCAAAAAGTGGAAACAACCCAAATGTTATCAATGA

FIG. 1AJ

GTAAATGGAATAACTCATTGTTCTATATGCAAGCAATAAAATATTATTCAGCTACTAAAA
GAAATGAAGCACTGATATATGCCACAAGATTGATGAATCTTGAAAACATACTAAGTGAAA
GAAGCCAGGCACAGAAGGCCACATATTACATAATTCTATTTGCATGAAAATGTTGAGAAT
AGGCAAATATATAGAGCCAAAATAATTTGTCCTTGGCACGGGCTGGCAGAATGGGACAAT
GAGAAGTGACTGCTAATGGATTTGGAGCCTCATTTGGAGGTGATGAAAATGTTCTAGATT
AGTTAGTGATGATGTGATAGTTGCACAACTCTGTGAATATTCTAAAAATCATTTTTTGAA
CCCCTTAAAGCAGTGAGGTTTATGGTATGTGAATTATATCGCAATAAAATGTTTTCTTTT
AAAAAGAAAGAACAAAAATGATGGGATATTTTAAAATTTTAAAAATTGAAGACTTTTTTT
TTTTTTAGAAAGTTCTGCTGCTGAAACCACAGGGAAGCAAAAAAGGTTGAACACACAATT
TGACATGTTAATGTAATGAGAGACTATAATAGGAATTATCCACGGGTTGTTTTATCTGTA
CTTTCTGACTAAAGTTTTTTTCCGTACTTCTATAGACTTTAAAATGGTCCATAGATGTGC
AAAAAATGAGAGAACCTATTCCATGAAACCATATATCAAGTCCCAGAGAGCAGAGGGAAA
ACCTTTTTTTTTTTTTTTTTTTGCAAAGAAGAAGTCATAGACTGTGTGAAAGAATAATGT
TGCGAGACAACAGATCTGGAGTTGGACAGGGGCAGGAGGCATAGTGAGAAGATCAGTTAT
TGCAGTTGTCATCCATAAGGGCCATCTGTACACTCTGAAAGTGGAGCTATTCATAGTGAG
AATGATGTTAAGAAAAGGAACAAATAAAATTACAGTCCTCGTTATAAGAATTTAGCATGC
AAATCTTATCAGAGCAGTACTGAGGTAAACAAAAAGTGTCAAGAAATCATGGGATTTAAT
GTGAAAAACTCCCTCAGTGTTGGAATACAGTCATCTTCATATGGTGGTGGGTGTAAGGGG
CAAGGAAAATTTTCATGGTCCCTGCTGAACAGGGAAATGTAAGGGGATTATTGTTTCATA
GAAGACCGCCAGTGCCTACCAAATATCTGTTATACTCTATTATGATGAAATGGGTAATAG
GTTAAGGAATACCATAAGGGGAAAGGAGACTTGTCCTACAAGTTTCTTAGCACTTAGCAA
ATGGAGCAGGCATTTGCTATGCATTAAAAAATAAGCATCATCCAAACTCTCAGACTCATC
CAGCCACAAACTTAACTTTTTGTTCCTCCTCCTCCCAGATAAAATTCTCGACTTATTTCC
ATTTGTCATCTTTTTCTCACTAACCGCCACCTCCACTGATGTCTCAGCCCACTTCAGTGT
AGCTTCAGCTTTCATCATTACAGTGAAACAGCTTACATGAAAGTTACCAATGATTTCTAA
AGAATATATATTTTTAAAGTTTATTTATTGATCTTTTGGCAGCATTAAGCAATGTTGTTT
GTGGTTTCATTGCTCATATACTTTCTTCCTACTTTGATTTGAATACTTTTTGCTTTGAAT
ACTTACCTTTCCTTCCCTGACCAGTAAATGCCACTTTGCTAGGTCTCTTCACAGCTCCAT
GCTTTTTTTCAGGTAGTCCCTTGCCCAGGTACTTTTTAAGTGAGGTGAGTATCAAATATA
TATACACATCAGACTAGTCCTCTGGGATACACACAATCACAAATACACTTAAACACTCAA
TGTACCTTTATTATAAATCTTGAAATGAGTTTTTATAAGTCTTGCAACCAAAGTTTAAAA
AAGAATAAATTCTTTTTTTAAATTGCTTTGGCTATTCCAGGTCTTTTGCACTTTCATAAA
AAATTAAAATTAGTACTTTCATTTCCAGAAAAAAGACTGTCGTGGTATTGAACGTGATTA
ATTGCATTAACTCTATAGATCAATTTGGGGAGAATTGCCATATTAACAATACTAAGCCTT
TTAATGCATGTCCACAATGAATATATTTATTTAGGAGTTCTTTATTATCTCTCTGCAATG
TTTCATCATTTTCAGTATATATATATATATATAATGAAATATATATACTTATACATATATTT
TATGAAATATATATACTTATATATATATTTTATGAAATATATATACTTATATATATATTT
TATGAAATATATATACTTATATATATATTTTATGAAATATATATACTTATATATATATTT
TATGAAATGTATGCCTAAAACACATTCTTTTGATATTGAAACTTTTAAAATTTAATTTTC
CATTTATTGCTAGTATGTAGAAGTATAATTGATTTTTTTGTTTATTGATTTAATGACCTG
CTCCTTGCTAAATTCTTTTATAAGTTCTAGTGGGTTTTTGGTAGATTCTTTAGGATGATC
TTTGTAAGCAATAATTTCTTCTCAATAGAACCAATCTGTAGGCATTTTATTTATTTTTCT
TTTCTTCTTGTATTGGCTCAAAGTCCAGTACAATGTTGAGTACGAGTGGTGAGAGAAGAC
TTGATTTTTTGAGTGGTAAGCCAACACTGCATTGCTAGAATAAATCTGATTGAGCAAATG
GTATTATCCTATTTATATATTGCAGGATTTAATTTGATAACATATTTTTAAAGAGATTTT
TATCTCTATTCATGAAGGATATTTAGTTGTTAGCTGTCTTTTGTTGCCATATCTTTGATT
ACAAAGATAAATGTGACCTCATGAAATTTGTTGGAACATATTATATTTTCTGTACATTTC
ATTAAAAGTCTGAACAAGATTGGAATTATTTATTCTTTACTGTTTGATTGAATTCATTAA
TGGACCTATCTGGGCCTGGAGATTTTCTTGTAGCATAGTTTGTAAGTACAGAGTCAGTTT
TGGTCATCTTTGTCTCTCAAGGGCTTTGTCCATTTCATGTAAGTTGGCAAATTCATTGTT
TATCCATAATGTTTTTAATGTTTGTAGCATGTTTGCCTCTTCCTCATAACTTTATCCTGG
TCACAAACATTTTTTTAAGACAGAGTAGGTTTTAAGGTCCATCATGTACATGCTATTTCCA
ATTCATAACTGTGGTAATACATTTTTCAGGGTGTATTTTTGCATTAAATATGATTTATAA
AGTTTATTCATAATAGTGAAATAAAAGTGGGGTGCATGTATTTTACTTAATCCTTCTCAG
TGCCTGCTTGATTGAAACCTCTGAGATTTACAATAATGTACTTTTAGGGATGCATTAAGG
ATTACTAGTGCATAGTTCCTGGAGCTCAGTAATGTCAGTTATTCCTCTTAATTTTATACG
GAGTTTCTCTGAATTCTCCATGTCTCTAGACAGCTTATCAATGGAGAAATTTATGTGTCC

FIG. 1AK

TCAAAATGAATGCAGGATTCAGCATCTTCTATCCTTATTTAGATCATTATCTAAAAAGGG
CATCACTACATTTTTTTTTCCCGATTTCAGGGACCATAGCTTTCTCTTTATGAAAACTGT
ATTTTTTTTTTTTTTTTTGAGATGGAGTTTTGCTCTTGTTGCCCAGGCTGGAGTGTAATT
GTGTGATCTCATCGGCTCATTGCAACATCCACCTCCTGGGTTCAAGCGATTCTCCTGCCT
CAGCCTCCTGAGTAGCTGGGATTACAGGCATGTGCCACCACGCCCAGCTAATTTTGTATT
TTTAGTAGAGGCGGGGTTTCTTCATGTTGGTCAGGCTGGTCATGAACTCCCAACCTCAGG
TGACCGAAAACTGTTTCTAATGGCGGCAGAAGTCATCAGATGCAGAATGTAGATTCTCTC
CTTCAGGGGAACAGTCAGTGATAGAATCACTAAAATTTAATTGATCTATCAGAGATCATT
TAGAAGACAGACAGTTCAAGATCATTTAGCAGACACATACAGGCTTTTCATGATAGGAGT
CTCCTGGAACATTCCAGCATCCATTGCTCATTCTTTTCAGTTATTTTTTAAAATTGCTTT
TTAAAATGAGAGTCACAGAAGAGAAAGTTCCTATCTCTCCCCAACCAGTGGGTTAAAAGA
TTGAGTTGAACCACTACTATGTAAAAAAGATTGTCTACATGACAAGACATACAGAGTGAG
AAGAAAAATAATTTATCCGATATTTTCCATTCAAGGGCAGGTCTTTGTTAACATCATTTG
CCTCTTCAAGAAAGAAAATGGTCAAAGGAAATGTCATATTAATTTATCTGTGTGGACATA
TAAGTAAAATTCTGTTCTCAAATTAAAGATTATCGAACAGACTTTGATCTGGTGGTGTAA
AAATCAACAAAATCTATCGAACATCTATTCTGAGAAACCACAAGGACACATTGGTCAGTA
CTGGTTTGCCGCACAGAGACAGAAAGTAAAAGCTGAATAATCTTAACAGAGCTAAGGTGG
CCTTTTCTTGTGTTTGTTGGCACATTTTCCTCTTTAAAAAATTATGCATGCTGAATTTTA
TTGTTCTGTTCACTAAACCCTATCAATCTTCATGAGCTTACAATTAAGAGAATATTGTAC
TTGGAGGGATTCCCTGCTATTATCAAATAACTTTGAAAAGAAATGGAAAAGTACAAGTTG
TGTAATTACTGTTACAAATTCCAGCTATTTGAAATATTAATGTAAGACCGCAAAAAATCC
TCAATGGGTTTGTGTGCATTTTAAAGGGCTGGACCACAAAACTGATTTCAAACAATTTCA
TAACTACAAATAGTGAACAACAAAAAATACTTGATTTTTTAAAAATATCCTTTCATTCAA
AGGTTTGCTTTGTCCGAACTCGAGAAGCAGAAAACCTGAAAAGCTACAGGTAGTTAAGTT
CTATCTCTCTGGCAGCAGATGGCAGTATTGATGCGTGAAAAATCCATAACAGGTTGCTTG
ACGTTACTTGCTGGGTTTTCCTCTGCTTTAAACTTTGGTATCTGAGCTGAACAAAAATTC
CTAATAAGATAATATGGCTGACATCCCTTTATCATTCTCCTTTCCCAAGCTTTGTTCTTT
TTACAAGGAAATATCTTTTCCACTTGCAGCTTTCTTTAGACATTGACAAAATTTTGATGT
TTTAACTTTTTTTTCCACACAAACTCCTATTTGGTATTCGTCTGAATTAACGCCAAGCAC
ATACTAAGGTCAGCAAATGCTCTGGAGAAACAGGCGCTCAAACCTCCCACACCTCAGGCG
TCTGGAAGCCTTTCCTTACTGTGTTTTCTAATTACTTCCCCAAAGTGGAACTTTCCTAAG
TCAAATTGCAATAAGGGTCTGTCTCTTCTCCTTTCAGATCCCTGGAACATCATCTGTAGT
TCAGAGAAAATGGAAGCCCCTGCAGCCTGTTTCACAGCCTCGAGGGCCAGGACAGCCAAC
GAAGTCCCGGATGAGCGCTGTGGCGGCTGAAATAAAGCAGATCCGAGCCAGAAGGAAAAC
AGCCCGGATGTTGATGGTTGTGCTTTTGGTATTTGCAATTTGCTATCTACCAATTAGCAT
CCTCAATGTGCTAAAGAGGTAAAACTTATCTGTTATTTGAAAATGAAATAGCCTGCCTTT
TCTTGATTCTTAATTAACTTTTTTTTTTTTTTTTAACTAAGCCAGAGAAAAATCTAAACT
TTCTGCTTAGATACCTTGTCAGGCCAGATGACTCAGTTATGTTGTTACCAGCAGGTAAGG
CGAACAGCCTTTAAGAGTGCTCAGACATGTGCTTTTGTCATGCGTATTCTCAGTTGCATG
GCAGACATAAAACAGATGTTTCTCCAATCTCTTCAAGCTAGTTGCTAAACCTTAGATGCA
GACAAAGTTCTAATGCGTAACAACTCATTTACAGCTTGCAGTTCTTTCTTGATGAGAACA
AACGGGTTTTTCAAAACTTCGTTTCCAAAAACATAGGCAATTGTGAGAGAATTATATCTT
AAGGATAAAAAGAGATAAGAACCTTATGTTAGTATTCTAATTATACTTAAAAGTGCATTG
GCGAGCACTTTTTAAAAAAAGCCATCAAGGCAGATATGTATGTCGAATGTCTAAACAGAA
GAATTCATTTCCTGAAGTCACTGAATGAAGCTCAGGGCAGATAGTAATAAAAATCAATGA
GGGAAAGTATGCTATTTGCTACAATGCAGGCACAACTATTAAGTTAAAAATTTTGACCCA
TGACATGAGCAGCAGATGCAGAGGCAGTGGTACACACTAAACTTCATGGCCAGCCAACTT
TATTGGGAATTATCGAAACTGTTCCACATAGACTGGTCCCAAGGCAATACCAATTCTTGT
TTACAACAGGCTTCGAACTTAAGCTAGAATTGCTCCTCTCACTTTGGCCTGATTCAGAAT
CAATATTATATTCCTCACAGCTGGGAACTCTGAAGAACAGCAGCTTTGGCTGGAGTCAGA
AGAAGTGGTATAATCAGCCGCAAAGGGTTCTCATTCTCTTTGGCCCCTGTTTTTGATGGT
TTAACGGCTTTTTCAATGGAGAAGAAATGGAGAACAAACTTCTGTTCAGTGATACTATTT
ACTACAGTCACAGCCTTAAAGATATATGATTTTTTTTGTGGCCTGGGTCCTTGAGACATA
TGCCAGCTCACAAGAAAATAGAAATTATTTTGCCCTCCATATCTTTTTGTGCTTTGCTTC
TTATTAATTATTATTATTATTATTATTATTATTATTGCTAACAGAAATTTAATACAAATT
TATTATGGCCACCTGCTAGATACTCTCTTCTGCTTTTAAGAACTTTATAAACATGTTATG
TTACTGGATGGGTTTTATTCTTTCTTTCTCTTTCTAATCTTTTTTCTCTTTTAGTCAGTC

FIG. 1AL

TAAATTCAATGAAAATTGGATTTACCTCTCTCTGGGTTACGTATTTGGATTTCCTGTATC
TCAGAACTTGCTCTTTCCTTTTATTTCCAACTACTTTTTTTGTCAATAATATATGTCTTA
TTCTTCTGACTCAAATCCCTTCCTTTCCAAGGAAAACAAATAACTTTCAAAGGAGCAAGG
CTGTGTTAAATTTAAGATATTTCAAGTTTTGGGGCATTCTACTCTTTTCCACAACATAAA
AACTTTTGAAAAAAAGAACTTGAAAATTGTTTTTCTTGTTACCACACACATTTTTTTTCA
AATGCTTATATTTATTTATCCTTGCATATGAAATTTGTTTTTCTTTCTCCCACAAAAAC
CATTCCTAGCTTTTTCTCCTTAAAACTTAACTTTTTGCCAAATTAGTCAAAAGCAATTTC
TTTACAACAGTTCAGGTTTGTCCAAGATTTCAAAGACATTTTGAGGTAAAGGGTCATAAC
ATAGTACAAATTTCTTTTGTCCGTATTATTTCACTCTATATAGTATTTTTGTAAAACTCT
AGTACTCTTTATACCAGAAATGGTATAAGGTACACCTTATACCAGAAATGCATTGTTGTC
ATGCCTTCTTGCTGTAACACACACACACACACACACACACACACACACACACACACACAC
TGATACAGACAATCGAAGATGGAGACTTTAGCAGGAAATATATATGATTTTTGGCCTATA
ATCTTATTGAGTAGCTGTAAGTTATCTGTTATAGGTTAGTGATTAGAATTTATAGATGGA
ATATTTCTAAGTATGGAGAAAATTTTTTAATAGTCTTTAAGGATAGCATAACAAAACATT
TTTTAAAGTTTAAAATAATACATGAAAAATTAACACTCATTAATTTTTAAAAATTACCAA
AATTCTGCCCATCGAGAACTGTTTCTTCTCTGGGTATTAAGGAGTCCCAGAAGGCAAGTT
TCAGATAGTCCAGGAAGATTGGAGTTGAAGGCATATGATACTTTGATCAATACATAAATG
AAAGTAGGAAGAAGTACTTGAAGACTATCATTTAGGAGTGATTTTTAAATGATACACATA
ATAGAATATTAATACAACATTATTCAATTGTATTTAGAAAGAAAATGAAATAAAGAAGAT
ATATATTCAACTTCCATATTCTTATTTACAAGAAATACTGCATCTGCTATTTGTGGGAGG
GAGAGACCCTTCTCTGACCTGATTTGGCTTTTGATTTATTGATTGTGCTGTGGAGGTTCT
GTTCAGGCACTGAAGTTATTCTAAACCAATTATGGGGTCAGAAACCAATCTGTGGTCAAT
TCCTGCAACTGAAGAGGACAGGAGTCAGACCATCCTCTACCAATAGCCTTGTTCACCTTT
GAATTTAATTATTTAAAAGACACTTTTCTGTTGTTTCTTTTCCTGCAGAGTATTTGGGAT
GTTTGCCCATACTGAAGACAGAGAGACTGTGTATGCCTGGTTTACCTTTTCACACTGGCT
TGTATATGCCAATAGTGCTGCGAATCCAATTATTTATAATTTTCTCAGTGGTGAGTTTTC
AACTGTTCTTCCATAAGCCACAATTGTAACCAAGGATGAGGAATCAATGAACACTCTTCA
ACTATATGAGGAGTTTAGTTGCTATGTGAGTTGTATTTTTTCCCTGACCTGATTTATCTT
GAGTTTCTTCTCTTTTGAGGCAAAGTATTTGTTACTGAACTCATCAGAGAAAATGAACTG
ATTTTTCCATGTCAAACGTATAAGAAATGTTATAATAGAAGAAAAGTAAACATTCTGAGA
AATCAATAACACAAAATCTTACATGACATACTTTAAACTCATGATTTACAAAAATATAAA
ATACTTTGTTCTGTTTTGCCTTGCTATATTATTCCTTTGCCAAAATGTGTAGCCTAATTG
AGACAGAATTGGGATCTATTCACTTTTAGATATTTTACTATATTTACGTTTCTCTTGTGA
GTATCATCTCTTGGATTTATCTCAATATTTCCCACTGACTACCAAAAATAGTATTACTCC
AAAATAACACATAAGTTAAATGATACACACATACATATACGTGTAACTTATACAATTTGT
ATCTGTTTATGGAATCAATATAATTATAAAAGTCATTTAAATCACTATTGTTTATTCACA
TTTTGCCCGACTGACTTTTAGAATTATTTTTAATTAGCTACCTTTTTACATTGCCTTAAT
CTCCAACTCATTGGCGATTTCTTTGTTATTTCTATCTTCAAATATATGGTGATTTTATGT
GGAAGAATAGAAATTCATTTTGTGGCATATTTAATAAAGCTTCTGCATCTTCCAACTTGA
TCTTTGGCCTTCTGGTTTGCATAGGTTTAAAAAAAAGGCAACAAATTAGATTGATGAGAA
ATAATTTTGTTCTATTTAAAAAAAAATCTAGCACAATGACTAAAGCTCTGAACCTCGCAC
TAAGCAGGTAAAGGCTATGAGGAAGTTGTAATGAGAAGTGTTTGAAGCAGAAGTCACAGA
ACCAGGTCAAAGTCCTAGTATGGAGGATAAAAGTGAGTTAGAGGAGGCAACTGATAATCA
CTGATAACTCATTATGTGACTGCTATTGTGCTGGGCCCGTGAACATTCATCTTCTCATTT
AATCACTGATAACTCAGTGCGTAGCTGAGGCTAAGAGAGAAGAAATGATTCGCAATACTG
CCATTCACACTAATAAAAGTGATTCATTCATTCTCATAGTTCTCCAATATCTCCTCCATA
ATTTAAAGACAAGGAATAGCTTCTACAGTATTTTTCCCCCTTCAGTTTTTGTTCTTTCTT
ATATAGATTATGAAACTGAAAATTTTCTGGATATTTGAGTGTATGTTTCTAGGTATTTTG
TGGATTTAATTGTTTCAGTATCAGTTATTTAGAGTAAAATGCAGGAGTAATTTTTGTATA
ATTTTGGCTTTGTATGACATAAGTTTCATTGTGTTTAATTATTAAATATCTCTGAGAGTT
CTTCTACTGATGATCACTTCCATTATAGTTATGTAGATAAAATATACCAATATGCGTAAA
TATATGAGGTTTGACTATAAAGGAATGAAGCAAATTCCAAGCCCCATATGTGAAAGGCAG
CCTCGTTATTTTATGAAAATATTCATTGTTTCAAGAGTCTACCAAGCTTCCAATAAACTC
AATTTCCTTATTCTATTTTACCCATCTTTGCAAAATATTACACCTCATTGTTAGTTTGGC
TCAAGGGAGCAACTCAGTTGTACCCTATTCATAATTTGTTGAAGCATTTATGTATAATTC
CTTTTCCTTTCATTCTCTCTGTTTGCCAGGAAAATTTCGAGAGGAATTTAAAGCTGCGTT
TTCTTGCTGTTGCCTTGGAGTTCACCATCGCCAGGAGGATCGGCTCACCAGGGGACGAAC

FIG. 1AM

TAGCACAGAGAGCCGGAAGTCCTTGACCACTCAAATCAGCAACTTTGATAACATATCAAA
ACTTTCTGAGCAAGTTGTGCTCACTAGCATAAGCACACTCCCAGCAGCCAATGGAGCAGG
ACCACTTCAAAACTGGTAGAATATTTATTCATATGACAAGGATACCTGAGTAAAACTATC
CTTTTTAAAATCACTGGGAACAGAAATTTTATTATCCTATGATGTGAAGCTAAAATTACT
TGTGGATCTTTTTTTTTTTTTAATCTATTGCTCTTTGGAAATAAAAAAAAAGTCAGTTTAA
AATGATTTCTCAACTTTTGATTTAAATATGTTAGAAGTTTAACCTTCAATTGAGCTTATT
TCAGGCTATTTCACTTTTAGTTTCATGTATTAAAATGTGTGTCAATTAAATGTTTAAACA
TTTCTAATTCTTTTTATAATCCCTTGTTATTTTAATCTCTCACATTCAGATTGGTTCCTA
AAAATTACCAGAATCTATCCAATGATTTTTTTTGCTACTAAAAGAAGTAGCAATTACTAA
TTCTGAATTAACAATAGACATGTTAGTTGACTTAATAGTTTTTTTTAAAAAAATCACAAG
ACTGTTGTTATAATGTGATATCTGAGAAAATATTTATATATAAAATAGCATATTGTGTTA
GGTAATTCAAAAACTATCTTACAAAACTATATACTCACTCATTTACACAATTTTCTCAGG
TTTGCAAATTGACCATTGCTAACATTTCTTGTCTCAACATATGGCCAGTAAGACTCTATC
ACAGTAAAAGTTTTAACGTAATTTCCATCTCTAACACTTTAACATTTAAGAATAAGCTAA
ATCACATCATTATATTCTTTTAACAACAACAACAAAAAGTGATATAGTCAGCCTTGCTGG
ATTAAATTAAAAATGCACCACTGTGCTAGGTGCTAGGGAATGAGATGGCGTCGATGCAAA
CATGCCTTCAAAAGAGCTTCAGTCTAGTGAGGGAGACATGTTGACAGAGTGCAAGGCAGC
AAACAATCTGGGGGACAATTCTTGGTCATGGCAGAGCAGTGAAGCTACCAAGGACAGTGG
TCTTCACCAGAAAGTTTGTAGCGCAGTTGCACTTTTTTTTTTTCTTCAATTTAATTACAA
TGACAGTTGATGTCAGTGGATTCCATCTGGGCCTGGGGCTGAGTACCAGGTGGTTAAAAA
ATAGAGGGGCTTGCTCTTAACTCACACATACATGAATAGACTATCGTATATTTTGTAGAA
AATGTAAGATCTGGGAGTCAAAGCACTGAGTATTCAAACTTATTCCCCTGAAAAATTCTT
CTGATTCAAATATTTACTTGAAAATTAAACTAAAAGTAAAAGAAGTGTTTATGAAAGATG
ATTTTCATCTCCTATTATGGTAACAGGTGTTCTGATTGTATTGAAACAAAAGATATGGGG
CACAGTGTTTAAGAAAAACTTTCATAGAAAATTAATTTTTGTTATTTTTTCATTTTTCCA
TTACACTCAGAGAAAAGTAAAAGAGCCTAATTATCCACAACTTGTTTTCAAATCTTGGAA
TTTGGGATTCTGTTACCTTGTGCCTTTTATGACTCAAAGCAAAAACTATCTTCTTATACA
AGGTTTATTGAGATCATATTGTAAAATATCAGCACTATATCAGTGAAAGCAAGGTATTTT
AACTCTCTCCTTTCTCCCCTTTGTATATTTTAGAACTTCTTTTCTTATTTATGCTGCATG
AAAGGAGAGTTGTAATTTTCGGATCGTGATGACAGCACTTTAAAAAGTTTGAGGATAACT
TCAAATAACGTTGATAATATGCCTTAATAGCCAGTAATAGCTCAGAGGAAGAGTAAATTC
CTTAGACCCAAATATACCTACTTATAATTTAAAAGAGAGAAAAGGGAGAGAGATTGAGAG
GGAAAGGGGGAGAGAAGGAAAAAACTGACTCAGAGAGCAGCAGTTATGTGACGTATGGGA
AGTCAGAATTCCTTTGCTCTAAATCAGTGATTCTCAAAATGTGGTTTCTATACCATCGGC
ATCAGCATCATCTGGGAACTTAGTGGACATGCTAACTTCCACCCTATCCCTCACCTACTT
AACCAGAAACTTTAGGGGTGATAGCCCAAAAGCTGTGTGTTAAGCACTACAGGTGTTTCT
GAAGCACTTTAAGATTTGAGATCCACTGCTTTAAGTGATACCATCTGACATCAGTTTATC
TGCCTGTGTGAAATAAAGTCTTTTACTGCACAGGTGTCTACAACAGGGGCCACCATCATC
GCTACCGTCAACGTGGTTGGATGTCTGAAAGAAGAAGCTGAGTATCAATGTTGACTCTCA
CTCATGTCATCTTATTAAAAAAAAAACAGTTTACAAAACAATTGCTACTGATAAATGCAG
TGTGAAAGACTGGTTTTAAGGCACTTGTGTGCTTTATGTCCACCCAGATAACTTGAGTTT
TTAACTAAAAGTTTCAAATCCCTATCTTCTTTATACTTACTAAAGTTCGTTTTGCAGAAG
CAGATAGTTTCTAAGAATGATCATTTCATGGAAGGAGATATAAAATAAAATAAAACCAGT
ACTTAAACTCTGGGAATGTAATAGGCCATGTACATAGCACTCAACATGTGAATCCAGGAA
TCCTTCTAAGAGGTCTAGATTTAGTATGGTTACCTTAATAGGACAAATGGTAAAGAAATA
GGTGTTCCCAAACTCTGCCAATCTTATGAAACAAAGAGTCAACTCTTTACCTCATTATTT
GCTAATGACACAAATGCAAAGACATCTTTTGAAAAGAATGTGTTGGGACTGTTTTATGCT
GTACCTTGAATGTGTATCTCTCCTTTTTTTGCTATATTTCAAAGATTTAATGTAAGTTGT
CAATGTCATTGAGTTCTTGTTATCAATAGGGATGATATAATTTTATCTAACATGGAATCC
ATTTTAACTTTGTTATTTCTGAATTTCTATGAAACCACAAAAACCTTCATACTTGAATTT
ATTTATTCTTGGCTAAAGATTACTCCCAGTTTGTGAGGAAATTTATTTCTGAGTTTCCAA
AGCTTGGAGAATTTATTGGATATTAAATACCTGTTATAAATTATTGATGAGTTAATTGCA
AGTAGCAGACACAATGATATTGAATTTCACTCCCAATACACATTGTTTTAATGAAGATTA
AGGTAAATATGTTTATAAAATTTAGTCTGGCTATGCTTAAACCTGAAATAGCAGAATGGC
AAAAAACCCCAAAGCTGTTTATGGACCCAAATTGTGAGGAGGGCTATTATTTTAATACTT
GTGTAATAATAGAATGCACTTGATGTAAATTGTAATAGCCATCAACTGCATTTCAAAAAC
CTTTCGCTAGCCACTACAATTTAGAAAGCTTTTCAGTGTCAGTTAGTTTTACAACAAATG

FIG. 1AN

CCTTTTCTACTTTCTACAAGTCACAAGTCAAAAAAAAGTAAATTCCACCAAGTTTATTC
AATTAGTTTTCAAATTGCATGAAGCAAAAAATAGATTTTTAGAGACAATATATAAATAGA
AAAAATATTGTAAAAGTCTACTCTATTACCTTATGTACCACAAAAAAATAAAGTACAAAG
GCATGAAAAACACTATTATTTCCCAAAGTTCAAAGGGAATTGTTTTCTACGCAACTACTG
CTACTAACAAGGGGACAACAACCCCCTCCACTTGCCACGTATTTTTATTCTCTTTTCTTT
ATATCTTTGGAGTTAAATGTCTTTTATGTTTTTCATGAAATGTATTCTATAATTGTTGTA
TTTCATGTGTGTAACATTATGTCAGTTGTTTTAACAATTATCTTATATCTTGAAATTCTT
TATGCCTGATTGTACTGTGTCTTCATGAAGAAATTTCTTATCAAATCCAATGTGATTACA
CACTTACTGCTGTAAAGGATGCGCATTATGTAGTTTTTAAGTAAAAACTATAGTGAGAAT
TCTATAATCACATTCACACTCCCCTCTCTATTGTATGAAAAATCTTGTTGTTGTTGATTA
GATAAGGTGGATATTCACTCATAGTTAATGTCAAATCTCTGCAGTTAAGGATTGAATTAA
GCCCTCTGGTGCAGTACCTAATGATCAAAACATTTTTTCCAATAAGTTTATATAACCAAG
GATAATAATGATATAAAAGGTTTTTAATGTTGTTTTTAAGAGCAGGTACTATAACAAAGA
AGGTTAACACTGGTACAGAAATATTTCATAAAAGTTATGAAAACCAGATAAATACAGTAT
TAAATTTTGGAGCTTTTATCTGAGTTGAGAGATTTAGTCTACATTGACTGAGATGAAATG
ATGAACTCATAATTTTCAATTTATTATCAGAATAATAAGTGACATTTACATAATTAATTT
TTTTCTGGGCCATTTTGTATAAGTCATTTAGGACTATTTTAAGTTCACTGGTAAATTTTA
AAATGTATATTTTCAGCTTTTCAATTTTTTTCAAAATAGTTCTGAGAAATTACAGAATCA
GATACTAAGGATATTAATTTAAAAATCAATTTTTATTCAGCACTATTTATTCTAACATAT
ATAAAAAATGAAGCCAAAGTAACCCGTCAAGGTAAATACTTGACTCCTAGGAAAATGTGA
TTTTAGTAGGCATCTCAAGAGGAAGTGAAACTTCTCGTGGTGAAATTACAAGAAAAACAA
GTTATTCAGTGGTGAGAATGTGTTGCTCTAAGCAATCCATTAGCACAGACTAGCTACTTG
GCCACTCCTCTTCCTTCTGGAGCCAGCCCTGAAGAGTGGTCACAGCATCTTCATTTTTAT
CCAGGCCAATGGCCATGCATGAGAAGTTGGGTAGCAAAATTCTTGAAGCACCTCTTTGTT
CTTGCTCTTCTTTCACTGTTTTCTCACTCTCCACCTGTAATGCTCACTGCCAGTTTTACC
ACCAAGCTAAGTATCAGCAGACCTCCCTCCACAGCGTGCCTTGCCCTGTAGAACTCCTGG
TCCTTCCTTCAGCCCAACCCCATCCAATTGCCTAGGTTCTTGTTGTCTCCTGAGATGAAC
AAGAGGCAAGTAGCTAATTTGAGAACAAATGAAGCAGAGCTGAAGGAAAAAGTAAAACAT
TTATTTTTTCATATCCCAAATTTTATAATTTTACATTTTTTTAAAACCCATTCATTTTCT
TCCCAGAACATTTATGCTTATCAGTGGTCTTCTGAATCTGTGACAACTCCCTTTTCAAGC
CCCAGCTAAGCTTCTTGCCTCAAGCCAGAAGGAATCCCAGTTTTGAGTCTTGTGTTAAGG
CCATGGCAGGTCAGTAGGGAGATTATCTGAGGAGGTACCGCTTGTGACACCTTCAGAAAC
AAAACAGCTATTGCCTTACGTTTCATAGGCCCAGGCCCTGAGCAATAGCAAAAAGATAAT
ACTTATTTTTTTAAACTGTTGTTTATTAGGTGATCGATTTCTAATTAATTTCAAAATATT
TAAGGTAATATTTTAATTACCGAGGAAGAATGGTACAAACAAAATGTTGTGGAACTGGAA
AATCCTCAGTGCTTGACAACATGAAACTTATTTAACTTATTATAGATGAGATAATGAGAA
CATCTTCAGAAAAGAAGCTATGTTCCTTAAAACAGGGGTACAGATTTAAAAGCTCTGTTT
ATATGGTTTTGGTAGACTAAGTGAAGAACTTGCCTATAAAGCTGAGTCTCGATCATATAG
CATATCCATTATAAAGTGAGAAAATTGCAATTTTAGAGTATTGTCAATACATCCAAAAAT
TTTTACATGATTTCTAAATGCAGATGTGTGTGTGTGTATGTCTACGTATGTCTCTCCATA
TGCAACAAGCAGTTAATTAGTCCAAATATATCCCACAGTGTAGATTAGTTTCATATCTCA
GCTCTTCAATGTCTCTTCTTCATTTAATTCACTCCTTGGTGTCTAGTTTTCCTCACTCTT
TTACAAATATCCAGGTTCTATATTTCTGCTTTTCTAGAGAGCTTTTTCCCTCAAGAATAT
ATTTTTCTTTTTCTTTCTTTCTCTTTATTTTTGTTTGTTTTTAACTAACATTCATATGGT
TATAACAATTTGAGACAAGTGAAAAGGAAAGATCTGTAAACTGCCTATCTCCTTTGAAAT
TCATTGCCAATAATCCTTAAGAATATAAAGTTCCTTGATGCCAAAGACCTTCTCATTAGT
GTTGCTGCCTGTTGTTTCATTGGTTCCCTAGAACAATGCCTGGCACATAAAAGTTATTTG
ATAAATATCTCTGCTATTAATGAATTAATAATAACTGCATGACAATTCTTTCCTCAATTC
ATCATTTTGCTTCATTTTCTCACAGTTGCTTCAATGTGTCTGTGGAACTATCTTTCCATG
TGAACAAAACACTCTACATTCTCAGTGTCTACAAAGCACATATTTCCTTTTATTAAAATT
AAACTTTGAGAGCACCAAATCCTAATGTCTAACCATCATCAAACTGGCAGATAGCACCAG
TATTCTTTTTGCTCACCAATTTTATGCCCAGGCATCTACTGTTTCTTTCATGAATAAAAC
CTGACACCTGTAAGAGGATTTATCATGGTAAACTTCTCTTTGTTACTGACATTTTCAGCC
TCTTGGGCTCTCCCCTCCTTACTTATACACATTGGCACCCAGCTTGAAGTCATACTCTCT
AGACCCTGGGTCAATGTGGGTAATGCATCCAGGAATCCAGCTTAACTCTTCCTTGGTCTC
TTTGATGTGACTGACCTTTATTTCTACATTTCTTCATCAAACCAGTCTCACAGTTTTGCA
CAGTGCAAATCACATGCTGCACCATGTGCTTATTATCTCCTATAACAACAGATGCTCCAC

FIG. 1AO

TGAAATGCAAAACTCTGTGTTAAGCCAACAACTGCTTCTCCATCCTTTCCTCCTATACGT
TTCTTCTCACTACAACTTCCCTTCTCAACCCCAAAGGGACTACTGGATTCTTTACTCTTT
TATTTTACCCCAGTCTATCAGTCCCATCCTGGACTTCCTTCCTTCTCTGCTTAGAGGAAA
GCAAGATGATCAGGTAGAATTGCACTTATGACTAGATATTATTTACTTCAAACAAATTCT
TACTATTTGTCCTGATGAAATTCATGACAGTTTTCATACAACAGAAAGCCTGCCCTCTT
AGAAGAGAAGAGAACTGAAAAGAAATGGTTGAAGTAAGGTAGAAAGCCCTCATGGAGTTA
GGTGGCTAGGCCAGCAGAGCTAGGCACTGTTCTCCTGTTCAGAATTGCACTCCTGATACT
CCAGATGGGAAGCCTGCCATGGCACTAACCACAGCACTTTTTATACCCTATCTCTGCTAT
TATGAGCCCACATTAGTTTTTCTTCTGCTTCAGAAATTGTTGCAAAAAATAATTTTATTA
TTTACAAATTATTTTTAAACCATATAAATCTGCTTAGTTTGATTTCTCAAACCCTCTAAA
ACTTACACTTCTTGTTGTCCAATCTTTGCTTTTAATTGGGTATAATTTGAGGCAGAAATA
AATTAATCTCATTTTTAAAAATGTACTAGCTATTAATAATTTTTAAATTTATCTTCTAAA
ATTGGAAAGTATCCACTTTAAATGCATCTGTAGCAAGGACTTTTTACATACATTCTGTAG
CTTTATTACTTCCATTGAGAACTGTTAAAATAACAGAACTTACCTCACTGTACGCTGGCT
TTTGAAAAGGCAGCAGAACTGTTTATCTGATTATCGAAGTAATCATATTACATTTCTTTT
TCTTTTCTAAGAGAAACCTTCTTCATGTGCTCAGTCAAACATTTTGGTGTTTAAGAATTG
ACTTATTAGGTCAGGCGCGGTTGCTCACGCCTGTAATCCCAACACTTTGGAAGGCCGAGG
CAGGTGGATCACTTAAGGTCAGGAGTTCGAGACCAGCCTGGTCAACATGGTGAAACCCCA
CCCCTACTAAAAATGCAAAAAAAAAAAAAATAGCAAGGTGTGGTGGTGCACATCTGTAATC
CCAGCTACTTGAGAGGCTGAGGTGGGAGAATCATTTGAACTCGGGAGGCGGAGGTTGCAG
TGAGCAGAGATCACACGACTGCACTCCAGCCTGGGCGACAAACAAGAATCTGTCTCAAAA
AAAACACAAAAAACAAAAAACAAACAAAAAAGAGTTGACTTAGTTAATGAAAATATTTTT
ATTAGGAAATTATACTTCTCTTTACAAAGTATGTATTATTTGTTGCATCTATATAGTCTA
TCAATTCTAAAAGCACACTTTATGCGAAAATGTAGTCTAGGCCTTCAGAATGTATTATTA
CAAGAAAGTATCTATCAACCATGTTTCATTTGTTTGCATGTTTTGTTTTGTTTCCAATAG
ACTATGAATATTCAGCTTCAAATGCTACCTCATGATTGTTACATTCCTGTTGTTGAAAGA
ACCCATCTCTTTCTTACCTTCTTGTCCCTAAATTGTGTTCTTCTTATAACTTACTTTGCA
CATAACCATAATGGAGTGAGATCATAGAATTAAGAGGATTGAGAAAGAAAAATACTTCCC
TCATTCCATTGGCAGTAATCTGTGATTCAAAAGTTAACAACATACCATGTATTCTTGTAG
GAGATTATTTCATGCTTATCACTGATCAACTTACATGCAGGTTAAAACCAGCCCTGAAAA
AATGCTCATCATCACTGGCCATCAGAGAAATACAAATCAAAACCACAATGAGATACCATC
TCACACCAGAAGAATGGCGATCATTAAAAAGTCAGGAAATAACACTTGCTGGAGAGGATG
TGGAGAAATATGAACACTTTTACACTGTTGCTGGGAGCGTAAACTAGTTCAACCATTGTG
GAAGACAGTGTGGCAATTACTCAAGGATCTAGACTAGAAATACCATTTGACCCAGCCATC
CCATTACAGGGTATATACCCAAAAGATTATAAATCATGCTACTATAAAGGCACATGCACA
CATATGTTTATTGCGGCACTATTCACAATAGCAAAGACTTGGAACCAACCCAAATATCCA
TCAATGATAGACTGGATTAAGAAAATGTGGCACATATACACCATGGAATACTATGCAGCC
ATCTGAGCAAACTATCGCAAGGACAGAAAACCAAACTCCGCATGTTCTCACTCATAGGTG
GGAATTGAACAATGAGAACACTTGGACACAGGGTGGGAAACATCACACACCGGGGCCTAT
CATGGGGTGGGGGTAGGAGGGAGGGATAGCATTAGGAGAAATACCTAATGTAAATGATGA
GTTAATGGGTGCAGTACTCCAACATGGCACATGTATACATATGTAACAAACCTGCACGTT
GTGCACGTGTACCCTAGAACTTAAAATATAATTTAAAAAAAAAAGCCCTAAATGCAACTT
GTTCAGATAACTGGAGCCATCTTCCTAGCTCTTTATTTCTCAGACAGTGTGGGTAAGTCC
TGCTCCGTACGAATGCTTATGTCAGTTTTGAAGTTCAGTACTTTCTTAAGAGCCAGAGTC
AGTCAAGATGTTCCCTTAACAAGATTTTTCAATGGGGTTACACATTAATGAGTTCTTTTT
CCTCCTTTAAGTATTTGAAAATTTTGGTTTAATAAAAGGTTTAACTATGATGAATTTAGG
ATCCTTTTTCCTGTTACAGAGCACAGAATAATAGTTAATATTTTACATACATATTGCAAG
TTCATGTTGCCACTAGGAGTGTCCAGAATAGACAATTGAAACAGCCTTCTAGCTACTACT
ATCAAAAAAGAGCTTTAAATAACATATTTTAATTAAATAACATTATTTTCTATAGCTATA
CCTCAATAAAACCATCAACCAATGTTTGTACAATTTGATGCCCCCACTCTAAGATTTTTA
GCTAGTGTAAATCAGAGTCTCCTATTTAATGAGACACTTTATCCAATCAGGTTGTGTTTA
TTATTCAACCAGATGATCTTGGAACTTATAACAAACTAGTAATACTTAAAGCTGGGCTTT
ATGTGCGTGATTTACTGGGATGTTTGCTTATACCTTGTTTCCAAGCTAAAAATATTGTGA
CCAGGTGTGTTAGTCTGTTTTGAGTTGCTATATAGGACTACCTAATGCTGGGTCATTTAT
AAAGAAAAGAGGTTTATTTGGATTATGGTTCTGCAGGCTGTACAAAGAGCATGACATCAG
CATCTGCTTCTGGTAATGCCCTCAGGAAGCTTTTACTCATGCCAGAAGGCAAGGGGAGCC
AGCGTGCCACATGGCAAGAGAGGGAGGAAGCACAAGAGAGAGGAGACGTACCAGGCACTT

FIG. 1AP

TTTAACAACCAGCTCTCACATGAACTAACAGAGTGATAACTCACTCAATACCCGGGGGAT
GGCACCAAGCCATTCATGAAGGATTTGCCCTCATGACCAAATACCTCCCACTAGGCCCAA
CCTCCAACACTGGGGGTCTCATTTCAACATGAGATTTGGAAGGGACGACTATCCAAACTA
TATCATCAGGATTTTCTGGCATGGACTACCAAGCCATTTCTGCTTCAAACTCCCCTGAAA
TTCTTGTTAAAAATGCAGATTCTTTGATACCACCCCCAATACACTATTTAGTCTGAGATG
AAACTCAAGGATTCTGATTTAATTGATCTAGACTAGCATTTGACCATTGATTTATCATCT
GGGATTCTAGGAAGTCAACCACTTATATGTTTTAGAGCAGACTTCATTATAATTGAGGAG
AATGTTTGTAGTCTGTGGGCTCCTCTGTCCACTTCTGATTGGGGCCCCTTTGCCTGATTC
TGACTGGATCAGGCAGAGTTTTATTCAAGCCACTGTCCTTTTTGGCTTCTTAATGTTCAA
AATATATTAACACAATCTCAGTTTTCTAAGAGCTAAATTATACGACTTGGTTCTTGTCTG
GTAACATAACTGCATTACTGGATCTTGTCAAGATTCAGAGACATTCTCCCAGTTTCAAAT
TTGTAACTAACACTGTTTGATCACAAAAAAGTTCTAAGCCAAAGCAAAACTCTTTCTACC
ACCACCAGATGGCGTTACTTTGGACTTACCTATAAATGGATTTCCAAATGGTTTTTCAGA
AACCAACTGGAGGTACTTAGAAAAACTTATGGAACTCACAACTATTCTTTGCATGTCAAA
AGCTATAACAGTAAATAATATTTGTGGAGAATATTCTGTAAGATTAGGCTGCCTTTCTTT
TCCTCCAGCTTATTTAAACTATATCCTTATATTAACCCTTGTTGGAGATGTGTCCTCTTA
TTGCACTGTATGTGAGTGTGTGTGTGTGTATCCCATCACGTTGGTATGATGATAGCACCC
TTCATTGAGAAGCTTTGCAAAAAGAATATAAGAACATGTTATTATGTTTACTTAAAAGTA
TAAGGCCGGGTGTGGTGGCTCACACCTGTAATCCCAGCACTTTGGGAGGCCAAGGTGGGA
GGATGACGAGGTCAGGAGTTAGAGACCAGCCTGACCAACACGGTAAAACCCTGTCTCTAA
TAAAAAATACAAAAATTAGCCAGGTATGATGGCACGCATCTGTAATCCTAGCTACTCAGG
AGGCTGAGGCGGGAGAGTCCCTTGAACCCAGGAGACGGAGTTTGCAGTGAGCCTAGGTGG
CGCCACTGCACTCAGGCCTGGGTGACAGAGTGAGACTCCATCTCAAAAAAAAGAAAAAAG
AAAAAAAAGTATTGAGGACATTGCTCATGACATTCCAAGGTTATATAAAAGAATATATAA
AAAGAAATTTCTGCCTGGACTTAGTGCCAGGAATACTTGTACTTTTCTTGCTTTCTTCTT
AAGAACATTGCACAATAGAGTATTTTTAAAAATTGTGCTTGCTGTTCAAATTGCCTGCTG
GAAGGATTAGAGGCAGATCTGTAGCATGCCGAGTCCCATCTTTGCATACAGGCTATCATG
ACAAACATTGTATGTGCTAATTCTATCTGGCTTCTCTTTATATTCCTATCTGTCTCTATT
TCCTGTCATTTTAATGTTTTAAAATTGTACTTTTTACTTAAATGGTTTTTGGAAGAAATA
AATATAAGTAAAGTCTGTTAGAGGCCCGGCGCGGTGGCTCACGCCTGTAATCCCAGCACT
TTGGGAGGCCAAGGCGGGTGGATCACAAGGTCAGGAGATTGAGACCACCCTGGCTAACAC
GGTGAAAACCCATCTCTACTAAAAATACAAAAAAAAAAAAAAAATTAGCCAGGCGAGGTGG
CGGGTGCCTGTAGTCCCAGCTACTCGAGAGGCTGAGGTGGGAGAATGGCATGAACCCAGG
AGGTGGAGCTCGCAGTGAGCCGAGATCTCACCACTGCACTCCAGCCTGGGCGACAGAGCG
AGACTCCGTCTCAAAAAATAAAAAAATAAAATAAAAAAATAAAGTCCGTTACAAAGCACAA
AAAAGAACGGCAAAGCCAACAAACATATGAAAAAAAGCTCATCATCACTGGTCATTAGAG
AAATGCAAATCAAAACCACAATGAGCCATCATCTCACGCCAGTTGGAATGGTGATCATTA
AAAAGTCAGAAAACAACAGATGCTGGAGAGGATGTGGAGAAATAGGAACGCTTTTTACAC
TGTTGGTGGAGGTGTCAATTAGTTCAACCATTGTGGAAAGCAGTGTGGCGATTCCTCAAG
GATCTAGAACCAGAAATACCATTTGACCCAGCAGTCCCATTACTGGGTACATACCCAAAG
GATTATAAATCATTCTACTATAAAGACACATGCACATGTATGTTTTTTGCAGCAGTACTC
ACAATAGCAAAGACTTGGAACCAATCCAAATGCCCATCAGTGATAGACTGGATAAAGAAA
ATGTGGCACATATAATATACAGCATAGAACACTATGCAGCCATAAACAAAGGATGAATTC
ATGTCCTTGGCAGGGACATGGATGAAGCTGGAAACCATCATTCTCAGTAAACTAACACAG
GAACAGAAAACCAAACACCACATGTTCTCACTCATAAGTGGCAGTTGAACAATGAGAACA
CATGGACACAGGGAGGGGAACATTACACATCGGGGCCTATTGGGGAATGGGGGCTAGGGG
AGGGATAGCATTAGGAGAAATACTTAATGTAGATGACGGGTTGATGGGTGCAGCAAACCA
CCATGGCATGTGTATACCTATGTAACAAACCTGCATGTTCTGCTCATGTATCCCAGAACT
TAAAGTATAATAATAAAAAAAAAGAAAGCACAAAAATAAAAGTACTTGGAAAAGTTTAAA
GGGTTAAATATTATGCAAAACTGAAAACTAGCTTCAGATACATTTAAGTTTATATCATGT
TAACAAGTTATTTCTTTCTAAAAAATTCTAACCTGTAACACAGAGAGTGGACTTGAACTT
GAAAATATGGTTAAGGTACAAATGCAGATTTGGGGTCCCAGTCTCCCAGACTGTGGCTTC
TATGGAAGAGATTGTACTGGCTCCAAATTCCACAGATGATTGAACAACTTGTTTCTGCCT
GTGTCAGAGCTGAAGAGTGAATATCTCCACTATATATATCTCAAAATCTCCCAAATGAAA
TTTGGTAACCCTCTATGCCATAACACATCACATTAATAATTTGTATTCAAAAGTCTCTCA
GAAAAGATTTTTGAAATGCCAGATACTTTAATTTTTTTATGTTTATATATTTAGGGTGTA
TGAGTACAGATTTCTTACATGCCTATATTGCATAGTGGTGGAGTCTGGGCTTTTACTGTA

FIG. 1AQ

GTCATCATCTGAACAGTGAACTTGTACCAAATAAGTAATTTTTCAACTCTCATCCACCCA
CCCTCCCATCTTTTGTAGTACCCAAGGTCTATTATCCCACTCTGTATGCCTGTGTACCTA
TTGTTTAGCTTCCACTTATAAGTGAACACATGCAGCATTTGACTTTCTGTTTCTGAGTTA
TTTTACTTAGGATAATGGCCTCCAGTTCCATCTACATGGCTGCAAAAGTTATGATTTTAT
TCTTTTTTATGGCTCCATTATATGTATGTGTGTGTATCTCAATTTTCTTTATCAAACCCT
CTGTTGATGGACACTTAGATTAGTCCACATTTTTGCTATTGTGATAAACATGTAAGTGCA
GGTATCTTTGTAATATAATGATTTCTTTCCCTTTGGATATATACCAGGTAGTGGGATTTC
TGGATCTAATGGTAGTTCTATTTTTAGTTCTTTGAGAAATCTCCATACTGTCTTCCATAA
AGGTTGTACTAGTTTACATTTCCACCAAAAGTGTATAAGCATTCCCTTTTCTCTGCATCC
TCACAAACATCCTTTGCTTATTGACTTTTTAATAACAGCCATTCTGACTAGTGTGAAATA
ATATTTTATTGTGATTTTAATTTTCTCTGATGATTAGTGATGTTGAGCATTGTCTCAACA
TCACTATGCTAGTGGCATGCATGTTTTCTTTTGAAAAAAAGTTTGTGTTCTTTGCCCACA
TTTTAATGGGGTTATTTGTTTTTTTTTTTCTTTGAGTTGTTTGAGTTCCTTGTAGATTCT
GAAAATTATTCCTTTGTCAGCTGCATAGTTTACAATTTTTTTCCCATTCTGTAGTTTGTC
TGTTCACTCTGTTGATTGTTTATTTTTCTGTCCAGAAACTTTAGTTTAAGTCCCATTTGT
CTATTTTTGTTTTTGTTGCATTTGCCTTTGAGGACTAGGTCATAATTTTTTGCCTGGGCA
AATGTCCTGAAGATTTTTTTCCAGGCTTTCTTATAGTATTTTTATAGTTTCGGGTCTTAT
GTTTAGGTCTTTAATCTATCTTGAGTTAATTTTTGTAGCTGGTCAGAGGTAGGTGTCCAG
TTTCAATCTTCTACATATGGCTATCCAGTTTTCCCAGCACCATTTATTGAATAGGGAGTC
ATTTACCCAGTAAATATTTTAGTTGACTTTGTTAAAAATCAGTTGGTTATAGGTGTGTGG
TTTTATTTCTAGGTTCTCTATGCTGTTCTATTCATCAATGTGTACATTTTTATACTAGTA
CCATGTTGTTTTGGTTACTATAGCTTTGTAGCATAATTTGAAGTCATAATATGATGCCAA
CAACTCTGTTCTTTTTGTTTGAAATTGCTTTGGCTTTTTTTCCTTGTGAGAGTTTGCTGA
GAATGATGGTTTCCAGCTTTGTCCATGTCGCTACAAAGGACATAATCTCACCCTTTTTTA
TGGCTGCGTAGTATTCCATGGTGTATATGTGCCACATTTTCTTAATCCAGTCTATCATTG
ATGGGGGGAGGGGGAAGGGATAGCATTAGGAGATATACCTAATGTAAATGACGAGTTAAT
GGGTGCAGCACACCAACATGGCACATGTATACATATGTAGCAAACCTGCACATTGTGCAC
ATGTACCCTAGAACTTAAAGTATAATAAAAATAAATAAATAAAATAAAATAAAATTGCTT
TGGCTTTCTGGACTCTTTTTTTTGGTTTTATATGAATTTTAGGATTTTTTTCTAATTCTA
TGAAAAATGGCATTGGTAATTTGATAGGGATTGTGTCGAATCAGTAGACTGCTTTAGACA
GCATGGTCATTTTAATAATATTGAATCTCTAATCCATGAGCCAGGGATATTTTTCCATTT
GTTTTTGTCATCTAGGGTTTTCTTCCATCAGTGTTTTGTAGTTCTCCTTATAGATATCTT
TTACCTCTTTGGTGAAATGTATTCCCAGGCATTTTACTTTATCTTATCTTTTTGTAGCTA
TTATAAATGGAATTGCTTTCTTAGTTTGGTCCTTGGAAATGCCAACTACATTTAAAATCC
TTTTCCATTTGATGGATTTCAGGTCTTGATGAACATCTCAGTTGTAATTTTCTTAAGATT
GAAAAAGTAAATATTTTTTCTATATGTATATATAAAATTGTCCTCTCTCAAAATTTTAAT
TCAATAACCTGCTAGATATCACTTTAGAATCTTGCAGTACTAGTTTTCTTCTCAATTAAT
TGTAGATCTTAGCCTTTTAATTTGGGCATGTTTTTCCCTATTAGGACTTAAGTTATTAGG
ACCTAAGTTTGTAGACAAGAACTATGTTATATTTGAGAAATTTGTGAGTCATGTACTGGG
CCTAGCACAGTGCCTCATAAGATGTAGACCCTCAATAAACTTGTTGAATAGGTTAATAAA
TAAAAAAGCCCCTATCACTCAATTTTTTTTTTTTTTTTTTAGATGGAGTCTCACTCAGT
CACCCAGCCTGGAGTGCAGTGGCACGATATCGGCTCACTGCAAGCTCTGCCTCCTGGGTT
CACACCACTCTCCTGCCTCAGCCTCCTGAGTAGCTGGGACTACAGACACCCGCCACCATG
CCCGACTAATTTTTTGTATTTTTAGTAGAGACGGGGTTTCACCTGTGTTAGCCAGGATGG
TCTCGATCTCCTCACCTCATGATCTGACCCCCTCGGCCTCCCAAAGTGCTGGGATTACAG
GCATGAGCCACCACACCTGGCCTATTTCAGTCAATTGTTAAAAGTGCTAAGAACAAGTGG
AGATCTTGTTAATGAAGAAAAAAAAAAATAGTATTTACTACTTACCTAAACACTCTACTAA
GAAGGGATATACAGATCAAAAGGATTAAATCTCTGCCTGCATTAAGCTAACTGTTTTGTA
AAGAAGAACGTAAACAAAGTCAAAAATGCATTTTTTAGGTGCTAGAGATTAGACAGGACA
AAATCTTCTGGCTCTGCCTAGAGTTAAGTGGCTTTGGGAGAGGCTTTGCTGTAGTTTAAA
GGCAGAGGTGGGGAAGGCCACTCTGGCCACAAGGACAGATCCACAATGGGATGGGGTATG
AAACAGCACGAACCCTTCAGGAAATTACACATAATTTAAAAGGAAAATGGGAGCCCATGG
CAGAAAATAGAATTGAACAGCAGGAAAAGGGTAGATAGTAAAAAGCATTTTATAATATTC
AAGGACATTTGAAACTTGTGGTATACAATGAGGAAGAATTTAAAAATTCTATACAGAGGA
GTGACATAGTTAGATTTGTGTTCTGGGGAGCATAATAATAGCATTACAGCGGGTGAATTT
GAAAGCTGGGCCTCAAAAGTTTAGATCTCAAATAGGTTTTTATGGGAGTATTCATCCTCA
TGAAACATGATTTGGAACTAAACCAAGGCAGTGGCAATGGGGCTGGAAAATAAACACTAG

FIG. 1AR

ATTTCATATCTAGATGAAGATTTGTGGAATAAGAGAGGCCACATTAATGTTTAATTCTAT
TTACAATGGATCCCAGCCACCATCCGCTTTAACACAGAGGTGCTTTTCCAGTAGCTAAGA
GGACTAGGTGCTTTAGATACATTTGTGAAGTTGTCCTCCCATTGTTAACATGCTTTTTTT
ATTGTCTGTGTGTAGGTTGATGGGGGAGGCAGAGTTAGGATCACACATAGAAGTTCAGTC
TTTGAAATGCTTTCTTTCTCTTTTTCCCCAAACAATGACCCCCACCTTTTCCTTCTGGCA
TATGTTGCCTCAAGACCCTAACACTGCTGCCAATCTGCTGGTCTTAGAGCCAAGAATCTG
CCACCACCTGGCCCACCACAGCCTGCTCTGCTAGCTGCTCTCCTGCCAATACTGGCCTTC
ATGTACAAGTGTAGGTTTTGAGGGTTCCGTTCTCTCCCCCTTTCTCTCTTTGAGTGTGGG
TTTGTGAGTGTGTGTGTCTTCTGTAATAAGAAGAAAACAGGCCACATTTTCTCTACTCGT
GTTATACACTTCCCGGAGTGTCTCACATCAAAACCTGTCCTAAGTCCAAGCCTTAGAAGC
TCTTTGCTGGCCCAGCCTACACTTGGGTTGTTACTTCTCAGGAGCTACCTTTCTGTCAGT
TGAGATTTTAACAACCCACCACAGTACTCCAAGCGTGCAGTCCCTCACATCTTGAAATCT
GTGCTTTGGCAGCAGCAGAATCAGGGGTCTGTGGATTCTGAACCCAGAATGTGTCAAACC
AAAGGGTGACATATTGGGACATTTAATAAGTCAGAGACTATTTCCCAGGAATATTTTTTT
GAAGCATTTAAACTAAAATACAATTGAACTGAGATCTCAAAACAGGAAAAATGAACTTGA
CAAGAATTAGGCTAAGCTGCATCTCATGACGTAAATATTCACATTTGCATATACATTAAC
AGAGTCAAGTCAAAAATTGATTTTTTATTGGATAGGATTAACTTTAGCTACAGAAAACAG
AAAGTTTAAATGACTGGCTTTAAAAAGCAAAAGTTTACTTGCTTTCATTTATATGCAATC
TGGGGGGTTGCGGGGGAAGATTTGTTTGTGGGTTTCCCATTCTCAAGGTGCCAGGCTCCT
GTGTTTCTGCCCCATATCCTTAGAGGGAGGGTTTCCTCCTCAGGATTGCCTTATGTGCAA
GGTGACTACTGAAGCTCCATTTTTTATGCCCAAATTGTAGCAAGAAAGAGAAAAGGAAGA
AGGAACAGAAAGGCACATGACATCACTTCAAATAAAATTAGGGGGAAAATAATAACAGAT
ATCTGATAGGAAACTAACAGTACCTTCTGCAATAATGATTACATTTCTGGAAAATAAATG
TTAAGATCCTTGAAAACAAGGAGTAATAGTTGAGGAAAAGCTTCTTAGCAGCCTGGGACT
AAAAACTTCAAAAAATTTAAGATAAAAATCTGAAAACTGGTAGAGAATTGGGGAGAAAAA
GAGAATTTGAACAAGGCATGCAAGAGTAAGAAAAATGTCATCACAAAATTACTAAGAAAG
CATAAAAGCAACTATATTTTATTAGAGTAAAAATAAATGGATTGAATAACCCTAGTAAAA
TAAATTCCAGCCATACATTGTTTATAAAAAGTGTATTTAAGGTGATTAGGAAAAAATAAA
ACTAAATTTAAGTGCAAAGATCTCCCAGGGAAGTCAAAGCAAAAATAAAGTCAGATGTTG
CTGTCATTAGACAAAGTAAAATTTAAGGTGAAAACATGACAAAGAGGGACATTAAATAAG
GATAAATGTACAATCAATGGTGACAAACTTTTATAAACTTGAAATTATATTAACAAAACA
TAAATCATGTAAAACTAAAATACCTTGATAAAATGCAAATTATCAGGTAACAAGAATATA
TCTATTGCAGAAAGTAATATATCAAACTAAAATAATGTGTATCTATTACAAGTATACAAT
ACTTTGTAGCCTACAAAATAAGAATATACGATTTCTTCTTAAAATGTTATACATTTACAA
TAATTAATAATTTGGCCACTCAGAAAACCTTGGTAAAGCAAGGAAAGTAGAGATATTATA
AGCCAACTTAATAATTTAGTAACATTGGGTAAAAATGGAAGAAGTATCATATTGTGGTTG
TGAACATAAGCTCTAGTTCTCCTAGTTTTGTGATTTGGGAAAGTTAATTATCTTCTCTCT
ACCTCGTCTTAATTTTCAGTAATATTAGGATAACAATAGTTTGTACATCATCAGTGTTTT
TTTTTTTTGAGGAATAAATGACTCACATGTATTAAACACTTAGATCCATTGTTAACATAT
AATATGTATAAATAATGTCAGTATAAATCAATGTCAGCCTAAAAAGTTAAGACTGTGATT
TTAAATAATACTAGATTTAGAATAAAATCAAAATTGAAATGACATTATTAACTTAAAAAT
AACAAAAAAAGAGAAGACTTTAAACACAATGGATGGAAAGCAGCTATACCAATAAAAGAC
AAAAATGTGGAGTATTATATGTTCTTAATGTTTTTAAAATTATAAAAATAAATAAACTA
AAACATAGAATTTTAAAAATTAAATGTTGGAGGGATTAGGTCAGATAAGAGAAATTTCTG
TTAGCAGCAGCTGAATTTTCTGCTAATAACAGAGAATTGTGAAAAGATGATTTCATAAAT
ATGGCAAATGTTTGTAATAGCCATCCTAGGAGCACGGATATTAGTAACTAATTGAGGAAG
TACTGTTGGGCAGTGTCAATATACTGGTTAAGAATAGAATTTAAAATAATGCTAATTATA
AGGCCAAAAAACTCAGTAATGCAATTTTTTTAGTATAATTCAGTAGGGGAGAAGGAGAGA
TAATTAAACTTGGAAATTGACATACAGTTGTCCCTTGGCATCCATGAGGAATTAGTTCCA
GGACTCCCTATGGATACCTAAATTCACAAATGCTCAGGTCCCTTATATAAAATGGCAAAA
TATTTGCATATAACTTACACACACCCTCTTTATAATTTAAGTCATTTCTAAAGTACTTAT
AATACCGAATGCATTATAAATGACTGTGGAAATAGTTGTTGTATTATTTAGGGAATAATG
ACAATAAAAAATATATGTATATGTTCAGTAACAGATGCCTTTTTTAAAAAAAAAATTGTTT
TTGATCCACAGTTGGCTGAATCTATGGATACAGAGCCCACATTTACTGAGGGCAGACTAT
ATTTAGAGTACTTAAGGATCACAAGGGACACACATCTGAGGGTACTGAAGAGTGGGAAGA
AATTACTAACCAGAGGGTCAGACTAGAAGGCAAGGAAGTGAAGCCAGGAGATGATTAGAA
AATAAGAAAATCATACAAGCCTGGAGATTATGTTGAAGTGTAAGAACATAATTAGAGTGA

FIG. 1AS

GAAACATGAGTCAAGGAAGAAGGAGATTGGTGCTTGAGAGATGTGGCAGACTGTATCTTT
CAAAGATGGCTACACCAATATATATCTCATTCCACAAGCTGTTTTTACCATGCTGTATTG
ACGCTCTTCCATATGGAGGTGGGGCCTATGTCCCCTCCCTTGAAACCAAATGAAACTTTG
TAATTGCCTTGATCAACAGATTGCAGTAGGAGTGATGCTGGATGATTTCAAAGGCTAATA
CACACAAGAAAATAATGGCTTTCATTTGACTCTTTCTTGGAACATGTGCCTTGGAAACCA
TGAGCTTATTTGCAAGAAGCTCAGCTATCCTAAAGTTTATCTACTGGGTAGACCAAGTGG
AGAAATTACACAGACATTGAGATTATGTTCAAGGGGTCTCAGAGGTTCAAGGCCTCCCAA
TTCAGGCACCAAACAAGTGGAGAAAAGGCTTTCAAGATCATCCCTCTGAAATAATTGTCT
GATTGAAACCTCAAAAGAGTCCCTGAGCCAGAACCATCCAGCCAAGCCACTCTCAAATTC
CAAATCCACAGACACCATGAATGACAGTAAATCATTATTGTTGTTTTAAAGCACATAAGT
TTTGGGGGGTTATTTACACACAGCAACAGAAAAAAAAACTGATGAATGGGAAACATGGAG
AGAAATGCAAATAGAATAAAATGGGAAGGAATACAAGGAGAGGAAAGTAGTATTGTGCAA
AATAGGCAATCGGATGACCCTCAAAAGGAAATTTTTTTTCTGAGCAACTTAATGAATATA
AGGTCAGATTAAATTGGAAGGTAACAGGTACAAATATCATTAATGCTAAATTCTATTTGT
AGTAAGTCAACTATTTGTAAATTATGCATTGGAGACCGACTTTACATCAATCAAAAGTTA
AATTTATTTAGAAATCTATAGAAGAAGAAAAAGAATAAAAGCCATTGGAAAAGTTTTTAC
AATTATTCCATTAAATAGACAAAGTCCTTTAAGGAAAGGGATTAAAATGAAGGTAAGGTG
ATCTGCTTAAAAATAATATAGCAATCTGGGAGCCATGGCTCATGCCTGCAATCCCAGTGC
TTTGGGAAATCTAGGCAGGAGGACCTCCCAAAGGAGGACTTGGAGTTTGAGACCAGCCTA
GGCAACACAGAGAGACTCCATCTCAAAATTTTAAATTTCTTAAAAGAAAAAAAATAAAAT
GAAATAATATTGTATTAATTCCAGTAAAAGCATCAGACCAATTTAGAATATGGATGAGAG
AGAAAAACTAGAAATAACACCACAACAAGGAAGGAGAAAGCTGGTCTCTGGCAGGGACTT
CTAATTTAGAGAAAGACAGATGATAGCAAACAGCAAAAGTTGTATTATAGATGTAACTTA
AAAACTAATTTGATTTTTATTTTTAGTCAGAAAACTGCTTTAGGTATGGAACAAGTATAA
CCTGGTATTTCCAGTATCTCTCTGTTGACCTCACATCTCTCTCCAGATACTGCCTCAATT
CTCTGCTTCTCTTTATAGCAAATTCCCTTGAAAGAGAGACTACCTGGATCAGAAATTCCT
CTGCTTCAATTTGATCCTGAATCCACTTCATCTAGATCTTCCTCACCAATTCCCCCAAAT
ATTTGTCTTATTATGGTCACATGGGACCTCTACTTTGCTATATCAGTAATTTTGTTCTCA
TTTTACTTTTTTGTAGTTAATTACTCCCTTCTCCTTGAAACACTTTCCTTGTTTGGCTTC
TAGGATGCCCTGTTCTCATGGATTTCCTTTCACTTCTCCAGTCATTTCTGTTTGTTTTTT
CAATATCTTCGTGATCTTATATTTTTAATGCGTCCTGCTAGCTTCCCAACTAGGTTTCCT
ACTTTCACCTTAATTCCCTATGGTTTATTCTCTACAAGAAAGGAATTATAATCCCTTAAA
AATGTCAATAAAACTCTATCACTACTCAATACTCTCCAAGGGGTCCTTATTTTATTCAAG
TAAAAAACTAAAGTCCTTACTATATGTCTGTAAATTCCCATAGGATCTGGCCCCACAGCC
CCTCTGGCCCCTGTCCATTCTGCCCCTTGCCAATTCTGCCCGGCCACAGTTGCCCAATAG
CTGGTCTGTGAACACATCAAGCACATACTTAATCTCAAGGCTTTTGCAATCATTCTTTTC
TCTAGTTGTAATCTCTCATTACTTATTCTGAGTGTCTTGTTTCTGCAGTTGCTTTACTTA
CTTGACCTATATAAAATAGTAATTCTTACCCCTACAACTCCATTATGTCCTATCTTCTTT
GCCTTGCCTTATGTTTTTTTCTTGGAGTTACAGATACCTGATGTAGATAGTATTTACTTT
TTTTATGCTTGCATTAATCACCTAGAATATAAACTCCAAAAGAGGAGCTATTTCTCTTTT
ATAATCTATCTAATATATCTTGGATATTTGCTCCCACCTAAATTTCATGTTGAAATGTAA
TTCCCTGTGTTGGAGATGGGGTCTGGTGGGAGGTATGTGGATCATGGGGCGGATCCCTCA
TGAAGGGCTTGGGCCATCCTTTTGGAGAGAAGTGGGCTCTGGCTCTGACTTCACACGAGA
TCTGGTTGTTTAAAAGTGTGCGACAGCTCCCCTGAGCTTCCTCTCTCACTTGCTCCTGCT
TTTGCCATGTGAAGTACCAGCTACTGCTTCATTTTCCACCATGAGTAAAAGATCCCTGAG
GCCCTCCCTCAGCAGTACATGTCCCTATGCTTGTTGTGCAGCTGGCAGAACCATGAGCCA
ATTAAATCTCTTTTCTTTTAAATTACTCAGTCTCATGTATTTCTTTATAGCAATACAAGG
TTGGCTTAATACATATCTCTAAAGCAAAAGCTGGGCCTGGTATGTAATAGGTGTTCAATA
AATATTTATTGAATAAATGAATAAATACTAGGCTAAATAAAGTTTAAAACATCATAATAG
AACACTGGGTAGATGTCAAGATGACAGTTTTGTTATTCACATATGGACATGGAAAGGTCT
TTGTGGTGCATTGTTAAGGGAGCAAACCAAATTACAGAACACTATATAGAGTAGAGCTGT
ATAAAATACATATGGTGTATGTTTATAAATATGTCTAGAAAAATTTGAAAGCTATATATC
AAATATCATATCATTTATCTTTAGAAGGCTAATTGCATATTTTCAATTTATTGTTTATAA
TTTTTTTTATCTATTATTATAGGTTACTTGTATAATCACAAAAGACAACTGAATAATTCT
TTTTGTCTTCATCAACTTTTATTTTAAGTTCTGGGATACATGTACAGGATGTGCAGGTTT
GTTACATAGGTAAACGAGTGGCATGGTGGTTTGCTGCACAGATCGACCCATCACCGAGGT
ATTAAGCTCAGCATCCATTAGTTATTCCTCCTGATGCTCTCCTTCCCCTTGGCCCACCAA

FIG. 1AT

TACACCCTAGTGTATGTTGTTACCCCTCATGTGACCATGTGTTCTCATCATTCAGCTCCC
CCATATAAGTAAGAATATGCAGTGTTAGGTTTTCTGTTCCTGTGTTAGTTTGCTGAGGAT
AACAGGTTCTAGATCCATCCATGTCCCTGCAAAGGACATGCTCTTGTTCCTTTTTATGGG
TGCATAGTATTCCTTGGTGTATATGTACCACATGTACAACTAATTTCCACAACAAAAAAT
GTACTATTACATGGATATAATGTTTATATTCTCTTCACAGAATTTGAGTCACTTGAATTT
TTGCTTTAACACTTAGAATTTGGAGGGTCTGTTTTCTTAAAAAAAATTAACACTTTAAAT
CCAATAAGTAAATGTGGAAGGTTGGTGGAAATAGTTAGCTGGAAACTCAGAATTGATATT
AACTTTCACCAAGCCTTTGTTCACATTATTTTCTTCTACAATTTATGAATGAATAATCCT
GCACTATCTATGCATTCAAACAATGATACATATGGTGCATATGTATATATGGCAAAAATC
TAAGAAATGTAGCCAAATATTAATATTGCTTACACGTAAGTAGTCAAATCATGGTGGTTT
TTTTTTATTTTCTTGATTTTGCAAGAAAATTAATAAAGAGGCTATTTACATTTTAATGTA
CAAATGTGTATACAAATATAATAGTTATGCTTTAAAAATCCAATAAATAAATGTAAGTAA
AACATTTCTGAATTTTTTAAAGATTTCTCAATAGATCTAGGTATTCTTCTTAACCAAATA
CTGATACTACCGTTAACCACTTCTGGAAAATTCTGGCAATTGGTCCCTTTGGGGAAGAAC
TAGAGGAATCACTACTATACACACTTACTGTGGTATTCAGTGCCCTTCCTCAAGGGGAAT
TCGCCTATCTTTTTTTTCTTAAGTAATATTTTATCTTTAATAGACAAATAATGGTTGTAT
TTATTTACGGGATACAAAGTGACATTTTGATGCAAGCATACCTTGTGGAATGATCAAATC
AGGCTAATTAACATATCTGTCATCTCAAATGCTTATCCTTTCTTCATTGTGGGAGCACTT
AAAATCAATTCTTTTAGCTATTTGGAAATATAAAATATATTATTTTCTAACTATATTTAC
TTACGATGTAGTGTAATAGATCACAAGAACCTATTTCTTCTATCTAACTGAAACTTTGTA
CTCTTTGACCAACATCTCCCCTTTCTTTGTCCATCCTCCTAGCCCAGCCTTTGGTAGCCA
TCACTGTACTCTGTATTTCTATCACTTTGCCTTTTTAAATTGCACATATAAGAGAGATCA
TGCAGTATTTGTTGCTTTGTGTCTGACTTATTTCCTGTAGCAGAATGTCCTTTAGGTTAA
TCCATGTTGTCATAAATGACAAAATTTCCTGCCTTTCAAAGGCTGAATAGTATTCCATTG
TTTATATATACCACATTGTCAAAATCCATTCATCTGTTGATGGGCATGTAAGTTGTTTTC
AAATATTGGCTTTATTAATAATGCGGCAGTGAACGTGGGAGTTCAGACATCTTGTTGACA
TACTGATATTAATTCCTTTGACTATATACTCAAAAGTGGAATTGCTGGACTGTGTGGTAA
TTTTAGATTTTTAGTAACATTCATACTGTTTTCCAAAATAACTGTATGAATTAACAATAC
CATCAACAATGTACAAGGGTTCCCTCTGCTCCACATCCTCATCAACACTTGCTAGTTTTC
ATGTTTTCGATAATAGCCAGTCTATCAGGTGTAAGATAATATTTCATTGTGATTTAATTA
GCATTTCTTTGATAATCAGAGATTTTGAGCCTTTTTTAATATATCTGTTGACCACTTTTA
TGTTTTCCTTTGAGAAATGTGTATTTAAGTCGTCTGCCCATTTTTAATAGGATCATTTGT
TTTCTTATTATTGAGGGGTTTGAGTTCCATGCATATTTTAGATACTAGCCTTTTATCCAA
TGCGTAATTTGCAAATATTTTCTCCCAATCTGTGGGTTGTCTCTTTAACCTGCTAACTGT
TTCCTTTCCTTCCTGCAGAAGCTTTTTAGTTTGATGCAATTCCATTTGTCTATTTTTGCT
TCCATTGCCTGTGCTTTTGGGGTTAAGAAATCTCTGCTCGATTACATTTATTGATTTGCG
TATATTGAACCAGCCTTGCGTCCCACGGATGAAGCCCACTTGATCATGGTGGATAAGCTT
TTTGATGTGCTGCTGGATTCGGTTTGCCAGTATTTTATTGAGGATTTTTGCATCAATGTT
CATCAAGGATATTGGTCTAAAATTCTCTCTTTTGGTTGTGTCTCTGCCAGGCTTTGGTAT
CAGGATGATGCTGGCCTCATAAAATGAGTTAGGGAGGATTCCCTCTTTTTCTATTGATTG
GAATAGTTTCAGAAGGAATGGTACCATTCCTCCTTGTACCTCTGGTAGAATTCGGCTGTG
AATCCATCTGGTCCTGGACTCTTTTTGGTTGGTAAACTATTGATTATTGCCACAATTTCA
GAGCCTGTTATTGGTCTATTCAGAGATTCAACTTCTTCCTGGTTTAGTCTTGGGAGGGTG
TATGTGTCAAGGAATTTATCCATTTCTTCTAGATTTTCTAGTTTATTTGCGTAGAGGTGT
TTGTAGTATTCTCTGATGGTAGTTTGTATTTCTGTGGGATTGGTGGTGATATCCCCTTTA
TCATTTTTTATTGTGTCTATTTGATTCTTCTCTCTTTTTCTCTTTATTAGTCTTGCTAGC
GGTCTATCAATTTTGTTGATCCTTTCAAAAAACCAGCTCCTGAATTCATCCATTTTTTGA
AGGGTTTTTTGTGTCTCTATTTCCTTCAGTTCTGCTCTGATTTTAGTTATTTCTTGCCTT
CTGCTAGCTTTTGAATGTGTTTGCTCTTGCTTTTCTAGTTCTTTTAATTGTGATGTTAGG
GTGTCAGTTTTGGATCTTTCCTGCTTTCTCTTGTGGGCATTTAGTGCTATAAATTTCCCT
CTACACACTGCTTTGAATGTGTCCCAGAGATTCTGGTATGTTGTGTCTTTTTTCTCGTTG
GTTTCAAAGAACATCTTTATTTCTGCCTTCATTTTGTTATGTACCCAGTAGTCATTCAGG
AGCAGGTTGTTCAGTTTCCATGTAGTTGAGCAGTTTTGAGTGAGTTTCTTAATCCTGAGT
TCTAGTTTGATTGCACCGTGGTCTGAGAGACAGTTTGTTATAATATCTGATCTTATACAT
TTGCTGAGGAGAGCTTTACTTCCAACTATGTGGTCAATTTTGGAATAGGTGTGGTGTGGT
GCTGAGAAGAATGTATATTCTGTTGATTTCGGGTGGAGAGTTCTGTAGATGTCTATTAGG
TCTGCTTGGTGCAGAGCTGAGTTCAATTCCTGGATATCCTTGTTAACTTTCTGTCTCGTT

FIG. 1AU

GATCTGTCTTATGTTGACAGTGGGGTGTTAAAGTCTCCCATTATTATTGTGTGGTAGTCT
AAGTCTCTTTGTAGGTCACTCAGGACTTGCTTTATGAATCTGGGTGCTCCTATATTGGGT
GCATATATATTTAGGATAGTTAGCTCTTCTTGTTCAATTGATCCCTTTACCATTATGTAA
TGGCCTTCTTTGTCTCTTTTGATCTTTGTTGGTTTAAAGTCTGTTTTATCAGAGACTAGG
ATTGCAACCCCTGCCTTTTTTTGTTTTCCATTTGCTTGGTAGATCTTCCTCCATCCTTTT
ACTTTGAGCCTATGTGTGTCTCTGCACGTGAGATGGGTCTCCTGAATACAGCACACTGAT
GGGTCTTGACTCTTTATCCAATTTGCCAGTCTGTGTCTTTTAATTGGAGCATTTAGTCCC
TTTACATTTAAAGTTAATATTGTTATGTGTGAATTTGATCCTGTCATTGTAATGTTAGCT
GGTTATTTTGTTTGTTAGTTGATGCAGTGTCTTCCTAGCCTCTATGGTCTTTACAATTTG
GCATGATTTTGCAGTGGCTGGTACTGGTTGTTCCTTTCCATGTTTAGTGCTTCCTTCAGG
AGCTCTTTTAGGGCAGGCCTAGTGGTGACAAAATTTCTCAGCATTTGCTTGTCTGTAAAG
GATTTTATTTCTCCTTCACTTATGAAGCTTAGTTTGGCTGGATATGAAATTCTGGGTTGA
AAATTCTTTTCTTTAAGAATGTTGAATATTGGCCCCCACTCTCTTCTGACTTGTAGAGTT
TCTGCCGAGAGATCCGCTGTTAGTCTGATGGGCTTCCCTTTGTGGGTAACCCGACCTTTC
TCTCTGGCTGCCCTTAACATTTTTTCCTTCATTTCAACTTTGGTGAATCTGACAGTTATG
TGTCTTGGAGTTGCTCTTCTCGAGGAGTATCTTTGTGGCATTCTCTGTATTTCCTGAATC
TGAATGTTGGCCTTCCTTGCTAGATTGGGGAAGTTCTCCTGGATAATATCCTGGAGAGTG
TTTTCCAACTTGCTTCCATTCTCCCCGTCACTTTCAGATACACCAATCAGACGTAGATTT
GGTCTTTTCACATAGTCCCATATTTCTTGGAGGCTTTGTCCGTTTCTTTTTATTCTTTTT
TCTCTAAACTTCCCTTCTCACTTCATTTCATTCATTTCATCTTCCGTTACTGATATCCTT
TCTTCCAGTTGATCGCATCGGCTCATGAGGCTTCTGCATTCTTCACGTAGTTCTCGAGCC
TTGGCTTTCAGCTCCATCAGCTCCTTTAAGCACTTCTCTGTATTGGTTATTCTAGTTTTA
CATTTGTCTAAATTTTTTTCAAAGTTTTCAACTTCTTTGCCTTTGGTTTGAATTTCCTCC
TGTAGCTCGGAGTAGTTTTATCGTCTGAAGCCTTCTTCTCTCAACTTGTCAAAGTCATTC
TCCATTCAGCTTTGTTCCATTGCTGGTGAGGAGCTGCGTTCCTTTGGAGGAGGAGAGGTG
CTCTGCTTTTTAGAGTTTCCAGTTTTTCTGCTCTGTTTTTTCCCCATCTTTGTGGTTTTA
TCTACTTTTGGTCTTTGATGATGGTGATGTACAGATGGGGTTTTGGTGTGGATGTCCTTC
CTGTTTGTTAGTTTTCCTTCTAATAGACAGGACCCTCAGCTGCAGGTCTGTTGGAGTTTG
CTAGAGGTCCACTCCAGACCCTGTTTGCCTGGGTACCAGCAGCGGTGGCTGCAGAAGAGC
GGATTTTCGTGAACCGCGAATGCTGCTGTCTGATCGTTCCTCTGGAAGTTTTGTCTCAGA
GGAGTATCCTGCCGTGTGATGTGTCAGTGTGCCCCTACTGGGGGGTGCCTCCCAGTTAGG
CTGCTCGGGGGTCAGGGGTCAGGGACCCACTTGAGGAGGCAGTTTGCCCGTTCTCAGATC
TCCAGCTGCGTGCTGGGAGAACCACTGCTCTCTTCAAAGCTGTCGGACAGGGACATTTAA
GTCTGCAGAGGTTACTGCTGTCTTTTTGTTTGTCTGTGCCCTGCCCCCAGAGGTAGAGCC
CACAGAGGCAGGCAGGCCTCCTTGAGCTGTGGTGGGCTCCACCCAGTTCGAGCTTCATGG
CTGCTTTGTTTACCTAAGCAAGTTTGGGCAATGGCGGGCACCTCTCCCCCAGCCTTGCTG
CCACCTTGCAGTTTGATCTCAGACTGCTGTGCTAGCAATCAGCAAGACTCTGTGGGCATA
GGCCTCTCCAGCATATAAACAGAACCAAAGACAAAAACCATATGATTATCTCAATAGATG
CAGAAAGGGCCTTTGACAAGATTCAACAACGCTTCATGCTAAAAACTCTCAATAAATTAG
GTATTGATGGGATGTATCTCAAAATAATAACAGCTACTTATGACAAACCCACAGCCAACA
TCATACTGAATAGGCAAAAACTGGAAGCATTCCCTTTGGAAACTGGCACAAGACAGGGAT
GCCCTCTCTCACCACTCCTATTCAACATAGTGTTGGAAGTTCTGGCCCAGGCAATTAGGC
AGGAGAAGGAAATAAAGGGTATTCGATTAGGAAAAGAGGAAGTCAAATTGTCCCTGTTTG
CAGATGACATGGTTGTATATCTAGAAAGCCCCATTATCTCAGTCCAAAATCTCCTTAAGC
TGATAAGCAACTTCAGCAAAGTCTCAGGATACAAAATCAATGTACAAAAATCACAAGAAT
TATTACACACCAATAACAGACAAATAGAGAGCCAAATCATGAGTGAACTCTCATTCACAA
TTGCTTCAAAGAGAATAAAATACCTAGGAATCCAACTTACAAGGGACGTGAAGGACCTCT
TCAAGGGAAACTACAAACCACTGCTCAATGAAATAAAAGAGGATACAAACAAATGGAAGA
ACATTCCATGCTCATGGTTAGGAAGAATCAATATCGTGAAAATGGTCATACTGCCCAATG
TAATTTATATATTCAATGCCATCCCCATCAAGCTACCAATGACTTTCTTCACAGAATTGG
AAAAAACTACTTTAAAGTTCATATGGCACCAAAAAAGAGCCCGCATCACCAAGTCAATCC
TAAGCCAAAAGAACAAAGCTGGAGGCATCACACTACCTGACTTCAAACTATACTACAAGG
CTACAGTAACCAAAACAGCATGGTACTGGTACCAAAACAGAGATATAGCTCAATGGAACA
GAACAGAGCCCTCAGAAATAATGCTGCATATCTACAACTATCTGATCTTTGACAAACCTG
AGAAAAACAAGCAATGGGGAAAGGATTCCCTATTTAATAAATGGTGCTGGGAAAACTGGT
TAGCTATATGTAGAAAGCTGAAACTGGATCCCTTCCTTACAGCTTATTCTAAAATTAACT
CAAGATGGATTAAAGACTTAAACGTTAGACCTAAACCATAAAAACCCTAGAAGAAAACCT

FIG. 1AV

AGGCATTACCATTCAGGACATAGACATGTGCAAGGACTTCATGTCTAAAGCACCAAAAGC
AATGGCAACAAAAGCCAAAATTGACAAATGGGATCTAATTAAACTAAAGAGCTTCTGCAC
AGCCAAAGAAACTACCATCAGAGTGAGCAGGCAACCTACAAAGTGGGAGAAAATTTTCGC
AACCTACTTATCTGACAAAGGGCTAATATCCAGAATCTACAATGAACTAAAGCAAATTTA
CAAGAAAAAAACAAACAACCCCATCAAAAAGTGGGTGAAGGATATAAACAGACACTTCTC
AAAAGAAGACATTTGTGCAGCCAAAAAACACATGAAAAAATGCTCATCATCACTGGCCAT
CAGAGAAATGCAAATCAAAACCACAATAAGATACCATCTCACACCACTTAGAATGGCAAT
CATTAAAAAGTCAGGAAACAACAGGTGCTGGAGAAGATGTGGAGAAATAGAAACACTTTT
ACACTGTTGGTGGGACTGTAAACTAGTTCAACCATTGTGGAAGTCAGTGTGGCGATTCCT
CAGGGATCTAGAACTAGAAATACCATTTGACCCAGCCATCCCATTACTGGGTATATACCC
AAAGGACTATAAATCATGCTGCTATAAAGACACATGCACACGTATGTTTATTGTGGCACT
ATTCACAATAGCAAAGACTTGGAACCAACCCAAATGTCCAACAATGATAGACTGGATTAA
GAAAATGTGGCACATATACACCATGGAATACTATGCAGCCATAAAAAAGGATGAGTTCAT
GTCCTTTGTAGGGACATGGATGAAATTGGAAATCATCATTCTCAGTAAACTATTGTAAGA
ACAAAAAACCAAACACCGCATATGCTCACTCATAGGTGGGAATTGAACAATGAGAACACA
TGGACACAGGAAGGGGAACATCACACTCTGGGGACTGTTGGGTGGGGGGAGGGGGGAGGG
ATAGCCTTAGGAAATATACCTAATTATAAATGACGAGTTAATGGGTGCAGCACAGCAGCA
TGGCACATGTATGCATATGTAACTAACCTGCACATTGTGCACATGTACCCTAAAACTTAA
AGTATAATAATAATAAAATAAAAAAATAAAGAATAGAATAAATAAAAACAAAAATAAATA
AAAAATAAAAAGAAATCTCTGCTCATATCCAGGCCATGATGGTTTCCCCCTGTGTTTTCT
TCAAGTAGTTTTATAGCTTCAAGTCTTATGTTATATTAAGTCTTTAATCCATTTTGAGGT
GATTCTTGTACAAAGGCTGAAGTAAGGGTTCATTTTGATTCTTCTGTGTGTGTGTATCCA
GTTTTCCCAACACCATTTATTGAGAAGTCTGTCATTTCCCCATGGTGTGATCTTGTTACC
TTTATGAAAATTTAATTGACCATAGGTGTATGGGTTTATTTCTGGGCTTTCTATCATATT
CCATTGATTGATATGTCTGGTTTTATGCCAGTACTATGCTGCTTTGATTACTGTGGATTT
GTAATGTAATTTAATGTCTGAGAGTGTGAAGCCTGCAGCATTATTTTTTCTCAAGATTGT
TATCTGTGGCTATTTGTAGTCTTTTGTGGTTTCATATATATTTTACAATTTTTTATTTCT
GTGAAAAATGCATTGGAATTTTCATATGGATTACATTTAATCCGCTTTGGGTAGTATGAC
CATTTTAACAATATTAATTGTTCTAATCCATGAGCATGGGCTAGCTTTTCATTTATTTGT
GTCATCTTCAGGTTTTTTCAACAATGTTTTATAGTTTTAGTATATGGATCTTTCACTTCC
TTGGTTAAATTTAGTCCTAAGTGTGTGTGTGTGTGTGTGTGTGTGTGTGTTTGTGTGTAT
GTGTGTGTGCATCAACTAACCATAGTCATGTGGGTTTATTTCTGGGCTTTCTATCATGTT
CCATTGATTACTTCTAAGTGAATGAGTGTGTGTGTGTGTGTGTGTGTGTGTGTTTAAGAT
ACTGTTGTAATTTTAAAATTTCTTTCTCAGGTTGTATGTTGTTAGTGTACAGAAATAATA
TTAATTTTGTAAGTTGATTTTGTATTCTGCAAATTCACTAAATTTGTTAATTTGTTTTAA
CAATTTTTTGGGTGTAGTCTTACAGGGTTTTCTATATATAAGATCATGTCATCAGTAAAC
AATTTCATTTATTCTTTTCCTATTTGGATGCTTTTTATTCTTACCCAATTGTTTTGACTA
GGACCTCCAGTACTATGTTGAACATAATTGATGAAAGCAGACATCCTTGTCTTGCTCCTG
ATCCAAAAGCCTTTAACTTTTCACCACTGAGTATGATGTTCACTGTAGGCTTGTTATATA
TGGTCTTTGTTGTGCTGAGAAACATTCCTTCTATAACTGATTTTCAAAAGTTTATCATGA
AAGGATGTTAAATTATTTCAAATGTTTTTTCTTCATCTATTGAGGTGATTATATTGTTTT
TATTCTTCATTCTGTTACTATGGTGAATCATATTTTTAATTGTTTTTTACTTGCATAAAT
TTATTTTGTGATAGGTAGAAAAGCACATCTGCAGACCTAGAAGCAGAGTGAATCTAAAAA
ATATTATTTATAATTATTATGAGTACACAATAGGTATATATTTTCATGGGGTACATTCAA
TGTTCTGATACAGGCATATGATGTGTAATAATCACATCAGGGTATTTGGAGTATTCATTA
CCTCAAGCATTTATCATTTCTTTGTGTTAGGGAATTTCAGTTTCATTCTTCTAGTTATTT
AAAATATACAATGAATTATTATTGACTGTAGTCACCCTGTTGTGCTATCAAATAGTATGT
CTTATTCATTTTATTTAACTATATTTTTGCACCCATTAACAATCCCCACTTGATTTGAAT
ATGGTAAGCCATTCTTGCATCCTAGGAATAAATTCCATTTGACCATGGTGAATGATCCTT
TTAATGTACTGTTGAATATAGTTTTTGGTATTTTGTTGAGGATTTTTGCATCCATGTTCA
TCAGCGATATTGGCCTGTAATTTGCTTTTCCGGTAGTTTCTTGTTTTTTTATTATACTTT
AAGTTTTAGGGTACATGTGCACAACGTGCAGGTTAGTTACATATATATACATGTGCCATA
TTGGTGTGCTGCACCCATTAACTCATCATTTAACATTATGGAAAATCTCCTAATGCTATC
CCTCCCCGCTCCCCCCACCCCACAACAGGCCCCGGTGTGTGATGTTCGCCTTCCTGTGTC
CATGTGTTCTCATTGTTCAATTCCCACCTATGAGTGAAAACACACGGTGTTTCTTAGTCT
GGCTTTGGTCTCAGGCTAATGTTGGCCTTACAAAATGATTGTGGAAATATTTCCTTCTCT
TCAATTTTTTGAAGAAGTTTGAAAATAATTATTACCAGTTCTTCTATAAATGTTGGGTAG

FIG. 1AW

AATTCATTTATGAAAATATCTTTTCCTGGGTTTTCCTTGATGGCGGACTTTTCATTACTG
ATTTAATTTCCTTGCTCATTACTGTTCCATTTATATTCCTCATGATTTGATCTTGGAAGG
TTATGTATCGAAGCCTTTATCTATTTCCTCTCCATCGTCCAATTTGTTTGCATGCAATTG
TTCGTAGTGGTCTCATAAGATCCTTTGTATTTTTGTACTATCAATTGTGATATCTTTTTT
CATTTCTGCTTTAGTTTACTTGAACCACCTGTATTTTCTCGTGGTTAATTTAGCTAAGGA
TTGTCAATTTTGTTTGTCTTTTTGGAAGACCAACGCTTAGCTTTACTGATCTCTTGTATT
GTTTTTCTAATTTCTATTTCATTGATTTTTGCTCTGAAATGTTTCCTTTCTTCCACTAAC
TTTAGGCTTAGATTGTTCTTCTTTTACTAATTCATTGAGGAGTAACATTAAGTTGTTTAT
TTAAGATCTCTCTCTCCTTCTCTCACTCTCTCTTTTGATGTAGGCATTTAGTGTTACAAA
CTTTCCTCTTAGAACTGCTTTTGCTGAATCCTGTAAGTTTTAATATGTTGTTTCCATTTT
CATTTTTCTCTAAATATTTTTAAAATTAATTTTTGAATTTCCTCTTTGACTCAATAGTTT
TTCAGGAGCATGTTGTTTAATTTGCATATACTTGTTAATTTTTCTTGGTTTCTCCTGTTA
TTGATCTATAGCTTTATATCATTGTGATTGAGAAAGATACTTGATATAATGTTGATCTTC
TGACACTTGTTAAGATGTTTTGTGGTCTATCAATTGATTTATCCTAGTGAATGTTACATG
TATACTTGAGAAAAAATGTATATTTTGTTGCTGTTGGATGAAATGTTCTGTATAGGTCTAT
TAACTCCATTGGTATACGTATAGTTCAAGTCATATTTTGTTATTAAAAATTTTTTGTCTA
GATAATAGTTCTGTTGTTGGAAGTGGGATATTAAAATTATTTACTATTATTGTGCTGCAT
TTATGTCTCTTTTCAGAACTCTTAATCTTTGATTTATATATTTAGGTGCTTCAGTGTTGG
GTGCATATATATTTACAATTGTTATATTATCTTGATGCACTGATCTTTTTATTATAATAT
ACTGACCTTCTTTATCTCTTTTTACAGTTTTTTTTAACCTAAAGTTTATTTGGTGTGAAA
TAAGTATAGCCACCCCTGCTCTGTTTTATTTGCCTGGAATATCATTTTCCATCACTTCAT
TTTCAACCTGTAAGTTTCCTTTAAGGTAAGGTGAGTCTTCTGTAGGCCCATATAGTTGGA
TCTTGTTTGGTATGTATCATGGTACTGTATGCCTTTTGACTACAGAATCTAATCCATTAA
ACTTTAAAGTAATTATTGATAGATGAGAGGTTGCTACTTCCATTTTATTGTTTTCAAGTT
GTTTTCTAGATCCTACATTTTTTTTCTTATATCTTGCTTTCTTTACTTGTGATTTGATTG
CTTTTTGCAGGGATATATTTTGAATTTTTTAAAATATTTTGTGTATCTATTATAGGCTCA
TGCTTTGTGGTTACATAAATCATCTTATACCTATAACAAGCTATGCCAAGTTGATAACAA
CTTAAGTTTGATCACTTACACAAAGGCTACACTTTTACTCTCCTCCTTCTAAATTTTATG
TTTTTGATGTCATTCTTTACATCTTTTTATAATATGCATACTTAACAAACTACTGTAGCT
GTAGTTGCTTTTAAGAATTTTGCCTTTTAACCCTTATACTAGAGAAATCCTTGATTTGTT
CACCATCATTACAATATTAGAATGTTTTGGAATTGAAAAATGCCATTAATTTTACCAGTG
CGTTTTATACTTTCATATGTTTTCATGTTTCTATTTTGAATCCTTTTCCTTCAGCTTGAA
GAACTCCCTTTAGCATTTCTTATAACGCAGGTCTAATGGTGAGAAACTCAGCCTTTGTTA
CTCTGAGAAAGTCTTTAACATCCCTCATTATTTAAAGACAGGTTTGCTAGGTATACTATT
CTTGATTGGCAGGTTTTTTTCTTTTAGAATTTTGAATATATTATCCCACTCCCTTGAGCT
TTCAAGGTTAATGCTGAGAAATTTGCTGATAGTTTTATCAGGGTTCTCTTATATGTGACA
ATTCAATTCTCCCTTGCTGCTTTCCATACTCTAAGTTTTGACAGTTTTGTTATGATGTGC
CTTGGTGTGAGTTTCTTTTCCTTTTTTAAATTTTAGATTCAGAGGGTACATGTGCAGATT
TGCTGCAAGGACATATTGTGTGGCGTTGGGCTTCTGTTGATCCCACCACTCAAGTGGTGA
ACATAGTATCTAGTAGGAAGTTTTTTGTTTTTTTGTTTTTTTTTTAGCTCTTAGACCCTT
CTTTTTCCCTTTTTGGAAGATGCAGTGTCAATTGTTTCTATATTTATGTCTGTGTGTACC
CAATATTTAGTTCCTACTTATGTGAAAGAACATGCAATATTTGGTTTTCTGTTTCCGTGT
TAATTTGCATAGGATAATATTTTCCAGTAGTCTGTCCATGTTGCTGAAAAAGACATGAGT
TTGTTCTTTTTTATGGCTTCACAGTATTTCATGATGTATATGTACTTGGTGTGGATTTAT
CCGGATTCATTTTATTTGGTATTCTTTGGGATTCCTGTATCTGGCTTTCTATTTTCTTCC
CCAGTACTGGGAAATTTTCTGCCATTATTTTTTGAATATGTTCTGTGCTTGTCTCTCTCT
CCTCCTTCTGAACACCTATAATGTATATATTGCTCTGATTGAGGGTGTCAGTATGTCTCT
TAAGATGTGTTCATTCTTTTTCATTCTTTTTCCTTTTTGCTGCTTAGATTGGATGATTTC
CAGTGACTTGTCTTTGAGTTCATTGATATTTTCTTCTGCTTAATCTCATTTGTGGGTGAA
CCTTTCTGTCAATTTTTTCAGTTTAGTTTAATATTCCTCAGCTCTAAGATTTGATTGATA
CTTTCATATACTTTCTCTTTGTTAAAGTTCTCTGTTTTTGCATTTCTCTCTGGACCTTAG
TGACAGTCTTTATAATCATTATTTTAAATTCTCTATTGGGTAAATTACATCTCTTCTATT
CACTTGGGTCAATTTCTGAACATTTATTTTGCTCTTTATTTGGAATATATATTTCTTGTT
TCTTTAGTTTCCTTGACTCTGTGTTGTTTACTGCACATTAGATAAGACAGCTGCCTTTCC
CAGTCTTATCAAACAGGACCTGTGTAGAAGAAAAATATCACTAGTCCATTTGACAAAAAA
TTTTAATGTGCCTCTCAAAGCTTTGTTTGTCCAGGCCACTGTTTCTGTTATTGGTGGCTC
CCAGGAGATTGGGATATGCCATGTCCTATCAATACTCTGTGAACTATAAGATAGAGGCCA

FIG. 1AX

GACTTTCAAAATGTAGCCAGAAAAATGTCAAGTATTAGATGTGTGGTCCAGTTCCTTCTA
TCCTCATGTTGAAATTGGGTGCAGGTGTTACTTCTCCACTCTCTCTGCATGAAGCCAGGG
AGAGGTACTATGGAAACTGCCTGTATTTGTGTTCAGGCCACACTTTTTGATTCTGGGAAG
ATAGCTTTGGGAGTGGGGCCACTGTTTGTCTACATCTTTGTTATCTGTGATCTAGAGTAA
GTTAGGAATGCAAAGCTCCACCACTCCCAAGCTTAGGCTGTTAAGAATTCAGTCCTTTGG
GTGGGAGCTGTAGAAGTTGTGACACTTAATTGTGAACAAACTCTTTTCAAGAAGAATAGG
TAGGCTATAAAATAATAGAAGAAATGAATAGAGCTATAGAAGTTGTGACACTTGGTATGT
GAACAAACTCCTTTTAGGAAAAATAGGCTGGGGACAAGCCAAGTTCTGCTTAGTCTACCT
GAGAGCTACTATTAGTCTGTCTTGTTAGCTCCCTGATGCAAGCTGGAGGTTAAGCTATGT
AGTTGTCACTGGATGAGTGTGCAGTAAGCTGCTAGAGAAAAAAAAAAAAAGGAGCTGTGC
ATTCTAGCCCCTGTTCTCCACTGCTCCCAAGAGATATAGTTCCTGGAAGAGTTTGCATGC
CTGTTTAAAACCACCTCTTTGTTCTGTGATCTAGGGAGACTTGTATATGCCTAGTCTCTT
CTGCTCTTAGAGCCAGGAGTTTTGGGATATAGTATTTCTGGTAAATGCTGTAAAAGGGCA
TTTTGTGGGTGAACACACTCCTTCCAGGGAGAATTGGGAGAGCTGGGATTATTGCTGAGT
TGAGCTGGAGGAAGTCTCAGGAAGTGTTAAGCTGCTGCTCAGGCTGTTAGAGAGCTACTT
TTTGCTTGCCCCTTTAACTCTCAGATGCGTTAGTTAGAAACCAGACTGTCAAGTAGCCGC
TAGGGGAGTATGCTGTAAACCTCTTCCAGGGAGAACCAGGTAGTGGTATTTTTGAGTCCT
GTCTCTGTACTAATTCTACTAATTCACAGTGTTAAAGCACCTGAAAAAGTGCTTGCACAC
ACATATAAAACTGCCACTGTTTTCCTGTGGTCTAAATAAACTTGTGTATGTCTAATTCTC
TCTAACTCCCAGAGTTGGTGAATTAAGAGCCAAACTGTTGGGCATCTTATAATTGGGGTG
CCATATGTAAGGTCCCAATCCTCTCCACAGGGAGAATCTGAGTGTTAGTGATTCCAGTTA
TATGGTGAAGTACCTGGAAGGGGTCCATGCTCAAGTATGCCTCAGATTTGTCTACCCATT
TGAAGTGCATGTTTGGGTTTTTATTTTGCTTTTGATGTGTTTTTTTTTGTCTTTTTTTTT
GAGACAGAGTCTCATTCTGTTGTAAAGGCTAGAGTGCAGTGGCACAATCTTGGCTCACTG
CAGCCTCTGCCTCCCTGGTTCAAGTGATTCTCCTGCCTCAGCCTCCCGAGTAGCTGTGAC
TACAGATGCGTACCACCATTCCCAGCTAATTTTTGTATTTTTGGTAGAGACAGGGTTTCA
TCATGTTATCCAGGCTGGTCTCAAACTCCTGGACTCAAATAATCCACCAGCCTTGGCCTC
CCAAAGTGCTGGGATTAAAGGCATGAGCCACTGCGCCCGGCCATGCATGTTTTCTTTCTT
GCCTGGTAGGCAGGAATCTCTCAACTTATTTCTGACTTTCTCTCACAGGGAATTAATTGA
GATGTTCATTCTGTGCATTTGTGAGTATTGGGAGTGCCAGGAGCTTCCTATTCTGCCATG
TTGCTGACATCAGTCTAAGGAAAACAGTTTAAAGAAAGTTCATCAAAAAGTAACAGTAGA
CACATCTGGGTGTCTTAAATATGAATACATTTCTTTCTTTCTTTCTTTCTTTCTTTCTTT
CTTTCTTTCTTTCCTTCTTTTCTTTCTTCCTTTCC

FIG. 1AY

SEQUENCE LISTING

```
<160> NUMBER OF SEQ ID NOS: 24

<210> SEQ ID NO 1
<211> LENGTH: 168575
<212> TYPE: DNA
<213> ORGANISM: Homo Sapiens
<220> FEATURE:
<221> NAME/KEY: CDS
<222> LOCATION: (21181)...(21403)
<221> NAME/KEY: CDS
<222> LOCATION: (95252)...(95430)
<221> NAME/KEY: CDS
<222> LOCATION: (101753)...(101996)
<221> NAME/KEY: CDS
<222> LOCATION: (110324)...(110439)
<221> NAME/KEY: CDS
<222> LOCATION: (124058)...(124278)
<221> NAME/KEY: CDS
<222> LOCATION: (127009)...(127130)
<221> NAME/KEY: CDS
<222> LOCATION: (128910)...(129139)

<400> SEQUENCE: 1

cgacttgatt ttattttttg catatggata tccagttttc acagcactgc ttgttaccct     60

cagcaaagaa cagttgtctg taaattcatg ggtttatgtc taggctctct gttctgttct    120

attggtcaac atatggtcat atatcactta actgcaggga agggatacat tctgagaaat    180

gcattattac atgatttcat cattgtgcaa acactataga gtgtagttac agaaacctag    240

tatctctagc tgtgttctta tgattcaaat ttgctttggt catttgagat ccatactggt    300

ggagtctaat tattcaaaac tagggaaaac agacaaacag aaaaaactaa gaccaagtta    360

gcagaagaaa gacaataaca aaggttagat caaaaataaa taatatagag aatgaaaaaa    420

ttagaaaaag tggacaaaac tacaatgtac ttttttgaaa agacaaacaa aattaacaaa    480

cccttacctt gactaaaaaa agagactcaa ataaataaaa ttggaaatga gacaggagac    540

attacaattg atgttaacaa aaagatcata aggtactatt atgaacaact atacaccaat    600
```

-continued

```
aaattggaca acctagaaaa aaaatggata aattcctaga aatacacagt ctatcaaact    660
gaaacaagaa gaaatagaaa gcctgaacat accagtaaca accaaggaga ctgagtaaat    720
aatcaaaaac ctcccaagaa gaagagtcta ggaccagaag tcttcacaaa tgaattctac    780
caaacattta aagtattaat gccaatcatt cattcttata ctcttccaaa aagaaagagg    840
gaatattttc aaactcattt tatgaggcca gcattattct gataccaaaa ctacgcaaaa    900
atactacaag aacataaaaa ctacaaatgt gggaattatc atgtatacat atgcaaaaat    960
cctcagtaaa atcctagcaa actaaattca acagtacatt aaaaagatca tatagcatga   1020
ccagtgaaat ttctccttag gacgcaagga taagtcaaca tataaaattg aatgtgatat   1080
accactttaa caaaatgaag gataaaaatc atatgatcat ctgaatagat gcagaaaaag   1140
catataacaa actttgacgt tgttgagaaa ttgaaagctt ttctctaaga tcaagaacaa   1200
agcaaggatg cccattcttg cttctattca gcatagtgct tgaagtccta gtctggacaa   1260
ttgggcaaaa ataaataaat aaataaatag ataaataaat aaataaatat aaataaataa   1320
ataaaatcca ccaaattgga aaggaagaag tgaaattacc tctgtttgta gatgagctga   1380
tctcatgtgt agacaacctt aaagattcca caaaaacaaa caaacacaca aacaaacaaa   1440
atagctagag caaagaaatg aattcagtac agttgcagaa tgcaaaatca gtatacaaaa   1500
agtacttgta attctatata atagcaacaa actatttcat aaggaaatta aggaaacaat   1560
ccccattaca atagcatcat aaataataaa tcttaagaac aaatttaacc aaggaggtga   1620
aagacttgtg tactgaaaac tataaaatgc tgataaaaaa attaaagaag atacaataaa   1680
tggaagatat tccatgccat ggtttggaag aattaatatt gctaaatgta catactaccc   1740
aaaacaacct gtagagtcaa tgcaatccct atcaaaatac caatattttt ttttttacag   1800
aaatgaaaac acaatcttaa cactatttaa accaattaaa caaacctatg atttcaattt   1860
ggtcaaatgt gttagaatgg atttcctttt attgttttga acttgtctct tccaaatttc   1920
aaagcctggt tcctaatttt tacttgaaat accaaataac aaacccactt aatgagctct   1980
gagccagttt tagtagccaa acttgtattt aaatagtgtg ttacatattt gcacaaaaag   2040
ccaacggagt ctaaatcaac actaattcac atcattacta gcaatctaaa acatcagatg   2100
ataattttgc tgttgtcttt caggcaagat attcaaccat tggtattaaa tgttttatat   2160
gaatgtgcgg tgttttattt cagaaacact tctctgaatt cccaaggcct aagagctatt   2220
catcatagag gtttgtggag gcggtagtta gacattttct acatgcataa tgttaattca   2280
ttcaaacatt atagaaaaaa agtttgtaaa gaagttaatt ttcaaggtga caaaaaaatc   2340
agattgaatc atgtttattt tatttcaatt taaactcgtt ggctatctta ggaaattcac   2400
attgtttttg aagaatatat gaacaaagtt tgattcatct tatctatata agcatgagag   2460
aaatacctag atgagagtga aaaatgacta attttgtgac cattgttata tcatagatta   2520
acttgttctc ttctacttct aagctgtgtg atcttgaaaa gtcatctaaa cttcaggtac   2580
catcctcact tgcaaaatga ggggaaaaac cccagcacct ttaatatggt gttatgtgga   2640
tgaaataagt taatatatat taagtgctta ggtttcatgc actttctata tagtattaat   2700
aatattattg ttacattatt atagttacat tattattttt attaatatta ttggaacatg   2760
aatggaattg ttgtggctca ttttaaagat gctgcaatgg agaccaagag aaattaagta   2820
taataatcct agttaaggta cagccatttc taattacatt ttccaactgc tgcttttact   2880
cctagcactc acaccaattc ttctcataat ctaataaata ctgaaattta aaacttataa   2940
agaacacata ataatcttat ttaattatca caacaatttc tgtggagtta ctattaatcc   3000
```

-continued

```
agagatgaag aatctaaaac tctaaattat caagcaacta ttccagcttt aaacaacagt   3060
aaaactggaa ttaaaactag agtttcttta tgaggccagt attactctta tactaaagca   3120
agacaactgt ctctctctca ctctctcttt ctctctctct gagacacaca cacacacaca   3180
caagcacaca cacacacaca ccagatcaat ataacttatg gatgttgatg caaaaatttt   3240
caaaaaatta atagcaaatc gaatccagca gtattttaaa ggactataca ccatggacaa   3300
atggggttta ttcctgggat ataaagttgg ctaaacttaa tgaaaatcaa ccagtgcaat   3360
aaataatagt aattaaaaaa acataattat ctcactagat gtacaaaaaa tgacaagatc   3420
caacatgttt tcaatataaa agcattccac agactaggaa tagaagggaa cttcctcaac   3480
tttacaaaga acatctacaa cgaaaccaca gctaacatca tatttaatgg tggaagactg   3540
aaatctctga atattttccc ctaagatcag aaaaagacaa agaggtctac taattctatt   3600
caacattgga aagatagttc tagtcaatta atcattaaaa aaaggcattt agattagaaa   3660
ggaagtaaaa ttacctctgg cagatgacat aatcttatac atggagaact cctagagatt   3720
acatacacac tcacaactac cagagttaat aaatgggttc tacaaagttg caggatacaa   3780
tatcaattct caaaaaacac ttgtatttct atacactagc aaataactct gaaaatgaaa   3840
ataacaaaac aattccactt gcaagagcat caaaaaagca tgaaaatctt aggaaggaat   3900
ttaccaagaa tgtacaagtt ttatgtactg aaaaataaaa aatgtcatta aaaatagtta   3960
aagagaatct aagcacattg cagttttctg actccaggcc cgggctcttg gatggcatct   4020
ctggatccac tcaggaccag ggagaacttg ttgccctgaa gggaaggaca caagtctgac   4080
tggctttacc acctgctgat tgtagaagcc tagggccttc agggaacaca ggtggtagcc   4140
agatagcagt taccatgggc attaggcatg acccagtgct atgttggctt ctagtttgac   4200
ccagcacagc ccaagggtgg taaccacatg ggtgcttgtg tcacccctcc ttaagttcca   4260
ggcagccagc aaagagagag tgactctgtt tgggagaaag taagggaaga gaataaaagt   4320
ctctgttggt aatacaagga attcttccag atcttatcca agacctctat gaatctgcaa   4380
cagccaaagc attattagtt ttcaggtttc cccagtgcag atatgactgc aatgatcaaa   4440
aacttagatt ataacactca agtcccattt gatacctgaa aagctttcca agaaagatag   4500
gcacaaacaa gtttggactg ggaggactac aataaatacc taacttctca atgcccagaa   4560
actgatgaac atccacaagc tttaagacca tccaggaggt ggctggcaag atggctgaat   4620
aggaacagct ctggtctgca gctcccagtg agatcagtgc agaaggtggt ggtttctgca   4680
tttccaactg aggtacccag ctcctctcat tgggactggt tagatagtga gtgcagccca   4740
cagagggtga gccaaagctg gatggggtgt cacctcactg gggaagcaca aggggatggg   4800
gaactccctc ccctagccaa cggaatctgt gagggactgc catgagggat ggtgcattct   4860
ggtccagata ctatgctttt cccatgttct tcacaaccct caggccagga gattccctcg   4920
ggtgcctaca ccaccagggc cttgggtttc aagtacaaaa ctgggtggat ctttgggcag   4980
gcaccgagct agctgcagga gttatttttc ataccccagt ggtgcctgga atgccagtga   5040
gacagaacca ttcactctcc tggaaaggga gctgaagcca gggaacccag tggtctagct   5100
cggtggatcc cactcccatg gaggccagta agctaagatc cactggcttg aaattctcac   5160
tgccagtgca gcagtctgaa gtcaacctgg gatgcttgag cttggtggag agagggacgt   5220
ccaccattac tgaggtttga gtaagcagtt ttcccctcac agtgtaaaca aagccactgg   5280
gaagttaaag taggtggagc ccacgacagt tcggcaaagc cactatagcc agaatgcctc   5340
```

-continued

```
tctagattcc tcctgtctgg gcagggcttc tctgaaagaa aggcagcagc tgcggtcagg   5400
agcttataga tcaaactccc atctccctgg gacagggcac ctggggaaag gggcagctgt   5460
gggtgcagct tcagcagact taaatattgc cgcaagctga ctctgaagac agcaggggat   5520
ctcccagcac agcgctcgag ctctgctaag gggcagactg cctcctcaag tgggtctctg   5580
acccctgtgt ctccagactg ggagacaccg cacagcaagg gtcgacagac acctcataca   5640
ggagagctcc ggctggtatc tggtgggtgc cctctgggga caaagcttcg agaggaagga   5700
gcaggcagca atctttgcag tactgtagcc tctactggtg atacccaggc aaatagggtc   5760
tgacgttgac ctccagcaaa ctccagcaga ccttcagcag acgggcctga gtgtaagaag   5820
gaaaattaac aaacagaaag gaatagcatc aacatcaaaa aaacaaaaac aaaaacaaaa   5880
acaaaaacaa aaacagcaca tccgcacaaa aaccccatct gaaggtcacc aacaccaaat   5940
accaaaggta gataaatcca caaagatggg gaaaaaccag cacaaaaaag ctgaaaattc   6000
caaaaaacag aatacctctt ctcctccaaa ggatcacaat tcctcaccag caaggggaca   6060
aaactggaca gagaatgagt ttgatgaatt gacagaagta ggcttgaaaa ggtgggtaat   6120
aaactcctct gagctaaagg agcatgttct aacccaatgc aaggaagcta agaaccttga   6180
aaaatggtta gagtaattgc taactagaat aaccagttta gagaagagca taaatgacct   6240
gatggagctg aaaactatag cacaagaact tcgtgcagca tacacaggta tcaatatcca   6300
aatcgatcaa gcaaagaaaa gaatatcaga gattgaagat caacttaatg aaataaagtg   6360
tgaagaccag attagagaaa aaagaataaa aaggaatgaa caaagtctcc aagaaatatg   6420
ggaatatgtg aaaagactaa acctacattt gattagtgta cctgaaagtg acggggagaa   6480
aggaatcaag ttggaaaaca ttcttcagga tattatccag gagaacatcc acaacctagc   6540
aagacaggcc aacatttaaa ttcaggaaat acagagtaca tcacaaagat actcctcgag   6600
aaaaacaacc ccaagacaca taattgtcag atgcaccaag gttgaaatac aggaaaaaag   6660
ttaagggcag ccagagagaa aggtcgggtt acccacaaag ggaagcccat cagactaaca   6720
gtggatctcc ctgcagaaac cctacaagcc agaagagagt gaaggccaat attcaacatg   6780
ctttaagaaa agaattttca acccacaatt tcatatccag ccaaactatg cttcatagtg   6840
aaggagaaat aaaatccttt acagacaagc aaatgctgag aaattttgtc accaccaggc   6900
ctgccttaca agagctcccg aaggaagcac taaatatgaa aaggaaaaac cagtatcagc   6960
cactgcaaaa acatatgaaa ttgtaaagac catcaacact atgaagaaac tgcatcaact   7020
aatgggcaaa ataaccagct agcattataa tgacaggatc aaattcacac ataacgatat   7080
taaccttaaa tgtaataggc taactgcccc aattaagaga cacagactgg caaattggat   7140
agagagtcaa gacccaacag tgtgctgtat tcaggagtcc aattcatgtg caaagataca   7200
tataggctcg aaataaaggg atggaggaat atttactaag caaatggaaa gcaaaataaa   7260
gcggaggttg caatcctagt ctctgataaa atagacttca aaccaacaaa gatcaaaaga   7320
gacaacaaag ggcattacat aatgataaag ggatcaatgc aacaagaaca gctagctatc   7380
ctaaatatat atgcacccaa ttcaggagca cacaaattca tcaagcaagt tcttagagac   7440
ctatagagac ttagactccc acgtaataat agtgggagac tttaacaccc cactgtcaat   7500
attaaacaga tcaatgagac agaaaattaa caagtacatt caggacttga actcagctct   7560
ggaccaagca ggcctaatag acatctatag gactctccac cccaaataaa tagaatatac   7620
attattctca gcaccacatt gcacttattc taaaattgac cacatcattg gaagtaaaag   7680
actcctcagc aaatgccaaa gaactaaaat cataacaaac agtctctcag accacagtgc   7740
```

-continued

```
aatcaaataa gagctctgga ataagaaact cactcaaaac cgcacaacta catggaaact   7800
gaacaacctg ctgctgaatg actactgggt aaataatgaa attaaggcag aaataaataa   7860
gttacttgaa accaatgaga acaaagacac aacataccag aatctctggg acacagctaa   7920
agtagtgttt ggagggaaat tcatagcact aaatgcccac acgagaaagt gggaaagatc   7980
taaaatcaac accctaacat cacaatgaaa agaactagag aagcaaaggc aaacaaattc   8040
aaaagctagc agaagacaag aaataactaa gatgagagca gaactaagga gagagagaca   8100
cgaaaaaccc ttcataaatc aatgaatcca agagctgttt tttttgaaaa gattaacaaa   8160
atagatagat cactagccag actaatgaag aagaaaagag agaagaattg tatagacaca   8220
ataaaaaatg ataaagggga gatcatcact gatcccacag aaatacaaac taccatcaga   8280
gaatactata gacacctcta tgcaaataaa ctagaaaacc tagaagaaat ggataaattc   8340
ctggacacat acaccttccc aagactaaac caggaagaag tcaaatccct gaacagacca   8400
ataacaagtc ctgaaattga ggcagtaatt aatagcgttc caatgaaaaa aagcccagga   8460
ccagatggat tcacagccaa attctacaag aggtacaaat cagagctggt accattcctt   8520
ctgaaactat tccaaacaac agaaaaagaa agactcctcc ctaactcatt ttatgaggct   8580
ggcatcatcc tgataccaaa acctggcaga gacatacaca caaaaaagaa aatttcaggc   8640
taatatatcc ctgattaaca ccgacgcaaa aatcctcaat aaaatactgg caaaccaaat   8700
ccagcagcac atcaaaaagc ttatccacca cgatcaagtt ggcttcatac ctggcatgca   8760
aggcttgttc aacatacgaa aatcaataaa tgtaattcat cacaaaaaca gaaccaatga   8820
caaaaaccac atgattatct caatagatgc agaaaaggcc ttcaacaaaa tttaacagcc   8880
cttcatgcta aaaactctca ataagctagg tatcgatgca atgtatttta aaacaataag   8940
agctatttat gacaaaccca tacccaatat catactgaat gggcaaaagc tggaagcatt   9000
ccctttaaaa actggcacaa gacaaggatg ccctctctca ccactcctat tcaacatagt   9060
gttggaagtt ctggccaggg caatcaggca agagaaagaa atagaaggta ttcaaatagg   9120
aagagaagaa gtcaaattgt ctctgtttgt ggatgacatc attgtatatt tagaaaaccc   9180
cattgtctca gcccaaaatc tccttaagct gataagcaac ttcagcaaag tctcaggata   9240
caaaatcaat gtgcaaaaat cacaagcatt tctatacact aataatagac aaacagagag   9300
ccaaatcatg agtgaactcc cattcaaaat acctaggaat acaacttaca agggatgtga   9360
aggacctctt caaggagaac tacaaaccac tgctaaggaa ataaaagagg atacaaacaa   9420
atgcaaaaac attccatcct catggatagg aagaatcaat atcatgacaa tggccatact   9480
gcccaaaata atttatagac tcaatgctat gttcatcaag ctaccaccga atttcttcac   9540
agaattagta aaaaactggc caggctcagt ggctcacgct tgtaatccaa gcactttggg   9600
aggccaaggc aggaggatca agaggtcagg agattgagac catggtgaaa ccccgtctct   9660
actaaaaata caaaaaatta gccgggcgtg gtggcaggcg cctgtagtcc cagctacttg   9720
gagaggctga ggcaggagaa tggcgtgaac ccaggagacg gagcttgcaa tgagccaaga   9780
tcctgtcact gcactccagc ctgagtgaca gagcaagact ccgtctcaaa aaacaaacaa   9840
acaaacaaca aaaaaaaaaa aactacctta aatttcttat ggaactaaaa aagagcccat   9900
atagccaaaa caatcctaag caaaaagaac atagctggag gcatcatgct acctaacttc   9960
aaattatgct acaaggctac agtaaccaaa acagcatggt attggtatga aaacagatat  10020
atagaccaat ggaacagaac agaggcctca gaaataaccc cagacatcta caactctctg  10080
```

-continued

```
atttttgaca aacctgacaa aaacaagcaa tggggaaagg atttcctatt taataaatgt  10140
tgttgcgaaa actggctagc catatgcaga aaactgaaac gggactcctc ccttacacct  10200
tatacaaaaa ttaactcaag atggattaaa gacttaaacg taagacctaa aaaccataag  10260
aaccctagaa gaaaacctag gaaataccat tcaggccata ggcatgggca aacacttcat  10320
gtctaaaaca tcaaaagcaa tggcaagaaa atcccaaatt gacaaatggg atctaattaa  10380
actaaagagc ttctgcacag caaaagaaac tatcatcaga gtgaacaggc aacctataaa  10440
atgggagaaa atttttgcaa tctgtccatc tgataaaggg ctaatatcca gaatctacaa  10500
tgaactccaa caaatttaca agaaaaaaac aaccccatca aaaagtgggt gaaggatgtg  10560
aacagacacc tctcaaaaga agacatttat gtggccaaga aacatacaaa aaaaagctta  10620
tcatcactgg tcattggaga aatgcaaata aaaaccacag tgagatacca tctcactcca  10680
gttagaatgg cgatcattaa aaagtcagga aacaacagat gctggagagg atgtggagaa  10740
ataggaacgc ttttacactg ttggtgggag tgtaaattag ttcaaccatt gtggaagaca  10800
gtgtggtgat tcctcaagga tctagaacca gaaataccat ttgacctagc aatcccatta  10860
ctgggcatat acccaaagga ttataaatca ttctatgata aacacacatg cacatgtatg  10920
tttattgtgg cactattaac aatagcaaag acttggaacc aacccagatg tccatcaatg  10980
atagactaga ttaagaaaat gtggcacata tacaccatga aatactatgc agccataaaa  11040
aaggatgagt tcatgtcctt tgcagtgaca tgaatgaagc tggaaaccat cattctcagc  11100
aaactatcac aagatcagaa aaccaaacac cacatattct cactcataag tgggagttga  11160
acaatgagaa cacatggaca cagggagggg aacatcacac accagggcct gtcaggcagt  11220
ggggggctag gggagggata acattaggag aaatacataa tgtaggtgac aggttgatgg  11280
gtgcagcaaa ccaccgtggc acatgtatac ctatgtaaca aacctgcacg ttctgcacat  11340
gtatcccaga acttaaagta ttaaaaaaaa aagaccattt atgaaaacat gaccttacca  11400
aagaactata taagtcactg gagaccaatc ctggagtgac agaaatatgt gacctctcag  11460
atggagaatt caaaatagct gttgtgagga aattcaacaa aattcaagat gacatggcaa  11520
aggaattcag acttctatca gataaattca aaaaagaaga tgaaataatt tttttaaaaa  11580
ttcatgcaga aattttggag ctgaaaaatt caattgatat acaaaagaat gcatcttacc  11640
agcagaattg atcctgcaga agaaagaatt agtaaatttg aaaacactct atttgaaaat  11700
atacagtcag aggagacaaa agaagaaaat taaaaacaat gaagcatacc tacaggatct  11760
agaaaatagc ctcaaaagca taaatctaag agttactggc cttaaaaagg aaggagagag  11820
agagagagag tgggataggg gtagaaagtt tattcaaagg gataacaata gagtatcagt  11880
attcaaatac aaggttatgg aacaccattc agatttaacc caaagaagac tacctcaaga  11940
catttaataa ctgaactctc attcaatggg aaaagtaaag tcctttcaat aaaggtgttg  12000
ggataattgg gtatgcaaaa aatgaatttg gataccttc ttgtgtcata tacataaaac  12060
cccaaaatag attaaagacc taagtataag agctaaaact atgaaactct tagaaagaaa  12120
cacagtaaat ttttgtgacc tttgattagg caatgatttc ttaaatatga taaaatatgg  12180
taaaagcaac aaaagaaaac atgaataaat tggatcttat caaaatttaa aactttttg  12240
catcgtagaa tactatcaag agtatgaaaa gaaaacctac aaaataggag aacatgtttg  12300
gaaatcatgt atttgttaag ggattagtat acagaatata tatatatata tatatatata  12360
tatatatata tatatatata tactcttaca cctcaactat aaagagacga ataacccaat  12420
ctaaaaaaat aggcaataaa tagctattag ttctccaaag tacatacaca aatgaccaac  12480
```

-continued

```
aagttcatca aaagatgctc atcatcttta ctcaggaggc aaatacagat taatattaca  12540
atgatattag acatggattt gtcatataca gactttatta agttagattc cctctatgcc  12600
taatttgttg agagttttta tcatgaagag atgttgcatt ttgtcaaatg ccttttctgt  12660
gtcttttgag atgatcatat ggttttcgtc ctttattttg ctgatatgat gtaccacatt  12720
tattgatttg catttattga atcatccttc cacccctggg ataaatccca cttgatcatg  12780
gtgtattatc tttttgatgt tttttggatt cactttgctg atattttgtt gaggatttct  12840
gcatctataa tcattaagga tattggcctg tagttttctg tttttatgtt gtattctagt  12900
ctgattttgg tatcagggta atgctgttct tgttgagcgt gtcaggaagt ccaaaagact  12960
tcttctttag tgttttggaa tagtttgaga attgttagtt tttttttttt ataagtttgg  13020
tagaattcag cagtaaagcc atccagttct gggcttttct ttgttaagag acttaaaaca  13080
cacacaacgc acacacaaaa tgaaatatca ctttccaccc attataattt acaaagtgga  13140
aaataactcg tgttgataag aatgtggaaa ccttgaaacc ttcatgcatt gccagtggta  13200
atgtgaaaga atcttgccat tgtggaaaac aatttgtcag ttcctcaaac agttcaacat  13260
agagttactg tatgaaataa ttcaactccc aggcatgcac ccaagagcat tgaaaacata  13320
agtacacaca aaaacttgta caagaacagt cagatcagta ttatatataa ttggcaaaaa  13380
atggaaacaa tccaaatatt catcaactgc tgaatagata aaatgtggca tatccatata  13440
attaaatact attcagccac aaaaataata aagtacggat agacactaaa acatggaaga  13500
accttgaaaa tattaagcta agtgaaagac ataagacaca aaacccaaca tttaaaggaa  13560
atttccagaa ttgtcagatc cactgaagaa gaaacttgag tgtttgccag catgtgggag  13620
gagaggaaaa tcagtagtta tgaggtttct ggaattagta gtgctgatgg tgacacaaca  13680
ttgtgaatat actataaacc actaaatgat acctctcaaa atggttaaaa cattactgtt  13740
gtgttatgtg aattttacct caattagaaa agaaaaaaat cttatcaata acaaagagaa  13800
atttccacac aaggtgggat cgcttccaca gtgctactca atgcagttta gcgattgcat  13860
ttgtattgga gtaaaagcat gtcacattgc ttttaacatt ggagtccaat acataaacct  13920
ctttcaccat aactatatgg agttcattgt atgtatattt attaaaatgg aattaagatg  13980
aatttcacaa cacaatggat catttttttt ttcatgtgga aaatcagaac acatgcctta  14040
atggttacat gccccacctg ctgctcacct aaaagtaaat ttcctctaac tcagacaaat  14100
atgttatttt caaggaaaag aagcccagag aactgagatc cagaagaaat aacatgtatt  14160
gaaagcacac agaagtattt caatgaactc aaacccaaga ttgtagaaaa ctctcatgtg  14220
cccctgggac tgatgtttga aaatacacat attttgctcc tactctttcc ttccccagat  14280
cccacccttc agagcacccg acgataatgg atagtttcta gcagggtgtc tggaatgggc  14340
aagtaccccc aaagttatag tttgtactgc aagacttgaa cccactcttt ttctgccctc  14400
tattattatt tttgcatttt aaccatttat tattttgaaa agaaaagaga atttttagaa  14460
tatggaaaga ggaagtgaat taataaaata gcacacccta catagagact gctaatccat  14520
ctccagtcta aagatttagt aataggcaag aatatacata tccaggaatt tccttggtgt  14580
tacataaaca aaggcggcac atatgtatat ttttcacaaa atattcactg tttgaagaag  14640
gaattactcc cttcaattga gttcaggcct gatcaacaag tagtgattgg ccaacagcta  14700
aatgcaaagt gcatgctaag tctggggata caaagatgaa tgagaaaaca tttatgccct  14760
taggagaaaa acaaatatct ttatctcaga gaatagagaa ggagattgat tctctttggg  14820
```

-continued

```
ggagatgtca tcctgaagag tataacaagt tcccctataa ttctactttt cagtactgtt  14880

taaaatacaa ctggattttt ttaaatatgt aaaatttata taattttaca aatgtctttg  14940

ttaagaatta aaactatcat tagtaaagga cacagctgga aaattgaaaa cattttggtt  15000

ctctactgtg gaaacagaat agagtaacag caaaaagcgt atttctggaa ttggaccctg  15060

acaactctgc ttaaacactc caccactttc tagctatatg accttgggta agttacttaa  15120

cttctttgtg tgtcagtttc ttcatttgta aaattggaat aatagatgct ttttttgaga  15180

cagtgtctca ttctgttgcc caggctggag tgcagtggcg tgaccacagc tcactgcagc  15240

ctcaacctcc tgagttcaag tgattctcca acttgagcct cccagatagc taggaccaca  15300

gacacatgcc accatgcctg ggtaattttt tttttaagtt tttcatagaa atagtgtctc  15360

actaagttgc ccaacctgga aaattggaat aataattcat aaaatcttcc tcctagattt  15420

gtgaagatca attgagttaa tgtatgtaac gtacttggca cagagcttgg cccatgtaat  15480

ctctcaatga gtgctaacat tacttgtctc acaaaaagtt acttacttcc gtctggcacc  15540

aactccctct ctcacttccc acaatctggt taccattcat tcttcagttc tcagcttaaa  15600

caatgtcttt tccatatggt ttcattgacg ccactttggg aaaatagatg tctcttctgc  15660

ttgcattttc agaccttttt aggtgtatac cttagggcat ttgctttact gaccaaaatt  15720

atttgccggc tactctgtgc ttttcatgac acactgaata agacaggaag agtgtttatc  15780

tatgctcaac ataagatagg catataatgg aagcttcgta tatatttgtt gaataaaaaa  15840

cataagggga aaatatcaga tctaataatg caggacagga ggcaagatgg aacggagaga  15900

accttgtctg agaagagaca taattaaaac agggcatggg aggtaataga aagattggag  15960

gaaaaagaga cagagagaca gaaatgtttg tggtaatttg tgacaagtag ctttgattgt  16020

tcatggccta atcttttagg gcatgaggtt atttcattct ctgtagccca ccgagagtgc  16080

gtacagtgac acatgttatg taagtcccct tttccctttt tataaatgtc tagaccccct  16140

gtgatttgag acttttctag aagaatttag ctgaagacca tattgttttt taaatgtagt  16200

atttggagcc tagaggtgcc agataacttc ctgcaaagct aatgcattta ttttgggaat  16260

atataagctc agtatcatca ttaccaacag tgctcagact tgattttatt ttcattccaa  16320

cagcaaagga aagaaagcaa cttctttcat gcttccatgc cactctgcat ctctctacct  16380

tcacagagtt tctcaataat ggcaacattt ccagttcacc aatggactga gagatcattg  16440

aggctagact agtcttatta atccttatac cccagctcct agccgaactc ctggacacac  16500

aatagatact cagatacatt tactgaaatg catatagaaa gttacacctg caaaaaagat  16560

gatctctcac caggaataag aaaatataat ctgggacagc ccatatatga gatctctaaa  16620

caacctacct ataaccacca agaaaaaaaa atacctgagt ttgagattta tttttccgtc  16680

tcatttttaa tatattccag ttagtgaaag agctaaaata aatgacaaga aaaatttaat  16740

ctaggtattt aaacagaatt attctgaatg ttgtgagcta catttctttt ttacctttta  16800

tttatacata gtatttgtat atacttatac aatatattta ttttgtatat ataaatatat  16860

tgtatttatt tatacatgta aatgtataat atatttattt atacatagta tttatatata  16920

catagtattt gtatatattt atagggtaca tgtaatattt tgttacacgc atagaatgtg  16980

taatggtcaa gccagaatat ttagagtatc cattacctta agtatttatt atttctctgt  17040

gctaggagca tgttaagtcc tctcttttag ctattttgaa atgtacattg atgttaacta  17100

tcattaacac agagtaattg atatgtatag caaataatat ttgcagtagg atatcacatg  17160

tttacttatt tatttattta tttattttta ttatacttta agttctaggg tacatgtgca  17220
```

-continued

```
caacgtgcag gtttgttaca tatgtatgca tgcgccatgt tggtgtgctg cacccattaa  17280
ctcctcattt acattaggta tatctcctaa tgctatccct ccccctccc ccaccccacg  17340
acaggttcca gtgtgtgatg ttccccttcc tgtgtccagg tgttctcatt gtttaattcc  17400
cacctatgag tgagaacata cggtgtttgg ttttttgtcc ttgcgatagt ttgctgagaa  17460
tcatggtttc cagcttcatc catgtctctg caaaggacat gaactcatcc ttttttggc  17520
tgcatagtat tccatggtgt atatgtgcca tattttctta atccagtcta tcattgttgg  17580
acatttgggt tggttccaag tctttgctat tgtgaatagt gccgcaataa acatatgtgt  17640
gcatgtgtct ttatagcagc atgatttata atcctttgtg tatataccca gtaatgggat  17700
ggctgggtca aatggtattt ctagttctag atccttgagg aattgccaca ctctcttcca  17760
caatgattga actagtttac actcccacca acagtgcaaa agtgttccta tttctccaca  17820
tcctctccag cacctgttgt ttcctgactt tttaatgatc gccattctaa ctggagtgag  17880
gcactggtct gaaaatatca attcatttaa ttcttttaac aaccttaagg ggatatcatg  17940
gtacaaattt agagctttct tttgtgtttg taaaatggat tgattccttt tccctacatc  18000
cagcagaaat atttgaattg aagagaagag taatacctaa gaactagaaa ttcctttctt  18060
atgtttcaaa agatatcaaa agatctaagg aagatattca catcaaaaat gagtattata  18120
atatttatta tctatggtgc acttgcaaaa aagaaaacaa gtaataatct gaagatttaa  18180
gtgaatattt tatgacattg gagtaccaca tatttagaag aaagcaccag agaaatcata  18240
gatagaagga aatggaatat ttgtaggatc aagataaata cagcttgtca taaaataaag  18300
caggtatcag gataaaatct tgaaaatatt ttcatttctc gttatttata acttcaattt  18360
actgtgatga ttaattgtag gtggaagatt tacgaagaga agactgaagt atagacaagt  18420
tgaagtgcca caaaatgaaa gctaatgaca ctgactactt aggaaatagc agactgggtc  18480
catatttata gattgtcaat gacaaggaat ttgcagatgt taatgaatat agatccgaac  18540
ttaagttgca acaacctttc ccactttgag atgaatagtg catggaagag taaaatgcag  18600
atgttaataa atcagaggaa gacatcgtgc cagagtataa agttgacaga tttatgccga  18660
tgaacttgaa caaagccaca gaaggcctac ttgtcaaatt tactggtgac aacaggtctg  18720
gagaaatggc taatgttttg gataatagca ttagaattta aggtctgttt aaacttcaaa  18780
ttaacagaat gaaattaata tatgcacata tcaattgggt cttttgctta tatatcatct  18840
cttaatagag ccttttttgaa caatcatttc taatgtgacc tttgggattt tctactcatc  18900
atcacctcat cctgtttggt ttgcattata gcatctatcc cttcctaacg ttttccctat  18960
gtatttgtta gtttgttttt ttttaatcta actttactag aaagtaaaat gcatggaaac  19020
agcaacctgt ttaactttgt atcactaaga gtggaaaaat aaccctcagg aaatatttgg  19080
taaaataata aaatgcccat tgatgccctt ctcttaaaaa gaaatttaat tagtgcagat  19140
tggggaaata caacaatatt tctcataaaa tgtgatatct atacaataac agaagtacta  19200
tgtcccaaaa agtattctat aaatagaaga aagaacagat ggttttgctg ctgattaatc  19260
catttatctt tcgtaaatca tctaatttcc ccaggaacag cttcctcatc tattaaaggg  19320
ggttagtaat agctaagccc tcaggggttt aaaaatgcat atgaaataat tttataaacc  19380
ataaagcaca aaacaaatat gaaaaattat gattggagga gggggtgggg tagttaacta  19440
aatctcagtg taaaccacca atgtcttgtg tgtgttgaaa aaataattac atataaaaac  19500
tggttgcatc caaagaataa tgtacttttt gcactggcaa gactcaaacc atattattgt  19560
```

-continued

```
tacttcctcc cagttacata ttttgcaaga tattgacaat tgtctaaagg aagaccaaac  19620

agatgtaggt gggagctact gtcatttgaa caacattgaa aagaaaaata ctaaaaaaga  19680

aacatgaggg catataaagg agcgctgggg ctgtgatgtt tattttgaat ctgtgaagca  19740

ttgtcatgtg gaagatttat tctgtgtagc accaagatgc aaactaggaa ttagaggtaa  19800

aagtctcaaa aagacaaatc gtggcttgag accttggttt aatgtaagaa acagttttct  19860

caccccttaga gcactcccat aaggatggaa gtagtgaatt gtggtggtca cattcaagct  19920

agatggggac atgtcagcaa tgttatcagg aggcttctac tctgaagctg aagttcagac  19980

aagatttcca ggctcttccc aagtgcaaga ttgtaattac ttaaatgcaa tatttttacc  20040

atgtttatta agaataaaag gatcatgaat tcacattctg acaaatgcta gaatacttat  20100

tattagagac aaaaccagtg catgagagaa tggcaggtga catcagccct gaatcaatgg  20160

gaagaaagac ccaatgggat gtggtattta ccagagagag cacttctgct tagattgcta  20220

catcctacag tgaatgttta atatcattga gtatattggt ggtctgtcat gcttgacaac  20280

attaactatg atcatattta tgacacttgg cgtccttcaa gaatttgtag ctctatttca  20340

catgacactt aactatcgca aatacaaatt ccagctaaat agacccttca gtttaaaaac  20400

agtctcattc tcaaatttta aggagaaagt gaagacggag atgtcttaaa gactcggcaa  20460

gtactaagtt ggcaaatgtc aaatgttaaa ataagtttat attaaatgtt aaagtgtttg  20520

cctggaatga cttttccatt gtcctgcttg agaaacacag aggcacctcc ttattgcttt  20580

tatatttgct ttacaaagac aaatgtatca acatgctctg tattaattgt atgttgacat  20640

ttttgtcata tccacagact gatgcatgtc tgtgcatggt ttataataag tgcacgtaaa  20700

aatagagaaa ataagtagaa aaagagagag atttaactct caccccccac cccccaaaaa  20760

aacagattaa attagttttc attacttttt ttttttttctt cagcttcagc tctccctcag  20820

cgagggagga ggctgtgggc tgcggactga gtgctggaat gaggagtaat tgagcttcag  20880

ctgagccgga cgtagctttc tcctcctggt gtcattgctg cagcctccag tgccgggtcc  20940

ctagttcctc agctgcctat cttcccggtg caacatcgcc tgtaaagaca gcaaagccac  21000

cgcagaagtt gcccggcaga agactccgga ggcattggct cagtaacttt tcacgtcatt  21060

ttctgctcgg gagccccttc tagcctctcc gcgcagcctt tcccaccgca aatcaccagt  21120

gctcatgggg caggcggaga ggagcttgca gcattgagcg gaaccggact tgagcccgtg  21180

atg tcc ggc acc aaa ttg gag gac tcc ccc cct tgt cgc aac tgg tca    21228
Met Ser Gly Thr Lys Leu Glu Asp Ser Pro Pro Cys Arg Asn Trp Ser
 1               5                  10                  15

tct gct tcg gag ctg aat gaa act caa gag ccc ttt tta aac ccc acc    21276
Ser Ala Ser Glu Leu Asn Glu Thr Gln Glu Pro Phe Leu Asn Pro Thr
            20                  25                  30

gac tat gac gac gag gaa ttc ctg cgg tac ctg tgg agg gaa tac ctg    21324
Asp Tyr Asp Asp Glu Glu Phe Leu Arg Tyr Leu Trp Arg Glu Tyr Leu
        35                  40                  45

cac ccg aaa gaa tat gag tgg gtc ctg atc gcc ggg tac atc atc gtg    21372
His Pro Lys Glu Tyr Glu Trp Val Leu Ile Ala Gly Tyr Ile Ile Val
    50                  55                  60

ttc gtc gtg gct ctc att ggg aac gtc ctg g gtgagtctcc tcccgggcag    21423
Phe Val Val Ala Leu Ile Gly Asn Val Leu
 65                  70

ccctcctagg ggctatcacc ccctctccgc cccgggctga gaaggctcta aagagacccc  21483

tccctccccc gggaagcaaa caaagaggtc gctgctctcg gatggggttt tctaataaaa  21543

taataataat aatagaaagt tttctgattt tccgaaccgg gaccgagccc tggaaaggtt  21603
```

-continued

```
attccctgtt ttgcaggaat aacggggaaa ccgcgtttct ttttcgagca cctagattac  21663
aagcgcaggg agaggggccg cggcagggat ctccaggtgg attttgttga gtgtgtgtgt  21723
gtgtgggtgg gtaggtgggg gagtcagtca tccctttgtg taacgtggct gggtgtttca  21783
ggggggttgg gacgagacag agcttgcaga atacaaagct acatccctaa ggagcaagct  21843
ctctgtggct gtggaagtca caaagcattt gtgagctagg tggcattgcc ctttggcgag  21903
gaggtttagt ctccagtcaa gaggtggtaa tgaaccagca gggagtggag acggaggcaa  21963
agcagggaag tgcactcact catagaagct gaattaaaca ggatccatgc ctggagcaag  22023
aaggaggggc atcggagaaa agtaccacag agatctcaat catccatcca tccattcatt  22083
cttacatcca ttcagccaaa tatttttttt tttcagtctg cttgttgcca ggctcaggaa  22143
ttattcatgt caactgtttg ttgttgtttt gttttgtttt gttttctcca aagatgagac  22203
taagcttaat gctaggctat ttgtcccggt ctaggtctgt atgcaaacac gggtttcctc  22263
gacccctcat ccccctcccc ctaaacaatt tctgagggtt ggggaggggg tgagatggca  22323
acatggtgag tgcgatgatg gaatgtatta gggcagttgg ggaatatacc tccagaaaag  22383
gggctttgga agggagggat aacttgaaat aaattgtgaa tggaaggaga gtgtaccttg  22443
atgaatgaag agtagaaggc tgggagactt ttcacatgca gagggcagtg tggaggaagt  22503
ctctgctgaa aatgacagga gatggaggag gctaggagtt gctcttgatt ttcatttata  22563
aaagaagaag aaggtgagtg aggtgagata ggctgggagg ctttgcagtc aaaagcaaag  22623
aacttgtagc tgcaatgggg actgacaagg aaattatcag gctttcagac taacctgatt  22683
tttgccttct ctcccaagtg tgttggtctg ggtagaaatc atcccgagta gtctctcacc  22743
aactcagcag gcagaataga tgatagtatg tgaatgacag gagttctcca gagtgttggt  22803
agaatgttat ttgaggagac aagaaacctc tgagaacttt agtacatttt taaatattat  22863
ttttagactg ttttcctttg gttgatttaa aagtaaaaat aaaggaaatc tttttgggat  22923
actaacaaaa tgaaacaaaa gtggaaatac acaagattag gattcttgtt ataagcataa  22983
ttctgttgat aataatccta atcttgcttt ccttcttctt gttacccatc cttaggatta  23043
catctcttaa gacacatggc taccagcata gcaacatttt actgcattat gccaacactt  23103
attgataagt gaataatcaa aattgaacat atattgagta cctactgtgt gccagagccc  23163
ttcatgtaca ttctctccct taaatatcaa aataacccac attagccaga agaagaaaca  23223
agacttagag aaataaaatg acgtattaag ggacataatt taaattcagt tccatttttt  23283
ctgacctcag atccagaatt ctccattgtt attccactct agagctaaaa agcatataga  23343
gaatagattc tctgctcctg attgtctgca agtttattag atgtgttcct gttctcctct  23403
gcatcaacgc ccactgccaa taaagtacaa tgagggatta atggcactgt cattctcttc  23463
accaaaaacc tttccagaga agcagtaatt tttttatgaa tagctatcaa tagtaactat  23523
ttgccttcct tattttaatt ttcggctgaa tctttgtggt aaaatgtgct cttctttgtt  23583
gttattgcat ttttaccttg catagacctt gtagtgaata gtctccatat cctaattgca  23643
tagtttaggg atacatgttt gctagcctgg ggagttttag tttcaagaag gaaacacctc  23703
tacagtaagg ctacttgttt cataatgtca aggaagatag cactgtccac agccccaagt  23763
gctgaaatgg ccaattccat tcagcctaaa aagaaagatt tactcaaagc actctgcctt  23823
aaagaaactg acagctattt tcctcaggac tgaataacac tgaaatcctc tctggttgaa  23883
ctgaaatgca ttcttttctg acatactgcc tgaaagttga tgaggtttag gtttgacatt  23943
```

-continued

```
taaacaaacg agtagtgtcg ttactcacag acaacttcct gctctttgat gtcactgtca  24003
aatttgcaaa atgaattaga ttgagaattg cttctttgcc cctctggtat aagtaatttt  24063
gcacatagag tggtaggaca ggatgtcaca tgatttatgc aaaataaaga tgcaatatta  24123
agtatgaagg taaaatacca cagtgtaggc agcagatgta atcactgagc cttcaggtcc  24183
agtcaccatt tgtactttca tataactgct tggaaaatct caaccttttt gggcttacaa  24243
atataatgcc atcagttaga agtcatcttc tccacaatgt cctttcatga agtgatgtaa  24303
taggatatgc tgtgggtagc ataacaaagt cttgattgtc ctcatctctt tttcttctcc  24363
ccatagtccc tctttatcac tatgccacct ctccactctc atatactcct cccaaagatg  24423
gaaagcagtt tcctggggga gtaaagtttt aaatagaatg ttatgagtat ttacattcaa  24483
tgaaaagctg taagcatgtt taatgtgaaa ttttaagttc taaggaagga gcatagggta  24543
aggttctttt tggaaggagt atcttttcag tatcttcaga ataatgccac ctataaccta  24603
ttcctaacta tgtcttctac tacagctaag tagatgtatc aacttattca attggtatat  24663
tgtgagcatt atcatttttt taaattagtg tgtatatcag gggagcctct ggggaaatgt  24723
aaagaaatgt gactgatgtt aatttttact cctgattcct tgaatgacaa ttgtagggag  24783
aaatgtgttc tagtcagttt aaacattaag tacctaggga aaatgatcaa ttttctgctt  24843
ctcatatctg cattcaaaga tatcatatgt ttcatctggt atgcttctgt catatctgtt  24903
gttgtctcca tatggaaaat aggaaaacat cagtctagct atgcttcttg cttcttgtgt  24963
gccattagca agttattgaa ctatccaagt caattttttt ataattacaa attaaagatc  25023
gataatgact gcattataga aatagtatca ggatataatg tacgtatacc ctctataaag  25083
acatataaag ggacacaggc atatacatat ttttcttgac acatagacac taattaatgt  25143
caatttttat cccttaattt tcatgactga actttttgtg atgtggtgta tagccagctt  25203
ctgccttcat gggccagtct gtatctctgt agctctttat ggcctctgcc ccagcctttt  25263
ccttaattgc atattttcct aaaaggtgtg aataaaatgg tgttggcaca cattactctc  25323
cttttccaca ctagctccac ccacccatct ccttcatact gattgcttaa cattgccttc  25383
ttgcctttaa atgaaagcca ttcctaacta ttggaatagt ttgctttctc tctcaactta  25443
aatttgcctg tgctgggtcc cattcattta gagtttttga gttgttaata ggttgttgat  25503
aggcaggtct atcactacta gtgttttaaa taacacacac attggtaata tgttgattta  25563
actcatacat tgttaaaata cattgtgaag tattcatagt taaaataaat tatccattaa  25623
gtaatttacc taataacagt ttacccaagt taggtgtgtg gaatggggaa atatttgtaa  25683
taagtttgct tcctacagag ttagtcttgt gtcagatatg taagtggtag aattgcaagt  25743
tcatgttact cctaagccta gagacattta ttttctgctt ctccgaatgc ccattttagt  25803
ttcatgggtg tttgtaaacc catccttacc tacacaggaa gcaaaaaggg gttatttcta  25863
aaccettttt agatatagaa ataatacatc actcatctcg gccaagactc aatagaatca  25923
tgaatagtga ctgtaaaagg taatattaac tattaggctt taaacctatt gtgcatttta  25983
gttttaaaat gcaaacatgc taatctgaat aagaattaat ctgatgcctc tacatttttg  26043
ctaaaatcat aactgtttag tcttacttag taaaataaat tatatctttg acttaaaatc  26103
ccaatgataa cttttaagat ggctatttca tagataacag caacatttat catggacaga  26163
caataatgag aataacatgt gcaactgata atttaaatgc aatgagttat ttctgtattt  26223
gaaaaaatat atttgggaaa tgggataatt aaaaaatacc agttttcaag agaccaaatc  26283
taaaactcaa acataaacac aatgctccag tttttagaaa actgtcttga ttgtagtagt  26343
```

-continued

```
gcctacatac taaattgtat catatgattt atattaattt tccttatttt gtattttaga  26403
ttatatttga aaattttcat gtactgcagc tatgttagca tctcaaagtc tccatattct  26463
cactccgctc cgaaacatcc actgctgatg ttatttaact agtgaaagaa gatccttcca  26523
tgtttcttct tatagcattc tgacatcttc tccaccctaa ggaatgctgg ctttattaag  26583
tatgtttcag tcaatgacat gtgattggtg aagctgacgg tatttgtctt cagttccttt  26643
tttccctgca aaggaaattt gttgaatatt tattgggtac tatatgccag gtactatatg  26703
tcaggctcca cttacatata ctctattgat gccttacaac aaacttataa tgagaagatt  26763
aataggtttt acaaataaga aaaatgaatt caaagagcaa tgctaactta ctcaaaagtt  26823
tagtcaggca gtaaatagca gcactaggtt tcaaatatgg atttaacaaa ttccatggtc  26883
catgcttatt ccattacttc atcctgcctc tttccttagc ttctaaccct gactggagat  26943
gcataggcaa aaagaggaag gaagagatac ttagatgtgc cctctagaca atttacagag  27003
ttgtttgggc atgttgccat gctgtttttc tgatagacta cagttcttca gctctgagga  27063
tgagctcatt tgataagcca atcaaggtcg ggctagggtt actttacaag agaaaatttc  27123
aaggtaaaat aggtgctgcc aaaaatgctt ttacctgttc aggggggttga ctcactggaa  27183
aaaaaatgtt agataattgt ggccaaggat tattttgtta ttgaaagtgc tatttttaga  27243
cacaatttga gcctgagagc ctaaacactt aacacttcac ataatctaca gatatttgtt  27303
tatttttctt tttgtcatgc attgccaaat aaatagtatt tatttaaaca aatcatgttg  27363
ctattgattt tattaaatag atgaactttt tttaattttt tttttttgag atggagtctt  27423
gctctgtcac ccagactggg gtgcagtggc acaatctcgt ctcactgctg cctccacctc  27483
ctggcttcaa gctattttcc tgcctcagcc tccccagtag ctgggattac aggcacatgc  27543
caccatgccc agctattttt tttttttttt gtatttttag tagagatggg tttcaccatc  27603
ttggctaggc tggtcttgaa ctcttgccct tgttatctac ccacctcagc ctcccaaaat  27663
gctgggattg caggcatgag ccactgtgcc tgacgtgaac aggtcaattt ctatatcacc  27723
ggacagtgtt cctggatcag aataatatat tatatgtatg aagaatcatt acctattaca  27783
tcagacatga aatgaccttt agatactgac tttgaaagag tttgagatgc tattggatga  27843
aacacatgac ccatatgacc agtcttttga attgctgact ctgagtataa aatgttttca  27903
tttcaccttt gttcacaatg agaagtgatc tcttaaccaa gtaaatgaat taaatcgata  27963
tttaaaataa cattaaattt cttgccagaa aaactgttct ttcataaaca aaaaacaaat  28023
tgctcaaaat aaatgactat atctttattt ctaaaaaatg tttagagatt attattattg  28083
ggtctttaca agtaatttgc cttcaatact aaacacatga gaacaatgtt taatatttat  28143
atagtatttt actcttcaga agatatttgt ccatattctc tctcagttat tcttcacaac  28203
aacattatga ggtaggtctt ttttaatgaa aaaaaactca agtgcttgaa gtgatttaaa  28263
atcactgtgg aagaaaagca tgggcataca gaaaagccaa gtggttgtgt gtcagcttgg  28323
gaaaagcttg caaatttcct gtatttcaag aggccaggat gaggtgtgta attatctttt  28383
actggtcttc agctatcctg tctttgatat gtgattgtgt caaaactatg aggaaaaact  28443
cacattaaca aacttcataa acttgttaaa cataaaataa taatttcgat gttttaattt  28503
acagtaagag tttattctta caagtcctta aatacccaaa gttctttcag ttatcatagt  28563
ctttttcagt agacagaaat ccatgtggac tgttattgtt ctgaatagct aggctatgcc  28623
atagtagcaa acaaaccctg aattttcatt ggcttagtat cacgaaagtt tatttcttgc  28683
```

-continued

```
tcatttaaca tctgaggtgg gttggagagt ctccttcatc caatgactca cagttcaggc  28743
agcctccaca ttttgtgcac tatccctaaa aggtggactc tgtggtaatc agtttccaat  28803
atggcttcca atgaccgccc ccgggccccg gccccacttc ctgatagtca catcatcgtg  28863
tagtcccttt gcatattatg ccagaattgg tctgggtgac caacagctca tagcagcagt  28923
gaaacgatgt cactttcaag attacataac aggagcttac agcttctggc tcaagtaccc  28983
actttctctc tagctcttgg atctcttctt ctggaggaag taagctgcct tgtggtgagc  29043
agctgttggc tggagttaaa atctccagcc agcagccaga gaggaaatac ggtctgttaa  29103
caacctcatg tgtgagcttg gaagcaaatc cttcagacca ggttgagtct tgaggtgact  29163
acaacagcca ctaccccaac ccacccccag cttcagtgca acttagtaac agacactgag  29223
tcagaactat tcagctaagc ttcttgcaga ttcctgacca ttcagaagct atgtcataat  29283
aaatttttgt tgtttgactt cagtttcggg ataagttgtt gcacagcctc taaagttgtg  29343
aactagaaga agtatactgg ctcttaacca cctttgccaa aaattaacac ttgtcagtca  29403
tggtcatatt catttggtcc aaatcaatca tatcgtatca acctaactac aaaggggatt  29463
gggagatggt gatgtctctg tcacagaatc tatataatag ttaaaagtat ttttaacttg  29523
catagactca gaacaagata atttggagga attcaatgct taatggcata ccactaagat  29583
aagctgatag atatatcgtt gcgatttggg tctctgacaa tagaggcaat tgataatatt  29643
aagagactat gtgccaatta ttgtgcttgg attgagggta caaaggtaat agaatccaag  29703
gaacctgcac tctttttgaa agatagacac ataaacacat acttttaaaa taacgtggta  29763
agtgctacta tgacagatgg ttgcacagaa tgtagtggaa gtatttgaga aggacactta  29823
gctctgctgg gggattagag agagatacag gaggagatga cacctaaact gagttttaat  29883
agatgaattc aagttaccca ggtgaagaaa attgggtaag gatgttctaa gcagaggaaa  29943
caacataagc aaaatcaaag aggcgtgaaa tagaatgagc tatgaagaaa gtgttaggca  30003
attgggtaag tccaatgtaa gtgcagatga ggagagtctg gaaatgaggc tgaagcagta  30063
aataaggatt ggccataaaa gaccttgtgt acaattctta agatctaggc tttgacactg  30123
ttgtttaggg ggagctgtta aaggatttta aattagagta ccatcattgg tttgcatttt  30183
ccatgagagc attttgagga aaatgcagag aataaataca tgaggggaaa gactagtgaa  30243
ggttttcaca ctggggtttg catcctgttt tggcaataag cttgttttaa tgaaaacaaa  30303
caaacaaact gacaataaag aacataatcc aaattctcca gataattact tccaggaggc  30363
tttctacgtg ctgcatacaa aacaaagaaa gaaaaacata aagtgagaaa acgaaggaaa  30423
aacaaggaaa gaagagaaag aaagaataca tattggaaaa actgttgctg tttttgtttt  30483
gctgaatatt taaatttgag aagcaatttc tctttttctt tttacttttt tttttgagat  30543
aaagtctcac tctgttgccc aggctggagt gcagtggcgc catttcagct cactgcaacc  30603
tccgccttcc aggtcccagt gattctcctg cctcagcctc cccagtagct gggacttcag  30663
acatgcacca tcacgagcag ctaatttttt gaattcttag tagagatggg atttcaccgt  30723
gttgctcaga ctgatcttta actcctgagc acaggcaatc cgcccacctt ggcctcccaa  30783
agtgctagga ttacaggcga gagccactgc acccaggcgc aggttttctt tatgatgttt  30843
taattatatc tttcttggaa catatatgta tgaatcttgc atgccatagg tctattaata  30903
ttttccaata ttctacatgg ttttttacta aaatcatttt tatgattagt tactgactga  30963
ggtttcaatg catcactgta ctcctagcta tctctcattt tagcttttac atcacatttt  31023
ggcctcacac tgaaacacaa aatattaaaa atttgagatc taataaacaa ttttcacatt  31083
```

-continued

```
ttccaactaa atccccactt ctttctaaat tttctacaac tttctaaaca ttctcacttg  31143
aaaatttatt ttaaatgaca tgtattttat tcaaacaatc aatgaagatg ctacattgac  31203
cccaagtgag cccttaggga atttccgtga atatttccct acaggttggc atggtaacac  31263
acttcacaat ttctaaatct gtggatagtt tagaagcttt tatttgctgt tcctagttca  31323
caatggaaat acaacaatga ttaaaaatta taatatcctt ttgtagattc ttagctttta  31383
ttcctactca gtgactctaa aatgaattta taaggcccat ggtttataac catgtgaggc  31443
cttgattttg tcactacatt gctagaaatg gggtcagaag gccaccagct ttaataattt  31503
aattcatcaa ttcggaatga atttgatgag tcaaccactt tggtagagaa ccatattgct  31563
cataaatact gttttgaagg caattcgtct ttcataaaat gtgaagattg tgctgatctt  31623
tctgggcagg gttatggagg tgtgattaaa tgcttaagaa accattttgt tattatatta  31683
aaccgaatca actttttatt attaaaaata gataaaaact tagcatcctc aattataata  31743
ctttatacaa aagtttccca attttatata gactgaagat aaaaatacat taacaaatct  31803
taccagctgg ttcaggaaaa taacttcata attattgaga catttatgtg tttgggcttg  31863
atttatactt tggacacagg aaaacctaga gagatctggt tctttgaaat catcagagat  31923
ggtgatggtg actcagagat tcctgaaaat cagtaagatt accctagttt atagacgtat  31983
gtgttatttt ttcccccagg cataatgaac tttataactt gtcattgaca agaagccaaa  32043
tcatcttaga gaaaaggggg agaataaaaa tttaagaact taaaaacaca taaataaaaa  32103
catgtacata cctcacacat gtgtacacac acagtttggg gattggatga tatgaataat  32163
ataattaata caccctaatt tttcatgcag gattaagaaa gtatcttcca aacattaaaa  32223
atgctgaaaa ctggacataa ggccttgagt ttcccaaatt caggacatat tttcaactat  32283
cccctgagta aatgaactat aacatttaca gaagtaaaaa tgataaatac actaaagatg  32343
aataagtcct tgaattaaca gccaaacaag aaggcgcatc ctttggatga ttgatcactg  32403
tagcatgatt tcttttcctt gaatagacaa tattccttga caatctttct gtaaacagaa  32463
tacaatgttt ccctaagcaa tatatgcgtg ctctagagtt ttcacaattt ctgatcctcc  32523
tatgactggc tcctgctcag ctcacactgc actttcatgg aagttctctt agaatgccag  32583
ctttgaatca ctgctccctc atgtgctgtg tgtgatagca tcccatttta gttttgtcat  32643
agaattgatt accatttcaa attgaattgt taatttattg ttcatttttc tgttgtctcc  32703
cttaagtaaa aggtaagctg catgagaata gtttcatttt ttttcctgtt tgccaatgta  32763
tcctcagtgc cgagaacagg ttcaggaata cagaattttt agttagcaaa tgaattaaag  32823
tgtaagactt ccagcaggag gaatttttta catataagta cattttttaa attaagcatt  32883
gcaggcttta aatttcttct atataaatat ttaaaataaa gcttcaataa tttgaattgc  32943
ttttgtgatt attttgtttt ataccttgag taacttatac atcaactatt ttgtagttat  33003
tctagtaatg attatgaaag accatttgaa aatctttccc cagcactgag atctccttga  33063
catgactaag tgatttatac tatgcaatta tattgctctt ctcaagaaaa gcaaaatgaa  33123
atttacaaat ttggtagctt tttgttcttt tgttttctca agtaagatac accaagattt  33183
ctttaaatga tacgctatat ttctgcaata actgagaaga acatgtaatg tgcaaaactc  33243
ttaaactctt tttgtttcaa aataattctt ggttgttttt ataaaagtct aagcaaatac  33303
ttaatgaact gtgtcccaaa tgaggtgaaa cagctgtgac agaatgttac tatgactctg  33363
tactttctat aataaaaagg gacagacata tcctcacctg agccttggga tgtttcaggc  33423
```

-continued

```
atgcccatag agcctaagct ttaggaatcc tctgtcattc ttttccattg ccagtgactt  33483
gtgccaattc tagggttctg gactgtgcaa acaatggaaa aaataataac actttcaggt  33543
ggcgcacaaa accaatgttc atagtagatg gatagttcta gacactttat ttaatagaga  33603
ataggagaaa cactaatccc atctaattct gccttcaaac tcctaaaata ttcatcatta  33663
tgaattaaaa aaaaaaatca aagtgtaacc tcacccagag aaagaagaca ttggggccag  33723
gtctggtggc tcatgcctgt aatcccagca ctttgggatg ctgaggcggg tggatcatga  33783
gttcaagaga tcgagaccat cctggccaac atggtaaaac cccatctcta ctaaaaaaca  33843
aacaacaaaa aaattagctg ggcttggtgg catgcgcctg tagtcccagc tacttgggaa  33903
gctgaggcag gagaatcact tcaacccggg agacggaggt tgcagtgagc caagatgaag  33963
ccactgcact ctggcctggt gacagagtga gactccgtct caaaaaaaaa aaaaaaaaaa  34023
aaaaaaaaaa aaaaaaaagg aaaacgaaaa gaaaagaaag cagatattgg taattctagc  34083
agatcctgga acaactgaac caaatttatt aatatgtatt attactgaaa atcagtaatg  34143
aacaaaattt acagaatggg cttcttggag ttgttacatt tcccttatta cataactctt  34203
caataaaagt gtttgtcata cctattttag ttaattctac aacaactagt gtgatagggc  34263
tattatttga tctttttttt tttttttttt ttttacaggt agtgacattc agtattagac  34323
agctgctatt gtgttagttg tctgaatacc tttacatatt atcaactggc cttttcattc  34383
ctgagttgtg agtaaatgct ctgtctccca gactggagtg cagtggcgca atctcgcctc  34443
agtgcaagct ccgcctcccg ggttcacacc attctccagc ctcagcctcc cgagtagctg  34503
ggactacagg cgcacgccac catgcccggc taattttttt ttcttgtatt tttagtagag  34563
acaggttttc accatgttag ccaggatggt cttgatctcc tgacctcgtg atccacccgc  34623
ctcagcctcc caaagtgctg ggattacagg catgagccac cacacccggc cataaatgca  34683
gtcttgtgtt ccccacttcc attcctcctt tgacagtaca gctatgctag tctgcgtagc  34743
aaattgaaaa aatatgacct gtgggattta aacaaaacac agtgtcatac acattttctg  34803
gtaaacttaa ccaaaaggga cttgggttcc ataactaatc accaatgcct cagtgatctg  34863
taactccttg taggtacctg atcacagtta ctaaagggaa agaggagcga ggaatacaag  34923
agcaaagtca agccagacat agattttatc tctttgtaaa caggagttca gaagaccgct  34983
ctgaatgctg agttagcatc agcaataata gaaatatatg cagattgttg atttgaagtc  35043
atgcaaagat atctttttca tccaaatgga ggcaaaagca tcatagagca ccagagggct  35103
aaatccaact gtagcagcaa aaggtacaca gaaaaataaa gcatcctgaa ccaacgcact  35163
gactttctag ggcttatcta atttggagct atttcctttt cttatttcat tcagcaaata  35223
tttattgaac acccacaatg tgtaatctgt tctattacat tctgtggagg aaatacagaa  35283
gtgaatgagg catggttctt acctacaagg aatttctaat cttgtggggg agactaacat  35343
gtaaacaata aactatagta tgaggattac tgaagaggca tatgctaagt ctcagaacat  35403
tgaaatataa gagttgggtt tgacatgggg aaagaaatac cttcttcact gaggaggtag  35463
cattttgagt tattgttgac atgtgaatac gattttgaaa agttccaaag aatgaaaaat  35523
tccacctaca ttggtgaagt actaagatta aatgcatgat agcttgaaga cacaaaaata  35583
attatttata aaccattcca aaaatcattc agggaattcc aataatacac aagtttttaa  35643
acacatttct gggtaatttt gagtaataag gtcttaatct cctctactgc tttcaattgt  35703
ttttgtggcc ttctttattt tgtgggtatc tggcccagtc ttgtctgtag tgtattatgg  35763
tggattggat taaacatgtt ttgcaatctc tggagtgatt ttaaaatgac ttgtgttata  35823
```

-continued

```
tcagagtttc ctaaagggag attaatttgg cttaatggta agaacggatt aaagttatga  35883
gataccagac actgggaaaa cagttagaag cctgttgaga ctcttcaggg cagttgttgt  35943
gagaatgaag ttaagacaat gggatagaat atgaaaaaaa atgaaacaaa catgagaggc  36003
agtctgaaga tggaagttgg caactcatca aatgtgagaa atttatagga acagaaaaga  36063
acctgctgat taatataaat tttctgccaa agaaagtaca gtggctctcc tcagcaaact  36123
aacatgggaa cataaaacta aacactgcat gttctcactt ataagcagag ctgaacaatg  36183
ggaacacatg gacacaggga gtgggacatc acacactggg gcctgttgtc gggactatgg  36243
gagggagacc atcaggataa atagctaaag catgtgggac ttaataccta ggtgatgggt  36303
tgataggtgt agcaaactat gatgacacac gtttacctat gtaacaaacc tgcacgtcct  36363
gcacatgtat cccagaactt aaaataaaat taaattatta aaaaaagaaa aagacagtgc  36423
ttgtcttatt cgttttttc ttaaaatggg aaatatgtaa tatatatcaa ctgtagtgta  36483
tagaagggtc atgatgaatt ggacaaagat acgtggagtt tgaattgcta gaggagtacc  36543
cacgtgcagt tgtccagcag aaatcagggc ttgttcccca acatgctatt cacaatcagt  36603
ctactactct caggtatttg tttttctgtg tggctatgca agcaatagat acagtttatg  36663
tgaaaatgtt ttagaaaatg tcttctggaa taattaaaag catacaaggg aatgtaaatc  36723
tcttaatgtg acaagacctt tttgccacaa taaacaaatt cattagttca aaaaatattt  36783
attgtgtgcc tattgcagca aacaaaacag acgaagctcc ttcttgtagg gaacttatac  36843
tctagtgata tttagtatat attttgacaa ttgaaccaac aggatttgct gacggattgc  36903
cttatgggta taagagaaag agaggagtcc acactttcat gccaggtagg ttgatggagg  36963
tgccatttac tgagatacag ggccgtagag gaggagtgtg tttgcagcag ggaaggagaa  37023
gactcaaaat ttggttttga tcatactaaa tttgatatag tacaggtaag tgtatggtgg  37083
ccattagaac atgaaggtaa gagtttagat aaggagacag gtatggtgaa atacatccaa  37143
tatttataac caatattatc ttttgtgtct gtaccttttt atacattccc catatatatc  37203
aaagactata gaagggactg gatagtgaat aagtgattat acataaattc ttttttacag  37263
attattttgc tcttgatttc tcctatgtaa atcatcacag ctacattttt taaaatctta  37323
aaaaggatta ctttgaacaa tgcatttaaa catccagaaa acaaaaacag gagtgcatgg  37383
taaaaattct gatttcagaa cgtatgcctg acttatcaag tcagaatttc agggagtgaa  37443
gaccctggaa tctacacttt aaatagagcc tcagttcacc aagtatgaga agtcctgtaa  37503
cagggaaaag taacctcctg ttatatttga tggaggccaa ttgacaagcc aagtagtttt  37563
ccatttgaca aaaattctat tgtaccaatg aagagctatc agaggggagt agattaaaac  37623
acctcccttg aaatggaatt tggcaagaaa gcaagaaatt acagcaaaaa gaccaataag  37683
aggaattagg ggcaatgaag gaaggagcaa agatgtggga acccaaaaag ttttcctagt  37743
aacaactttg aaattatatt tttagtatat taaatttaaa gtagagttat tagtgcatac  37803
attggtgtaa tttattatta tattaagcca acaatatact tttaaactta tacaactttg  37863
caaaaaagta caaatcagaa gtctgggcta agtagaatgc ataatagaat cagtagtgca  37923
aaatattgtt ctatattttc tagcttatga ttttctatat aaagtcagtc tttcaggatt  37983
aaaatgaatg tcacttcttt ttaccatgtg tcctttaaat tattaaaatc tatacacata  38043
ttgctataca tagtaaatat agttagtcaa ttatgtcatg gaaagaattg aagggttgtt  38103
ataaatttaa aggtgtttca ctatacaaaa acattgtgaa atactggtgc tgatttagtt  38163
```

-continued

```
ctagtatctc tgatatatta aatcataaat gtcaggagtt attggtcaca aaataaacac  38223
cagaattata tgacagtcta aaaacaaaaa caaaaaactt cagcaacaat attgaagata  38283
tggaagtgcc agaagaataa ggattaagac aatgaataaa aatctcttcc aaggactggt  38343
ctacactaag agtttagaaa tgcatttttt tttcacagaa atatccttaa tcctctatat  38403
agaaatgaga agaaaacata agactttagc aagctccatc taatccattt gcagacatat  38463
ggttacctat cttttcttca atatattgga gtttgcaaat attctacctt caaagaatag  38523
gtgttaccaa aacattgtct gcaagatttc taagatttga aatatatttg ctatagtagg  38583
ttagagatga gacattttta ctttaaattg caataattca gacttaaaat ataaaatgtg  38643
taagtctaaa tttttttct attcattgca aatatatctt atatatacat aaaatcctgt  38703
gtatactcat atgaacttta aggaaatatc agaggcatca gtaatagata acttgcatct  38763
cttttacatt cagttcaagc tactcaaatt ttaatctttt gttttcattc caacaaaaaa  38823
aattaggatc tgccttggct tttgctaaga aagtaattat tggctggaca tggtggctca  38883
catctgtaat cccagtactt tgggaagctg aggtggacag attgcttgag ctcaggagtt  38943
caagactatc ctgggtaaca tggtgagaac ctttctctaa acacacacac acgcgcacgc  39003
gcgcacacac acacacacac acacacacac acaaattagc tgggaatgat tacacgcctg  39063
tggtcccaga tacttgggag gctgaggtgg gaaaatcacc tgagcccagg aagtcgaggc  39123
tacagtgagc cgtgattcca ccactgcact gcagcctggg tgacaaaaag aaagtcatta  39183
tcttcaacac tgtgcataca cacttttctg catctagatc ccaaattttt gttttgtatt  39243
tacatagaac attgataagt aaggtaagta ttaattgata aaacatttca aactcatttt  39303
tcactaaatc caatggcctt cctcttttgc atgaagtctc taagaatcat gttaatctac  39363
atactcaatc tacgtaacaa ctggatatat cctgtagttg ttgcccattt ttctgctaaa  39423
tgttatcttt agcactaagc atgagtatga ggaaacagta tctgtgctca gattccagaa  39483
atgaagaaaa tgtactggag gtcttttgga taatggctac aaggtcacag ggactgactc  39543
ctttggaagc tcagcgataa ccattttcag agagaatatg tcaacatctt tcagtctaga  39603
acttgatgtt ctgctgagat ctaatctggg ggtgtcctac tattgaatag gtataaacta  39663
aataaaaata gtgagagaac attcatgtgt tcactcattc attccttcat caaacaaata  39723
ttgaaagtct attaattggc aagcactctt ctgacattag aaggagcaaa gataaaaaag  39783
atattatcat taacctcaag gacatgacag catcatggga aggccagaaa tgcaatatgt  39843
taaagtaaaa cacagtgtag tgtttactac taaagagata taaacagagt actgtggtct  39903
aaaatcatat atataacatt tgcttaatgg atgagaagga aactttaact tcaggaggca  39963
gagcattaag aaagtgaatg acaggagggt caaaagaaaa agccgacagt gttgcagagg  40023
cagggcataa aggagctaaa cctttgctac cttcagtttt tattatccac agaacgacaa  40083
agaaacaaca acaacaacaa aactttggat ttgagggttt tttgtttttc ttttttttt  40143
ttttcctctc attccaagca tcaaaccttg ggatttattt accttctagc aaaccaaaat  40203
ttatgggggc attcctatgg tcctcacctc accccatttt tctgttttac ctatgaaact  40263
tgatcaaaat actgtctcca catttctcat aaaatacatt agtttaattt tctactatta  40323
ctttctttta gttgatttaa aaaaaggtca tttatgacct atttaggtta gcatcattaa  40383
ttttatcaat gtaagaatat ggtagtacag tgtgaattcc attaatggat atgttgatac  40443
catgggtttc tctgaccttt cctcttccgc tcctccctga tgattggttc tgagcttatt  40503
atcatgtcag caatgaaaca gaaaagggag aaaaatctca agtaggttgt ctgtctcttt  40563
```

-continued

```
aacactgaat aaagattttt ttttctctaa cagacttaaa aatagtgccc taaaaatgtt  40623
ttgtttcatt tgtctgaatt cccattcttt cccgtgatca tagatagttg agctaaaaaa  40683
agaaaaaaca aaaaacaaaa ataaacattg tgtcctacat ttgtattaac tttcttagga  40743
atgagaagta gaatcttaaa aaccttagaa tgggagtttc caagctagct tgcaggcttg  40803
agttttattg ataatacctt taggatgcat gtattattag aaacatcagt tatttacaag  40863
ttcacctatt taaaagtcta ataggaaaaa atatttcatg ttgctaagta tgtgacttcc  40923
ctttaaaaga taataatgct ttccctttaa acaacaatag taaaagaagt agagttcctt  40983
ttaaacacat acttttatat tataacccat tctgtttaaa aaatagcagg catataatct  41043
agaaatgcaa ataatttagt gaaattttta aaattattct acatataatt aaatatggat  41103
attcgttttc aaatatcaaa taataaaata tgtctgagat gctgactaat ccttaattat  41163
aggtgtgatt tctacttcac catcaatact atggtactcc aaatcttaac atgagtctga  41223
ttttctaata aacatgatga aaaaagttat ggaaaaattt tgagatttac tttgggaggt  41283
tctattgtgt tctgttcagc ttcataatat tcagtttcta tgagtttggt atttaattat  41343
gtgtgtttgt cattcagtag gctggaagta tgaccattgg gagatcaaaa cgataagaca  41403
ttaatgacag tgctttatca ctgaatctag tacttttttt aatgaaagag atgttggcct  41463
cttgtattgt tataaaacaa cacaatttta tggctttaaa ttaaagtaca atcataacag  41523
aagacaaaat tagattaaaa aacaaacatg gagtgactca tataaaatat ttagaaacca  41583
ataatacaga tagagacaca ttagttcctc tagacattgt gttttccagt aaaatgatca  41643
ccaaacttac caggaaaatg ataattatca gattatttac tttcagaatt aaaggcagga  41703
agagaaaaaa atgaatgaag aggaaacaca gtaaccatat aggacaataa gagtgaatga  41763
agataaaatg aaaaatcaat aagatatcga ctttcttaaa agacaaatat cacaatagga  41823
aacacctcag aaagggaaat ctcaagaaaa taataaactg aaagaagaaa acatatcaaa  41883
acaacttgag gactgacaaa gttttaaaat gtatttagat aaagatacca tgaggaaagt  41943
gatcaaggtg ttctaggtaa tcactgaaga taaaactaaa aatagcttaa attaaaatca  42003
gatagagaga aggtaactga aacaggcata gaaagaaagt aagaaggaat acaatcctga  42063
acatcttaac aatgtctcaa atgtcaggaa ttgatccagt ttttggctgc acaacagagt  42123
ggctatagtt aacaataatt cactgtatat ttcaaaataa ctcaaagagt agaatcggaa  42183
tgttgctaac acaaagaaat gataaattct tgaggaaatg gatatcccaa ttaccctgat  42243
ttgatcttta cacattgtat gcttatataa aaacagtatt catggccggg cgtggtggct  42303
cacacctgta atccctgcac tttgggaggt cgaggtgggc ggatcacaag atcaggagat  42363
tgagaccatc ctgtgaatgg tgaaaccccg tctctactaa aaatacaaaa aattagccgg  42423
gtgtggtggt gggcgcctgt agtcccagct actggggagg ctgaggtggg agaatggcat  42483
gaacccagga ggcagagctt gcttgcagtg agctgtgatt gcaccactgc actccagcct  42543
gggcgacaga gcgagacttc gtctcaataa aacaacaaca acaacaacaa caaaaacaaa  42603
aacagtattc ataataatta aaataaatta tttttaaaat aaaataaaat atcagtaatt  42663
taaatttttc ctatagcata gagatctgta attaatactt gtcgatcatt gttgtttctg  42723
tcttcccaac aactacactc ctgtttcttc acattccccc ttcttctaac agcactacat  42783
ctttctttag gaaactatcc ttttgccatt tcatgtatat ggtggggtgg gggagttatc  42843
aatcacagta ccccagcaga tgggaccaga ggcaaaaatg cctgaccttc tcccatcccc  42903
```

-continued

```
caaccacagc agcaaatgaa ttataatttg atgcacaagg aagtatcgga gcttttgtgt  42963
tgggttttac atatcacctg tgggagataa atgaactttt ccccacctaa cctttagcca  43023
cttgggatga ttagacatag aggtgcctaa gatctttccc tttgccacat taaaaacaaa  43083
tcatctatgg cacgagcata caagaccagc tttcagagac acaaaatgat ggagagaacc  43143
atgatactag ttttagacct agtcactgag actttctctg ctccttccca gttacctgag  43203
ctttattttg tttacattta tcagatttga atggctgtac ttcaaagtac tgattaaaat  43263
aggaaccaac ctatatgatt caggtggtga gaaggaagaa aaagagagaa aatgaggtta  43323
acaaaagaga ataaagaaaa agaaagaagg aaaacaagaa actctgacta cctctcctct  43383
ttgacatagt ttacacttct gacagattgt tcttctctaa atttatgtag agattagagt  43443
gaggatgatg tatgcactgt agcatgggtg gtcttccagg aagccttgac tgaatgaggc  43503
aaggagtatg ttgctccctc agtaacctca aatttacctg caagcctgat aaaaatctaa  43563
cactaacact aaacccaatc ttatctacag ccctaactgc accctaatat taacaaccct  43623
acctctgtac ttcaaaacta aaactaattc tgattttact cccatctgcc ccttttaccc  43683
taaaaccaac tgtaaaacta aatttaactc taaacgtaat cctaaaacta agaattaact  43743
aacaatttta tctctatacc caactgttaa ccccaagcct aactctaatc ctatctctaa  43803
cctaacatta accacaaacc tacttctaac tctaatccta accataacct caaatctaac  43863
tctgattcca attgtaatct aaacaccaac ccacccctac ccttttatcc caaatccatc  43923
tgaaaccctc atcagaacac aaattccaat tctacttccc accctgactc tgactctaaa  43983
cataggccca aatataactc taactcgaag tcaaaaactt aacaaacctt atcttgaaac  44043
tcaaccttta cactaacccc aattctatct gtaatcctaa ccctaatatt atcatcaaac  44103
ctatgtctaa cacgacctcc aacccaaaac caaaactaac ctcagaccta actctacatc  44163
taattataac ccaaacccca ggctgctact taccataacc ctgaaactaa gcttgatcct  44223
ttctcttttt tttgagatgg agtctcgctc tgtctcccag gttgaagtgc agtggcgtga  44283
tctcggctca ctgcaagctc tgcctctcag gttcatgcca ttctcctgcc tcagcctccc  44343
gagtagctgg gactacaggt gcccgccacc atgcctggct aatttgttgt atttttggca  44403
gagatggggt ttcaccctgt tagcaaggat ggtctcaatc ccctgacctt gtgatctgcc  44463
tgcctcggcc tcccaaagtg ctgggattac aggcatgagc caccacgccc agccgaccct  44523
ttctcttaac ctacactaac actaactgta aacctagctg taactctaat tgtaaaccta  44583
acctgattac tcactacaaa ggtccctcta attctaacaa gaaactcaat cctatctcaa  44643
ttccacccaa ccccaaaagt aaatctaaac ttaaacataa ctcaaaatgt atctcaaacc  44703
ttaaccttca cgaaactaca tgtagcacta atgtaaccct aagcccaatc ctatcagtaa  44763
cactaatgct aaaacaaacc ccaatctgta tctctacccc atcactgaca ctacccaaat  44823
cccaatattt aatgctaatc attaagtctc aaactaactc caaacttatc tttaactata  44883
tctccaaccc taaccctaac attaacccca aacttatcat taatcataca tctagctcta  44943
aacctaaccc caactttaac tcttacccta gctctaaaat taaccccaac actatctcaa  45003
actgtaatcc taatgctaac gttcaggcta cttttaaccc tcaccctaca caaaatcctg  45063
cacctaaact caaccctaac tttaaaccta cctctaatcc aaacactaaa tttaaatctg  45123
gatcacgact tgggcatact agcacccact agtgttctgg gtgtcatttc tttgcttcac  45183
tctcatccag ctttctttac taattttgga taatgaatca gaaaatagtg gtgtggaatc  45243
agggtctttg aattattgta ttatccagag tttgtcctgc tgcaaatgat aaaacactga  45303
```

-continued

```
aaattagctt aacaaggaaa aaaataaaaa tgtgtgtgca ggggagaagt aggagagtta  45363
ttggctcaag gaacagaaga attcagtact gagtttcaca aatacctgga ttccctagtc  45423
cccatactgc catcaggatc caatctgtca ctcactccaa tctcttcctc ctccctgttg  45483
gattcattgt taggtttcct gtggcaagat gaaatggcct caggcctgta acacaatagg  45543
atcaattaca acagaagata gtatttctgt tttcctggtt gctcaagcct aaattccaag  45603
attagtttat atcaaaccta gttagttttg ctcatgtaag ggattactgc aactgggtac  45663
actaatatga agagtgggag agttggttaa gggggttctc tgaaaggaga attaggttac  45723
tgttaatggg agaatgagaa atgggtattg taatgacaaa aacacacacg actaccacaa  45783
atgttgagga agaattttcc tttatgatca tctagcccaa ctttttaatt tctaattttg  45843
tggttttgac cagtttttttg tttttttttt taatgcagca tgtcataaag ttgggaatac  45903
ttcacatttt gtctttgaaa atttggagag tacttaaaaa gatttacaaa ggggaggatt  45963
gaattatttt aggaatgtaa atggtggtct tctgtctcag gcaatgtaga tgcttgctag  46023
aaaacagctg actcatgact gttttctttc taattcatta atatgaatta tttcaaactg  46083
caaagttatc tcctttcttc tcctaatcta tccacttaga gtatacatgt tcaaattaat  46143
gtattgaact aatttttcta gtaatacatt ctatgcatta caaaaaatagc agtgggaagg  46203
tgaaaacaaa atgcagttat gcatttatct ctaaatgtgt tcaacatctc ttatgcgtac  46263
ttcaaaataa ttacatttgt ttaattttga aaaaaatatt aacaagaagt tgtaatttgg  46323
ggaaaattta aagctggcga aaaaggcttc atcataattg acaatatggg aaaatactgt  46383
attaaaatcc taggtttctc ccttgtttgc atgaaggaaa tgaaaaaatat ataagggaag  46443
gatttaatca gtcaggcaaa aatctaaatt catcacaggt ttattcactg catactatca  46503
atgtgcccag tacctgaatg aatatattaa agaaatccac ctcttgtaca atgaatgtaa  46563
atgagcagag tgtggtgatt aaaggttggt atttggtgct gggtagaccc agctttgcca  46623
cttactgccc aagtaaatat tgccatccat cagatatctc cacctatcag acccaccctg  46683
ttgtaataac aagattaaaa tctgtatcac taaaacttta aaagaattta tagccgaatc  46743
tagaaatctt tcactataat ttatctttcc ttaaaatgtc gttttttttt caattttact  46803
atatatgttt ttgtacttgt ttgctgtctt gtgtgtgtgt gtgtgtgtgt gtgtgtgtgt  46863
gtgtgttttt gaaacggagt cttgctctgt cgcctaggct ggagtgcaat ggtgggatct  46923
tggctcactg caactcccgc ctcctgggtt cacgtgattc tcctgcctca gcctcctgag  46983
caactgggag tacaggcgca caccaccaca cccagctaat tttttgtatt tttagtagag  47043
atggggtttc actatgttgg ccagactggt gttttttgaa aagacttttt cctgattcag  47103
aaggtgggac tcacaattgt aattctgcta atggttgtct ttcagtctat caattgcttc  47163
ataaatgcat ccactgttcc ttcttcttct gccctgctta taattttcca tgagtccata  47223
tatcttttta cactgtcttt agtcttattc actaaattaa aaactaattt ttgatatttg  47283
gtattcatga caagacaatt agtagaattt tgatgcttct tgtctgcaat tacagaatca  47343
atatattttc tatattattg tatattctct aaatcttatt ttgtataata gctttcagca  47403
tgttctttaa ttctgtttag atatttagaa agtatttgtt gttattctgt aatttatttc  47463
aatattcaat tatagtttaa tattttgtta tctagtgttg tcttgatttt gatatacgta  47523
ctgattttgt agatccaaat tcctctttcc tatcagagaa tgcaattttt tacttggata  47583
aataagaatc atatctcctc tgcttgctac cgtattgcat acattcatgg gtagagaaag  47643
```

-continued

```
agttaagctg atgagagtag gaattaaggt agacctgttt ggtaggttct cccagatttc  47703
agaggacaga catctttttt tccctgcctt ggtcatttaa actttttgga ttttggatta  47763
agtgtaggca gggaaaatgt atcagatatt tttatttttc tttggtgcca tttgtccttc  47823
tctgctttag gcagagaagc atatgtagtc caagaatgtg cttttctatc cagctacatc  47883
aataataaca attagtaaaa ttctacttaa acttagacct ttgctgttct cttttctctg  47943
cttgtgttaa gtcatgctca tgattctggc agttttccac agtaccatgt acagaaagct  48003
tgaataaggt acatctagaa tactcatata tgttcacttc aaaaacacat ttttgtggaa  48063
ttctaaatgc aaatctcaat agtgcaattc taatttacaa tgagaaaaaa ctaagggatt  48123
ttttctggtg attctttttg ctcatttata aatatgtttt taaatggtaa gcaaatatat  48183
aaattaagct tttccttacg tagctacatt gatttactag tggtggaaaa ggttaagcaa  48243
aactaatttt catgagtgta aatgaattag taagtgacat atgcaatgct taaggggaat  48303
ttgcataaat ctatgactga tactcaacct cttgcttagc gagaagataa ttaaaatatt  48363
ttatacttca agaagaccta gttttccaaa ttatttacat ccacaaactc agattttata  48423
gcaagtaaga aaagttaagt cagaagcata tactattaac agctacttac attgctcaaa  48483
tttaatatac gattgctgct tttgttggtt ttgaaatgtt tcttgaccat ggatctgaat  48543
aatgaagtta ttcaagaagc aactttaaga atgttatatt cttagaaaga agctatagat  48603
acaataatat taaaaaatta aatgtaagtt cctgcactca cagtagaggt aagttcaagg  48663
ttataagaga gcttatagat tctgagattt ggaaagaaga gaatagaaaa aacttttcag  48723
attaaataat gtgttaattg tgcttctaaa acagctttgg tgatcttaat aaaataaata  48783
ttgtttttat ttccattttt gcttttcaga caagaaatgc tacttgatgg ctgcatatat  48843
ttgttttgtc tcttttcacc acctactctt gctaaatact ctcaacccac tcatgaaatt  48903
aaagcacatt ggaaaacatt tatcaactac ctgtaaatac aacctatgct ctcttttgtg  48963
gaggtgatag acattcatca atggaatagt tgatctaaat cctagtcttc attatcttgt  49023
tttatacatt cttgtcttaa tcagtttggg ctgctctaac acaataccat agactaggtg  49083
gctgatgaac aacagaaatt tgtttccgac tgttttggag actgggaagt ccaagatcga  49143
attttatgtc tggtgagggc ctgtttccta attaataaac atctgttgtc tcatatgtcc  49203
tcacatgata gaaggggcaa aggagctctc tgatgtctct tttttagaat attaatctcg  49263
ttcatgaagg ctctgctctc atgacctatt ccttcccaaa gggcccactt ccaaagacca  49323
tcatattagg gattaggttt caacaaatga agccaggggg aggttggtaa acattcaatc  49383
tatagcaatg cctatctcca ggagctgcct gtggaaacac ttttatctga tatggtagtt  49443
taaagcatgg cagggataag tggtatgagg aaaactctcc ctgccaccca acgcacacat  49503
cccacttaag cttcagcagc tccaatttta tctgtgtaat atttggttcc acatcaaagt  49563
tgttttgaat atacttccat taccttaaaa aatgtaaaaa cactgcttta aaaagccaag  49623
cctattccct tttcattatt cagagttctt ccagttttac cgttacatca aattagaact  49683
acataattag gaacccctct ctaaatttgc ctctatacag agaaaaactg tgcctgaaac  49743
tttattaaaa ctcaataaag gaaatatgta tgaatgtata tatataattt ctctgaagga  49803
cagaatttgt acttcgttcc atacataaaa actcatttga caaataacaa gcatagctcc  49863
aagctcaaag aatagcttaa tttttcctga ttagtttata tctctcttat taatcaatga  49923
catttaatat tacaaccata gcttggggtt ttagtttatt tgctttctat cttttttata  49983
ctgtcggcct acctgtgccc aactatgtta tagtcagggg ttggtaaaat aaagacaaaa  50043
```

caaatcctgt cttcctggag atcaccttca ctgggggttg agaaacaata agaacaagta 50103 gtaagtaaaa tatgtacatt aaaattttag atgaagttaa gtgctatgga aaaaagtaaa 50163 atggaagagg tgttatggag tacctgttcg ggtatgggtt caatttacaa gtggatggtc 50223 accttctcac tgataaggtg acatttgagc aaaagtcttc agcaggaagg gagaatgcca 50283 tgcagttatc ctaggaaaga acatttccaa tataagtaac agccagtgca aaagccctga 50343 tgtagatgca taccttaggt atacgagtaa cagtaagaaa ttagtggcac gaaagacaga 50403 tgtacttgga aaccaaaaag aatctctggt aagaaattgt aagtcattgt aaggacttaa 50463 ggtttttttt tttcctctcc aaatgagatg gagatccatt agaagggttt gcgtagagaa 50523 ataatatgat ctgacttata tttaacagga ctactctttt gctgaattga aaattgtctc 50583 taagggtgta tatcagatct tatattgatc ttacccttct ctgttcaata tttaacacac 50643 aagcctgtta aatagtccat tcccaacttc tgtgacttct tgcttgagag cctttctatc 50703 ccctctcata agggctgtga gggcctaatc tgcttaccta tccagcaggc tgggaatgac 50763 acagagcact caccaggagc actctcaacc tatgactcat ggaagttggt agatgaatac 50823 cccagctctc atattccttg ggtggaagag ctctgagatg tgtgttctac accattaccc 50883 agagggcacc ctctggatta ggctcaagtt gctgacagta gtatcttgct gactaacata 50943 atttttatta attttctccc catttgacct tatttctcca tttttctaat agtgttcatt 51003 ggtatcactt ccaaaataaa ttacctttac ttgaatattt ttcttagaat cttctataca 51063 aacctgagct aatactgggg caaagagtgg aagcagggaa atattttgta ggtgttgtgg 51123 tgatgtagga cagagcctga tagcttggat caaggtggta gcaaaggaga ttgtagaagc 51183 tatcacactc tttatatatt ttgaagacac agccaagagg tttggtggaa aaatggattg 51243 tgagaagtaa taaaaagagt gggagagaaa gtcaaggatg tcaccaaagt tgtcctaagc 51303 aagtggaaac ttagatttgg gagaatcaaa aatcctaaaa tatccaaatc ctctcccctg 51363 ccttcccctc ccctcccctc cccttccctt tggagatagg gtcttgctct gtttcacagg 51423 ctgtagtcta gtttcgcgat ctcgactcac tgcagcttcg accccctggg ctgaagtaat 51483 tcttctactt tagcctccca ggcagctggg actacaggat tgcactaatg tgcccagctg 51543 attttttta gttttttta tttttagtgg agatgaggtc tcgctatgtt gcctgagctc 51603 aagcaatcca ccctcctcag actcccaaag ttctgggatt acaggtgtga aacactgtgc 51663 ctggcccaac attttatttt caaatattta agttttgaat gtctattcga taaccaagta 51723 aagaagtcaa ctagaatata tgagaatgga gttttctaga gaagtctggg ttgaggatgt 51783 acttttggga aatggagcac atacttggta tctaaagctg tgagccgaga tgagatcact 51843 aggtaggtaa atatagataa attagagaaa atatctaata attgagacat ggagtactat 51903 cataaatttt gaaaagacaa gaaaatgtga gagatcgaga agaatggctg gggaagaagg 51963 aatctaaggt agtgaagaga ttgaaatgtg tcaaggagag aagagagtaa ttagctcaaa 52023 tgctactgat aagtaaagtg aaatgtagaa tgaaagtcaa ccataaaatt tggcattatg 52083 gggatcatta atgaccttaa agaaagtgct tttagtgtag taatagaaag atgcagaaag 52143 taagtagagt gaattcaaat tcaacagaga atagacagag aggaattgaa gacatttata 52203 ctgacaattc cttccaagac ttctgctatt aaaaaaaata aaaaaagaag gagaaatggc 52263 aagtgtttgg aggccaattt atactcaaga ataatttctt gagttggttt tttgtgtttg 52323 tttgtttttg attggttagt gtgtttattt tttagacggg attggagaaa tactttcatt 52383

-continued

```
tgtgttttta cccatgtttt cagccttgcc ctggctgcct ggtataacgc aactctattt  52443
gttattctgc tattatagtt tccctagctt gaattttttt acacccttat tataattgta  52503
gcgttgcatg cctatttcaa aacatctcat gtaccccata aatatataca tctactatgt  52563
acccacaaaa attagaaata aaaaaattta aaaattatga ttttttaaaa tttgttaaat  52623
aatgtttact gactctttta tttgttgaaa tcattcattt tttggaatat caggtccaat  52683
taaatattta atcagacttt gagaaggatt taataagacc aataaataac caagtattag  52743
ttgaaggaaa tttcagatat tttggtagca gaaggaactg agttatggct caagagtttt  52803
ttaataagtg tgagtggagt tatacaaact actcattaaa atctttattt gaatttgtaa  52863
tatctgaaac cattttcata ttgaagaatc acttaaaata gtcataaaat gtaaaattgc  52923
aagacaatta aaaacaaaaa tatgatttca cgactgtgat agtacctgag aaatttcttc  52983
atctccttag taagagaagt attacaccta tttatagtta ttttatgaaa ctagctaaga  53043
tgaattatgt agaaaagata cagattttca aacagaaact agaattaatg gaagctatgt  53103
gagactataa agagtttaat agttattttg attttttttt atgagtgcaa ggagtatagc  53163
gaaaaatagc atctacctat aaggatttgc aaagccagta atctttctaa aaatatcagc  53223
aaacccagaa ttaaggctta tgttcttagc tcattgtaac tagatcaaaa ataaagaagg  53283
ccaaataaag gtatgtgaca tttgttgaaa acctgaagtg tcctatatgc agaaatattt  53343
ttatcattta attaatttca gaaacttctt aacatgacat gatcctcttg aaaagatcac  53403
atcaaaaaag gcaaaataat tgcataatta ttgtagaata atttttgtgt gagtattttt  53463
gacttagtgt aagtttccaa gttcaggatt tatcatgcag tgaaaaaaaa tacacttgtc  53523
tagaagacag gagacttcat tatattcctc tctttacaat taattaacgt aagaccattt  53583
aaaatatgcc taattttcca ggcattggtt tgctttgcta taaaatggga ggatagaaaa  53643
taactttcaa aatatcttat aaatctaaga atctttgcat cttataaatc taagaatctt  53703
tggaaattca tagattattg agatggagtc tcgttgctat gcattgtagc aaagttggaa  53763
ataaattcta aattttattt catttatatt gatcaataaa ttgttacatt tcactaatac  53823
aataaggaaa atttatttta cctgagtgta tgtctagctt gtgaaataaa aatgctcaat  53883
tatgaaagca tttattgcca ttttgaatga aaaatgtaat atgtagaaca gaattttttt  53943
tgccttgaac tcagttaaat gtagaaattg ataaggactt gcattttcat gaacttaata  54003
attatctgtc ttttcaatgg tctccatatc aagtctgaga aatatggatg tgatttattt  54063
taaacctcac catttgaagt aaatctaaag attccattag gttatgagca tataggatac  54123
aaggaccata ttgacagttt tgtgggattg tattaggata aaagggtagg aacaatgggg  54183
agaaaattat agcttacaat agggaagaac caaaaattgt tgcaaaatga tggaacaggc  54243
tgaaagaatg atataacctc ctaaacactt caaatgttta agcagttcat tgtaccaggg  54303
ccattgtagc aaatatttc tgtcttgggt ggaaggtcag tcaaggtgac tgataaagtt  54363
tcttctaacg ataaaatagc acaactcact ttttttctaa cctctaagag tatattaata  54423
tcaaaagaag gcaagcaaca aactacttct gaatgttaat atatatctgc attcatttta  54483
aaagtctgct acaactacag atagaggaac agtttgtagt atccgtgatc ctagaacaaa  54543
tttagctttt aatatcttgt caactttttt gttttagtat ctcttccttg gaactagctg  54603
agctttaatg gcatcatcat gtgatatgac ttgagattta tatttggaag agctttgaaa  54663
aatcacggat tgttacccta atgaggtgtt attcagtctt ttaaacaaga gcaatttctt  54723
tacaaaaagg agcagaattc ttaattgtat ctgtaaacct ccatttaaga atgaattact  54783
```

-continued

```
tggctgggca tggtggctca cacctgtaat cccagcactt cgggaggcag aggctggtgg  54843
atcacttgag gtcaggagtt tcagaccagc ctggcccaac acggtgaaaa acagtctcta  54903
cgaaaaataa aaaaaaaaaa aaaaaaaaaa aatagccagg tgtggtggtg tgtgcctgta  54963
atgccagcta ctcgggaggc tgaggtgaga gaatcacttg aacctgggag gtggaggttg  55023
cagtgagcca agattacacc attgcactcc agtctgggtg acagagcgag actccacctc  55083
aaaaaataaa aaataaaaaa aaaaagaatg aattgctcat aaatgtgcct cactgatgat  55143
taaatttaat cctgcaagat tatgtctttt gatggaaatg agagggttta tacaaagttt  55203
tattcgtgat gttatctatg tcatctattg atttctgctc tgattcatgt ggatgaagtt  55263
acacctcaca ctttaagctg gtgtcagtct tcccattttc tgctgtgatg tgtactcaag  55323
atctccagat tacatctgta atgtaatgca gccatgattg tttataggta catttagatg  55383
aattcaatga tgagttatgt tgtaataagt gtcagattta gatgaaccat acaaataaaa  55443
gaaccatgca ttaaaatgac aaatgtgtaa aagcattatt tgggccttaa gtcaaggccc  55503
aaatgtggat actggtactg agacatcttt cagaaaggag gtatgaagta ctgaaaaata  55563
tttacaaaat gaagactact tttatcttac ttatcatgat tcttttatta catatgcatt  55623
ttctaagata actatagtgc attagtttgt actatgttaa tataataata gggtaaatca  55683
aacaatgttt tctaaatcca ttaaaataga gttccctaag ggagttaaaa caattacgtt  55743
ctactgtata ttattggcat gcttcaggag acatgattta atctctagac tatcagaatt  55803
caagaactag tgagtcatat aacaaaggag gcttaatcat gccatttaag tgtcatggaa  55863
aaaggtttat tggtcaggaa aaattaatta gaaaaaagtt ataaaatact tcactaagaa  55923
aataaaatgt caggaagccc acttagacaa tgagtgaaaa tgaaacaaat tcaagttttt  55983
acaatatttg gtttctatag gattgcttca ttgttttggt ttttgttttt ccccataagc  56043
tgatctcaga aacttttcct ctacatgaag aggctgtcat tttttcatgg tgtgtgtttg  56103
ttcacatgcc acacagacaa tcaattatga agaaaggaga gactcgtagg aggcagggcc  56163
aggctgttca cacttttaaa ctaggtagcc acaaatgagg cttagttaca aaaacttgaa  56223
aactggattc ttcccaatgt attatacatc cccaaagaaa tgatgaagtt ccttactctc  56283
ttctctttgt ttttgtaaat cttaccactt caagtgttgg caatacttac tttaaagtag  56343
gttttcatat tggcttagat tttttttca ttaacttgca atttgtggtt gggaaatgat  56403
ctgcttttg tttcaggttg tttaatgttt tccaatgtaa tattcttctt gcactccagt  56463
gagtttattt acaaaacatt taatgtcatt tgcgtcttcg aagaacaatg tattcggtta  56523
gaacaaaagt gagctcctgc atagagctta tgatggttta taattggtaa attattacct  56583
tggtcaagtt tgtaaactaa taaagggagt agaaaacttt tagataaaaa aaactacctc  56643
attcaaaggg accgttcacc cacaaaatgc ctttttgttt atcttttgga atgacaccat  56703
tggaaactca gtatggccac ttttatggta ataataaaag tcatatataa aaaggattat  56763
tagaaatgtg ttatttctta ggcaggtatg cttatttaaa gtatgtatgc atacatactt  56823
taaactacta aatacaaata aattagtagt acagtcatta ggattgctct tagtttgtta  56883
gtgttggaat agacttttgg attttcttcc tagcttagat tgatacaatg tgatggggac  56943
ttgctctcca aacacaggaa taggtggcct gcagacacac tctgtgatgc tgtaattcta  57003
atcctcactg aatatatcag ggtggacat ctggcctggg gcaattcaga tactttttct  57063
taaaatttat actacaaatt caaaagtggt aactcatctc tgccatcact tatagtagaa  57123
```

-continued

```
taagacccac tgttgcagtg gggaattgag aaacccagtc cacagggaga acaaacatgg  57183
agaataaaat aagtaaatta gaacaggaaa aatgccaaaa cacacagaca tgaccctgat  57243
agttttccat ttcctgatca ctgtcccttc ctgtggctgg ataaggaact gtctctaggc  57303
tctgtaagac atatttgcat ccttacgaca aatttctact ccttttcata aactagactt  57363
gggttcttta acttgcaaca gcaacaacaa taaacgattt tgttgggtac aatctgattt  57423
tattaacttc tggatttaaa agcccttcta aatgttgatt ggcattgttt ttacttccta  57483
agagtacgct catgcaccac atagtgatgt tttggtcaac gacagactgc atttacgact  57543
gtggtcccat aagattataa taccatgctt ttctgtactt ttctatgttt agatatgttc  57603
agatacacaa atgcttatca ttgtgttata attgcctaca gtgttcagta cagttacatg  57663
ctgtacaggt ttatagccta ggagcaattg gctataccct atagcctagg tgtgtagtag  57723
gctataccat tagatttgtg taagcatacc ctatgatgtt tgcacaatga tgaaatcacc  57783
taaggatgca tttctcagca tatatcccag tcattaagca aagactgact ctattattag  57843
gtctatttta ttctatagca tttgatcatg agatatgtga aaataaatat aatttttaga  57903
agtacaataa ctttcaaatc ctgaatgttc tgtactttcc atctcacaag cattttgcaa  57963
agcatcaaat ggtataagcc agattactgt taaggcaact tggaattaat atgctgctca  58023
gttctggaaa aggcatattc tgtaaatata gatgagagaa tatagacttt ttccctctct  58083
tcttacaatc cacattctat tcagtatttc atttacttga ggggttatat gctacttatc  58143
tttatctgtt gtggagtgag gacacattcc aaatgccttg gtattattaa aagcccttca  58203
tgatgtggcc ccatctttta tgacttttcc ttttcaactg tgccctctag ccttatttga  58263
tttctctcaa attcttaaac acagcatgct tcactgacct ttaagccttt gcacatacag  58323
tgttgatgtg gagcttcctg accaactcct aattctcctt caggcctcaa tttaaacatc  58383
acttcctctg ggaagctttc tattattccc aaggtactgg gatatgttct tgcacagcat  58443
gctgggctaa tgtcacaatg gctaccttgt tttattgtta gtatttgatc agcgacacct  58503
tgccagggag cccctgagta ttgtctgagc agaaactatg gctatcttgt cccctgttta  58563
gcacagggct tctctaaaag tgggcttctc taaaagtaag tgctcaagaa caacaacaaa  58623
aagtgttaca ttaataaaca cacacacata catacaaaga aatacctgtc tttctccata  58683
tctcaagatc atgctgaaaa gccagcattc atgaacaaat tcctgtgcga agattgagaa  58743
tgaaagatga ataagaggta tctttagaac ccaattatgg ctgccgttgt tccctgagtg  58803
tgaggcttgc tgttagagtg acagaaggaa ttttgactac tcaagaccat acaaatttgg  58863
aaatgactcc aaagtaaaca tggttagata actacacatt ccattccccc ttttttattt  58923
ctatagaatc ccaactttgt tcaagtagta acatgcccag cttcagaaat gagtcatgat  58983
ttttctaaag caacaatatc aatcttcttt cccttcccca gtgattggta tggaagtgga  59043
catttcagca agttttagcc aataacgtga attctgtttt gaagcatcta agaaagattt  59103
tgctttctgc tgtaaatcaa aagcagaaac aggagaagat tcttttgggc ctctttccct  59163
cttcctggcg tggaagtagt tgtgagagca tatgataccc aaagtttcgg tagacatttt  59223
ataattatgt gatgaataac ctaaggataa ttaaacatat aaaagaatgg agaaagactg  59283
agtctgtttt actccacaag atgctgaacc aaccctgaga cataatttat ctggattctt  59343
aaataactag tgtctttgtg gtttaagctg ttctttgtaa acaaacatat cataagtgat  59403
taagtgatgt tatcttcctt taaggcaatc aaaatgcatc tgacaaatgg ccatctaatt  59463
taaaattcca actatgtaga catctcaaac aaagtcagta tctcaaaaaa tatactacaa  59523
```

-continued

```
aaattctcat gtgtccattg gggataactt ccaatgctct ttcattggta ttgtagctat  59583
ggcatttgat ttccaattgt atgtggatca ggtagttgca gggtgactct caagggcgag  59643
aagaaagtaa gagtacatga aaaaaaagag gaagagagag agcagacaag aaggaagaac  59703
aagacaaagt caaaccctag gtagaaataa gaaggagcta gtacagaaag caaatgccta  59763
aggtgttgga gaacatagaa aggtagagtg gaatgaaaaa gaaaaaaaca ctaaatagca  59823
gcacatagaa tcttggggtt tcagggatat tgtttatgaa aggttagaat aggcaacaat  59883
ctaccttgtg gcatcttctt aaaattatca acatataaaa caaacaataa ttatttaaat  59943
tacctgtcat atgggtcttg tcatttattt ataatttaag gagaattaaa actgaactag  60003
ttgctgggga gtgacatcag caagatggag atatagaaat cttcaggacc tccttccgtc  60063
catggaacca ctgactcaaa aatgacaaat ggaaaaaatt tactttctga gaaatcaaga  60123
agccagttaa gaggctcctg tatctcagat gagtgcaaag ccagctgcaa cagagccagc  60183
agaaaatttg ttgtactcac tcttcatggt cacttctggc atagcacagt gcaatctaga  60243
agaaattctc ggctcctgac tactttcttg gaaaagaaag agaaaaatgt accatatgtc  60303
taatattctg atggggatgg ggtgtgggct gctcaaagga ctagcttccg tcatgcctaa  60363
atacaagtgc taattgggaa gtccacaatg ttgggggctg cagaaaacaa gggcaacagt  60423
ttggactagc atgcactcat ttgccgcagt tcctcctctc acttcataga atgagtagaa  60483
gaacccttaa ctctcaaggt ttttttcctg gggagagaaa gagtcaaagc aattatacaa  60543
tattatggct ttgtgggagt gatgtatcca aaaaaaaaaa aaatgagttt ttaccacacc  60603
aatctcagag tgcagatgga acctagcata ttctagatgc ctgggggcca ttgagaacaa  60663
aagagagcta ggcaactttc agcagctcca gaagaactgt ggtaccacag atagacacca  60723
aagggaggaa gagattacaa gctcctgaaa aaagaaatga gcaattcatt ctaattgaga  60783
atttacacac actggtacag ataagatgaa tttgcaaaaa aagaatagag gccccagaat  60843
ttctagctgg gttttttggt gaaggccttt ctctgtatca agctagtccc taaagactgg  60903
gtgaggtggt ttttgtttgt tttacatttt tattttaaaa gatggggatc tcactttgtc  60963
acccagactt gagtgcagtg atgcaatcat aactcactgc agcctcaaac tccaagggtc  61023
aagtgatctt tccacctcag cctcctgagt agctgagact agagacacat gccactgtgc  61083
ttgattaatt tttatttttt tatttttttt cgtagagatg tggtctcact ttgttgttca  61143
ggctggactt gaactattga cttcaaggga tcctcctgac tcagcctccc aaatcattgg  61203
gattacaggc atgagccacc atgcctgacc tgttttgttt tgttttaaaa aactcagaaa  61263
aatttcaaaa tagcaattat aaagacaatg agcttagaaa accaattaat ggacaaaatg  61323
taactataag taaagagata catgtaaaaa gaatcaaaca aaatttgcag tggaagaata  61383
tgataaccaa attgaatatt acattagagg agtttaatac tagatttgaa caagcagaag  61443
aaagaatcag ggaacttgaa gatgggtcat ttgtaattat tcagtcagag aaacaaaaag  61503
aagactaaaa aagagtgaag aaaccctaag gacatcatca agtagaccaa tatgtgttat  61563
cagagtttta gaagaaaaag acagaaaaat aggcataaag catcattgac aaaataatga  61623
cccaaaacct cccaattatg aaagacaata gatattctga atccagagca caatggcctg  61683
caactaagat gaacccagaa aagtctatac ttcagcacat tataatctaa ttatcaaaag  61743
ccaaggacaa agaaggaatt ttgaaagcag aaagaaaata gtgactcatc agatacacaa  61803
gggctgtcat gagaatatca gcagatttct cagcagaaaa cttgcaaaac agaaataagt  61863
```

-continued

```
gggattacat attcaaagag ctgaaaaaaa gtctgccaac aaaaaatcct ttatccagaa  61923
gaattttctt caaaatgaag gagaataaag gatattccag ataaacaaaa gccaagggaa  61983
tccatcacaa ttaaacctgc cttacaagaa atgctaaatg aagttgttca agttgaaata  62043
aaagaacgct gaacagcaac acaaaagcat ataaaagtat aaagctcatt ggtcaaagat  62103
agatataaag gaaaaacaac gggatattat aatggtggtg ggtaacttac tcttcatcct  62163
ggtatagaag ttaaaaaaaa ccacaagtat taaaataact gtaactataa aattattaat  62223
gaatacacaa tgtaaaaata tgtaatttgt gatactgata acataccatg tgtggagggg  62283
agaagtcaaa gtgtagagtt ttaaataaga ctgaggttag gtttttatca ccttaaaata  62343
gattgttata atatgtttga tttaagcccc atggcaacta caaagaaaat acctacaggt  62403
aataaacaaa agaaaatgag aaagaaatga aagtgtgtct cagtccattt ttattttgct  62463
ataactaaac atctgagact aggtcattta tagagaaaat aaatttattt cctgcagttc  62523
tggaggctgt gaagttcaag actgagttgc tgcctctgtt gaggggcctt cttattgcat  62583
cataacatgg cagaaggcat cacatgacaa aaaagcaaca gcaagagcca aactggcttt  62643
tatcataggc ctagtttgtg acaccttaca tagtcctatg aaaacccatt aagccattag  62703
cccattaatc cattaattca tgaatagatt aatacatcca tgtggggaaa gccctcatga  62763
ctcaaacctt tctcaaaaaa cccatctctt aatactgtta cattagtatt aagttttaac  62823
atgagtttca gagtctagaa atattcacac catagccttt cacccatgac ctcccataat  62883
ttatgtcctt atcatatgca aataccttca ttccattccc gtagccccga agtcttaacc  62943
tgttctagca ccaactctaa aatacgaagt caagagtctc atctgagact caaggcatga  63003
tccatccttg ggcaggttcc ctttcagttg tgaaatcaaa acaagtcata taattctaaa  63063
atacagtgct ggtacaggaa taagacagac attcccttgt cgaaagggaa aataaactag  63123
aagaaggggt taatggtccc caagcaagtc tttaacacag cagggcacat attaaattgt  63183
aaagctaaag aatactcttt tttgggtcca tgttaagcat tctctgcaca atgtggggaa  63243
cacattgagc cactctgccc ctatggcttt gctgtgctca gaacacactt cagctttctc  63303
agattggaat tgctcattgg tgcctgcagc tttcccaggt gggcactgca cactgctggt  63363
gtttctataa ttctaggatc tcaaaggcag ctctggctct caccccgtat ttttactcaa  63423
cattgctgta gtggggctct cagccatggc tctgtccctg tgacaagtct ctgcctgggt  63483
ccccatgctt ttagatacat cctctgaagt ctaggtgaag gccatagtgg ccctacaact  63543
cttgcattct gtatccctgc agaattagca ccaggtggac actgccaagg cttatggctt  63603
ttgctttctg gagcagtgag gtaagctaca cttggagcct cttgagccag ttggagtggc  63663
tgaggaatga tgcgctcaca tgaagggagc agaggagtcc tgagcagccc tgggcagcaa  63723
gctgtggaga gtaccctggg cctgtcccct gaaactattc taccctcctt ggcccctggg  63783
cttttcatga gaggggggcag tcttaaaaat atgcaaaata cttttcaaac attctcctca  63843
ttgtcttaat gaataacatc tgactccctt ctatcagtgc taatctcttt agcaagcagt  63903
tttgctgttt acatggctaa gcaagctgca aacttttcaa atcattttgc tgtgattccc  63963
tttaattata catctgtctt taagtcatgt ttttgctcct gaattggcca aaagtaacca  64023
cacagccaaa agtagccaaa cagcatcatg aatgctttgc tccttaaaaa tttcttctat  64083
aagatatttt actttattat tgtcaagtct ggccttctac acagccctag agtatggaca  64143
cagttccagt aagctttttg ctactttata ccaagtatga cctttattcc aggttctgat  64203
accttgttcc ccctttctgt ctgaaacctc ataacggcct tcattgtcta tatgtttact  64263
```

```
agtattttgg ccataatcac ttaaataatt tataaaatga ttcagacttt ccctagtctt  64323
ctcatcctct gatccttcac cagaagcacc cttaacactc tatttacagc aatataagat  64383
tttttttgcc tgctcctcca aacccttcca gcctttgtcc attacccatt tccaaagcca  64443
cttgcacatt tttaggttga gcatcagcct cacttcttgt taccaaagcc tgtattaggg  64503
ttctccagag agacaaaacc aatgggatat acagaagggg atttgttagg gaaattggct  64563
cacacagtta tggagactga aaagaccaag gtcaagggga cgtatctggt gagaaccttc  64623
tcattgtatc ataacatggc agatggcatc acatgctaaa agagcaagaa caatagccaa  64683
actggatttt ataacagacc cactcttgac gactatccta ttcctgtgat aagccattaa  64743
tctgtgaatc catgagtaaa ttaatctatt catgagggct ctgcctctat tgtcccttaa  64803
aggccccact tcttaatact gttacattgg ggatgaagtt tcaatatggg tttcagagga  64863
gacaaacatt caaaccatag tgatgtcact acaaaaaaat taatgaaaca caaaggagta  64923
cagtaagaga gcaaaataca gataaaagtg ctatatgata tatagaaaac aataaaatgg  64983
caatagtagg agtttatctg tcagtagtta ctttagccat aaatgaacta aactcaaaca  65043
aaagacaaag attagctgac tggatttaaa aaatactata tgctgtctac aagaagtaca  65103
aggagcccac tccaaatttg tagacacaca taggataaaa ttaaaaggat ggaagaaagt  65163
attccatgtg aatggtaacc agatgagagc agggctcatt atacttatat cggacaaata  65223
aattgtaagt caataattgt cacaaggaac aaagaaggac aatatgtaat attaaaagag  65283
tcaattcacc agaaagatat aacaatttta aacatatatg tattcaatct tagggcttta  65343
aaatatataa acaaatatta atggaactga agggagaaag acagcaatac aacaatagta  65403
ggagatttta attctcagct ttctttttct agagacagag tctcactctg tcactcaggc  65463
tggagggcaa tggtacaatc tcagctcact gcaatctcca cttcccagac tcaagtgatt  65523
ctcccacttc agcctgctga gtagctggga ctgcagacat gcaacaccat acccagctaa  65583
ttttttaact ttttgtacag atgaagtctc gtatattgcc cagctggtct taaactcttg  65643
ggctcaagtg atccttcacc tgggcctccc aaagtgctgg gattataggc atgagccacc  65703
gtgctcagga cccaactttc aaaaattgat agaacatcca gacagaagat caatgagaag  65763
cggattgaac aacgtagacc aaataagcct aacaaacata tgcagaaaat tccatctaac  65823
agcaccagaa tatgcattct tctaatgcac acacacatat tatccagaat agatcatatg  65883
ctgtgtcaca aaacatgttt taacaaattt aaaaatacag aaatcatatc aaatatcttt  65943
tctgaacaca gtggaatgaa actataaatc aattataaaa ggaaactggc aatttcacca  66003
atatgtgtac attaaacaat aaattcttga acagtccatg agtcaaagaa gaaattataa  66063
gggatatttg aaatgtttca agataaatga aaatgtctca agatgaaata aaaagacaac  66123
atatccaaat ttatggaatg caacaaaagt ggcaagagtt aagtttatag tggtaagtga  66183
ctacattata aaagaaaaaa gattttaagt aaacaaccta actttacacc tcagaagtgg  66243
aagaaggaga aaatactaag cctaatgtta gcaaagaaag gaaataataa aaattagaaa  66303
aaataaatta aatagaaagt agaaaattac tataataatt aatgaaacta acagctgctt  66363
tttaaagatc aataaaattt acaaaccttt ggctagaata actaagaaaa aagagagaag  66423
actcataaat aatattgtaa ataaaaaagg agctattgca atcaaagagg caggaacaat  66483
aaagattttc aggctattct gtataattat acactaacaa attggataac ctagaagaaa  66543
tgtataaatt ctcagaaata cacaacctac caagactgaa tcaagaagaa atacagaatc  66603
```

-continued

```
tgaacagatc tgtaactagt aaggagatta aatcaatgat cagaaacttc ccaaaaaaga  66663
aaatcccagg atcagaaaac ttcactggag aattctgcca acatttaata gaaaaaaaaa  66723
tgccaattct tctcaaactt ttgcaaaaaa ttgaagagga cgaagcattt caaactcatt  66783
ttatgagtcc agcattttcc tgataccaaa atgagataaa gatattacaa cgaacacaca  66843
cactttcaaa caagctacag gccactatct ctgatgaatg taaatgcaaa agttgtcaat  66903
aaaaaatagc aaactgaatt caacagtgca ttaaaaggat cacacactgt gaccaagttg  66963
aatttatctc tggaatgatg aatggtttaa catatgaata tcaatcaatg tgatacacta  67023
tattaacaga acaagggata agatcacatg ataatctcta taaatgctga acaatcattt  67083
gacaaagttt aataccottt cgtaataaaa atactcaaca aactatgaat agaaggcatg  67143
tacctcaaca caataataaa ggtcacatat caaaagctaa cagataacat catactcaat  67203
ggtaaaaact gaaagctttt cctccaagat caggaactag gtaagaatgt ccattcttgc  67263
catttctcat caacgtatta ctagaagtct ttgctagaac aattatgcaa gaataagaaa  67323
taaaaagcac tgaaatcagc aaggaagagg gaaaattatc tctattccca gatataataa  67383
tcttatatgt agaaaattct aaaaatcaca caaggaaact gttgcaacta gtaagttcat  67443
caaaattgca gaacataaaa tcgaaatgca aaaatcagtt atgtttctat acaatagcag  67503
caaactctct gaaaaagaca ttacaatccc acttacaata ttatcaaaaa tgactaaaat  67563
gtttagtaat aagcttaacc aaggaggcta acgacttata cactgaaaac cataaaagca  67623
ttaccaaaaa ataattttaa aagacacaaa taaatagaaa gataattctg ttttcatggg  67683
ttagaaaact cgatattgtt aaaatgtgca cactgctgaa agcaatttat agatcctata  67743
caatcttacc aaaattatga tgtcattttt ttcagaaata gaaaaaaaat ctgagaacca  67803
tggatactta gaaaatctgg agaaagaaga gcaaagtaga gggtctcatg cttcctgact  67863
tcaaaacata ttccaaagcc attgtaatag aaacagttta gcactggcat aaagacagat  67923
atatgaactt acaaaccagc atagcgagcc cagaaataag cccacacata cattgtaaaa  67983
taatatacaa agcacaaaga ctatggacag gatagtctct tcaacaattg tgttgggaaa  68043
actagatagc catattcaaa ggactgaaat tagaccctac tcaaaaaatc aagtcaaaat  68103
gaattaaaaa ttaaagatct gggccgggcg tggtggctca cgcctgtaat cccagcactt  68163
tgggaggcca aggggggtcag atcacgaggt caggagatcg agaccatcct ggctaacaca  68223
gtgaaacccc gtctctacta aaaatacaaa aaattagccg ggcgtggtgg tgggcgcctg  68283
tagtcccaac tactcaggag gctgaggcag gagaatggcg tgaacctcag aggcagagct  68343
tgcagtgagg tgagatcacg ccactgcact ccagcctggg ggacagagca agactccatc  68403
tcaaaaaaaa aaaaaaaata caagatctga aactatgaaa ctcatagaga aaaacaggag  68463
aaaagtttta taccattggt tttggcaata atttcttgta tacgacacca aagaacaggc  68523
agtaaaagca acaaaaaata gataagtgga actacataaa attaaaaact gatgcacaga  68583
aaataaataa aaagaaaaaa cagagtgtaa aagcaaacca tgaaatggga gagaatattt  68643
gcaaaccata tatctgataa tgggttagta ttcaaaatat ataaggaaca cctacaactc  68703
aatagcaaaa aactaaccca attaaaaatg gacaatggac ctgatggata tctctccaaa  68763
gaagatgtaa aaacagccaa cagatacatg aagagtgctt aacatcatta gtaattaggg  68823
aaatgcaaac caaaccacat gagctatcat cttacacctg gtaggatgac cattatgaaa  68883
caaaagaaag agaattaaaa aaaaaaaagt gttgaaaggg atgtggagaa actagaacct  68943
ttgtacagcc actgtgaaaa aatgtttgga agttcctcaa aaaaattaaa aataaaacta  69003
```

-continued

```
tacgatccag taatcccact tttagatact tttccaaaat atttgaaaac aggaactcaa  69063
agagatattt gcactctcat gtttattgta gccttattta caatagtcaa gaggtggaaa  69123
caaatgaaat atataatgac agatgagtca ataaaatgtg gcatgtacat atcatggaat  69183
attattcagc attacaaaag aagaaaatct tataatatgc tgcaacatag acaaaccttg  69243
aggaccttat actaaataaa ataaaccagt cacagaatga caaatactgc atgaatatac  69303
ttctatgaag tatctaaagt agtcagtcat agaagcagga agcagaacgg cagctgccag  69363
gtcctgggag taagagtaag aggaaagttg catttcagtg ggtatagagt ttaaagcatg  69423
caagatgaaa aagctctaaa gatctgatgt acaataatat gcatataatg aacaatattg  69483
tactgttcac ttaaatatgt gttaggtcca tgttatgtga tttttaccac attttttga  69543
aagcaagttg ctaaagaatt tgccaaatgg aattatagtg acacgagttc aaataaaatt  69603
aaaaaacgag aaacagtaga gtttacttaa tttgttaata tatccatatt atcattttag  69663
ggaattttta ctaaagcaga gtatataaac tatctttttt tgttctaatg atccatttgt  69723
tttagtttgt ttcccatttt tatgtagcta gactgccagt taatctccta aaattattgg  69783
caccatattt cccatttttt ctggcttttt tattagtaac tgggatcctt gcagctgtat  69843
ctatgtgatg ccaaacaatt aggttgatca attctgtgac aacaagccat ctggttactt  69903
tagtgaatag gcccttactt acctttcata agttgattct attctccttt gtgccttctc  69963
tttaaattac cattatcctg taaccataaa ttaaaaatac agcatcgctt ttaaaacatc  70023
ctgaagtaat ttttaacact acaaaagaga agaaatttcc tttgtttggt gttctttgac  70083
cctaattagc atttaggaac aaactacact tgcaaaatta ttttcgattg gtagagggaa  70143
gaaaagggtc tttttattac tatgtatttg taattacttt tgtcacttat gttattcttg  70203
tgtctaaatt caactctaga tttattctct gttgatattt tttatcactt gagaatattt  70263
tagtttttca acctctatat ggcgggctat cactccaaat ttaggttaaa ctgtaggttg  70323
atttaaaaat ctggctatga tgcagaaaaa ttcgggcaac ttacctagaa aaaaaaaagt  70383
agttatattt cagtacttct tttacctaat cagccatttt aaaataattt tgttcattat  70443
caatatggag gaaattattt atatgcaggg aagttattta tatgcagagc tgttaatggc  70503
agcaatctgc atgacaaatt tctacttaat aagcaatgaa atagttggat aaatgtgtat  70563
ttctacatgg gtgaatttcc caaaattcac acttcaaaga cagttgctga catttttca  70623
atgagagatt ttattagata atgagtcatc ttagagttat cttgtaagta ttctttagtc  70683
ttaatttaaa tttaaatgaa agtcaattca aagtgttgta ttttcttaaa taaattttgt  70743
tttataaaca ttagaaatta aataggacta ccatatggtc tagcaatcac acttctgggt  70803
atatatccaa agaaaatcag ttcagtatgt caaagagatg tttcgtattc attgcagctt  70863
tattcacaat agccaagata tagaatcaat ctaagtgccc atcaatggat aaacgtagaa  70923
aacatgggct gggtgcggtg gctcacgcct gtaatcgcag cactttggga ggccgaggcg  70983
ggcagatcac gagatcagga gatccagacc atcctggcta acacggtgaa accccatctc  71043
cactaaaaaa aaatacaaaa aaaattagcc gggcatggtg gtgggcgcct gtagtcccag  71103
ctacccggga ggctgaggca ggagaatggc gtgaacccgg gaggcggagc ttgcagtgag  71163
ccgaggttgt gccactgaac tccagcctgg gctacagaac gagactccgt ctcagttaaa  71223
aaaaaaaaaa ggaaagaaaa cgtggtatat atacacaatg gaatactatt tagcctttta  71283
aaagaaggaa accctgtcat ttgcaacaac atggatgaac ctgaaaaaca tgttaagagg  71343
```

-continued

```
aacaagtcag gcacaaatac ttaatgatct cgcttatatg tgaaatctaa aaaagttgac  71403
ttcatggaaa tatagagtag aatggtgatt atcgggtgct gggagttggg gtaagatgtg  71463
gttggggaaa cggtcaaaga ataaaaaatt tcagttaaag aggaagaata cattcaagag  71523
atctattgta catgttgaat atagttagta acaatatttt gtatcctcaa attgctaaga  71583
gagtagattt taagtgtttt tgacacaaaa actgataatt atgtgaggta atacattttt  71643
taattagctc cctttagcca ttccacaatg tatacatctt ttaaaacatc atgttgtaca  71703
tgacaaatat atacaatttt tatttgtcaa cttaaaaaat attaaagatt taatgtagat  71763
aaatgaaaga aaattaggaa ttaaggtaca aaaattattt atagtgttta ttattggtct  71823
atgtttacat agtatttctt tgtctccatt agtgtgttat acaaataccc aactagaaac  71883
atgactttac aaatggtgta tctgatcttt tatgtcccta gttattattt tagccctgtc  71943
ttttttttta ataaaacata ttctgctttt tcttgtcctc atccttctat gagttgaatt  72003
agtgactcta ctccaaagta atggtgttgc tttctcagac catatggtga tacaaaggca  72063
tatgagttat cataagcatg gtctgtgtag gcaaagcatg taactccaca aatgcttctt  72123
gagagattct aatataatct gtgccagacc tgcacaaggc atagagaata aaaatttgca  72183
ccccacacag tcactcctca ttcattcatt caacaataat caagtacctg gtaatgctaa  72243
tgcagtgtac tataattcca tatacataaa ctaatatttt taagatacat gaaggttatg  72303
ttataactaa tagtcaatgt atttttaaaa ttactgtaat caaattgtaa ttgtaattaa  72363
gtattttctt aatcaacaga aactaaaagt ataatttcca tcaactcctt ttaagtataa  72423
atgtaattaa atgcctggca cattcttcac attatataag gatctttata cttaagacat  72483
ttgggaaacc ctacttaggc ttatcattga caaaacattt tcaaaatctt ttcatttggt  72543
cctcaccaca atactgttaa aaagacagcc taagctgttt tgtgcttcct ccctagttgg  72603
gcatccctgt gcaatgagag ggacaaacaa ggtggtttta aggtcagaaa catccaattg  72663
cagcatcatt gggaaatttg taagagcagc ttttataaaa tgtcaccaac tcatgtatct  72723
ttaaaagatg tgctgaatct tatgccttga gatttttctt agtttcctta ttttctattc  72783
ccctcccact ttctctttgt cccttggtgg cttcattaat cccatattac aatacaaagt  72843
aaataatagt gctctgaagt gcttcctatt tgttcaggat gaagtctgaa aaatgaaact  72903
gcaatttttt ttcttttgag acaaagtctc actctgttgc ccaggctgga gtgcaatggt  72963
accatttcag ctcactgcaa cctccgactc ccaagttcaa gtgattctcc tgcctcatcc  73023
tccccagtac ctgggattac aggcatgcac caccacgcct ggctaatttt tgtattttta  73083
gtagagatgg ggtttcacca tgttggccag ggtggtctcg agctcctaac ctcagatgat  73143
ctgcacacct tggcctccca aagtgctggg attacaggtg tgagccactg agccctgcca  73203
aaaactgcaa ttttatctta ggggacaggt aagcataaaa acatccaaaa tcatgtattt  73263
atgtttaggc tctgcttgta gagtgatacc aaattccagg tgtttttttt tttttttttt  73323
tttttgaga cagagtctgg ctctgtcgcc caggcctgga gtgcagtggt gagatctcgg  73383
ctcactgaaa gctccgcctc ccgggttcac accattctcc tgcctcagcc tcccgagtag  73443
ctgggactac aggtgcccgc caccacgccc ggctaattgt gattctttac attatcaaag  73503
aattcatgaa aacaggatat gaagattagt gaaggattct tttcattagc aaagtaactt  73563
ttcttatttc aaatttaaca catctattta taaaagttat agaatttaaa ttttaaaata  73623
tgaatgaaga aaaacaaaat cagcataaca tagtaataca tataattgat atgtactatt  73683
ctgttacttg gattcattac ttaacccttg cagtattcta tgattttttt ttaatccatg  73743
```

```
tgttacagtt agggcttaga aagatttaag cacctagcca aaattatgca ttatgttaag  73803
tggttgatat ccacttattg acaaatatgt attgattgag aattagtcat ggagatatca  73863
atgggttatt ttgattactt tttccattac tcccaagtgg tcaggattag ttttagatta  73923
tttaagtagg ttggctgagt tcacaaaagc tattactatg gggaccttaa ttgaaatcta  73983
actctatcca attctatttc ttttccctat ccctcgaatg ggtgtatgtg tgtgtgtgtg  74043
tgtttgcaca cataaaaacc tgttctaatt ttatgcaaca tggaaagcat taatgtttaa  74103
catgtatgtt tgaacaggga attttgtact gcattaaaga ttattcctgt gtattacata  74163
caatcaaata tttgactatt gactgtctta gtatgttcat ctaattgttt cctattccca  74223
tgaaaactgt atcagtctga gaacagctac tatatgatat gcatcactag tctccccatg  74283
gtgcataata cttgatataa attagatgct gttggttata cttggcgggg ggaaagggga  74343
cactaaaaag gaagagtcaa tttctactgt gaacaaagca aaaagcaaaa ggagagataa  74403
atggaattaa attaaaaatg aaattgagag tgtagataaa tctatgtaat gaagatgcta  74463
gtaacatagg aagagaaata agataggggta taacagtgat tatttttcct aataagtagt  74523
gtcatggcag ttggaagaca agagattatc caagcactgg ttatagtctg aaagatgagg  74583
tggtagctta cttgtttggg cctcaggcat tgcagtacaa acagacagtg agggaggagt  74643
caattaagac ttatacaaat gcagaagtca tggttgaggt agtgagagga tttccaggac  74703
agtgatgaat aacagaacct cagcagaagg agcatgtgga cccaaagcat catacgaata  74763
atgataggac caagggaaaa gaagtcaagc ggaatgggga tagacaaaag ttttgaaatt  74823
tatgtgtaag agttgaatga agaaagttat taataagact tacacaacaa agaatttcta  74883
catagaagtt gaaaagacag caacagagtt tagagtttag gaaaaaaaat taaatattaa  74943
attttaatat gtaatattgt aggatttgaa taccttaaag ctgaaattca gtttttgatg  75003
ctgcttctta gcatctttgt cttgacatgt atatcaaaat gtaagaatgt ctgtatctta  75063
caatctgtga ttcttgagaa gtcaatgcca tattattcac tacattcatt ctttcttatt  75123
ggaaccataa tactttcttc aataataatg tcagtagaca ttctaaataa ataaaaaata  75183
tccaataaca tgccccaatg tttcacaggt atcacaccaa tagcccctga gatattgtca  75243
cattccattt atctgcagaa gtcttattca actttctgta ttaagtacca agaaatttct  75303
taggcaatta gtaagttcac ttgtattctt aaaacttcac agaatgaaaa attaaaaatt  75363
ttaatctctt tttctagaac aattgtttta caaagacttt tcaaggtttt ttaatcctat  75423
tttttgacaa aataacatat tttaatgaaa gtaaacatgt agaaatgact taaccaaaac  75483
tagctattga caacttttca gcactttttt ttgggtgaat tcaggaacaa actttgtatt  75543
cattttatta atccactaag tagggttgct tcacttcctt ggttactgtg catgtggacg  75603
aggctgattt tcatggtggg atgttaaaag gagggatttt tgcaaatcaa accacagaac  75663
catcacctca cacttgttag gataacaaac attagcaaaa ccaaagatga caaatgctag  75723
caaggatgtg gagaaattgg aactcctgta tatgctgaca gaaatataaa atgatgcagc  75783
cactataaaa attttttgtt tttgagaatg tgtcttgcta tgttgtccaa gctggcatca  75843
aactccaaga ctcaagtgat cctttcacct cagcctcctg aagagctgga actataggca  75903
tgaaccactg tgctggcttg gaatattttt attttcctca aaaaatcaaa aatagaatca  75963
ccatatgagc cagcaattcc atttttgggt atatatccaa aataatttaa atcaaaatgt  76023
tgaagagata tctgcactct cacattcatt gcagtagtct tcacaaaaca acctaaatgt  76083
```

-continued

```
ccatccatgg attaatgggt aaagaaaata tggtctacac atacaatgga atattattca  76143
gccttaaaaa agaagggtat ctttctgaat gcaacatcat agatgaacct gcaggacgtt  76203
atgctaggtg gaataagcca ggtatagaag gacaattatt gcatgattct acttacatta  76263
ggtatttgaa atagtcaaac tcatggaaac agagactaga atggtagttg ccaggggctg  76323
ggaggaggca gaaatgagga actgctgtcc aatgagtatg tagtttgaat tatgaaaaaa  76383
tgaataggtt ctagagatct gctgtacaac attgtgccta cagttaatga tgcagtatta  76443
tgcacttaaa catttatcaa gagaggagat gccatgttga gtgctctttt cacaatgaaa  76503
gtacagtaaa atgaaatgaa atatacagca ggctttacac acaccgcttc acaggcaaaa  76563
actacttggg aaacaaaatg gaaggtcccc agagtcgtga gggaagtaag gtatggtaca  76623
gggtcaaaat ggctgtacct ggagctctct gactggtcag gcaccaacca gcaatactct  76683
catgccttaa ttatagttta ctgctgagat aattgagaat gagagctcat atttactaac  76743
caggatatga atagactgag aactttaaat aactttcctt taattccata aaaatctcca  76803
ttctgtttta aagtctttag tacagatttt agatgtaata aactgctaag atttgagcaa  76863
caactataag cataataaat ggtttgcttt atgggcagtt ttacactaat gcctctaata  76923
ataataacag tagcaataac aaaaatgaca ggattcttag gacttcatta ctcagagcat  76983
aatccctaga aagcagcagt cattatctaa cccagaaact cccaagagtt tgcttaacac  77043
tttaaaatgt ataatctaaa ttaaagaaaa tatgagtaaa tggtattgtt tcccctgaat  77103
tgaagtaata tgggatgtgt tgaaagaata catcaagaca tttttcactg tcacctagcc  77163
tgatgactga catagattaa ttactacata aatttcctct tccatttaat actgataaac  77223
agatttatgg gacttaaacc acagtacaca gttttgtatt ttgtacgaaa tggataatca  77283
cattttaaaa catgtgtaag gcatatttgc aaacttgaaa cgtcgtcttc cataaatata  77343
tgctgaatga atgaattaat gaataaaaat tgaggcaaaa actcaggtgt ggctcagtca  77403
tctgaatgtt attatccaat gaaacaggtc aaagattttt tttttttttt acggttcatt  77463
tctagccaat aagaccaagg ttcattcact tcacctctgt atagaatcct ttgttggggg  77523
ctgcgaggag gcagtaagaa gtatcacatc taatcttttc cataattagc caagttagtt  77583
ggtacttccc ataactctga tacccatagg cccttgctat ttctagactt gagtgtcatt  77643
cagaaatatg gtttaggcga gcactaggaa agatacacag tttttctaaa acacattatc  77703
caatcaatat tctacttata aaagtcaact acacacactt cagtcatgag gtaaaaaaat  77763
gaaatttata cataacactc acttatgttt atcactcact tatatttata ataatagaca  77823
tacaggtatt ctattaaagg aactttttaa tgtttgacca gaaaaaattt caatatccct  77883
ttttattaag tttaagttac tgtaatgaaa ttaaacatgt gaagggagac taatactctc  77943
ttttaagaga agtaagaatg aaatatccat ataaaataca ctgcattatt ctctttgttt  78003
caatggcaaa tagaatcaaa aggaataacc cactttattt aacggaatat ctgaaagtgt  78063
tccacttatt tatttctaat tttaactatg gaaagtactt gcattttttt ttaggaaaga  78123
aagccaagat tttataaagt aaaaatctgc tttgtgtgcc tttccaaatt agaagagaaa  78183
tgtatcatct taatacagca gattcagtta ttataaagac ctactccatc caaaaaattg  78243
agtgaaataa aaagaaattg acttacttgt taaagagaaa agattgccaa ggcttgcaga  78303
cttgtgaggt ggttaaataa caaactaaag actagcgaat atgagctatt ttgtttgacg  78363
tgccttccat ttaataaatg ctgtatcaat ctagctgttt ctctattttt aatcatacat  78423
tttgttgttg ctctaaattt aatcttacct tatacattgt ataatagatg tcccttaaat  78483
```

-continued

```
acatcaaatt taacgtgttc caaagaaaac tcataatctc ctcatctcca tccacctcac  78543
tcctcctgct gtgatcagtc tctccgtttt tgttcattgt ccatcatctt ctacagaaca  78603
gatgtgtcct aacccacttt cctaaacaca tttttgtata caaaataatt tcctttttt  78663
aatttcagaa ctctattctg acaaacattt ggcttcaacc tgtaattaaa aacttaacaa  78723
tacttaatag ttgcctcaaa gagcatcccc tctttgtcaa tgtgagacta tttacattaa  78783
tttacatgta attcagtttc atactcattc actggggtgt gaatattagt caaacgggca  78843
attaattaat acaatcttta tatattcact tattaaaatg caccacacaa ttcctaattt  78903
attgagagtt ctcactaaat ctatgggatg taaattttga aacagctgca gctgtttatg  78963
ccattgctct tgttgtccaa tagagccaag tggacattct tttttgttgt tgttctttcc  79023
ttgaatagag tcgaaattat gaatctaact ttctccgaca tgttgtctaa aaggatatca  79083
tcttacctta ctcagtgtga gccctaaaac taggaaatgt ttatcaatct ctgattgcag  79143
atcaagttta actatcaaat acagattaac ttttcagcaa aaatttgtta aatattcaga  79203
gatagaaatc ttgatgttgg atgacaaaga tcacttgtga agaactttat taagttttat  79263
ttggttgaaa aatctataat ttttagtgaa caactatcat ccattatgtt ccaagctttg  79323
tgacaactgt ttttatgtcc attaaaacag tcctataaaa taggtacaag tatctcaatc  79383
ttatacatgt caaaactaaa gcacagagat gctaaataac ttgactaaac aagatattga  79443
aggtgaagtc tgagatagat ttttaactcc gaagtgcata aactttacct ctatattatc  79503
tgtcttcaaa aagaatgatt ttaaagatta ggctttttta tttcagaaga aaatattttt  79563
acacaattct agattcttaa cagtaatttg aaggaatgaa tgtctgatga ttcaagaaaa  79623
gtgaggtaca ttttaaagga aaagtgacag acaaaaaatg gatttttgaa aaatgaataa  79683
agctgctttt tttttttga tggtgtcttg ctctgttgct cacgctggag tgcaatggtg  79743
caatctcagc tcactgcaat ctccgcctct cggattctag tgattctcct gcctcggcat  79803
cccgagtagc tgggattaca ggcgcccacc accagactca gctaattttc tgtatttttt  79863
agtaaacatg gggttttacc atgttggcca ggctggtctc aaactcctga cctcaggtga  79923
tccacccacc tcggcttccc aaagtgctgg gattaccggc atgagccacc acgcatggcc  79983
aaagctggtt tttaaaaggg atcattgtac attattatca aatttcattt gaacgtcaaa  80043
aattctgagg caagaaggaa attgagccca ggagtttgag accagcctgg acaaaatggc  80103
aagaccccat ctttacaaaa acaaaaataa aataacacta gccaggcatg gtggtgcaca  80163
cctatagttg tagctacttg ggaagctgag gtggaaggat tacttgagta cagagaagag  80223
gttacaatga gggaggatcg tgccactgca ctctagcctg ggcaaaagag caagaccctg  80283
tctctaaaga ataacaaata aataaataaa gtctggacaa gcctaaaatc agtaatattt  80343
ggggaatatg caaatagtct ttgctttatt tactcaatta ttgaaactat attcaaaaat  80403
aggaagtaaa acatgattta atattattta gtaagttaaa catgttataa taatttggaa  80463
atccatgtat gttagttaaa tatacattac tataaaatgt aaatcagtgt ggtttgtagc  80523
agagacctgg attttttatc tttgtagtgt acctacacca tcacagaaag gtttgccatc  80583
agtctctaga ttaggtgcaa attcatttaa tgtgatccat cctattatct aaaaggtcat  80643
tctgttgttt tcagccttca tctaagacac tctcagatac tatttcagga atttatgaca  80703
gcaaaatgat ataaggtgac aaagtagaaa taggtgctat gctgctttac ctatattgag  80763
ttattttctt ctctccagga tcagatatta atgataaatt ctctaacatc aaaaaataaa  80823
```

-continued

```
acctaggtca tataaatttt acacaatcaa tgtcagtcac tcagcaacca ttgagaatct  80883
actatgttta gaatggaaca cctgacttat agaaaaaaag gtaaaagatt ggttttgtaa  80943
aatgacacat acaatttaag aaaaaatagg ctatctatat tagatagtta aaagaagatt  81003
ttaaaatacg ataagaagag aggggagaaa tggctagatt aatttgagga ttacctagtg  81063
ttaaaataag tccagattta aatcaagttt attaattctg aaaaagatca catcctaaag  81123
aaggcatcaa attgacccat aaatgtggat aaaacttctg taagataatg aaagccctag  81183
agagtaatgt tcaactccat tttctaattg gcaacaaatg tataatatgg gtacaccaga  81243
atatctaact caaaaagtgg ggaaaaaaac tcaaaaagta cgaaatgttg gcaaaaatgc  81303
agacagctag gacactcata ccagctggta agtgtaaaaa ctagtactgc accaagcact  81363
ttagaaaact taacggcagt tatgtagtaa tggtgatcat atgcatactc tatgatagca  81423
atttcactgt tagatatata actaacagaa atttgcacat atgtgtcaga agacgtacat  81483
aagaatgtta gtaacagccc tgtttacaat agccctgaat tagaatgaac caaaatttcc  81543
atcaattgta gagtatttca atgataatat aatcacacac tggaatgaaa atgatggaac  81603
tactactaaa catacaacct ggatcttaca aacataatca taagtgaaag aaattagaca  81663
caaaataaca cataaatgtt gattccacat agataaagtt aaaaacagat aacaattaat  81723
ctatggtgtt acaaatcagt atacggattt ccttttgttg gcaggggga tgttgttgga  81783
gaggaaatag gaagagagct tctggggtgc cggtcatatt gtacttctca gtctgaatag  81843
tagttacaag ggtatgtaca ctctgctgta atttgtccag tgatacatga tggtttgtac  81903
atttttatac atgtgtgata attcaataaa aatatctgaa aagctacaac agcagtggca  81963
acaacaaagc ccattaacca caagaaataa tcatgtaaat tgttttcttc aaataaatgt  82023
gttgtaaata acttctctca ctctttggca tatatttttg tcctcttttg atatacccta  82083
attttaggtt tgtttaattt ttcaaacatg tcctttatgt ttaatacatt tgaggaaatc  82143
tgcttaagaa atgcttatct actccaacat cttatcaatg ggaattttat ttttttaact  82203
gtcaaattta gatctataag taacctggaa tttatgtttg tatatgatgt gatgtagaaa  82263
tcaaattttt attttttcta tgtagatatc aatttattca gtatcatttg tagaaaagat  82323
acttctttga taatgcagta catggcactt ttgtcatatg tcaagagtcc ttatatacgt  82383
aggtgtggat ctcaactatt tttgtttgtt ttgtttttgt tttggatctc aatttttatt  82443
ctattccctt gatctacatt tatatccttg taccagtact atactgtttt gtttactgac  82503
actttgtatt aatatttgat agctaatgta aatccttcaa atttgttttt ccataatata  82563
atactgacta attttggccc attatatttt tatataaatt ttgaaatcag cttgccagtc  82623
tttaccaaag gaaagctagc attttaattt ggaatgcatt gaatccatat atcaatttta  82683
gagaaaactc acagccttac aatacttatt cttcgattcc atgagtaggg tatatccccc  82743
tatccattta ggttattttt catattcctc atattttaca gtgcagaaat catgtgtttc  82803
tcattatttt tttcctagat gttgaacatt tattattcta ttgtcaatag tatcatctat  82863
ttaaattgca ttttctagtt gtttttattt aatagaaaca taattgattt tgcatatata  82923
cattatattt tatatatcaa tttcatgtgc tcttatgtta catattgttt tatattcagc  82983
aagtgttact aaggtattta ttaagattag tagtttatct ggagattctt tcacacttaa  83043
taagtatgcc ctctgtggat aatgataggt tttatttaat cctttccaaa cttcattatt  83103
ttatttattt ttattgcttt attacccttg ctccagcaca atgctaaata gaaattacca  83163
taaaagactt tgtgcactta ctcctgatca ctgagggaaa gactatttat gtgaattagt  83223
```

-continued

```
atttgtagat attaactttt gagaatttag ctgtcaatcc caatatgaca acttggaggt  83283
gatgcatttt tttcttcctg ctttaagatt tttcctttcg tcactggttt ttcagcagtt  83343
ttatgataat ataagtgggt gtgattttct cttatattta tcctggttga aatttatagc  83403
acttcttata tctacaaata tataccttta attcgttttg aaaaattctt agataatgta  83463
tttgccttgc caatatcttt ttaaagattg cttttgtctc atgctacttc tatacacaca  83523
tattgagaat ccaatcacag gtataataga attttcacca tgtgttatgc acactcttct  83583
gcattttcct tttttcctct ctgttcttta gcttggatat tttctattag tttgtataat  83643
cctattagat ggttttatct aatctttctt tctgttaaat ctctttgttg tgtttccagt  83703
tcacatattt ttaagttcta taatttcctt ggactatttt tctatttttt atattcttta  83763
taatatatct actttcttga cattattaat tcaatcattt taaaatttct gaaatatttt  83823
atgaaaaatt gtagaaatta ttttatgttc tagataatat tatcttcttt cacagagaat  83883
ttgcttttgc tttggccagc agctagtgtt gggacagaaa accactatcc cgtcagtcac  83943
tggaggcttt ggaagctggg cttcattctt taggagagct tgtctacttc agatttatcc  84003
ctatcagagt tcataacttg gagttacagc tgaaagccag ggttgtttac ctacttgata  84063
ggccttgaac tccaattatc atcttatttt tggttaggta ctaaatttcc ggctcagcat  84123
ctcatattat cagctttgtt ctctgtttct cttctcctgt tcttagctag agtttgcaaa  84183
ttgccaaaaa ctttgagaag aaaagaggct aaatgccaga gcatctccct cttgcatttt  84243
ctccaggata ttggcctttg atgtcccttc tgccttagta gctttccaat gtcttaaaga  84303
aatgtgtaac acttctggtt gttttaggtg ggaagtttgt tctgcagtaa gcttatctgc  84363
cgttaccaga aatagaaact attttgtaat agtaaaacaa atgtatactt tcgtactaca  84423
atatttagta cttcagagaa caattggcac tttctggata ttctcaacca ggagtatgtg  84483
gttgaaactg cacagttttc tggagatgat ttaggttctt cccttcttac tctaattctg  84543
tcactggttg atcttatcca ctccacaagc tttaatcaca atttctattc tgatgaatcc  84603
caaatattta catgtaaaga aattatatcc cctggagtat agaaccataa atctaaatgc  84663
caactgggta ttgacactag gataactcac aggtgcttca aaattacata tacaaagttg  84723
aatttctcat cttctatcta ctcttacaaa gctacctcat tatcctttat cccctagctc  84783
agtgagcatc cccagctgtc aagcaatata cctgctaatc atcctcagtt cttcttactc  84843
tctcatcctc atatctaatc cctcactaag gcctgatatt tcaacctcgt tattattttt  84903
ggcattcacc tttttccatt ttttggttac caacttgctt tcttggaatt ttaaaactgt  84963
cagtattaat ctctctgctt gcaacataaa gacatatatt ttccacatat tccgcctaag  85023
taatctttga aaaatagtag taagatattg ccattctgtt gcttaaaatc tgtcagtaat  85083
tttgtaattt tccaattctc catagtctgt aggacaatat ccaaatgttt taactgaata  85143
cacacacaca gaaacacaca cacacgctca cacacatttt atgattcata ctttgagttt  85203
aattgaaaga tagaacatct ataagatgaa aacagttgta gtcagagatt ctggtatgca  85263
aagtaggaga gagagccaag aactagaggt ataactttga attataatat tgggttggtc  85323
ttctatagat gagacataaa gttgtgagag tcaataagaa caactaaaga aagataatga  85383
aagaacaaaa gacaagtgga ttaaagacag atatgcggtg aaagagaaaa gcatttctac  85443
agaaaagacc cccaaaataa gttcattgca ggtagtaaga tgaacagaag tcaaatgtct  85503
tggggaggat cggattggtt gcttgtgtat gttaattaat gcaaaagggt caaagagaag  85563
```

-continued

```
gactgacttt atggccctgt agaactctga gaacagggtc aaaatccaga tgcatttcta  85623
agacatcaca ctgggaacgg ggacttgtaa tgagttatct acaaagtgta aaaagatgtg  85683
ggtaaccaaa aggttgtcat ttcctccaaa acaaattttc ctggagtgaa actgtaacta  85743
ccaggtatag tcattaatag aactgcagac actaagacta tggaaccttc cgtcttccta  85803
accttctcct caggccagcc ttaaaggcct gtgaagatct attaataaca ctgctgtttt  85863
gttctctggc agctcttggt gccagaaggc ttggtgccaa tttgtggttg agcccctcct  85923
tgggagaaat catgccattc agagacagct gataagtcaa gcctattttc ccactttctt  85983
cactgtattt ttcctgtctg aagaacttgt ttatggattt gatttctgta gagataataa  86043
tcacaggatt cagtggtata gcattcctct atgcattttc tccctgcaca tttgtgtgtg  86103
tgaagatact ctttctaaat ccctttcaag acaaattatt aattgtgata tattaattat  86163
tctccactgt acctaacggt tatcaacact acagaggcac cattggttga caaaagtgag  86223
agcttttctc aacattaaca taatgagcaa gtggcaatga gaaaatattt gtccaattag  86283
agacttttat attttctttt cttgaggaaa taaaacccga aacacattta agatacattg  86343
ctgtttgtgc ataggcggta aatttttttt tttttttttt tttttgagac ggagtctcac  86403
tctgtcgccc aggctggagc acagtggcac gatctcggct cactgcaacc cccgcctccc  86463
gggttcaagc gattctcccg ccttagcctc cggagtagct gggattacag gcgcatacca  86523
ccatgcccag ctaatttttg tatttttgta gagatggggt ttcgccatgt tggccaggcc  86583
ggtcttgaac acctgaccgc gggtgatccc cccgcctcgt tctcccaaag tgccgggatt  86643
acaggtgtga gccaccgcgc ccggccagta aatagttttg aagttttatt taatcccagc  86703
actttgggag gccgaggcag ggggatcacg aggtcagaag atctagacca tcctggctaa  86763
caccgtgaaa ccccgtctct actaaaaata caaaaaaatt agccaggcgc ggtggcgggc  86823
gcctgtagtt ccagctactc aggaggctga ggcaggagaa tggcgtgaac ccgggaggcg  86883
gagcttgcag tgagccgaga tagtgccact gcagttcggc ctggacgaaa gagcgagact  86943
ccagctcaaa aaaaaaaaaa aaaaaaaaaa aaaaagagtt ttattcatat tcatattaga  87003
taaccatttg ggtggcacat ttcacaacac agatgcactt cttaagagtc ctccatccgt  87063
cagcgttgta aaaaaggaag tggcacgttt gcatgtagtt cttctgagac ggagatttag  87123
ggacaacttt gccaaggtgt gtaggtggag aatgggagat tgagacaggc atattggctc  87183
aggaagacaa gggagtaaaa ctagcaatag aaaggagggc caatgccgta acagtgtgat  87243
ggagtgaaaa caagaaaaag gaaaatgcct caggatttgg tggagagttt gttttacctt  87303
tttaagataa tactcctggt cagcttccca ggttcttaag tctggatact gtaatgattt  87363
tggatgactg cattccatga cctgtttcaa ggtaggtttt ttgaaaatag gagttaaata  87423
taggctttct tccctatgta ttcagttgcg tttttttctt tttcatttag aaatgttgtt  87483
ttatttcacg ttctcttatt tatatttaat tgagatggtg ttggccattt tatccttctt  87543
tttttttgtt ttcttttctt tttttatttt attattatta tactttaagt tttatagtac  87603
atgtgcacaa tgtgcaggtt agttacatat gtatacatgt gccatgctgg tgtgctgcac  87663
ccattaactc gtcatttagc attatgtata tctcccaatg ctatccctcc ccctcccccc  87723
accccacaac agtccccaga gtgtgatgtt ccccttcctg tgtccatgtg ttctcattgt  87783
tcaattccca cctatgagtg agaatatgcg gtgtttggtt ttttgttctt gcgatagttt  87843
actgacattt tatccttctt taaacattat tttctatcta gaaaatccaa cttcaaataa  87903
atatactcag ttctacatta taaaaagtat tacaatgaat ttaatgctta aaactcattc  87963
```

-continued

```
cggaagtgac gatggaagca ggttcaaatg ctttcactga cactttgtgg caaagtgtgg  88023
aactacagta tatttttcca agttgtttcc tgatatattt tttatgtaca taacaatcaa  88083
taaattgtta tgctatttat ttatgtactt atatgtaaat taaacaacca agaaatcgca  88143
aagtgtttta ttaagatgat atctaaactg aaatatcaca acttactaca aataatactt  88203
tgtttcaaaa ataatttgaa ttgcatataa aaatcacagt tgctgtgatt aacattgcat  88263
tgatatattg gaactaaggt ttttggaaaa attgtgtttt ctttcaatct tttaaaaaat  88323
accatattta taaaatgagt cattaagatt atccctaggc attttcattc tgtattgaag  88383
gtttttgagg gacatcatta ttagttcaaa gtgtgtttca cattttgtag tctgtcttac  88443
tatggcaact aatttttttt tttttttttt ttttttgtga gagggagcct cactctgtcg  88503
cccaggctgg agtgcagtgg tgaaatctcg gctcactgca gcctccacct cccgggttca  88563
agcgattctc ctgcctcagc ctcctgagta gctgggatta caggctccca ccaccaagcc  88623
cagctaattt ttgtattttt tagtagagac aggatttcac tatgttggcc agtctggtct  88683
cgaactcctg atctcagggg atccacccac ctcggcctcc caaagtgctg ggattacagg  88743
catgagccac cactcccagt cggcaactaa tttttaaaat tgtggtaaaa tatacataat  88803
atacaattca acaacttaat cagttttaag tgtatagttc aatgacatta agtatattca  88863
ccttatagtg caaccatcgt cactatccac ctccagaaca tttaaaattt tttaaaactg  88923
aaactcttca ctcatggaac aataatgcct ccttcccctc ttctcctagc ccctgggcaa  88983
aaaaaaaatc tactttctat ctgtctgata tgattgctct gagtacctca tataagtgga  89043
atcatgtaat cattgtccct ctctgttttt accttatttt aatataatca aaactaaata  89103
aataagcaaa ttcttaaaat aaaattgata tatttagtac agatcctttt gagacactca  89163
gtggtccact aattatgtac catatccaat cacatcacaa tatcataaat tttatagtca  89223
attattagtt ggcatttcaa ggcccaagta tatgtttaat aagagacaca atcttacata  89283
tgcagtttac atgtttttaa tctagtctta gcaccagcat atcaccttag tttacatttg  89343
tctaagtgca agtattggtt ttggaatgta attttgctca tatacaatct gtaagatact  89403
aaaacaaaag ctagtttatt ataagtgaaa taatggcaaa ggccatttta aaaatattgt  89463
attattttcc catttgaaaa tcagtttagt ctttagccca caaaataaca ggaaaataac  89523
ttaaatcata aaaactatat ctgaatatta tttaacatat tttataaaga tatccttctt  89583
tggatcatgg ctgcagatgt tttcatgcag cttgagccac tttccatgtc ttacggagaa  89643
tgtgcaggag ctatatatca tcagattctt tcagagaaag aaccggtaag acaaatgaca  89703
gtctgaaaga taaaggaaaa aaataattga tatcttcttg gcacctctgc atttcaaaaa  89763
tactatttca ataaagtcca tgttagaggt ggaattcaag aattcactga atctgcattc  89823
ttgccttctg ctatcctctt ttgccctcat ttgctcaatt attcctcact cctggttaat  89883
gaaggcaggc ttttaaatac agactaacca taaattgact ttaatattgg tgtttaatgg  89943
ttattcacag aactgattta aaatgtggta tcaagttcag gtcctgggat ttaccaaagt  90003
tcatcagagg acacagtaca tggcgaattg agaaccatag cctactttat gtctaagaga  90063
atattgacaa acagctaagt tctctgtgag ctctcagatt tcactcaaaa gaaatgaaga  90123
aagtaaattc tctgtttaga ctttgtgcct tttttctcct tttaaagaat ttgctcatcg  90183
gaaaatatac cataccaatg gcagcaacat actataagtt tatgagcaaa tcaattccat  90243
ccatagttac tgcagaatgt attataggca gtatttttgt tgggagaaaa gcagcagaaa  90303
```

-continued

```
cttagcaaag taagggaaag agaaaaagca gcttataatg ataaagagcc tttgtgcccg  90363
tagagagata agaaaaaata caaaagaaat ccataatgat ccacaataat tttagaatgc  90423
aatttatggc catgaagggt acaacatgtg attgggtatc aaagaagaaa gaagtcatgt  90483
taatttaggc taattaaaag atattttgtg aagcagaaag ttttttattt tgttggttga  90543
ccagttgatt ttggacagtt ttggatacta tttaattggt taaaaagcta ttgaaatgga  90603
gtatcaacca tttccagaca gaggaatggc atgagtgatg gtctgggcac ggaatatgtt  90663
tgacacacag tgaaatatca gattcactct gatgctctgt gtattttacg ggaaacatta  90723
taagggataa agggcaaaaa ttcaacagaa acccagttac tattggccat ctgagaattt  90783
tgtactgtcc aggagaaaag agagctctca ttgaaatgga agagttaata caacaagaca  90843
ttgtgcttgt ctgtactcct atatatttta tccattaaag gaattaatgg attttatcca  90903
ttttatgaca tttattattt tatgacactt atccattaat gacattaatg gataaaacat  90963
ataggagtac agacaggcac aacgcatggg gaaactatta ggaggtcact gcaatactct  91023
agctaatggt tacaacaatc tgacattggg tatttgcaat aggaatagaa agaatataat  91083
agaggaaaga gatattttgg agatttcaag cataattaat gggagaaaat ggaagcttat  91143
acttcagaga agcacaaagt ccagtgataa gtttaagttg tataaattta gtgtgctctc  91203
aggagaaggt gatgtttact ttgtactttt acaaccttgc acgggtgagt gggttactga  91263
ataaacaaat aaatgtttgt gtaacacaaa tttagagaat gtgcagttgt agatatatat  91323
gtagttctga atagtccatt taaagacaga tactaggttt tcttccaggg tttctagagt  91383
ttcgggtctt acatttaagt ctttaatcca tcttcagttg ctatttgtat atggtgagag  91443
atatgggttt agttttgttc ttccgcatat ggctaatcca attttcccag caccatttat  91503
tgagtaaggc gtccttcccc agtgtctctt tttgttgagt ttgttgaaga taaattgcct  91563
gtaggtatgt ggttttattt ctgggttttc tattatgttc tattgatcta tatgtctatt  91623
tttatactat taatagtatc atgctgtttg ggttactata ggcttatagc ataatttgaa  91683
gtcagttaat acgataccca cagctttgtt cattttgctt aagattcatt tgactatttg  91743
ggcatagcca cagtctttaa atatttgaat ggacataatg tgaaaaccac acttaagata  91803
tgtttaaacg gcacagtaat attatctaac acaaactcaa aattcaaatg tatccagttg  91863
tcccaatagc tttctttata aatatctttt tttcttttta tttcttctta ggattgaaag  91923
gtaaatatcc tagcatctac acaagggaac cgatgtgtgt gtgtatatat atatatatgt  91983
atatatatat acacacacac acacatagga atacatacat gtatatatac cagtatacac  92043
atagaataca taggaagatt ttttatatat atatatatat atatatatat atatatatat  92103
atatatatat atatatcttc cccaaaagtg tgccttggct tttaaaaaag cttacaagat  92163
ctcaaactgt cttaatagac tgacagtaac caaatcaatc atccttctca ttgttgctct  92223
gagtagattg cacctggaga aatgattgca ggtatggata gctcacttag agctattact  92283
gataatctga agtgtgttca gaataaaata accagggtga tggggaatga aaagcccata  92343
agtttcacat gatggattct gattatcttt aggctggaga agcataggct agggaagtgg  92403
gcatagctgt tgttgttaaa tacttgaatg aatgcctttt tgatttgaat tgtgtttctc  92463
caaaaatata tgattaagtc ctaatgatca ttactcagaa tgtgacctta tttggaaatg  92523
gggtcattgc agatgtaatt tgatatggta aagtcatatt gcagtagggt gggcctttaa  92583
tccaatatga ctgggatcct tatgagatga tggccatgtg aagatagaaa cacagtagaa  92643
tgtcatgcac tgacaaaggc agaaattgga gttatactgc acaagctaaa gagcaccaaa  92703
```

-continued

```
gattgcctga aaaccacaag aaaataggaa gagactaaga agaactttac tacagctttc  92763
agagacagga cagccctgct gacaccttga tttgagagtt ctagctccag aactgtgaga  92823
caataagttt gtattgtttt aagacaccag gcttatggta ctttttttaca gcagccttag  92883
aaaacaaata caatgtacat atataggtaa agcttattca ttcagttcca agaaataatt  92943
aggatcttgt aagcagaaac gaagggaaaa cagaacatga acaagaactt gctagtaatt  93003
aaagccactg caaaatgaac tcaagggctc cagcaggttt taaattacct ggtattataa  93063
atgttcaagc aggatgaatc agagatggtg cagaggtgat tattcatgca tcagatggaa  93123
ggttagactg aataatctcc aagtgaaaaa attatatgat cctatcttaa agccctgtca  93183
aatagaggtt ggtagcttcc ttttcatttt ctgcttcaat caagaggata tatggatgat  93243
atagcttggt ggataacact taaattgaag acctagtact tagttttact tttacttact  93303
ctagtactta atttttctta ggtaggcccc ttaacttctc tctccttatt ttcccacctg  93363
ttaaacagag atattaatgc tattcacttc ctagtgttat tatgatgaaa ctagttaata  93423
atttaaaaaa tgcttagaac aaggcacagc acatagtaat gactaaagaa agaagtgctt  93483
ttgaacatat atttgctcta ctattgtcta gattgtctag atataatgca ttaagtcttc  93543
ccaccagtgc cattgctcgt gtccaaaata cagagttaaa agattagaaa taattgcatg  93603
ttttctaaga gtcctgcgca ttttcctaga tccaatattg tactatttgg acaatttatt  93663
gaccaagtac cagaaatata atatttttgc caattttctc ataacaaact gtgataatgt  93723
gtatgtcaac tgctagggtg ggtttgtgtg tgtgtgaata tgtgtgtgtg tgtgtttcaa  93783
gtgtttatag aaaataaatc actcaatggc ataattttca aataataaag actacagtta  93843
ccctgattaa ggttcacctg agttttggat attaccacgt gagagttaga ggacaatgtg  93903
aagttttcaa aattaaatcc tctgaaatcc aggtatcttg ttaaattgac atctgttggt  93963
agctgacagc caatttcagc ttcaggaact agtaagaaca ttttccagct tatgaaacta  94023
ttaataaatg ttacataatt gtccaaagaa atcctcattc agtgattcaa atttaacaaa  94083
attaggtttt atttattcgc tatgtaaaga tactaatccc tgcattattt gggtgcatgg  94143
gtgacagctc tgacaggttt gtgatgcccc agacaaattc agtaactttc agtgaagcaa  94203
acccatgaat agatgtgatg gcagcgtgta cacctatata attccagagc tagtgattat  94263
gtaactttta tatacgtcag accgaaggaa gacagagaat ggaggaactg ggtgttcttt  94323
cagtaaagag caactgaatg agacagtaca tcttttgaac tggggatata ctacaaggca  94383
atgagggagg ctggctatga aagtattgaa aaatatgttt gattgctggg tgatgtttag  94443
aggccctaag gtaatagaaa ggagacaaaa ttgagagtct ggaacttata tgtactttat  94503
tacagtactc tcattttcac caaagaaggc aacccatgtg gtgaaaagac cacaagcatt  94563
ggagctaaag ccaagttata gctgtagttt tatattttgt gagcccatat gtcctcagac  94623
aagtttcgtg agttaatttc ctttgtctca gcttcctctt ttataaaatg tgggtgatat  94683
cattgtccct taagattgtt gtcagcatta aacaacataa gtatatgaac catctagctc  94743
ggtatttggc aatggtagga gctgaataat tgttagctct taccttaaaa aattatttgt  94803
taaaagttcc aaatgcagcg ttcaggagaa gatatgggtc aaggtcatgg atgaggcaaa  94863
cactacaatt caataaaaat tgttagttct taatttatct taactcagca accgtttctt  94923
gagactctac tacatattga gtactgaggg aatagaaaga tgaatcaaag accattttaa  94983
aacatctggc atttgcaatt caaaatcaag taaaaataaa tacagcctta tgatttattg  95043
```

-continued

```
agaaatgtca tgcaaggtaa atgaactgat tttaagcatg tacttagcat tcacacagat  95103

tgacagattc agtgaaaaca cggcacagcc ttcaattatt tttcttttta aatacatatt  95163

tgtggacttt atagaaatac tgacagtgtt tcctcaccaa tacctatttt ctttgttgag  95223

tgactattcc tttttctttt caaattag tt tgt gtg gca gtg tgg aag aac cac  95277
                             Val Cys Val Ala Val Trp Lys Asn His
                              75                  80

cac atg agg acg gta acc aac tac ttc ata gtc aat ctt tct ctg gct    95325
His Met Arg Thr Val Thr Asn Tyr Phe Ile Val Asn Leu Ser Leu Ala
     85                  90                  95

gat gtg ctc gtg acc atc acc tgc ctt cca gcc aca ctg gtc gtg gat    95373
Asp Val Leu Val Thr Ile Thr Cys Leu Pro Ala Thr Leu Val Val Asp
100                 105                 110                 115

atc act gag acc tgg ttt ttt gga cag tcc ctt tgc aaa gtg att cct    95421
Ile Thr Glu Thr Trp Phe Phe Gly Gln Ser Leu Cys Lys Val Ile Pro
                120                 125                 130

tat cta cag gtaattgttt ttaatgcttt tttgaagcta ctaaaaagaa           95470
Tyr Leu Gln

tgttcagcca tagcgatggc ccttatggta aattaactag tgagttgaga aatatatttg  95530

cctaaggcat tgacaaactg aaggaaaata atacttgaga atttctggag aaataagtta  95590

agttctgggt aaaaattaag caatgaactg ccaaatcatc attagatgct gcacaaacat  95650

ttttgcacaa cttttttgat tactaatttg attccaaaag tttgattttg cacaaacttt  95710

ttttattcca aatttgatcc caaaagtttg attttgcgca aactttttttg attcctaatt  95770

tccccattgt taaataagaa acttgaacca attaatgatt taaccaatta atgatctccc  95830

caaaccaatt attgatcttt ctcttgaacc aattaatgat ctgccagtcc aagtcattga  95890

gcatatttgt ttttacaagt gattttattt tatactgaag aattaagacc tacttggtca  95950

aatcagtgcc atgaacaggt tttagtgtag attctaattc aaactaccgg atttggaatc  96010

tccgttctgc cattcaccaa ttgtatgcta tcaagccaaa tagttgtaat tcacttattt  96070

aaaagaataa tttaaatgag atctacctca tatggttgct gtgaccattt acttacataa  96130

ttcatataaa taagttggca cagtgattac cctctggaag agatgatctt ataaaaacag  96190

tatattctca ataaacatca attatcagca tcagaatcat cattactagg tgttttttctt  96250

tccttaagag tgaaaacagc ttcttttttct atttaattgc catttcagta attaagaatg  96310

aatactttca gagattagtg ttctgattgt tattatagct ctaaaatttt tgaaacaaaa  96370

gattcatcag ataatgttca cattcactca tccatcctaa aagatggatt tcccttagga  96430

attggacagc aaatgaaatg gtgaccactc tctgcttgtc ttcccatagc tttcctgcac  96490

cctcagtttt tacgccatgc agtctcccag atggtgccta taatatttta agaaaacaga  96550

aaataagctc ccagtaacaa aaaattaggg aggggtcaca aatagcctat tactagacat  96610

tatgccgatt aggcttttgg aatgaaatgt tgcaaagaga tatttagttc aatagttcct  96670

caattacctc ttataaaaag aagtgaaaaa tttttaaggt taaacattgt ttatagaata  96730

gtaagtggaa aatactatag aagttataag ctccatgcat atattatgtt taattataaa  96790

gctagtttgg atcagcctgc tgaaaatcat gaatggatta caaaacgaac agtagcacat  96850

ttttttgtgt gtgaggaaaa actacatggg acaatagaga aaaatattct catagaggaa  96910

aagttagtaa gaaatgaatg gctctggtgg tgtttgcata gaggcactag gaaagtaata  96970

catttcagat aattctaata tttcattatc tctgtggtac ttccagaaag ccttttacct  97030

ctcttggttt caataactac ccaggagaat attttgagga ttctcttaag ttttgggatg  97090
```

-continued

```
gctgcagttg cccagaatct tcaactgact ggtaacattt catgttctct ctgtgaaaca  97150
gaagattccc tggtgggaag tgaagtgata agggcaggtg cagtcatgtg ctaatgcaca  97210
gcgatagctt tctgcagagc aggcatctca gagtttcctg tgagtatttg cattagagga  97270
cagaatggaa gcagtgtaac cagtgagtga tgcagagcat gggtatctct tataatcact  97330
tacagtcctc tttcacacag cagaactatt taacaagtcc tacagttcaa ggaatatcct  97390
catctctgga aggattctgt ctgcctctct gcacacagtg tccaatctaa tcaattcctt  97450
agctgctcct cttctccata gagcaaggga aaaaactact gggtaaccac atgatgcaaa  97510
agactagatc catttgttac cccatctaac attacttctt gatggaaagg tgtaaatgca  97570
ccaagagatt ggtgcacagg taaaactagt atctccaaat tcttcatatt tattgcctca  97630
tttttcatag aatgttccca aatgcaatga acagtgccaa tgggcaataa acatataatt  97690
taaatttgag cagattttct ccctagttgt gacattctgt aactaatgac ttatatccct  97750
gatatgatat ttatgtctta ctgaatattt aaaaacatgt tacatcatgc ccagccacat  97810
tttaaagtta tttggttgca ttttagatta cttggacgtt tattaatttg ctataattta  97870
tatgttcttt ttcttctaaa tacaatacag cctttagatt tatgagtgat atgctgtaac  97930
gcattggcaa atgcacaaaa atctcaaaag tctcacaaat gttataaagc ttagctgaat  97990
aattaaaatg actcttttgt atctttaata attgcataac tccaagacca ttaacatgta  98050
ttcagctatt tgctgaacaa ttatcatgta tttcacttct cttccaacaa tgacaagagc  98110
attggttact ttttcagagt gatttttttt aactgcagaa gacgccctac acagaaaatg  98170
ccagaaaaaa aagaagccaa gtgagatgtg ggaggtgggc agtgggtggt caaacaagct  98230
ccctctcttt cagtcatact ttgaaacctt tctacctatt agtgcttatc atccaaatct  98290
gtgatttggc aaaattttca tttctcctta tagtgaatct ttaagatacc tttgccgtat  98350
ctatttgcta gtataaaaca gtggacttct ctactaaagg aaatccccaa acattatcct  98410
gtgcgaaggg tgcccatagt ataggtcaaa gaccaagtac ctgaaggcag aagaaagttc  98470
ccattatctc actccacttc attctcaaca ttcataatcc acactagatt catttctcaa  98530
atgacttact attcaacaaa cttgagctaa tatcagaatc caaatgaaaa agacacccag  98590
aagtgcactc ttagaagtta aaagcaacaa caaaactttc acttataatt acttatgata  98650
aaatgcaatt ttacatcacc tccaagaaaa tcttatacat tgcacataat tgtatattaa  98710
tgtgttaatt gcacaagcaa atatagtagg tcaaacaatg aatattagct cactgattgt  98770
caagggttca ttcaatggat tggttcattc tactgttaga tacatcacac tagcatattc  98830
ctccctttc tgtgtgatga agggcagtgc tccctgggtc actattggca ctggatgtca  98890
gtcttccaag tgaactgata tgaattgatt attatgacct aatggcatta ggaaacacta  98950
gaaatgacat tgatatttga accatgctac atctatccca tttatccatg ttgattaaat  99010
taatggatta taaattacta aggcttgatg aacactttgt acttctaatt gctagagagg  99070
attgatatat ctctagccca gaagctatga aaaggcgact gtgcgaatct atacaaccat  99130
agttctattc ccaggttagc aatggtattg aggggcccta ggtgcttaac ttatttgcag  99190
agaaggaatg gaggttgtag agaataaggt gatactggtt tgagaaagag agttgaaggt  99250
accctcaggt agcactaaga aatttctagg agtcactaat caacttaagc ccattctcat  99310
agagtccagc cccttaaaat tacacttaaa atgaaattag cctccaataa tttagcaaag  99370
gttaggcttt cacttgtaat ttctatgaat attcttctct gaaaagcaat ctgttccaat  99430
taaaatatag aacttcagac tcaagaatga aagataaaac taatagtatc atcatcatta  99490
```

-continued

```
ttattattat aatcataaga aatagtaaac acacagcact tatatgccag ccctggaata  99550

gacattttca tctcaactaa ctgtccatac aattccatgg ttaggtacta ttaatcatcc  99610

acattttaca gatgagaaaa ctgaggaatg gagaggttaa ataatctcct taagatcact  99670

ccatatgtca gatgggattc atgcccagaa aacctggttg cagactcgat tccagctata  99730

ctcttctgcc tctcccatag agaaacaaaa gaatcatact tgataagaat cttatcctgt  99790

tgatttactt catttagcac acacacacac acacacacac acacgcaaca cacaacacac  99850

aacacacaca ttaggcctaa agctgtaaag tgagtgactc aatagtgtgc agctagctga  99910

tcagagagag agaacagata gttcatcctg acagcccaga gactttctgc actgttgcac  99970

tggatcttag atctctttca ctcatttgta cctataatca acatatcaac aagaaaggtc 100030

ctcatgtaaa agacagagat aactaccctt tccacatatt atgagatcaa tataaccagg 100090

acagaaaaat agaagaagat gactggacta tatctactgc cttcaattaa ggctcaccac 100150

tattaatgga ttaacaaata tttgttttaa agacacatgc aagtatacgt tcactgcagc 100210

actattcaca ataacaaaaa cgtggaatca acctaaatgc ccatcaatga tagactggat 100270

aaagataatg tggtacatat acaccatgga atactatgca accataaaaa agaatgagat 100330

catgtccttt gcagcaacat gaaaggtgct ggaggccatt atccttagca aacaaatgca 100390

ggaacagaaa agcaaatact acatgttctc atttataaat gggagctaaa tgatgagaac 100450

acatggacac ataaagggga acaacacgca ctggggcctt tcagagggta gagggtggga 100510

gaagggagag gatcaggaaa aataaccagt ggatacttgg attaatacct gggtgatgaa 100570

ataatctgta cagcaaacac ccatgacaga catttatcta tataacaaac ctgctcatgt 100630

acccctgaaa ttaaaataga agttaaaaac aaaatatttc ttaaatgcat aatggatatc 100690

aaatgttgta tcagatattg gggacacagt tgtgaaaaaa acagaagcag tccctcctac 100750

cacagagctt tgttccaata gagaaaacag atgataaata agcaaattaa gcaaataatt 100810

tactacatta tacatgctga aagaaaaata aataacaatc tgtaaaaaaa aatgtaaaag 100870

aaatcagaag tctttttaaa gggagagggg attctgagag tgatatcaga atcaatattt 100930

catccagtat aagagagcac attgaacata attacattaa ctaataatgt ggatatatga 100990

atttttaaaa ttttttgttg ttgttatttc cttaaagtgt caagttaaag aatgatttgt 101050

ggcattgtta attatataca aattttgact gggtgaactt acctagtttt tggaatcaca 101110

ttgactaggc tagcagtgag caaactgtca taaggagatt cgcatacaaa attctctttt 101170

aatatgactc gtaactttcc ttgggtgcta catgttgaaa atgcactgat gtacaaatag 101230

cccttattat ttgaaaatat gaaataagct acccataatt taaaaatgtt aattaaatat 101290

aatttcaatc aaatttctat gtggtaattt agaagaaaga catattattc tttataattg 101350

aggcttttcc agtttggact aaacatatgt gttttttttt ttctatatga gggtatgatt 101410

tcttccaatc aatggaaaaa ttacaggaca aaataattac agtaattatt taaagaatgc 101470

catattataa attaagacat ttggagtaaa aaaagattgc aaagttttca tcataccttt 101530

tcatgtttaa caataaattt acatttaaaa gtatatttct aatatttcat ttttgtgata 101590

taatttcttt ttaaatagaa agcacttgca tggattgttt atttttggca gctttgaatt 101650

tgcttatatg ttgtgactac ctttctcata tagtaaatat attaagagta attcttttaa 101710

cagctggtgc ttctctatta ctatgatctt tcttttctct ag acc gtg tcg gtg    101764
                                               Thr Val Ser Val
                                               135
```

-continued

```
tct gtg tct gtc ctc aca ctg agc tgt atc gcc ttg gat cgg tgg tat   101812
Ser Val Ser Val Leu Thr Leu Ser Cys Ile Ala Leu Asp Arg Trp Tyr
    140                 145                 150

gca atc tgt cac cct ttg atg ttt aag agc aca gca aag cgg gcc cgt   101860
Ala Ile Cys His Pro Leu Met Phe Lys Ser Thr Ala Lys Arg Ala Arg
155                 160                 165                 170

aac agc att gtc atc atc tgg att gtc tcc tgc att ata atg att cct   101908
Asn Ser Ile Val Ile Ile Trp Ile Val Ser Cys Ile Ile Met Ile Pro
                175                 180                 185

cag gcc atc gtc atg gag tgc agc acc gtg ttc cca ggc tta gcc aat   101956
Gln Ala Ile Val Met Glu Cys Ser Thr Val Phe Pro Gly Leu Ala Asn
            190                 195                 200

aaa acc acc ctc ttt acg gtg tgt gat gag cgc tgg ggt g gtaagtacct  102006
Lys Thr Thr Leu Phe Thr Val Cys Asp Glu Arg Trp Gly
        205                 210                 215

tatggcccat caactgacat ttatattaca gcagcaaatt gaaaattgga ttagcatagc 102066

cattgtaaag ctgggcttat atattttatt gacatttgtg aatacagttt tgcaagagca 102126

tgaaaaccaa cttgaatttc aaaacaattt cacagaataa ctctacctat ctgaatcctt 102186

tggaaatgtt atctattatt ttctcatttt catatctttt ggataggaaa tgaaaggaga 102246

ttattctaca attcagattt gattatttta gtttttctta aactctttaa acaaaaagca 102306

atatggaata caaatccgat tatgtattct ggaatgatcc acgatttata agatggttca 102366

acactgtgtt gtctagtgtc agggtcccta atgggcttca aatacaactg aatttttca  102426

ttttaagacc atgtcctgga tcacatggtc ctgggaacat ggccagagtc agcatgtggt 102486

tctctaagtc aaataatcca aatttgtttt ctctattcat aatacattat tgctactcgc 102546

ataattatta tccagtttaa gaattatatt aattatgaat caatctggtt tcccatctga 102606

caagtatgat gtgaaattta agcaatcagg tttgaaggct ttatgtttct ttggttagaa 102666

attcttagag tcagtctgag gtttttgtgt aacagtgaga atactgctat caacacctgg 102726

tgctagcaca aatctgggca caggaaagaa tgacagaaaa taaaataacc ctgcatttca 102786

gcatagcatg cactgattcc aatatatcat atgaaatata tatttaaaaa aaaaccaatc 102846

tgacctcttc taggtaagta tactaaaaat ggctgatatt tagagaattc atatgttaac 102906

attgtttttt attagaaaga tgtatcaaaa caagcagtgc acaccaggga ctgattaagg 102966

ataatattct taaatattgt aatctttgaa tttctgttat ttcctacctt ggtgtttgta 103026

ctagaacacc gaaaggaaaa aaagccaatc actgatatat taggcatata ctacaggata 103086

tatctacagc aagataatat ttaagagagg ctgggattat ttcatatatt gttgcaagac 103146

ctataataac taaaatttta taatttgctt tatctattac cccaaatatc aaatatctgt 103206

cttttattgg gatttacttt tcctttttaa cattccaact tttttttgct gtatttttct 103266

ctgtatcatt ttcagttttt tccaatttc caaattaata gtgcagacaa aaaaaaaatc  103326

aatggaaatt tccaaaatgg taggaatatt tatgaagtgt cttatgtccc attcatttaa 103386

tgctcaaaca ccaccttgag aacttagtat atgtcaggca ttgtgcccac ctggagagaa 103446

acagactctg cttacgggag cacactctat ataataaggc tcaaaggcca ataaacaaat 103506

ttttataggg taatcagtat tttaatatat ttatatacaa aatgctgaga acacaaatga 103566

gagaacaaac tcagttctgg ccatttgaac aaaagtttac agaggaactg ctaacattcc 103626

agcagaacat taaagataag caaaaattct ccagactgag aagagggaaa aggatgtcca 103686

gaaagcaaga aaatccacat catggatact acattacaaa gcagaaagag tgaatcagca 103746

cttgtagttt ctggaacata ggggcaggta gtgtaaataa ttgaattttg aaacaagatg 103806
```

-continued

```
ggttggggac tgactgtgac atgtctctta tacgatcctt ttacactggt ttatatttag 103866
aaagcctaaa aaggtctttc tcagaatcct gtattaaact cgagactaaa tttaacccta 103926
gaaagattat attatttttt caagattatg aagcaaatag gtacatttaa atctaaagct 103986
tccaacttgt aagttgggat tccttaagtt ttatagggat tgctattaga taaaatataa 104046
aaatattttt caatatgtgt cagcagtatt ttctctaata ttccggcaat tagtttcact 104106
tatatgttta tgggttgctt ttataagctt ttcttttttt aatgtttccc tgaataatca 104166
agtaacagta acctccatta acaaaaagat tgcaaagtca tggattcctg ttcagttatt 104226
atgattatgt aaatagacgt atgattttta aattacctct gagtggtaaa tataaataca 104286
taaagctcat ttctactctg atattttatt acataactct agcatggaca ttttcattaa 104346
aaaaaggaaa caattgttga atatgtaaaa acctaaactt agccttcaga agtcatttaa 104406
gaaaactatt tgaaggtgat tttataatag cctataatta aatgcttgta aagactaaaa 104466
ttaagtatta ttggactgaa ttgattagct acaaaatcca acttagtaaa agctatacag 104526
tcatttaaat attaaatgaa attgctaaga atatttttaa gaaaaaataa ttcaaggcag 104586
atttttatct ttcttattag atatttatta tgatgatttc tacatagcat gtaaaatcat 104646
tgttcatgta aactatttat aagtccatgt tcgacttata atgttaaacc tttgtatatg 104706
tgtgattgtc acaacttttt aaaaaaccat aggaaagtat attttacagt gtcatctctc 104766
taaattcaaa tatttttaaa ggccaactgt catttagcct gatttttaaa actattgtaa 104826
aatatcttct atttgagatt aattcataat ctgtgtttct tatctttatt ctaagttaaa 104886
tcaataatgt agttataaaa gtagagagta gaatcataat tatcctacaa ccaatgtggc 104946
agtggaaaaa aatttggaaa agcaatttgg tcagttgata catatctatc aaataacttt 105006
tggaaaagtt ctgtaaatgc tgttttactc atggtgcaaa ataactgaga actctgtcta 105066
actaaaaaat ttaccagcaa tatgtaatta tatatggata aatgatttct aaaactaatt 105126
atattcatta ttgcctatta cttcttcata aaaagaacca taagccatga tttctggcag 105186
acacacacaa cactcaagaa catataaata atgtaaatac ttattttaat aacctttaaa 105246
atatacattt gtatgtgttc actgtttgct tcagtcacat catttcatac ttctaaaatt 105306
attaaattaa cccacaattt cttgcttgct tggtttgtaa atgcataatt ctacaggaaa 105366
gatcctacag aaagaaattc tttgctgggt gtggtggctc aagcctgtaa tcccagcact 105426
ttgggaggcc gagatgggcg gatcatgagg tcaggagttg gagaccagcc tggccaacat 105486
ggtgaaaccc cgtctctact gaaaacacaa aaattagctg ggcatggtgg tgggcgcctg 105546
taattccagc tactcgggaa gctgaggcag gacaatcgct tgaaaccgaa aggcggaggt 105606
tgcagtgagc cgagatcatg gcactgcact ccagcctggg caaaagagca agacaccatc 105666
ttcaaaaaga gagaaaataa ctctttttgt acactcaatc aaagttatat tttcttcact 105726
attcattcat ccagtgttta attagcatgt acccttggtc aattgttctg gacactggag 105786
attagtagca tctctctttt tgaatattac tgacaaattg ttctttggta ggctaaaaaa 105846
aaaaaatgga accattttta cagtcaaagt aattatggca tctggcctat tatgaggttt 105906
gaaagcatat aaatatgtgt ataagtctat taatgggaag atttattaaa catatttatt 105966
agggagaaga tagtaaaaca tattaaagat tcaggtaaac ttaatgaacc cctaaacttt 106026
gaaaagacat tccatgttga atattgggaa attatattta atttacttgt tcattcaatt 106086
cctgataagt gtaccatgaa agaggaatgt ttctagtttc tagataatta agataacatg 106146
```

-continued

```
ctggctgaat aatgaacctt aagtcatctg agagaaatta agttttgcct gtcaaatata 106206
caatataact ctttaatctc tgatttcaaa gactaaagat ccacatttgt tccttattag 106266
ttagtttcat atatatatat ataaaattta tttagattgt gcttattcat cagttgagta 106326
aaaacagtaa tttttaatga ttatcaatat ttaaaacttt tttaaattaa agtaatgctt 106386
atgtgaaaca aattttgtgt agttatattc taggttatat acaaatgtct taaatacatt 106446
gaagacattg cttatgaagt acagaaagac ttcaaagata ttttcatcac acataattta 106506
aaatttcaat ggcatatctg agtttttaat cagcttagac tatcatgttt ccctagttat 106566
ctattataat ctccttattc aaacaatcta tcctaccctg gaaggataat tttgcttgat 106626
ctttttttcca tatcagtgtt cattataata atttgcattt agcagtcaat tacatatttt 106686
ttctaattat tcataaatat accaaccaca taggagcttt tgctaccatc tattcaaaac 106746
gccaaactgt tatcacagtg atgctatcca tagctgcagt ggaaaaaatt tacctctcaa 106806
atctactttc ctctatccac tcaattggtc ttatgcagac aacagggctt cgcaggtatg 106866
taagcttcaa agttatatag attttgtcat gaggaaagct catgtgacac ctcttcaaaa 106926
caaataaaag ttcaaagcct cttaggtgcc tgggaagtgc tgagatcact ttcagattcc 106986
tttgaaattg gcccgccata tgctgtgtag gctgtggcac ttcaaaggga aagactgtta 107046
tttctcaagt cagaatgctt gaatgttatc actttttatg taactggcct gctttacagg 107106
atcaacttga aagaaagttg gaaactgatg aggtaggtga gtgctacctg ggccagagag 107166
tagctaaaaa tgacacctca aattggtctc ttagacctgc caacacatgc atcctactga 107226
ccctgctgaa gactgcagcg gataaagaca tctaaaccaa aagagaagat gggtttagaa 107286
gcatgaatat ggagaaaatt agactcaaac tcaactgcat ctgaaagaca gcctatggaa 107346
ataagattgt ggaggatatt aaactcataa atatgttaaa atatatccag caagaatcaa 107406
atgcatgatt gctcaataaa tattatctat tattatgaca atcatcatgc ttattattga 107466
ttaatcctga ctgtaaactg ctcttatcac aaatctgatc acataaccaa gctttcatgc 107526
ttctacatcc cctttatgaa gtaatgaaaa gaataaaata catagaggta atagcattat 107586
tcctcaacaa tactatggga taaaccccct tgtcaataga aaagtcaaaa caaagtatgt 107646
aaattttaga agaaaaacaa aacagctctg ttgtgttagc attcaattag aattataatg 107706
agttaattac atttaatatc tatggaatct atgcaagata tattgcttcc tcttttacat 107766
tgcagtaaaa gtaggtagac cattgtgata tattcgaata caagtacaaa aatatcttct 107826
aaaatctaca gggaactcaa acaaatcagg aagaaaaaat gcaaacaatc ttatcaaaag 107886
ttggctaaga acatgaatag acaattctca aaagaaggta tacaaatagc caacaagcat 107946
atgaaaaaat gttcagtatc actaagaatc agggaaatgc aaatcaaaac cacaatgcaa 108006
taccactttt ttttttattt tttattttat tttttgatgg agcctcgcac tgtcgcccag 108066
gctggagtgc agtggcatga tctcagctct ctgcgacctc cacctcccaa gttcaaacga 108126
tactcctgcc ttggtctccc aaagtactgg gattacagac gtgagcctgt aattggtgtc 108186
tggccaatac caccttactc ttacaaggat ggccataatc aaaaagccaa aaaattaagg 108246
acattggaat gaatgtggtg gagagggaac acttttacac tgctggtggg aatgtaagct 108306
agtacgacaa ctatggaaaa cagtgtggag attccttaaa gaactaaaag tagatctact 108366
atttgatcca tcaatctccc tactctggta gctacccaga ggaaaataag ccattatact 108426
aaaaagatac ctgcacatgc atgtttacag cagcacaatt cgcaaatgga aaaatataga 108486
accagcccaa atgcccatca atcaatgagg gaataaaaat atgtggtatg tatatagcat 108546
```

-continued

```
agaatactac ttagccataa aaaggaacga aataatggca ttcccagcaa cctggaggga 108606

tttggagacc attattctaa gtgaagtaat tcaggaatgg aaaaccaaac aacatatgtt 108666

ctcactcata agtgggagga tgcaaaggca taagaatgat aaaatggact tcaggtactc 108726

aggggaaagt gagggagagg gggtgaagga taaaagacca cagattgggt aaagtgtaca 108786

ctgcatgggt gatagatgca ccaaaatctc agaaatcacc actgaagatt catgtaacca 108846

aacaccaact gtttccccaa aacctatcgg aataaaaaat taaaaaaata catacataca 108906

aaaattcaga ttcccgacat aatatataaa tatatattat atgttatata taatattata 108966

tataaatata taatgtatta tagttatata taatattata tataaatata taatgtatta 109026

tatgttatat ataatattac atataaatat ctattaatat atattattta tattatatct 109086

aaatatataa tatataactt attattatat attataatat aacttatata ttatatataa 109146

tatatataat ataatataac ttattatata ttatatattt atatataaat aaaatatgta 109206

ctatattaat atatgaatat atctaatatt aatatacaat atataaattt ataaatatat 109266

aatgattata tattatataa tatataaaat atatattatg tagggaatct gaatttattt 109326

atgtatttat gtacatatat aaggtaggga atatatatat atgtattagg tagggaatat 109386

atatatatat atatatatct tctagagcat ttacaaagtt agtaatcaat ataatttaga 109446

aaagctaaaa tattaaacca caatgccatg aagtgattaa tcgacttatt cgtaagtgtc 109506

taatctgtga tgtgtatcat ttgtgtacat aggattaatt ataaataaaa aattactaca 109566

gtcctagagg tgtttatgct taataagtga gaaaatattc atattggatt ggagaaaata 109626

aatgttataa agccttaaaa ttctcatttt tattaaaagt atatacatgt atttttaata 109686

aaagcataca cacaccacag acatactatg cttaaagagg aattttgtat atgttccaat 109746

aagtcaacaa aaataatcat tgtcaaattt gtattgtatt tagttttcaa aatttttttc 109806

acatttgtat ttggagatac aactgagaat agcctcccat ttctcaggga acttacattc 109866

taataaggaa caaccaactg agtttatatt ttcttcccat tttaaccaaa gcattagttt 109926

ttaggttttc attgattcat gtcccttttt gtaaataaaa gtttagaaca acccaaatta 109986

attttgttaa ttagccagat gtaatcaagt caaataaagg gccttttaat aactgaacac 110046

ttgactttgg gtagcacaaa ttaagaaata gctaatgctt atttttctga gtacattaag 110106

tgaaattacg acttcacatt tggcatgtgt atacccatat actgagtaaa ataagttgtt 110166

aaatattatg aattattttt ccccttttgca tacataatat gacaatgaaa tcatataaaa 110226

ggtaaatatg cactttgaag aaaagcattg acatgtatct tttttaaaag tccatcaatt 110286

gtaacgtaag gttttgttgt tttgactttc atcctag gt gaa att tat ccc aag   110340
                                         Gly Glu Ile Tyr Pro Lys
                                                         220

atg tac cac atc tgt ttc ttt ctg gtg aca tac atg gca cca ctg tgt   110388
Met Tyr His Ile Cys Phe Phe Leu Val Thr Tyr Met Ala Pro Leu Cys
            225                 230                 235

ctc atg gtg ttg gct tat ctg caa ata ttt cgc aaa ctc tgg tgt cga   110436
Leu Met Val Leu Ala Tyr Leu Gln Ile Phe Arg Lys Leu Trp Cys Arg
        240                 245                 250

cag gtatatagtt tcaaatattt tgcgtgcatt attcctccac acataatttg       110489
Gln

ttatttgtta ttccttccaa atattttgtc tgtgcttttt ttttaggatg cacttataaa 110549

caaaatttaa gaatgcattg aaccaatata acatgttcat aaaagtatta tattgtgtgt 110609

tcttttaaag taatgagaac ccagacatag aaatatgtct aggcattttt agagtaatat 110669
```

-continued

```
tcaggaaatg tattttataa actgattaag tactttacat tttaaataaa atttaacatc 110729
tgtgattaat tgtcttttgt ctaggaataa cactaatttc gctttctatg agaaatagca 110789
aataaaaatt cctttagaga tttttgagac tctaagtctg aaaggttata tttgtaatca 110849
gatttattta aaacattgga acatataggt taaatctcca acttcaaaga tcttattttt 110909
tagaatatta taagaatcag gcagaatgta taattttaaa aactgtatat aatgctgatt 110969
tggggttact acactttgtt agataattct gctgtatcag tgaatgtttg tattcattca 111029
ctcagttatt cattcctgaa atacatatca tgaacttttc acatacatgt ctcacacaaa 111089
agctaaaaat tctacttttt gccattgagg aattcatagt ctagaggagg ggcatcatca 111149
gatgcagggc gaaaattact ttaaatataa gcacagagaa tcagagcaaa atgtactaaa 111209
accatatcta atacaggaaa ggtaacattt aacttaaacc ttgatgattt gaaggatatt 111269
accaacaaac acatttagtg gtttgtaaga tagagacaaa aaggatatgg ctcagtctct 111329
cccattttgt aaaatgtatc ttaaaatgcc acaattctta gagatgtatt tctctcgttc 111389
tctaaactta ctgccgatac ttactttatc aggcttgtgg aaggacatgc cattagtctg 111449
ttttctctga cacattttat ccaactgaaa agatttactg gagtcacctt aattcattaa 111509
aaagatttca caaacacttt atttggtctt tgaggatgtg tctttgtttt tttaatcaac 111569
acttgttatt caaagcattt ttcaagatca tctttcactg actggatatg agcaacactc 111629
atttttttta acactatatg gctcataatt tcaatatttt ctcttttcct ctgctattac 111689
aaagaagtca tttcttttat gaccttacaa gtgaaaccag tagcaacatt tattaacatt 111749
ttgtttccca tcatttttta ctataaaaac taatgtggac cactataaaa tatgagtggt 111809
gattttctag atgttggtga cagttttctc agcactctcc acctccctat gaagccaatg 111869
cttatatttt agggtgtttg ttactgcagc atcctgcttc ctagtaccta ttattgtatc 111929
tgtcaggttt tgctaggtta ttattcttct attaaaaaat gtggtttgca acaacagttc 111989
tgtttcactc ctattacagg tcagtgggga gggctggctg gggcactgtg ctccatttgt 112049
tttctcattc cagaacctag tctgaagaaa tggcactttc tgggacatgg cattctgaga 112109
ctgagagaaa aagaaaactg gaagaaaagt atattttctt ttaatgtctt ttatgaaccg 112169
gcatgtgtta catctcactt ttcattggct aaaacaagtc acgtggttaa acttgatcat 112229
gaagagggga cacattcttc tctgacagaa agacatcaca catcacaggg taatggggag 112289
cttcctacaa gctggggatg aatgatctgg aatgatacac tatacagaag tcaaaaacac 112349
aagggccaga ctgcatgaat ttaaatcctg actccaccaa gtagtagtga catgaatttt 112409
gtaaatggct taaattttg tgactccctt tattaacttt aaaatggggt tgtatagcat 112469
cttcctcata ggtttggtac atgcattcag gtgtgtccaa gggagagaac accgtcgtgg 112529
gttctcagtt tctatttcta tttgggccag taaaacccct tcctatccct cttttctgct 112589
tattactaga gacagaaact aaaaaccagg gcttcaggct gctaaaagcc taaaacaaaa 112649
caaaacaaaa ctacaacaac aaaataaggt gggttggaca agcttgctta gatgaattaa 112709
ctcaagtgcc taaatataga cagtgctcat taaacaaaat atcttaatgg atgttgttta 112769
ataatggcct ctcaactaat tgtacttaca tttaaatagc aagcatgtgt tgaattggta 112829
tatgtgacta ttttttaaaa aatgcacatt gaaataccag tatggtgctt cttatttgtc 112889
tggttcttct actctactaa gataaagata gtctcgctgt catctttgta tccctataaa 112949
tagcacgtgc tcagcacaca tcagttgctt ttttcataag aacaaagtga gtagaatagg 113009
```

-continued

```
agaaagtgct gggaaagttt agagaggaca tagagaatct attgcccagt tactccgata 113069
aacatttgta gaaatggatt agaatctgaa aaatttcttg aaggggaaaa agcaattaat 113129
gagcatgtag gaataaagat attttagatt tagattcaga ttttgttggg gaatgttcag 113189
tgttaagatt atcccctatt tccttatttt tactagttag tgtgcattgt ataaaaggta 113249
tgcttataat ttcttattca tttatttaca aattgacata cctttaaaac tctttcaagg 113309
ttgcaatgta tctgtcttgt tacttttaca tggtaaaact ttaccatgat accatggtta 113369
ccctaaagtt tacatggtac catcagagaa aatgttttaa aaagtttgtt aaatgaatga 113429
gtgacaccaa aatccaaaca ttttaatttt ccaccattta agcatatagt ttgacatttc 113489
ccaaactcta aaataaattt taaaataaat tgcatcacag attcataaat aatccacatt 113549
cttttcatga attatcctca ttagtacaag ccacatgatt cagaagattt gcagtaaaat 113609
gcttgggctg tgaaactaaa gtcatttaca aaacagattg gaatggaaaa taccaagttc 113669
agctgaactc actttagcag ccacaataaa gtgaattaac cccaaatgcg tgattacata 113729
gaattctgct tgagcaactc tcaatttcca actgttagtg tctataaaca aagttgtaag 113789
gcattatgcg tgccataggc tacatcaagt gagccatcaa atgaagagct tgtcctattt 113849
gcttaaaatt acagagatgc atgaaatctg ttatgtactt ttgaattagt aagtgtaaga 113909
ttattagtga gcaaattgtg tgtccttgtc tgactttctc aagaagttta agcctcatta 113969
aaagaattag ctaatgcatt gctgtgaact acttaaattc tctctctctc tgtttttttt 114029
tttttttttg gcaattcgac tcagagtact caggaaattc tacagattat ttgctaaaac 114089
ttattttttt aaagaactta gcttgcttga ctctttcatt tatctgtcag catttttttct 114149
agttcagacc cttcatataa ttcaacacta aatcttaatc gtcatgtgct tgtgttaatt 114209
tatttcacat ttattaagca cgtactctgt gtcagctatg gtgtgaggta ctgaggatgg 114269
actgtaatag atatttgggt ctgaaactat agttcagctt ctcagggcct ttgaaagacc 114329
ttcttgttcc cagctcttat cacaaagttt tctgctgctc tttattcagc actcttctaa 114389
gggaacttaa gataaataat atttgatgat gacaaatcag tctagtgtga gaaaataggc 114449
agcaaacaaa ttacaattgc aggggcagaa tcaggaaggc agtaactcga gtccatacaa 114509
aaaaaaataa ggagcaccag taaaggtaac tacataggta aatactgtag acagaataaa 114569
catatttatc ttctgttatc tgatgtaaag aacaactgca taaaataata gctataaaat 114629
tgtgaagatt caccttataa tgtatacaga tgtagttcaa aaaaggagga ggaaatggag 114689
ctgtattgga gcaaatttgt tttatactat tgaaattaca ttggcataat ctaagcagct 114749
tgtttagatt aagttgctaa ttttaattcc tggtgtaacc actaagaaaa taatttttttg 114809
aagaatgtag aaatataggt aaagtaacaa aagaattaaa atagtataca gaaaatattt 114869
aacacaaaat aaagcagtag tgaggaaata gaggaagaca agagatacaa tatatataag 114929
tcacaaatag taaaatggca gatatatatt atattttctt aataattaga ttaaatgtaa 114989
atggatacaa tacttcaatc aaagggcata gattgacata atagataaaa accaaccaat 115049
aatttaaaaa aacccatgat ccaactttat gctgtctaca agagacatac cttgtattca 115109
gatatacaaa taggttaaat gtaaaataac agaagaagta ctaaaataat cacaaaaagg 115169
gagttaatgt ggttatacta aaattagaca aaataaattt taacaaaata ttactataca 115229
tagagaggga catttcataa tgatgatgga gttgatccat caggaagata taaaagttgt 115289
aaacatacat gcatttagcc actgaaaccc aaaatatacc aagcaaaaag tagtagaatt 115349
aaggagacaa gtaggcagct agacaattat agttgaaaat gttaatactc acttgcagta 115409
```

-continued

```
atggatagaa aacacaggca gggtgcggtg gctcacccct gtaatcccag cactttggga 115469
ggctgaggcg ggtggatcac gaggtcagaa gattgagacc atcctagcta acatggtgaa 115529
acctcgtctc tactaaagat acaaaaaatt agccgggtga ggtgggggc acctgtagtc 115589
ctagctgctc aggaggctga ggcaggagaa tggcgtgaac ccggggggtg gagcctgcag 115649
tgaacagaga tcgtgccact gcactccagc ctgggcaaca gcaagactcc gtctcaaaaa 115709
aaaaaaaaaa aaagaaataa agaaaaaaca ggcagaatag caacaaggaa ataaaagatt 115769
taaacaaact atgaaaccac tgggcttaac agatatttta gaacactcca ccaaaaacag 115829
aagaatgcat atttatccca tttgcacata aaacattttc caggttttct gactaaagtc 115889
agaaacaaga caagtatgtc tgctacaacc attttcattc aatgttgaac agaactgatt 115949
cttttcaggg caaacaggca agagataata ttaacaataa taaaaaataa aaggcatgac 116009
gatcacaaaa taagaggtaa actatttcta cttgtaggtt atgtgatatt ttatatagaa 116069
aatcctaacg aattattttg caaaaaaata cattagaaca aataaatgag ttcagctagt 116129
tttcaggatg aaagattaat atatatacaa aaatcaattt catttttata cattagcaaa 116189
taaaaattta aaatgaaatt aacaaaaaat aatttaaata gcatcaaaat taatcaaata 116249
cctagaagta gatttaataa aagaagctta ataagagact tcatccaggc ttgattgctt 116309
atgcctgtaa tctcaacact tttgggagac tgaggcggga ggatcacatg aggccaggag 116369
atcaagacca gcatagtcaa cgtggtgaaa ccatgtttct actaaaaaca caaaaatgag 116429
ccaggcatgg tggtgcagtg caagactata atcccagcta ctcaggaagc tgaggcatga 116489
gaatcatttg agcctcagag gtggaggctg cagtgagcta agactgcacc actgcactcc 116549
agcctgtgtg gcagagttag actcttgtca aaacaaaaaa aattcttcag cataaacatg 116609
tatatttagg gaatgtccag aaattataga gacatggatt ccatgcagca gttataattc 116669
cctaaaaaga gaattatgaa ttcactgtat tgctgaggat tctaacataa ccaccaaaga 116729
tccagggaga aaattaccct atttttgtat ttaaaaagat gcatttatta aatgatgtgg 116789
tactagtctc tatataggca acaaaaataa tgaaaaggaa atagctctgg attattaaaa 116849
ataaatagtc tgttaatcaa atcaattaaa tagataatgt tccttcaaca ttttcaagtc 116909
ctatacatga atatcattta caatcataat tattagcaac ttcaatgagt aggccacagt 116969
tatacaagtt tcttgagtca gtttggaact atttccattc aagcaacata tagtccattt 117029
ctgtaacatt ttgttctcca tcattatatt cagtctcaga aaggttacca acacagtcct 117089
tgaatcacat gtagtacagg ttaagcatct ctaatcccaa aacctaaaat tctagctgct 117149
ctaaaatccc aaacttttga gagctaacat gatgccagaa gtggaaaagt cccctgctat 117209
ctcatgtgac aggtcgtgtc aaaagtcaac aaaaactttg tttcatgccc aaaattatta 117269
aaaatgttat ataaatttgt ttaaagacta tttgtattgg gtgtttataa aatgtaagta 117329
agttttgggt ttagacttaa gtcacatcta caagatatct ttttatgtat atgaaaataa 117389
tccaaaatcc aaaaaaactc acatctgaaa cacttttggt ctcaagaatt tcagataagg 117449
gatattcaat cggtacacaa catatacacc tacaattaca aaatatcatt gaaaaaactt 117509
aaagaaggac tacctaaatt aaaagatatt ctgtgtttat ggattggaag attcaatctt 117569
gttaaaatag aaataatctt caaattaatc catgaattca atacaattcc tatgaaaatc 117629
ccagatggct ttgtattttg gacacaaatt gacaaactga tcctaatatt aatgtggaaa 117689
tgcaagggat agagaagagc caaaataatc ctgaaaaaga aatggaaaac ttacttccta 117749
```

-continued

```
atgtcaaatc ttaacaaaaa gccacagtaa ctaagacggt gtggtacttc catacagtta 117809
gtcatataga tcagtggaat agaattcatg gtccagaaat aaactcatat ttatgattaa 117869
ttgagtattg ataaaggttt taacacagtt caatggcaaa aatcatagtc ctgacaacaa 117929
atggtgttaa gacaattgta tatccacaag caaaaggatg gagttgaacc tcacctcaca 117989
ccacattcaa aacttaactc aaaatgaatc atagatttat atgtaagagc taatctctta 118049
gaagaaaaca cagaagaaaa tcatcatgac cttggcttaa ccaataggtt ctaaatataa 118109
caccaaaacc aaaagcaaca aatgacaatg tagatacatt agacattatc aaaacaaaaa 118169
cttttgtgct tcaaactgca ccattaaaaa cgttaaaagt cagcccatat aaatgcagaa 118229
aatatttgca aatcatatat gtgttaagga atttgtatcc agaatataca aagaactctt 118289
atgaattaat aatttaaaaa aattacaagt aggcaaagac ttgaataaac aattctgcaa 118349
agaagatata caaatggtca ataagcacat aagaaggtgc ttaacatcat tactcattag 118409
agaaatatta atcaaaatca tgagatacct attcacactc aacaggatag atttgtttta 118469
aaaggctgta atcattattg gtaaggatgt ggagtaattg gaatccttct acattgttgg 118529
tgggaatgca aaacgatgta actgctttgg aaaacagttt ggtagttcct taaaatctta 118589
gagaattacc acattaccca ctaattcaat ctctagttat agacccagag aactgaagac 118649
atgtttacac aaaaacttac acatgaatgt tcataacagc atataattca tagtagccaa 118709
aaagtggaaa caacccaaat gttatcaatg agtaaatgga ataactcatt gttctatatg 118769
caagcaataa aatattattc agctactaaa agaaatgaag cactgatata tgccacaaga 118829
ttgatgaatc ttgaaaacat actaagtgaa agaagccagg cacagaaggc cacatattac 118889
ataattctat ttgcatgaaa atgttgagaa taggcaaata tatagagcca aaataatttg 118949
tccttggcac gggctggcag aatgggacaa tgagaagtga ctgctaatgg atttggagcc 119009
tcatttggag gtgatgaaaa tgttctagat tagttagtga tgatgtgata gttgcacaac 119069
tctgtgaata ttctaaaaat catttttttga accccttaaa gcagtgaggt ttatggtatg 119129
tgaattatat cgcaataaaa tgttttcttt taaaaagaaa gaacaaaaat gatgggatat 119189
tttaaaattt taaaaattga agactttttt tttttttaga aagttctgct gctgaaacca 119249
cagggaagca aaaaaggttg aacacacaat ttgacatgtt aatgtaatga gagactataa 119309
taggaattat ccacgggttg ttttatctgt actttctgac taaagttttt ttccgtactt 119369
ctatagactt taaaatggtc catagatgtg caaaaaatga gagaacctat tccatgaaac 119429
catatatcaa gtcccagaga gcagagggaa aaccttttttt tttttttttt tttgcaaaga 119489
agaagtcata gactgtgtga aagaataatg ttgcgagaca acagatctgg agttggacag 119549
gggcaggagg catagtgaga agatcagtta ttgcagttgt catccataag ggccatctgt 119609
acactctgaa agtggagcta ttcatagtga gaatgatgtt aagaaaagga acaaataaaa 119669
ttacagtcct cgttataaga atttagcatg caaatcttat cagagcagta ctgaggtaaa 119729
caaaaagtgt caagaaatca tgggatttaa tgtgaaaaac tccctcagtg ttggaataca 119789
gtcatcttca tatggtggtg ggtgtaaggg gcaaggaaaa ttttcatggt ccctgctgaa 119849
cagggaaatg taaggggatt attgtttcat agaagaccgc cagtgcctac caaatatctg 119909
ttatactcta ttatgatgaa atgggtaata ggttaaggaa taccataagg ggaaaggaga 119969
cttgtcctac aagtttctta gcacttagca aatggagcag gcatttgcta tgcattaaaa 120029
aataagcatc atccaaactc tcagactcat ccagccacaa acttaacttt ttgttcctcc 120089
tcctcccaga taaaattctc gacttatttc catttgtcat ctttttctca ctaaccgcca 120149
```

-continued

```
cctccactga tgtctcagcc cacttcagtg tagcttcagc tttcatcatt acagtgaaac 120209
agcttacatg aaagttacca atgatttcta aagaatatat atttttaaag tttatttatt 120269
gatcttttgg cagcattaag caatgttgtt tgtggtttca ttgctcatat actttcttcc 120329
tactttgatt tgaatacttt ttgctttgaa tacttacctt tccttccctg accagtaaat 120389
gccactttgc taggtctctt cacagctcca tgcttttttt caggtagtcc cttgcccagg 120449
tactttttaa gtgaggtgag tatcaaatat atatacacat cagactagtc ctctgggata 120509
cacacaatca caaatacact taaacactca atgtaccttt attataaatc ttgaaatgag 120569
tttttataag tcttgcaacc aaagtttaaa aaagaataaa ttcttttttt aaattgcttt 120629
ggctattcca ggtcttttgc actttcataa aaaattaaaa ttagtacttt catttccaga 120689
aaaaagactg tcgtggtatt gaacgtgatt aattgcatta actctataga tcaatttggg 120749
gagaattgcc atattaacaa tactaagcct tttaatgcat gtccacaatg aatatattta 120809
tttaggagtt ctttattatc tctctgcaat gtttcatcat tttcagtata tatatatata 120869
taatgaaata tatatactta tacatatatt ttatgaaata tatatactta tatatatatt 120929
ttatgaaata tatatactta tatatatatt ttatgaaata tatatactta tatatatatt 120989
ttatgaaata tatatactta tatatatatt ttatgaaatg tatgcctaaa acacattctt 121049
ttgatattga aacttttaaa atttaatttt ccatttattg ctagtatgta gaagtataat 121109
tgattttttt gtttattgat ttaatgacct gctccttgct aaattctttt ataagttcta 121169
gtgggttttt ggtagattct ttaggatgat ctttgtaagc aataatttct tctcaataga 121229
accaatctgt aggcatttta tttatttttc ttttcttctt gtattggctc aaagtccagt 121289
acaatgttga gtacgagtgg tgagagaaga cttgattttt tgagtggtaa gccaacactg 121349
cattgctaga ataaatctga ttgagcaaat ggtattatcc tatttatata ttgcaggatt 121409
taatttgata acatattttt aaagagattt ttatctctat tcatgaagga tatttagttg 121469
ttagctgtct tttgttgcca tatctttgat tacaaagata aatgtgacct catgaaattt 121529
gttggaacat attatatttt ctgtacattt cattaaaagt ctgaacaaga ttggaattat 121589
ttattcttta ctgtttgatt gaattcatta atggacctat ctgggcctgg agattttctt 121649
gtagcatagt ttgtaagtac agagtcagtt ttggtcatct ttgtctctca agggctttgt 121709
ccatttcatg taagttggca aattcattgt ttatccataa tgtttttaat gtttgtagca 121769
tgtttgcctc ttcctcataa ctttatcctg gtcacaaaca ttttttaaga cagagtaggt 121829
tttaaggtcc atcatgtaca tgctatttcc aattcataac tgtggtaata cattttttcag 121889
ggtgtatttt tgcattaaat atgatttata aagtttattc ataatagtga aataaaagtg 121949
gggtgcatgt attttactta atccttctca gtgcctgctt gattgaaacc tctgagattt 122009
acaataatgt actttttaggg atgcattaag gattactagt gcatagttcc tggagctcag 122069
taatgtcagt tattcctctt aattttatac ggagtttctc tgaattctcc atgtctctag 122129
acagcttatc aatggagaaa tttatgtgtc ctcaaaatga atgcaggatt cagcatcttc 122189
tatccttatt tagatcatta tctaaaaagg gcatcactac atttttttttt cccgatttca 122249
gggaccatag ctttctcttt atgaaaactg tatttttttt tttttttttg agatggagtt 122309
ttgctcttgt tgcccaggct ggagtgtaat tgtgtgatct catcggctca ttgcaacatc 122369
cacctcctgg gttcaagcga ttctcctgcc tcagcctcct gagtagctgg gattacaggc 122429
atgtgccacc acgcccagct aattttgtat ttttagtaga ggcggggttt cttcatgttg 122489
```

-continued

```
gtcaggctgg tcatgaactc ccaacctcag gtgaccgaaa actgtttcta atggcggcag 122549

aagtcatcag atgcagaatg tagattctct ccttcagggg aacagtcagt gatagaatca 122609

ctaaaattta attgatctat cagagatcat ttagaagaca gacagttcaa gatcatttag 122669

cagacacata caggcttttc atgataggag tctcctggaa cattccagca tccattgctc 122729

attcttttca gttatttttt aaaattgctt tttaaaatga gagtcacaga agagaaagtt 122789

cctatctctc cccaaccagt gggttaaaag attgagttga accactacta tgtaaaaaag 122849

attgtctaca tgacaagaca tacagagtga gaagaaaaat aatttatccg atattttcca 122909

ttcaagggca ggtctttgtt aacatcattt gcctcttcaa gaaagaaaat ggtcaaagga 122969

aatgtcatat taatttatct gtgtggacat ataagtaaaa ttctgttctc aaattaaaga 123029

ttatcgaaca gactttgatc tggtggtgta aaaatcaaca aaatctatcg aacatctatt 123089

ctgagaaacc acaaggacac attggtcagt actggtttgc cgcacagaga cagaaagtaa 123149

aagctgaata atcttaacag agctaaggtg gccttttctt gtgtttgttg gcacattttc 123209

ctctttaaaa aattatgcat gctgaatttt attgttctgt tcactaaacc ctatcaatct 123269

tcatgagctt acaattaaga gaatattgta cttggaggga ttccctgcta ttatcaaata 123329

actttgaaaa gaaatggaaa agtacaagtt gtgtaattac tgttacaaat tccagctatt 123389

tgaaatatta atgtaagacc gcaaaaaatc ctcaatgggt ttgtgtgcat tttaaagggc 123449

tggaccacaa aactgatttc aaacaatttc ataactacaa atagtgaaca acaaaaaata 123509

cttgattttt taaaaatatc ctttcattca aaggtttgct ttgtccgaac tcgagaagca 123569

gaaaacctga aaagctacag gtagttaagt tctatctctc tggcagcaga tggcagtatt 123629

gatgcgtgaa aaatccataa caggttgctt gacgttactt gctgggtttt cctctgcttt 123689

aaactttggt atctgagctg aacaaaaatt cctaataaga taatatggct gacatccctt 123749

tatcattctc ctttcccaag ctttgttctt tttacaagga aatatctttt ccacttgcag 123809

ctttctttag acattgacaa aattttgatg ttttaacttt tttttccaca caaactccta 123869

tttggtattc gtctgaatta acgccaagca catactaagg tcagcaaatg ctctggagaa 123929

acaggcgctc aaacctccca cacctcaggc gtctggaagc ctttccttac tgtgttttct 123989

aattacttcc ccaaagtgga actttcctaa gtcaaattgc aataagggtc tgtctcttct 124049

cctttcag atc cct gga aca tca tct gta gtt cag aga aaa tgg aag ccc  124099
         Ile Pro Gly Thr Ser Ser Val Val Gln Arg Lys Trp Lys Pro
         255               260                 265

ctg cag cct gtt tca cag cct cga ggg cca gga cag cca acg aag tcc   124147
Leu Gln Pro Val Ser Gln Pro Arg Gly Pro Gly Gln Pro Thr Lys Ser
    270                 275                 280

cgg atg agc gct gtg gcg gct gaa ata aag cag atc cga gcc aga agg   124195
Arg Met Ser Ala Val Ala Ala Glu Ile Lys Gln Ile Arg Ala Arg Arg
285                 290                 295                 300

aaa aca gcc cgg atg ttg atg gtt gtg ctt ttg gta ttt gca att tgc   124243
Lys Thr Ala Arg Met Leu Met Val Val Leu Leu Val Phe Ala Ile Cys
                305                 310                 315

tat cta cca att agc atc ctc aat gtg cta aag ag gtaaaactta         124288
Tyr Leu Pro Ile Ser Ile Leu Asn Val Leu Lys Arg
            320                 325

tctgttattt gaaaatgaaa tagcctgcct tttcttgatt cttaattaac tttttttttt 124348

tttttaact aagccagaga aaaatctaaa ctttctgctt agataccttg tcaggccaga 124408

tgactcagtt atgttgttac cagcaggtaa ggcgaacagc ctttaagagt gctcagacat 124468

gtgcttttgt catgcgtatt ctcagttgca tggcagacat aaaacagatg tttctccaat 124528
```

-continued

```
ctcttcaagc tagttgctaa accttagatg cagacaaagt tctaatgcgt aacaactcat 124588
ttacagcttg cagttctttc ttgatgagaa caaacgggtt tttcaaaact tcgtttccaa 124648
aaacataggc aattgtgaga gaattatatc ttaaggataa aaagagataa gaaccttatg 124708
ttagtattct aattatactt aaaagtgcat tggcgagcac tttttaaaaa aagccatcaa 124768
ggcagatatg tatgtcgaat gtctaaacag aagaattcat ttcctgaagt cactgaatga 124828
agctcagggc agatagtaat aaaaatcaat gagggaaagt atgctatttg ctacaatgca 124888
ggcacaacta ttaagttaaa aattttgacc catgacatga gcagcagatg cagaggcagt 124948
ggtacacact aaacttcatg gccagccaac tttattggga attatcgaaa ctgttccaca 125008
tagactggtc ccaaggcaat accaattctt gtttacaaca ggcttcgaac ttaagctaga 125068
attgctcctc tcactttggc ctgattcaga atcaatatta tattcctcac agctgggaac 125128
tctgaagaac agcagctttg gctggagtca gaagaagtgg tataatcagc cgcaaagggt 125188
tctcattctc tttggcccct gtttttgatg gtttaacggc tttttcaatg gagaagaaat 125248
ggagaacaaa cttctgttca gtgatactat ttactacagt cacagcctta aagatatatg 125308
atttttttg tggcctgggt ccttgagaca tatgccagct cacaagaaaa tagaaattat 125368
tttgccctcc atatcttttt gtgctttgct tcttattaat tattattatt attattatta 125428
ttattattgc taacagaaat ttaatacaaa tttattatgg ccacctgcta gatactctct 125488
tctgctttta agaactttat aaacatgtta tgttactgga tgggttttat tctttctttc 125548
tctttctaat ctttttctc ttttagtcag tctaaattca atgaaaattg gatttacctc 125608
tctctgggtt acgtatttgg atttcctgta tctcagaact tgctctttcc ttttatttcc 125668
aactactttt tttgtcaata atatatgtct tattcttctg actcaaatcc cttcctttcc 125728
aaggaaaaca aataactttc aaaggagcaa ggctgtgtta aatttaagat atttcaagtt 125788
ttggggcatt ctactctttt ccacaacata aaaacttttg aaaaaaagaa cttgaaaatt 125848
gtttttcttg ttaccacaca catttttttt caaatgctta tatttattta tccttgcata 125908
tgaaatttgt tttttctttc tcccacaaaa accattccta gctttttctc cttaaaactt 125968
aactttttgc caaattagtc aaaagcaatt tctttacaac agttcaggtt tgtccaagat 126028
ttcaaagaca ttttgaggta aagggtcata acatagtaca aatttctttt gtccgtatta 126088
tttcactcta tatagtattt ttgtaaaact ctagtactct ttataccaga aatggtataa 126148
ggtacacctt ataccagaaa tgcattgttg tcatgccttc ttgctgtaac acacacacac 126208
acacacacac acacacacac acacacacac actgatacag acaatcgaag atggagactt 126268
tagcaggaaa tatatatgat ttttggccta taatcttatt gagtagctgt aagttatctg 126328
ttataggtta gtgattagaa tttatagatg gaatatttct aagtatggag aaaatttttt 126388
aatagtcttt aaggatagca taacaaaaca ttttttaaag tttaaaataa tacatgaaaa 126448
attaacactc attaattttt aaaaattacc aaaattctgc ccatcgagaa ctgtttcttc 126508
tctgggtatt aaggagtccc agaaggcaag tttcagatag tccaggaaga ttggagttga 126568
aggcatatga tactttgatc aatacataaa tgaaagtagg aagaagtact tgaagactat 126628
catttaggag tgatttttaa atgatacaca taatagaata ttaatacaac attattcaat 126688
tgtatttaga aagaaaatga aataaagaag atatatattc aacttccata ttcttattta 126748
caagaaatac tgcatctgct atttgtggga gggagagacc cttctctgac ctgatttggc 126808
ttttgattta ttgattgtgc tgtggaggtt ctgttcaggc actgaagtta ttctaaacca 126868
```

-continued

```
attatggggt cagaaaccaa tctgtggtca attcctgcaa ctgaagagga caggagtcag 126928

accatcctct accaatagcc ttgttcacct ttgaatttaa ttatttaaaa gacacttttc 126988

tgttgtttct tttcctgcag a gta ttt ggg atg ttt gcc cat act gaa gac   127039
                        Val Phe Gly Met Phe Ala His Thr Glu Asp
                            330                 335

aga gag act gtg tat gcc tgg ttt acc ttt tca cac tgg ctt gta tat   127087
Arg Glu Thr Val Tyr Ala Trp Phe Thr Phe Ser His Trp Leu Val Tyr
    340                 345                 350

gcc aat agt gct gcg aat cca att att tat aat ttt ctc agt g         127130
Ala Asn Ser Ala Ala Asn Pro Ile Ile Tyr Asn Phe Leu Ser
355                 360                 365

gtgagttttc aactgttctt ccataagcca caattgtaac caaggatgag gaatcaatga 127190

acactcttca actatatgag gagtttagtt gctatgtgag ttgtattttt tccctgacct 127250

gatttatctt gagtttcttc tcttttgagg caaagtattt gttactgaac tcatcagaga 127310

aaatgaactg atttttccat gtcaaacgta taagaaatgt tataatagaa gaaaagtaaa 127370

cattctgaga aatcaataac acaaaatctt acatgacata ctttaaactc atgatttaca 127430

aaaatataaa atactttgtt ctgttttgcc ttgctatatt attcctttgc caaaatgtgt 127490

agcctaattg agacagaatt gggatctatt cacttttaga tattttacta tatttacgtt 127550

tctcttgtga gtatcatctc ttggatttat ctcaatattt cccactgact accaaaaata 127610

gtattactcc aaaataacac ataagttaaa tgatacacac atacatatac gtgtaactta 127670

tacaatttgt atctgtttat ggaatcaata taattataaa agtcatttaa atcactattg 127730

tttattcaca ttttgcccga ctgactttta gaattatttt taattagcta ccttttttaca 127790

ttgccttaat ctccaactca ttggcgattt ctttgttatt tctatcttca aatatatggt 127850

gattttatgt ggaagaatag aaattcattt tgtggcatat ttaataaagc ttctgcatct 127910

tccaacttga tctttggcct tctggtttgc ataggtttaa aaaaaaggca acaaattaga 127970

ttgatgagaa ataattttgt tctatttaaa aaaaaatcta gcacaatgac taaagctctg 128030

aacctcgcac taagcaggta aaggctatga ggaagttgta atgagaagtg tttgaagcag 128090

aagtcacaga accaggtcaa agtcctagta tggaggataa aagtgagtta gaggaggcaa 128150

ctgataatca ctgataactc attatgtgac tgctattgtg ctgggcccgt gaacattcat 128210

cttctcattt aatcactgat aactcagtgc gtagctgagg ctaagagaga agaaatgatt 128270

cgcaatactg ccattcacac taataaaagt gattcattca ttctcatagt tctccaatat 128330

ctcctccata atttaaagac aaggaatagc ttctacagta tttttccccc ttcagttttt 128390

gttctttctt atatagatta tgaaactgaa aattttctgg atatttgagt gtatgtttct 128450

aggtattttg tggatttaat tgtttcagta tcagttattt agagtaaaat gcaggagtaa 128510

tttttgtata attttggctt tgtatgacat aagtttcatt gtgtttaatt attaaatatc 128570

tctgagagtt cttctactga tgatcacttc cattatagtt atgtagataa aatataccaa 128630

tatgcgtaaa tatatgaggt ttgactataa aggaatgaag caaattccaa gccccatatg 128690

tgaaaggcag cctcgttatt ttatgaaaat attcattgtt tcaagagtct accaagcttc 128750

caataaactc aatttcctta ttctatttta cccatctttg caaaatatta cacctcattg 128810

ttagtttggc tcaagggagc aactcagttg taccctattc ataatttgtt gaagcattta 128870

tgtataattc cttttccttt cattctctct gtttgccag ga aaa ttt cga gag gaa 128926
                                              Gly Lys Phe Arg Glu Glu
                                                  370

ttt aaa gct gcg ttt tct tgc tgt tgc ctt gga gtt cac cat cgc cag   128974
```

-continued

```
Phe Lys Ala Ala Phe Ser Cys Cys Cys Leu Gly Val His His Arg Gln
375                 380                 385                 390

gag gat cgg ctc acc agg gga cga act agc aca gag agc cgg aag tcc   129022
Glu Asp Arg Leu Thr Arg Gly Arg Thr Ser Thr Glu Ser Arg Lys Ser
                395                 400                 405

ttg acc act caa atc agc aac ttt gat aac ata tca aaa ctt tct gag   129070
Leu Thr Thr Gln Ile Ser Asn Phe Asp Asn Ile Ser Lys Leu Ser Glu
            410                 415                 420

caa gtt gtg ctc act agc ata agc aca ctc cca gca gcc aat gga gca   129118
Gln Val Val Leu Thr Ser Ile Ser Thr Leu Pro Ala Ala Asn Gly Ala
        425                 430                 435

gga cca ctt caa aac tgg tag aatatttatt catatgacaa ggatacctga      129169
Gly Pro Leu Gln Asn Trp
    440

gtaaaactat ccttttttaaa atcactggga acagaaattt tattatccta tgatgtgaag 129229

ctaaaattac ttgtggatct tttttttttt taatctattg ctctttggaa ataaaaaaaa 129289

agtcagttta aaatgatttc tcaacttttg atttaaatat gttagaagtt taaccttcaa 129349

ttgagcttat ttcaggctat ttcactttta gtttcatgta ttaaaatgtg tgtcaattaa 129409

atgtttaaac atttctaatt ctttttataa tcccttgtta ttttaatctc tcacattcag 129469

attggttcct aaaaattacc agaatctatc caatgatttt ttttgctact aaaagaagta 129529

gcaattacta attctgaatt aacaatagac atgttagttg acttaatagt tttttttaaa 129589

aaaatcacaa gactgttgtt ataatgtgat atctgagaaa atatttatat ataaaatagc 129649

atattgtgtt aggtaattca aaaactatct tacaaaacta tatactcact catttacaca 129709

attttctcag gtttgcaaat tgaccattgc taacatttct tgtctcaaca tatggccagt 129769

aagactctat cacagtaaaa gttttaacgt aatttccatc tctaacactt taacatttaa 129829

gaataagcta aatcacatca ttatattctt ttaacaacaa caacaaaaag tgatatagtc 129889

agccttgctg gattaaatta aaaatgcacc actgtgctag gtgctaggga atgagatggc 129949

gtcgatgcaa acatgccttc aaaagagctt cagtctagtg agggagacat gttgacagag 130009

tgcaaggcag caaacaatct gggggacaat tcttggtcat ggcagagcag tgaagctacc 130069

aaggacagtg gtcttcacca gaaagtttgt agcgcagttg cacttttttt ttttcttcaa 130129

tttaattaca atgacagttg atgtcagtgg attccatctg ggcctggggc tgagtaccag 130189

gtggttaaaa aatagagggg cttgctctta actcacacat acatgaatag actatcgtat 130249

attttgtaga aaatgtaaga tctgggagtc aaagcactga gtattcaaac ttattcccct 130309

gaaaaattct tctgattcaa atatttactt gaaaattaaa ctaaaagtaa aagaagtgtt 130369

tatgaaagat gattttcatc tcctattatg gtaacaggtg ttctgattgt attgaaacaa 130429

aagatatggg gcacagtgtt taagaaaaac tttcatagaa aattaatttt tgttattttt 130489

tcatttttcc attacactca gagaaaagta aaagagccta attatccaca acttgttttc 130549

aaatcttgga atttgggatt ctgttacctt gtgcctttta tgactcaaag caaaaactat 130609

cttcttatac aaggtttatt gagatcatat tgtaaaatat cagcactata tcagtgaaag 130669

caaggtattt taactctctc ctttctcccc tttgtatatt ttagaacttc ttttcttatt 130729

tatgctgcat gaaaggagag ttgtaatttt cggatcgtga tgacagcact ttaaaaagtt 130789

tgaggataac ttcaaataac gttgataata tgccttaata gccagtaata gctcagagga 130849

agagtaaatt ccttagaccc aaatatacct acttataatt taaaagagag aaaagggaga 130909

gagattgaga gggaaagggg gagagaagga aaaaactgac tcagagagca gcagttatgt 130969
```

-continued

```
gacgtatggg aagtcagaat tcctttgctc taaatcagtg attctcaaaa tgtggtttct 131029
ataccatcgg catcagcatc atctgggaac ttagtggaca tgctaacttc caccctatcc 131089
ctcacctact taaccagaaa ctttaggggt gatagcccaa aagctgtgtg ttaagcacta 131149
caggtgtttc tgaagcactt taagatttga gatccactgc tttaagtgat accatctgac 131209
atcagtttat ctgcctgtgt gaaataaagt cttttactgc acaggtgtct acaacagggg 131269
ccaccatcat cgctaccgtc aacgtggttg gatgtctgaa agaagaagct gagtatcaat 131329
gttgactctc actcatgtca tcttattaaa aaaaaaacag tttacaaaac aattgctact 131389
gataaatgca gtgtgaaaga ctggttttaa ggcacttgtg tgctttatgt ccacccagat 131449
aacttgagtt tttaactaaa agtttcaaat ccctatcttc tttatactta ctaaagttcg 131509
ttttgcagaa gcagatagtt tctaagaatg atcatttcat ggaaggagat ataaaataaa 131569
ataaaaccag tacttaaact ctgggaatgt aataggccat gtacatagca ctcaacatgt 131629
gaatccagga atccttctaa gaggtctaga tttagtatgg ttaccttaat aggacaaatg 131689
gtaaagaaat aggtgttccc aaactctgcc aatcttatga aacaaagagt caactcttta 131749
cctcattatt tgctaatgac acaaatgcaa agacatcttt tgaaaagaat gtgttgggac 131809
tgttttatgc tgtaccttga atgtgtatct ctcctttttt tgctatattt caaagattta 131869
atgtaagttg tcaatgtcat tgagttcttg ttatcaatag ggatgatata attttatcta 131929
acatggaatc cattttaact ttgttatttc tgaatttcta tgaaaccaca aaaaccttca 131989
tacttgaatt tatttattct tggctaaaga ttactcccag tttgtgagga aatttatttc 132049
tgagtttcca aagcttggag aatttattgg atattaaata cctgttataa attattgatg 132109
agttaattgc aagtagcaga cacaatgata ttgaatttca ctcccaatac acattgtttt 132169
aatgaagatt aaggtaaata tgtttataaa atttagtctg gctatgctta aacctgaaat 132229
agcagaatgg caaaaaaccc caaagctgtt tatggaccca aattgtgagg agggctatta 132289
ttttaatact tgtgtaataa tagaatgcac ttgatgtaaa ttgtaatagc catcaactgc 132349
atttcaaaaa cctttcgcta gccactacaa tttagaaagc ttttcagtgt cagttagttt 132409
tacaacaaat gccttttcta ctttctacaa gtcacaagtc aaaaaaaagt aaattccacc 132469
aagttttatt caattagttt tcaaattgca tgaagcaaaa aatagatttt tagagacaat 132529
atataaatag aaaaaatatt gtaaaagtct actctattac cttatgtacc acaaaaaaat 132589
aaagtacaaa ggcatgaaaa acactattat ttcccaaagt tcaaagggaa ttgttttcta 132649
cgcaactact gctactaaca aggggacaac aaccccctcc acttgccacg tatttttatt 132709
ctcttttctt tatatctttg gagttaaatg tcttttatgt ttttcatgaa atgtattcta 132769
taattgttgt atttcatgtg tgtaacatta tgtcagttgt tttaacaatt atcttatatc 132829
ttgaaattct ttatgcctga ttgtactgtg tcttcatgaa gaaatttctt atcaaatcca 132889
atgtgattac acacttactg ctgtaaagga tgcgcattat gtagtttttta agtaaaaact 132949
atagtgagaa ttctataatc acattcacac tcccctctct attgtatgaa aaatcttgtt 133009
gttgttgatt agataaggtg gatattcact catagttaat gtcaaatctc tgcagttaag 133069
gattgaatta agccctctgg tgcagtacct aatgatcaaa acattttttc caataagttt 133129
atataaccaa ggataataat gatataaaag gtttttaatg ttgtttttaa gagcaggtac 133189
tataacaaag aaggttaaca ctggtacaga aatatttcat aaaagttatg aaaaccagat 133249
aaatacagta ttaaattttg gagcttttat ctgagttgag agatttagtc tacattgact 133309
gagatgaaat gatgaactca taattttcaa tttattatca gaataataag tgacatttac 133369
```

-continued ataattaatt tttttctggg ccattttgta taagtcattt aggactattt taagttcact 133429 ggtaaatttt aaaatgtata ttttcagctt ttcaattttt ttcaaaatag ttctgagaaa 133489 ttacagaatc agatactaag gatattaatt taaaaatcaa tttttattca gcactattta 133549 ttctaacata tataaaaaat gaagccaaag taacccgtca aggtaaatac ttgactccta 133609 ggaaaatgtg attttagtag gcatctcaag aggaagtgaa acttctcgtg gtgaaattac 133669 aagaaaaaca agttattcag tggtgagaat gtgttgctct aagcaatcca ttagcacaga 133729 ctagctactt ggccactcct cttccttctg gagccagccc tgaagagtgg tcacagcatc 133789 ttcattttta tccaggccaa tggccatgca tgagaagttg ggtagcaaaa ttcttgaagc 133849 acctctttgt tcttgctctt ctttcactgt tttctcactc tccacctgta atgctcactg 133909 ccagttttac caccaagcta agtatcagca gacctccctc cacagcgtgc cttgccctgt 133969 agaactcctg gtccttcctt cagcccaacc ccatccaatt gcctaggttc ttgttgtctc 134029 ctgagatgaa caagaggcaa gtagctaatt tgagaacaaa tgaagcagag ctgaaggaaa 134089 aagtaaaaca tttatttttt catatcccaa attttataat tttacatttt tttaaaaccc 134149 attcattttc ttcccagaac atttatgctt atcagtggtc ttctgaatct gtgacaactc 134209 ccttttcaag ccccagctaa gcttcttgcc tcaagccaga aggaatccca gttttgagtc 134269 ttgtgttaag gccatggcag gtcagtaggg agattatctg aggaggtacc gcttgtgaca 134329 ccttcagaaa caaaacagct attgccttac gtttcatagg cccaggccct gagcaatagc 134389 aaaaagataa tacttatttt tttaaactgt tgtttattag gtgatcgatt tctaattaat 134449 ttcaaaatat ttaaggtaat attttaatta ccgaggaaga atggtacaaa caaaatgttg 134509 tggaactgga aaatcctcag tgcttgacaa catgaaactt atttaactta ttatagatga 134569 gataatgaga acatcttcag aaaagaagct atgttcctta aaacaggggt acagatttaa 134629 aagctctgtt tatatggttt tggtagacta agtgaagaac ttgcctataa agctgagtct 134689 cgatcatata gcatatccat tataaagtga gaaaattgca attttagagt attgtcaata 134749 catccaaaaa tttttacatg atttctaaat gcagatgtgt gtgtgtgtat gtctacgtat 134809 gtctctccat atgcaacaag cagttaatta gtccaaatat atcccacagt gtagattagt 134869 ttcatatctc agctcttcaa tgtctcttct tcatttaatt cactccttgg tgtctagttt 134929 tcctcactct tttacaaata tccaggttct atatttctgc ttttctagag agctttttcc 134989 ctcaagaata tatttttctt tttctttctt tctctttatt tttgtttgtt tttaactaac 135049 attcatatgg ttataacaat ttgagacaag tgaaaaggaa agatctgtaa actgcctatc 135109 tcctttgaaa ttcattgcca ataatcctta agaatataaa gttccttgat gccaaagacc 135169 ttctcattag tgttgctgcc tgttgtttca ttggttccct agaacaatgc ctggcacata 135229 aaagttattt gataaatatc tctgctatta atgaattaat aataactgca tgacaattct 135289 ttcctcaatt catcattttg cttcattttc tcacagttgc ttcaatgtgt ctgtggaact 135349 atctttccat gtgaacaaaa cactctacat tctcagtgtc tacaaagcac atatttcctt 135409 ttattaaaat taaactttga gagcaccaaa tcctaatgtc taaccatcat caaactggca 135469 gatagcacca gtattctttt tgctcaccaa ttttatgccc aggcatctac tgtttctttc 135529 atgaataaaa cctgacacct gtaagaggat ttatcatggt aaacttctct ttgttactga 135589 cattttcagc ctcttgggct ctcccctcct tacttataca cattggcacc cagcttgaag 135649 tcatactctc tagaccctgg gtcaatgtgg gtaatgcatc caggaatcca gcttaactct 135709

-continued

```
tccttggtct ctttgatgtg actgaccttt atttctacat ttcttcatca aaccagtctc 135769
acagttttgc acagtgcaaa tcacatgctg caccatgtgc ttattatctc ctataacaac 135829
agatgctcca ctgaaatgca aaactctgtg ttaagccaac aactgcttct ccatcctttc 135889
ctcctatacg tttcttctca ctacaacttc ccttctcaac cccaaaggga ctactggatt 135949
ctttactctt ttattttacc ccagtctatc agtcccatcc tggacttcct tccttctctg 136009
cttagaggaa agcaagatga tcaggtagaa ttgcacttat gactagatat tatttacttc 136069
aaacaaattc ttactatttt gtcctgatga aattcatgac agttttcata caacagaaag 136129
cctgccctct tagaagagaa gagaactgaa aagaaatggt tgaagtaagg tagaaagccc 136189
tcatggagtt aggtggctag gccagcagag ctaggcactg ttctcctgtt cagaattgca 136249
ctcctgatac tccagatggg aagcctgcca tggcactaac cacagcactt tttataccct 136309
atctctgcta ttatgagccc acattagttt ttcttctgct tcagaaattg ttgcaaaaaa 136369
taattttatt atttacaaat tatttttaaa ccatataaat ctgcttagtt tgatttctca 136429
aaccctctaa aacttacact tcttgttgtc caatctttgc ttttaattgg gtataatttg 136489
aggcagaaat aaattaatct catttttaaa aatgtactag ctattaataa tttttaaatt 136549
tatcttctaa aattggaaag tatccacttt aaatgcatct gtagcaagga ctttttacat 136609
acattctgta gctttattac ttccattgag aactgttaaa ataacagaac ttacctcact 136669
gtacgctggc ttttgaaaag gcagcagaac tgtttatctg attatcgaag taatcatatt 136729
acatttcttt ttcttttcta agagaaacct tcttcatgtg ctcagtcaaa cattttggtg 136789
tttaagaatt gacttattag gtcaggcgcg gttgctcacg cctgtaatcc caacactttg 136849
gaaggccgag gcaggtggat cacttaaggt caggagttcg agaccagcct ggtcaacatg 136909
gtgaaacccc acccctacta aaaatgcaaa aaaaaaaaaa tagcaaggtg tggtggtgca 136969
catctgtaat cccagctact tgagaggctg aggtgggaga atcatttgaa ctcgggaggc 137029
ggaggttgca gtgagcagag atcacacgac tgcactccag cctgggcgac aaacaagaat 137089
ctgtctcaaa aaaaacacaa aaaacaaaaa acaaacaaaa aagagttgac ttagttaatg 137149
aaaatatttt tattaggaaa ttatacttct ctttacaaag tatgtattat ttgttgcatc 137209
tatatagtct atcaattcta aaagcacact ttatgcgaaa atgtagtcta ggccttcaga 137269
atgtattatt acaagaaagt atctatcaac catgtttcat ttgtttgcat gttttgtttt 137329
gtttccaata gactatgaat attcagcttc aaatgctacc tcatgattgt tacattcctg 137389
ttgttgaaag aacccatctc tttcttacct tcttgtccct aaattgtgtt cttcttataa 137449
cttactttgc acataaccat aatggagtga gatcatagaa ttaagaggat tgagaaagaa 137509
aaatacttcc ctcattccat tggcagtaat ctgtgattca aaagttaaca acataccatg 137569
tattcttgta ggagattatt tcatgcttat cactgatcaa cttacatgca ggttaaaacc 137629
agccctgaaa aaatgctcat catcactggc catcagagaa atacaaatca aaaccacaat 137689
gagataccat ctcacaccag aagaatggcg atcattaaaa agtcaggaaa taacacttgc 137749
tggagaggat gtggagaaat atgaacactt ttacactgtt gctgggagcg taaactagtt 137809
caaccattgt ggaagacagt gtggcaatta ctcaaggatc tagactagaa ataccatttg 137869
acccagccat cccattacag ggtatatacc caaaagatta taaatcatgc tactataaag 137929
gcacatgcac acatatgttt attgcggcac tattcacaat agcaaagact tggaaccaac 137989
ccaaatatcc atcaatgata gactggatta agaaaatgtg gcacatatac accatggaat 138049
actatgcagc catctgagca aactatcgca aggacagaaa accaaactcc gcatgttctc 138109
```

-continued actcataggt gggaattgaa caatgagaac acttggacac agggtgggaa acatcacaca 138169 ccggggccta tcatggggtg ggggtaggag ggagggatag cattaggaga aatacctaat 138229 gtaaatgatg agttaatggg tgcagtactc caacatggca catgtataca tatgtaacaa 138289 acctgcacgt tgtgcacgtg taccctagaa cttaaaatat aatttaaaaa aaaaagccct 138349 aaatgcaact tgttcagata actggagcca tcttcctagc tctttatttc tcagacagtg 138409 tgggtaagtc ctgctccgta cgaatgctta tgtcagtttt gaagttcagt actttcttaa 138469 gagccagagt cagtcaagat gttcccttaa caagattttt caatggggtt acacattaat 138529 gagttctttt tcctccttta agtatttgaa aattttggtt taataaaagg tttaactatg 138589 atgaatttag gatccttttt cctgttacag agcacagaat aatagttaat attttacata 138649 catattgcaa gttcatgttg ccactaggag tgtccagaat agacaattga aacagccttc 138709 tagctactac tatcaaaaaa gagctttaaa taacatattt taattaaata acattatttt 138769 ctatagctat acctcaataa aaccatcaac caatgtttgt acaatttgat gcccccactc 138829 taagattttt agctagtgta aatcagagtc tcctatttaa tgagacactt tatccaatca 138889 ggttgtgttt attattcaac cagatgatct tggaacttat aacaaactag taatacttaa 138949 agctgggctt tatgtgcgtg atttactggg atgtttgctt ataccttgtt tccaagctaa 139009 aaatattgtg accaggtgtg ttagtctgtt ttgagttgct atataggact acctaatgct 139069 gggtcattta taaagaaaag aggtttattt ggattatggt tctgcaggct gtacaaagag 139129 catgacatca gcatctgctt ctggtaatgc cctcaggaag cttttactca tgccagaagg 139189 caaggggagc cagcgtgcca catggcaaga gagggaggaa gcacaagaga gaggagacgt 139249 accaggcact ttttaacaac cagctctcac atgaactaac agagtgataa ctcactcaat 139309 acccggggga tggcaccaag ccattcatga aggatttgcc ctcatgacca aatacctccc 139369 actaggccca acctccaaca ctggggggtct catttcaaca tgagatttgg aagggacgac 139429 tatccaaact atatcatcag gattttctgg catggactac caagccattt ctgcttcaaa 139489 ctcccctgaa attcttgtta aaaatgcaga ttctttgata ccacccccaa tacactattt 139549 agtctgagat gaaactcaag gattctgatt taattgatct agactagcat ttgaccattg 139609 atttatcatc tgggattcta ggaagtcaac cacttatatg ttttagagca gacttcatta 139669 taattgagga gaatgtttgt agtctgtggg ctcctctgtc cacttctgat tggggcccct 139729 ttgcctgatt ctgactggat caggcagagt tttattcaag ccactgtcct ttttggcttc 139789 ttaatgttca aaatatatta acacaatctc agttttctaa gagctaaatt atacgacttg 139849 gttcttgtct ggtaacataa ctgcattact ggatcttgtc aagattcaga gacattctcc 139909 cagtttcaaa tttgtaacta acactgtttg atcacaaaaa agttctaagc caaagcaaaa 139969 ctctttctac caccaccaga tggcgttact ttggacttac ctataaatgg atttccaaat 140029 ggtttttcag aaaccaactg gaggtactta gaaaaactta tggaactcac aactattctt 140089 tgcatgtcaa aagctataac agtaaataat atttgtggag aatattctgt aagattaggc 140149 tgcctttctt ttcctccagc ttatttaaac tatatcctta tattaaccct tgttggagat 140209 gtgtcctctt attgcactgt atgtgagtgt gtgtgtgtgt atcccatcac gttggtatga 140269 tgatagcacc cttcattgag aagctttgca aaaagaatat aagaacatgt tattatgttt 140329 acttaaaagt ataaggccgg gtgtggtggc tcacacctgt aatcccagca ctttgggagg 140389 ccaaggtggg aggatgacga ggtcaggagt tagagaccag cctgaccaac acggtaaaac 140449

-continued

```
cctgtctcta ataaaaaata caaaaattag ccaggtatga tggcacgcat ctgtaatcct 140509
agctactcag gaggctgagg cgggagagtc ccttgaaccc aggagacgga gtttgcagtg 140569
agcctaggtg gcgccactgc actcaggcct gggtgacaga gtgagactcc atctcaaaaa 140629
aaagaaaaaa gaaaaaaaag tattgaggac attgctcatg acattccaag gttatataaa 140689
agaatatata aaaagaaatt tctgcctgga cttagtgcca ggaatacttg tacttttctt 140749
gctttcttct taagaacatt gcacaataga gtatttttaa aaattgtgct tgctgttcaa 140809
attgcctgct ggaaggatta gaggcagatc tgtagcatgc cgagtcccat ctttgcatac 140869
aggctatcat gacaaacatt gtatgtgcta attctatctg gcttctcttt atattcctat 140929
ctgtctctat ttcctgtcat tttaatgttt taaaattgta ctttttactt aaatggtttt 140989
tggaagaaat aaatataagt aaagtctgtt agaggcccgg cgcggtggct cacgcctgta 141049
atcccagcac tttgggaggc caaggcgggt ggatcacaag gtcaggagat tgagaccacc 141109
ctggctaaca cggtgaaaac ccatctctac taaaaataca aaaaaaaaaa aaaattagcc 141169
aggcgaggtg gcgggtgcct gtagtcccag ctactcgaga ggctgaggtg ggagaatggc 141229
atgaacccag gaggtggagc tcgcagtgag ccgagatctc accactgcac tccagcctgg 141289
gcgacagagc gagactccgt ctcaaaaata aaaaaataaa ataaaaaaat aaagtccgtt 141349
acaaagcaca aaaaagaacg gcaaagccaa caaacatatg aaaaaaagct catcatcact 141409
ggtcattaga gaaatgcaaa tcaaaaccac aatgagccat catctcacgc cagttggaat 141469
ggtgatcatt aaaaagtcag aaaacaacag atgctggaga ggatgtggag aaataggaac 141529
gctttttaca ctgttggtgg aggtgtcaat tagttcaacc attgtggaaa gcagtgtggc 141589
gattcctcaa ggatctagaa ccagaaatac catttgaccc agcagtccca ttactgggta 141649
catacccaaa ggattataaa tcattctact ataaagacac atgcacatgt atgtttttttg 141709
cagcagtact cacaatagca aagacttgga accaatccaa atgcccatca gtgatagact 141769
ggataaagaa aatgtggcac atataatata cagcatagaa cactatgcag ccataaacaa 141829
aggatgaatt catgtccttg gcagggacat ggatgaagct ggaaaccatc attctcagta 141889
aactaacaca ggaacagaaa accaaacacc acatgttctc actcataagt ggcagttgaa 141949
caatgagaac acatggacac agggagggga acattacaca tcggggccta ttggggaatg 142009
ggggctaggg gagggatagc attaggagaa atacttaatg tagatgacgg gttgatgggt 142069
gcagcaaacc accatggcat gtgtatacct atgtaacaaa cctgcatgtt ctgctcatgt 142129
atcccagaac ttaaagtata ataataaaaa aaaagaaagc acaaaaataa aagtacttgg 142189
aaaagtttaa agggttaaat attatgcaaa actgaaaact agcttcagat acatttaagt 142249
ttatatcatg ttaacaagtt atttctttct aaaaaattct aacctgtaac acagagagtg 142309
gacttgaact tgaaaatatg gttaaggtac aaatgcagat ttggggtccc agtctcccag 142369
actgtggctt ctatggaaga gattgtactg gctccaaatt ccacagatga ttgaacaact 142429
tgtttctgcc tgtgtcagag ctgaagagtg aatatctcca ctatatatat ctcaaaatct 142489
cccaaatgaa atttggtaac cctctatgcc ataacacatc acattaataa tttgtattca 142549
aaagtctctc agaaaagatt tttgaaatgc cagatacttt aattttttta tgtttatata 142609
tttagggtgt atgagtacag atttcttaca tgcctatatt gcatagtggt ggagtctggg 142669
cttttactgt agtcatcatc tgaacagtga acttgtacca aataagtaat ttttcaactc 142729
tcatccaccc accctcccat cttttgtagt acccaaggtc tattatccca ctctgtatgc 142789
ctgtgtacct attgtttagc ttccacttat aagtgaacac atgcagcatt tgactttctg 142849
```

-continued tttctgagtt attttactta ggataatggc ctccagttcc atctacatgg ctgcaaaagt 142909
tatgatttta ttctttttta tggctccatt atatgtatgt gtgtgtatct caattttctt 142969
tatcaaaccc tctgttgatg gacacttaga ttagtccaca tttttgctat tgtgataaac 143029
atgtaagtgc aggtatcttt gtaatataat gatttctttc cctttggata tataccaggt 143089
agtgggattt ctggatctaa tggtagttct atttttagtt ctttgagaaa tctccatact 143149
gtcttccata aaggttgtac tagtttacat ttccaccaaa agtgtataag cattcccttt 143209
tctctgcatc ctcacaaaca tcctttgctt attgactttt taataacagc cattctgact 143269
agtgtgaaat aatattttat tgtgatttta attttctctg atgattagtg atgttgagca 143329
ttgtctcaac atcactatgc tagtggcatg catgttttct tttgaaaaaa agtttgtgtt 143389
ctttgcccac attttaatgg ggttatttgt tttttttttt ctttgagttg tttgagttcc 143449
ttgtagattc tgaaaattat tcctttgtca gctgcatagt ttacaatttt tttcccattc 143509
tgtagtttgt ctgttcactc tgttgattgt ttatttttct gtccagaaac tttagtttaa 143569
gtcccatttg tctattttttg tttttgttgc atttgccttt gaggactagg tcataatttt 143629
ttgcctgggc aaatgtcctg aagatttttt tccaggcttt cttatagtat ttttatagtt 143689
tcgggtctta tgtttaggtc tttaatctat cttgagttaa tttttgtagc tggtcagagg 143749
taggtgtcca gtttcaatct tctacatatg gctatccagt tttcccagca ccatttattg 143809
aatagggagt catttaccca gtaaatattt tagttgactt tgttaaaaat cagttggtta 143869
taggtgtgtg gttttatttc taggttctct atgctgttct attcatcaat gtgtacattt 143929
ttatactagt accatgttgt tttggttact atagctttgt agcataattt gaagtcataa 143989
tatgatgcca acaactctgt tctttttgtt tgaaattgct ttggcttttt ttccttgtga 144049
gagtttgctg agaatgatgg tttccagctt tgtccatgtc gctacaaagg acataatctc 144109
accctttttt atggctgcgt agtattccat ggtgtatatg tgccacattt tcttaatcca 144169
gtctatcatt gatgggggga gggggaaggg atagcattag gagatatacc taatgtaaat 144229
gacgagttaa tgggtgcagc acaccaacat ggcacatgta tacatatgta gcaaacctgc 144289
acattgtgca catgtaccct agaacttaaa gtataataaa aataaataaa taaaataaaa 144349
taaaattgct ttggctttct ggactctttt ttttggtttt atatgaattt taggattttt 144409
ttctaattct atgaaaaatg gcattggtaa tttgataggg attgtgtcga atcagtagac 144469
tgctttagac agcatggtca ttttaataat attgaatctc taatccatga gccagggata 144529
tttttccatt tgtttttgtc atctagggtt ttcttccatc agtgttttgt agttctcctt 144589
atagatatct tttacctctt tggtgaaatg tattcccagg cattttactt tatcttatct 144649
ttttgtagct attataaatg gaattgcttt cttagtttgg tccttggaaa tgccaactac 144709
atttaaaatc cttttccatt tgatggattt caggtcttga tgaacatctc agttgtaatt 144769
ttcttaagat tgaaaaagta aatatttttt ctatatgtat atataaaatt gtcctctctc 144829
aaaattttaa ttcaataacc tgctagatat cactttagaa tcttgcagta ctagttttct 144889
tctcaattaa ttgtagatct tagcctttta atttgggcat gtttttccct attaggactt 144949
aagttattag gacctaagtt tgtagacaag aactatgtta tatttgagaa atttgtgagt 145009
catgtactgg gcctagcaca gtgcctcata agatgtagac cctcaataaa cttgttgaat 145069
aggttaataa ataaaaaagc ccctatcact caattttttt tttttttttt ttagatggag 145129
tctcactcag tcacccagcc tggagtgcag tggcacgata tcggctcact gcaagctctg 145189

-continued

```
cctcctgggt tcacaccact ctcctgcctc agcctcctga gtagctggga ctacagacac 145249
ccgccaccat gcccgactaa ttttttgtat ttttagtaga gacggggttt cacctgtgtt 145309
agccaggatg gtctcgatct cctcacctca tgatctgacc ccctcggcct cccaaagtgc 145369
tgggattaca ggcatgagcc accacacctg gcctatttca gtcaattgtt aaaagtgcta 145429
agaacaagtg gagatcttgt taatgaagaa aaaaaaaata gtatttacta cttacctaaa 145489
cactctacta agaagggata tacagatcaa aaggattaaa tctctgcctg cattaagcta 145549
actgttttgt aaagaagaac gtaaacaaag tcaaaaatgc attttttagg tgctagagat 145609
tagacaggac aaaatcttct ggctctgcct agagttaagt ggctttggga gaggctttgc 145669
tgtagtttaa aggcagaggt ggggaaggcc actctggcca caaggacaga tccacaatgg 145729
gatggggtat gaaacagcac gaacccttca ggaaattaca cataatttaa aaggaaaatg 145789
ggagcccatg gcagaaaata gaattgaaca gcaggaaaag ggtagatagt aaaaagcatt 145849
ttataatatt caaggacatt tgaaacttgt ggtatacaat gaggaagaat ttaaaaattc 145909
tatacagagg agtgacatag ttagatttgt gttctgggga gcataataat agcattacag 145969
cgggtgaatt tgaaagctgg gcctcaaaag tttagatctc aaataggttt ttatgggagt 146029
attcatcctc atgaaacatg atttggaact aaaccaaggc agtggcaatg gggctggaaa 146089
ataaacacta gatttcatat ctagatgaag atttgtggaa taagagaggc cacattaatg 146149
tttaattcta tttacaatgg atcccagcca ccatccgctt taacacagag gtgcttttcc 146209
agtagctaag aggactaggt gctttagata catttgtgaa gttgtcctcc cattgttaac 146269
atgctttttt tattgtctgt gtgtaggttg atgggggagg cagagttagg atcacacata 146329
gaagttcagt ctttgaaatg ctttctttct ctttttcccc aaacaatgac ccccaccttt 146389
tccttctggc atatgttgcc tcaagaccct aacactgctg ccaatctgct ggtcttagag 146449
ccaagaatct gccaccacct ggcccaccac agcctgctct gctagctgct ctcctgccaa 146509
tactggcctt catgtacaag tgtaggtttt gagggttccg ttctctcccc ctttctctct 146569
ttgagtgtgg gtttgtgagt gtgtgtgtct tctgtaataa gaagaaaaca ggccacattt 146629
tctctactcg tgttatacac ttcccggagt gtctcacatc aaaacctgtc ctaagtccaa 146689
gccttagaag ctctttgctg gcccagccta cacttgggtt gttacttctc aggagctacc 146749
tttctgtcag ttgagatttt aacaacccac cacagtactc caagcgtgca gtccctcaca 146809
tcttgaaatc tgtgctttgg cagcagcaga atcaggggtc tgtggattct gaacccagaa 146869
tgtgtcaaac caaagggtga catattggga catttaataa gtcagagact atttcccagg 146929
aatatttttt tgaagcattt aaactaaaat acaattgaac tgagatctca aaacaggaaa 146989
aatgaacttg acaagaatta ggctaagctg catctcatga cgtaaatatt cacatttgca 147049
tatacattaa cagagtcaag tcaaaaattg atttttttatt ggataggatt aactttagct 147109
acagaaaaca gaaagtttaa atgactggct ttaaaaagca aaagtttact tgctttcatt 147169
tatatgcaat ctggggggtt gcgggggaag atttgtttgt gggtttccca ttctcaaggt 147229
gccaggctcc tgtgtttctg ccccatatcc ttagagggag ggtttcctcc tcaggattgc 147289
cttatgtgca aggtgactac tgaagctcca ttttttatgc ccaaattgta gcaagaaaga 147349
gaaaaggaag aaggaacaga aaggcacatg acatcacttc aaataaaatt agggggaaaa 147409
taataacaga tatctgatag gaaactaaca gtaccttctg caataatgat tacatttctg 147469
gaaaataaat gttaagatcc ttgaaaacaa ggagtaatag ttgaggaaaa gcttcttagc 147529
agcctgggac taaaaacttc aaaaaattta agataaaaat ctgaaaactg gtagagaatt 147589
```

-continued

```
ggggagaaaa agagaatttg aacaaggcat gcaagagtaa gaaaaatgtc atcacaaaat 147649
tactaagaaa gcataaaagc aactatattt tattagagta aaaataaatg gattgaataa 147709
ccctagtaaa ataaattcca gccatacatt gtttataaaa agtgtattta aggtgattag 147769
gaaaaaataa aactaaattt aagtgcaaag atctcccagg gaagtcaaag caaaaataaa 147829
gtcagatgtt gctgtcatta gacaaagtaa aatttaaggt gaaaacatga caaagaggga 147889
cattaaataa ggataaatgt acaatcaatg gtgacaaact tttataaact tgaaattata 147949
ttaacaaaac ataaatcatg taaaactaaa ataccttgat aaaatgcaaa ttatcaggta 148009
acaagaatat atctattgca gaaagtaata tatcaaacta aaataatgtg tatctattac 148069
aagtatacaa tactttgtag cctacaaaat aagaatatac gatttcttct taaaatgtta 148129
tacatttaca ataattaata atttggccac tcagaaaacc ttggtaaagc aaggaaagta 148189
gagatattat aagccaactt aataatttag taacattggg taaaaatgga agaagtatca 148249
tattgtggtt gtgaacataa gctctagttc tcctagtttt gtgatttggg aaagttaatt 148309
atcttctctc tacctcgtct taattttcag taatattagg ataacaatag tttgtacatc 148369
atcagtgttt tttttttttg aggaataaat gactcacatg tattaaacac ttagatccat 148429
tgttaacata taatatgtat aaataatgtc agtataaatc aatgtcagcc taaaaagtta 148489
agactgtgat tttaaataat actagattta gaataaaatc aaaattgaaa tgacattatt 148549
aacttaaaaa taacaaaaaa agagaagact ttaaacacaa tggatggaaa gcagctatac 148609
caataaaaga caaaaatgtg gagtattata tgttcttaat gttttttaaa attataaaaa 148669
taaataaact aaaacataga attttaaaaa ttaaatgttg gagggattag gtcagataag 148729
agaaatttct gttagcagca gctgaatttt ctgctaataa cagagaattg tgaaaagatg 148789
atttcataaa tatggcaaat gtttgtaata gccatcctag gagcacggat attagtaact 148849
aattgaggaa gtactgttgg gcagtgtcaa tatactggtt aagaatagaa tttaaaataa 148909
tgctaattat aaggccaaaa aactcagtaa tgcaattttt ttagtataat tcagtagggg 148969
agaaggagag ataattaaac ttggaaattg acatacagtt gtcccttggc atccatgagg 149029
aattagttcc aggactccct atggatacct aaattcacaa atgctcaggt cccttatata 149089
aaatggcaaa atatttgcat ataacttaca cacaccctct ttataattta agtcatttct 149149
aaagtactta taataccgaa tgcattataa atgactgtgg aaatagttgt tgtattattt 149209
agggaataat gacaataaaa aatatatgta tatgttcagt aacagatgcc ttttttaaaa 149269
aaaaattgtt tttgatccac agttggctga atctatggat acagagccca catttactga 149329
gggcagacta tatttagagt acttaaggat cacaagggac acacatctga gggtactgaa 149389
gagtgggaag aaattactaa ccagagggtc agactagaag gcaaggaagt gaagccagga 149449
gatgattaga aaataagaaa atcatacaag cctggagatt atgttgaagt gtaagaacat 149509
aattagagtg agaaacatga gtcaaggaag aaggagattg gtgcttgaga gatgtggcag 149569
actgtatctt tcaaagatgg ctacaccaat atatatctca ttccacaagc tgtttttacc 149629
atgctgtatt gacgctcttc catatggagg tggggcctat gtcccctccc ttgaaaccaa 149689
atgaaacttt gtaattgcct tgatcaacag attgcagtag gagtgatgct ggatgatttc 149749
aaaggctaat acacacaaga aaataatggc tttcatttga ctctttcttg gaacatgtgc 149809
cttggaaacc atgagcttat ttgcaagaag ctcagctatc ctaaagttta tctactgggt 149869
agaccaagtg gagaaattac acagacattg agattatgtt caaggggtct cagaggttca 149929
```

-continued

```
aggcctccca attcaggcac caaacaagtg gagaaaaggc tttcaagatc atccctctga 149989
aataattgtc tgattgaaac ctcaaaagag tccctgagcc agaaccatcc agccaagcca 150049
ctctcaaatt ccaaatccac agacaccatg aatgacagta aatcattatt gttgttttaa 150109
agcacataag ttttgggggg ttatttacac acagcaacag aaaaaaaaac tgatgaatgg 150169
gaaacatgga gagaaatgca aatagaataa aatgggaagg aatacaagga gaggaaagta 150229
gtattgtgca aaataggcaa tcggatgacc ctcaaaagga aatttttttt ctgagcaact 150289
taatgaatat aaggtcagat taaattggaa ggtaacaggt acaaatatca ttaatgctaa 150349
attctatttg tagtaagtca actatttgta aattatgcat tggagaccga ctttacatca 150409
atcaaaagtt aaatttattt agaaatctat agaagaagaa aaagaataaa agccattgga 150469
aaagttttta caattattcc attaaataga caaagtcctt taaggaaagg gattaaaatg 150529
aaggtaaggt gatctgctta aaaataatat agcaatctgg gagccatggc tcatgcctgc 150589
aatcccagtg ctttgggaaa tctaggcagg aggacctccc aaaggaggac ttggagtttg 150649
agaccagcct aggcaacaca gagagactcc atctcaaaat tttaaatttc ttaaaagaaa 150709
aaaaataaaa tgaaataata ttgtattaat tccagtaaaa gcatcagacc aatttagaat 150769
atggatgaga gagaaaaact agaaataaca ccacaacaag gaaggagaaa gctggtctct 150829
ggcagggact tctaatttag agaaagacag atgatagcaa acagcaaaag ttgtattata 150889
gatgtaactt aaaaactaat ttgattttta tttttagtca gaaaactgct ttaggtatgg 150949
aacaagtata acctggtatt tccagtatct ctctgttgac ctcacatctc tctccagata 151009
ctgcctcaat tctctgcttc tctttatagc aaattccctt gaaagagaga ctacctggat 151069
cagaaattcc tctgcttcaa tttgatcctg aatccacttc atctagatct tcctcaccaa 151129
ttcccccaaa tatttgtctt attatggtca catgggacct ctactttgct atatcagtaa 151189
ttttgttctc attttacttt tttgtagtta attactccct tctccttgaa acactttcct 151249
tgtttggctt ctaggatgcc ctgttctcat ggatttcctt tcacttctcc agtcatttct 151309
gtttgttttt tcaatatctt cgtgatctta tatttttaat gcgtcctgct agcttcccaa 151369
ctaggtttcc tactttcacc ttaattccct atggtttatt ctctacaaga aaggaattat 151429
aatcccttaa aaatgtcaat aaaactctat cactactcaa tactctccaa ggggtcctta 151489
ttttattcaa gtaaaaaact aaagtcctta ctatatgtct gtaaattccc ataggatctg 151549
gccccacagc ccctctggcc cctgtccatt ctgccccttg ccaattctgc ccggccacag 151609
ttgcccaata gctggtctgt gaacacatca agcacatact taatctcaag gcttttgcaa 151669
tcattctttt ctctagttgt aatctctcat tacttattct gagtgtcttg tttctgcagt 151729
tgctttactt acttgaccta tataaaatag taattcttac ccctacaact ccattatgtc 151789
ctatcttctt tgccttgcct tatgtttttt tcttggagtt acagatacct gatgtagata 151849
gtatttactt tttttatgct tgcattaatc acctagaata taaactccaa aagaggagct 151909
atttctcttt tataatctat ctaatatatc ttggatattt gctcccacct aaatttcatg 151969
ttgaaatgta attccctgtg ttggagatgg ggtctggtgg gaggtatgtg gatcatgggg 152029
cggatccctc atgaagggct tgggccatcc ttttggagag aagtgggctc tggctctgac 152089
ttcacacgag atctggttgt ttaaaagtgt gcgacagctc ccctgagctt cctctctcac 152149
ttgctcctgc ttttgccatg tgaagtacca gctactgctt cattttccac catgagtaaa 152209
agatccctga ggccctccct cagcagtaca tgtccctatg cttgttgtgc agctggcaga 152269
accatgagcc aattaaatct cttttctttt aaattactca gtctcatgta tttctttata 152329
```

-continued

```
gcaatacaag gttggcttaa tacatatctc taaagcaaaa gctgggcctg gtatgtaata 152389
ggtgttcaat aaatatttat tgaataaatg aataaatact aggctaaata aagtttaaaa 152449
catcataata gaacactggg tagatgtcaa gatgacagtt ttgttattca catatggaca 152509
tggaaaggtc tttgtggtgc attgttaagg gagcaaacca aattacagaa cactatatag 152569
agtagagctg tataaaatac atatggtgta tgtttataaa tatgtctaga aaaatttgaa 152629
agctatatat caaatatcat atcatttatc tttagaaggc taattgcata ttttcaattt 152689
attgtttata attttttta tctattatta taggttactt gtataatcac aaaagacaac 152749
tgaataattc tttttgtctt catcaacttt tattttaagt tctgggatac atgtacagga 152809
tgtgcaggtt tgttacatag gtaaacgagt ggcatggtgg tttgctgcac agatcgaccc 152869
atcaccgagg tattaagctc agcatccatt agttattcct cctgatgctc tccttcccct 152929
tggcccacca atacacccta gtgtatgttg ttacccctca tgtgaccatg tgttctcatc 152989
attcagctcc cccatataag taagaatatg cagtgttagg ttttctgttc ctgtgttagt 153049
ttgctgagga taacaggttc tagatccatc catgtccctg caaaggacat gctcttgttc 153109
ctttttatgg gtgcatagta ttccttggtg tatatgtacc acatgtacaa ctaatttcca 153169
caacaaaaaa tgtactatta catggatata atgtttatat tctcttcaca gaatttgagt 153229
cacttgaatt tttgctttaa cacttagaat ttggagggtc tgttttctta aaaaaaatta 153289
acactttaaa tccaataagt aaatgtggaa ggttggtgga aatagttagc tggaaactca 153349
gaattgatat taactttcac caagcctttg ttcacattat tttcttctac aatttatgaa 153409
tgaataatcc tgcactatct atgcattcaa acaatgatac atatggtgca tatgtatata 153469
tggcaaaaat ctaagaaatg tagccaaata ttaatattgc ttacacgtaa gtagtcaaat 153529
catggtggtt ttttttatt ttcttgattt tgcaagaaaa ttaataaaga ggctatttac 153589
attttaatgt acaaatgtgt atacaaatat aatagttatg ctttaaaaat ccaataaata 153649
aatgtaagta aaacatttct gaatttttta aagatttctc aatagatcta ggtattcttc 153709
ttaaccaaat actgatacta ccgttaacca cttctggaaa attctggcaa ttggtccctt 153769
tggggaagaa ctagaggaat cactactata cacacttact gtggtattca gtgcccttcc 153829
tcaaggggaa ttcgcctatc tttttttct taagtaatat tttatcttta atagacaaat 153889
aatggttgta tttatttacg ggatacaaag tgacattttg atgcaagcat accttgtgga 153949
atgatcaaat caggctaatt aacatatctg tcatctcaaa tgcttatcct ttcttcattg 154009
tgggagcact taaaatcaat tcttttagct atttggaaat ataaaatata ttattttcta 154069
actatattta cttacgatgt agtgtaatag atcacaagaa cctatttctt ctatctaact 154129
gaaactttgt actctttgac caacatctcc cctttctttg tccatcctcc tagcccagcc 154189
tttggtagcc atcactgtac tctgtatttc tatcactttg cctttttaaa ttgcacatat 154249
aagagagatc atgcagtatt tgttgctttg tgtctgactt atttcctgta gcagaatgtc 154309
ctttaggtta atccatgttg tcataaatga caaaatttcc tgcctttcaa aggctgaata 154369
gtattccatt gtttatatat accacattgt caaaatccat tcatctgttg atgggcatgt 154429
aagttgtttt caaatattgg ctttattaat aatgcggcag tgaacgtggg agttcagaca 154489
tcttgttgac atactgatat taattccttt gactatatac tcaaaagtgg aattgctgga 154549
ctgtgtggta attttagatt tttagtaaca ttcatactgt tttccaaaat aactgtatga 154609
attaacaata ccatcaacaa tgtacaaggg ttccctctgc tccacatcct catcaacact 154669
```

-continued tgctagtttt catgttttcg ataatagcca gtctatcagg tgtaagataa tatttcattg 154729 tgatttaatt agcatttctt tgataatcag agattttgag cctttttaa tatatctgtt 154789 gaccactttt atgttttcct ttgagaaatg tgtatttaag tcgtctgccc atttttaata 154849 ggatcatttg ttttcttatt attgaggggt ttgagttcca tgcatatttt agatactagc 154909 cttttatcca atgcgtaatt tgcaaatatt ttctcccaat ctgtgggttg tctctttaac 154969 ctgctaactg tttcctttcc ttcctgcaga agctttttag tttgatgcaa ttccatttgt 155029 ctatttttgc ttccattgcc tgtgcttttg gggttaagaa atctctgctc gattacattt 155089 attgatttgc gtatattgaa ccagccttgc gtcccacgga tgaagcccac ttgatcatgg 155149 tggataagct tttgatgtg ctgctggatt cggtttgcca gtattttatt gaggattttt 155209 gcatcaatgt tcatcaagga tattggtcta aaattctctc ttttggttgt gtctctgcca 155269 ggctttggta tcaggatgat gctggcctca taaaatgagt tagggaggat tccctctttt 155329 tctattgatt ggaatagttt cagaaggaat ggtaccattc ctccttgtac ctctggtaga 155389 attcggctgt gaatccatct ggtcctggac tctttttggt tggtaaacta ttgattattg 155449 ccacaatttc agagcctgtt attggtctat tcagagattc aacttcttcc tggtttagtc 155509 ttgggagggt gtatgtgtca aggaatttat ccatttcttc tagattttct agtttatttg 155569 cgtagaggtg tttgtagtat tctctgatgg tagtttgtat ttctgtggga ttggtggtga 155629 tatcccttt atcatttttt attgtgtcta tttgattctt ctctcttttt ctctttatta 155689 gtcttgctag cggtctatca attttgttga tcctttcaaa aaaccagctc ctgaattcat 155749 ccattttttg aagggttttt tgtgtctcta tttccttcag ttctgctctg attttagtta 155809 tttcttgcct tctgctagct tttgaatgtg tttgctcttg cttttctagt tcttttaatt 155869 gtgatgttag ggtgtcagtt ttggatcttt cctgctttct cttgtgggca tttagtgcta 155929 taaatttccc tctacacact gctttgaatg tgtcccagag attctggtat gttgtgtctt 155989 ttttctcgtt ggtttcaaag aacatcttta tttctgcctt cattttgtta tgtacccagt 156049 agtcattcag gagcaggttg ttcagtttcc atgtagttga gcagttttga gtgagtttct 156109 taatcctgag ttctagtttg attgcaccgt ggtctgagag acagtttgtt ataatatctg 156169 atcttataca tttgctgagg agagctttac ttccaactat gtggtcaatt ttggaatagg 156229 tgtggtgtgg tgctgagaag aatgtatatt ctgttgattt cgggtggaga gttctgtaga 156289 tgtctattag gtctgcttgg tgcagagctg agttcaattc ctggatatcc ttgttaactt 156349 tctgtctcgt tgatctgtct tatgttgaca gtggggtgtt aaagtctccc attattattg 156409 tgtggtagtc taagtctctt tgtaggtcac tcaggacttg ctttatgaat ctgggtgctc 156469 ctatattggg tgcatatata tttaggatag ttagctcttc ttgttcaatt gatcccttta 156529 ccattatgta atggccttct ttgtctcttt tgatctttgt tggtttaaag tctgttttat 156589 cagagactag gattgcaacc cctgcctttt tttgttttcc atttgcttgg tagatcttcc 156649 tccatccttt tactttgagc ctatgtgtgt ctctgcacgt gagatgggtc tcctgaatac 156709 agcacactga tgggtcttga ctctttatcc aatttgccag tctgtgtctt ttaattggag 156769 catttagtcc ctttacattt aaagttaata ttgttatgtg tgaatttgat cctgtcattg 156829 taatgttagc tggttatttt gtttgttagt tgatgcagtg tcttcctagc ctctatggtc 156889 tttacaattt ggcatgattt tgcagtggct ggtactggtt gttcctttcc atgtttagtg 156949 cttccttcag gagctctttt agggcaggcc tagtggtgac aaaatttctc agcatttgct 157009 tgtctgtaaa ggattttatt tctccttcac ttatgaagct tagtttggct ggatatgaaa 157069

-continued

```
ttctgggttg aaaattcttt tctttaagaa tgttgaatat tggcccccac tctcttctga 157129
cttgtagagt ttctgccgag agatccgctg ttagtctgat gggcttccct ttgtgggtaa 157189
cccgaccttt ctctctggct gcccttaaca ttttttcctt catttcaact ttggtgaatc 157249
tgacagttat gtgtcttgga gttgctcttc tcgaggagta tctttgtggc attctctgta 157309
tttcctgaat ctgaatgttg gccttccttg ctagattggg gaagttctcc tggataatat 157369
cctggagagt gttttccaac ttgcttccat tctccccgtc actttcagat acaccaatca 157429
gacgtagatt tggtcttttc acatagtccc atatttcttg gaggctttgt ccgtttcttt 157489
ttattctttt ttctctaaac ttcccttctc acttcatttc attcatttca tcttccgtta 157549
ctgatatcct ttcttccagt tgatcgcatc ggctcatgag gcttctgcat tcttcacgta 157609
gttctcgagc cttggctttc agctccatca gctcctttaa gcacttctct gtattggtta 157669
ttctagtttt acatttgtct aaattttttt caaagttttc aacttctttg cctttggttt 157729
gaatttcctc ctgtagctcg gagtagtttt atcgtctgaa gccttcttct ctcaacttgt 157789
caaagtcatt ctccattcag ctttgttcca ttgctggtga ggagctgcgt tcctttggag 157849
gaggagaggt gctctgcttt ttagagtttc cagtttttct gctctgtttt ttccccatct 157909
ttgtggtttt atctactttt ggtctttgat gatggtgatg tacagatggg gttttggtgt 157969
ggatgtcctt cctgtttgtt agttttcctt ctaatagaca ggaccctcag ctgcaggtct 158029
gttggagttt gctagaggtc cactccagac cctgtttgcc tgggtaccag cagcggtggc 158089
tgcagaagag cggattttcg tgaaccgcga atgctgctgt ctgatcgttc ctctggaagt 158149
tttgtctcag aggagtatcc tgccgtgtga tgtgtcagtg tgcccctact ggggggtgcc 158209
tcccagttag gctgctcggg ggtcaggggt cagggaccca cttgaggagg cagtttgccc 158269
gttctcagat ctccagctgc gtgctgggag aaccactgct ctcttcaaag ctgtcggaca 158329
gggacattta agtctgcaga ggttactgct gtctttttgt ttgtctgtgc cctgccccca 158389
gaggtagagc ccacagaggc aggcaggcct ccttgagctg tggtgggctc cacccagttc 158449
gagcttcatg gctgctttgt ttacctaagc aagtttgggc aatggcgggc acctctcccc 158509
cagccttgct gccaccttgc agtttgatct cagactgctg tgctagcaat cagcaagact 158569
ctgtgggcat aggcctctcc agcatataaa cagaaccaaa gacaaaaacc atatgattat 158629
ctcaatagat gcagaaaggg cctttgacaa gattcaacaa cgcttcatgc taaaaactct 158689
caataaatta ggtattgatg ggatgtatct caaaataata acagctactt atgacaaacc 158749
cacagccaac atcatactga ataggcaaaa actggaagca ttccctttgg aaactggcac 158809
aagacaggga tgccctctct caccactcct attcaacata gtgttggaag ttctggccca 158869
ggcaattagg caggagaagg aaataaaggg tattcgatta ggaaaagagg aagtcaaatt 158929
gtccctgttt gcagatgaca tggttgtata tctagaaagc cccattatct cagtccaaaa 158989
tctccttaag ctgataagca acttcagcaa agtctcagga tacaaaatca atgtacaaaa 159049
atcacaagaa ttattacaca ccaataacag acaaatagag agccaaatca tgagtgaact 159109
ctcattcaca attgcttcaa agagaataaa atacctagga atccaactta caagggacgt 159169
gaaggacctc ttcaagggaa actacaaacc actgctcaat gaaataaaag aggatacaaa 159229
caaatggaag aacattccat gctcatggtt aggaagaatc aatatcgtga aaatggtcat 159289
actgcccaat gtaatttata tattcaatgc catccccatc aagctaccaa tgactttctt 159349
cacagaattg gaaaaaacta ctttaaagtt catatggcac caaaaaagag cccgcatcac 159409
```

-continued

```
caagtcaatc ctaagccaaa agaacaaagc tggaggcatc acactacctg acttcaaact 159469
atactacaag gctacagtaa ccaaaacagc atggtactgg taccaaaaca gagatatagc 159529
tcaatggaac agaacagagc cctcagaaat aatgctgcat atctacaact atctgatctt 159589
tgacaaacct gagaaaaaca agcaatgggg aaaggattcc ctatttaata aatggtgctg 159649
ggaaaactgg ttagctatat gtagaaagct gaaactggat cccttcctta cagcttattc 159709
taaaattaac tcaagatgga ttaaagactt aaacgttaga cctaaaccat aaaaacccta 159769
gaagaaaacc taggcattac cattcaggac atagacatgt gcaaggactt catgtctaaa 159829
gcaccaaaag caatggcaac aaaagccaaa attgacaaat gggatctaat taaactaaag 159889
agcttctgca cagccaaaga aactaccatc agagtgagca ggcaacctac aaagtgggag 159949
aaaattttcg caacctactt atctgacaaa gggctaatat ccagaatcta caatgaacta 160009
aagcaaattt acaagaaaaa aacaaacaac cccatcaaaa agtgggtgaa ggatataaac 160069
agacacttct caaaagaaga catttgtgca gccaaaaaac acatgaaaaa atgctcatca 160129
tcactggcca tcagagaaat gcaaatcaaa accacaataa gataccatct cacaccactt 160189
agaatggcaa tcattaaaaa gtcaggaaac aacaggtgct ggagaagatg tggagaaata 160249
gaaacacttt tacactgttg gtgggactgt aaactagttc aaccattgtg gaagtcagtg 160309
tggcgattcc tcagggatct agaactagaa ataccatttg acccagccat cccattactg 160369
ggtatatacc caaaggacta taaatcatgc tgctataaag acacatgcac acgtatgttt 160429
attgtggcac tattcacaat agcaaagact tggaaccaac ccaaatgtcc aacaatgata 160489
gactggatta agaaaatgtg gcacatatac accatggaat actatgcagc cataaaaaag 160549
gatgagttca tgtcctttgt agggacatgg atgaaattgg aaatcatcat tctcagtaaa 160609
ctattgtaag aacaaaaaac caaacaccgc atatgctcac tcataggtgg gaattgaaca 160669
atgagaacac atggacacag gaaggggaac atcacactct ggggactgtt gggtgggggg 160729
agggggggagg gatagcctta ggaaatatac ctaattataa atgacgagtt aatgggtgca 160789
gcacagcagc atggcacatg tatgcatatg taactaacct gcacattgtg cacatgtacc 160849
ctaaaactta aagtataata ataataaaat aaaaaaataa agaatagaat aaataaaaac 160909
aaaaataaat aaaaaataaa aagaaatctc tgctcatatc caggccatga tggtttcccc 160969
ctgtgttttc ttcaagtagt tttatagctt caagtcttat gttatattaa gtctttaatc 161029
cattttgagg tgattcttgt acaaaggctg aagtaagggt tcattttgat tcttctgtgt 161089
gtgtgtatcc agttttccca acaccattta ttgagaagtc tgtcatttcc ccatggtgtg 161149
atcttgttac ctttatgaaa atttaattga ccataggtgt atgggtttat ttctgggctt 161209
tctatcatat tccattgatt gatatgtctg gttttatgcc agtactatgc tgctttgatt 161269
actgtggatt tgtaatgtaa tttaatgtct gagagtgtga agcctgcagc attatttttt 161329
ctcaagattg ttatctgtgg ctatttgtag tcttttgtgg tttcatatat attttacaat 161389
tttttatttc tgtgaaaaat gcattggaat tttcatatgg attacattta atccgctttg 161449
ggtagtatga ccattttaac aatattaatt gttctaatcc atgagcatgg gctagctttt 161509
catttatttg tgtcatcttc aggttttttc aacaatgttt tatagtttta gtatatggat 161569
ctttcacttc cttggttaaa tttagtccta agtgtgtgtg tgtgtgtgtg tgtgtgtgtg 161629
tttgtgtgta tgtgtgtgtg catcaactaa ccatagtcat gtgggtttat ttctgggctt 161689
tctatcatgt tccattgatt acttctaagt gaatgagtgt gtgtgtgtgt gtgtgtgtgt 161749
gtgtttaaga tactgttgta attttaaaat ttctttctca ggttgtatgt tgttagtgta 161809
```

cagaaataat attaatttg taagttgatt ttgtattctg caaattcact aaatttgtta 161869 atttgtttta acaatttttt gggtgtagtc ttacagggtt ttctatatat aagatcatgt 161929 catcagtaaa caatttcatt tattcttttc ctatttggat gctttttatt cttacccaat 161989 tgttttgact aggacctcca gtactatgtt gaacataatt gatgaaagca gacatccttg 162049 tcttgctcct gatccaaaag cctttaactt ttcaccactg agtatgatgt tcactgtagg 162109 cttgttatat atggtctttg ttgtgctgag aaacattcct tctataactg attttcaaaa 162169 gtttatcatg aaaggatgtt aaattatttc aaatgttttt tcttcatcta ttgaggtgat 162229 tatattgttt ttattcttca ttctgttact atggtgaatc atatttttaa ttgtttttta 162289 cttgcataaa tttattttgt gataggtaga aaagcacatc tgcagaccta gaagcagagt 162349 gaatctaaaa aatattattt ataattatta tgagtacaca ataggtatat attttcatgg 162409 ggtacattca atgttctgat acaggcatat gatgtgtaat aatcacatca gggtatttgg 162469 agtattcatt acctcaagca tttatcattt ctttgtgtta gggaatttca gtttcattct 162529 tctagttatt taaaatatac aatgaattat tattgactgt agtcaccctg ttgtgctatc 162589 aaatagtatg tcttattcat tttatttaac tatattttg cacccattaa caatccccac 162649 ttgatttgaa tatggtaagc cattcttgca tcctaggaat aaattccatt tgaccatggt 162709 gaatgatcct tttaatgtac tgttgaatat agtttttggt attttgttga ggatttttgc 162769 atccatgttc atcagcgata ttggcctgta atttgctttt ccggtagttt cttgtttttt 162829 tattatactt taagttttag ggtacatgtg cacaacgtgc aggttagtta catatatata 162889 catgtgccat attggtgtgc tgcacccatt aactcatcat ttaacattat ggaaaatctc 162949 ctaatgctat ccctccccgc tccccccacc ccacaacagg ccccggtgtg tgatgttcgc 163009 cttcctgtgt ccatgtgttc tcattgttca attcccacct atgagtgaaa acacacggtg 163069 tttcttagtc tggctttggt ctcaggctaa tgttggcctt acaaaatgat tgtggaaata 163129 tttccttctc ttcaattttt tgaagaagtt tgaaaataat tattaccagt tcttctataa 163189 atgttgggta gaattcattt atgaaaatat cttttcctgg gttttccttg atggcggact 163249 tttcattact gatttaattt ccttgctcat tactgttcca tttatattcc tcatgatttg 163309 atcttggaag gttatgtatc gaagccttta tctatttcct ctccatcgtc caatttgttt 163369 gcatgcaatt gttcgtagtg gtctcataag atcctttgta tttttgtact atcaattgtg 163429 atatcttttt tcatttctgc tttagtttac ttgaaccacc tgtattttct cgtggttaat 163489 ttagctaagg attgtcaatt ttgtttgtct ttttggaaga ccaacgctta gctttactga 163549 tctcttgtat tgtttttcta atttctattt cattgatttt tgctctgaaa tgtttccttt 163609 cttccactaa ctttaggctt agattgttct tcttttacta attcattgag gagtaacatt 163669 aagttgttta tttaagatct ctctctcctt ctctcactct ctcttttgat gtaggcattt 163729 agtgttacaa actttcctct tagaactgct tttgctgaat cctgtaagtt ttaatatgtt 163789 gtttccattt tcatttttct ctaaatattt ttaaaattaa tttttgaatt tcctctttga 163849 ctcaatagtt tttcaggagc atgttgttta atttgcatat acttgttaat ttttcttggt 163909 ttctcctgtt attgatctat agctttatat cattgtgatt gagaaagata cttgatataa 163969 tgttgatctt ctgacacttg ttaagatgtt ttgtggtcta tcaattgatt tatcctagtg 164029 aatgttacat gtatacttga gaaaaatgta tattttgttg ctgttggatg aaatgttctg 164089 tataggtcta ttaactccat tggtatacgt atagttcaag tcatattttg ttattaaaaa 164149

-continued

```
tttttgtct agataatagt tctgttgttg gaagtgggat attaaaatta tttactatta 164209
ttgtgctgca tttatgtctc ttttcagaac tcttaatctt tgatttatat atttaggtgc 164269
ttcagtgttg ggtgcatata tatttacaat tgttatatta tcttgatgca ctgatctttt 164329
tattataata tactgacctt ctttatctct ttttacagtt ttttttaacc taaagtttat 164389
ttggtgtgaa ataagtatag ccacccctgc tctgttttat ttgcctggaa tatcattttc 164449
catcacttca ttttcaacct gtaagtttcc tttaaggtaa ggtgagtctt ctgtaggccc 164509
atatagttgg atcttgtttg gtatgtatca tggtactgta tgccttttga ctacagaatc 164569
taatccatta aactttaaag taattattga tagatgagag gttgctactt ccattttatt 164629
gttttcaagt tgttttctag atcctacatt ttttttctta tatcttgctt tctttacttg 164689
tgatttgatt gctttttgca gggatatatt ttgaattttt taaaatattt tgtgtatcta 164749
ttataggctc atgctttgtg gttacataaa tcatcttata cctataacaa gctatgccaa 164809
gttgataaca acttaagttt gatcacttac acaaaggcta cacttttact ctcctccttc 164869
taaattttat gtttttgatg tcattcttta catcttttta taatatgcat acttaacaaa 164929
ctactgtagc tgtagttgct tttaagaatt ttgcctttta acccttatac tagagaaatc 164989
cttgatttgt tcaccatcat tacaatatta gaatgttttg gaattgaaaa atgccattaa 165049
ttttaccagt gcgttttata ctttcatatg ttttcatgtt tctattttga atccttttcc 165109
ttcagcttga agaactccct ttagcatttc ttataacgca ggtctaatgg tgagaaactc 165169
agcctttgtt actctgagaa agtctttaac atccctcatt atttaaagac aggtttgcta 165229
ggtatactat tcttgattgg caggtttttt tcttttagaa ttttgaatat attatcccac 165289
tcccttgagc tttcaaggtt aatgctgaga aatttgctga tagttttatc agggttctct 165349
tatatgtgac aattcaattc tcccttgctg ctttccatac tctaagtttt gacagttttg 165409
ttatgatgtg ccttggtgtg agtttctttt ccttttttaa attttagatt cagagggtac 165469
atgtgcagat ttgctgcaag gacatattgt gtggcgttgg gcttctgttg atcccaccac 165529
tcaagtggtg aacatagtat ctagtaggaa gttttttgtt tttttgtttt ttttttagct 165589
cttagaccct tctttttccc tttttggaag atgcagtgtc aattgtttct atatttatgt 165649
ctgtgtgtac ccaatattta gttcctactt atgtgaaaga acatgcaata tttggttttc 165709
tgtttccgtg ttaatttgca taggataata ttttccagta gtctgtccat gttgctgaaa 165769
aagacatgag tttgttcttt tttatggctt cacagtattt catgatgtat atgtacttgg 165829
tgtggattta tccggattca ttttatttgg tattctttgg gattcctgta tctggctttc 165889
tattttcttc cccagtactg ggaaattttc tgccattatt ttttgaatat gttctgtgct 165949
tgtctctctc tcctccttct gaacacctat aatgtatata ttgctctgat tgagggtgtc 166009
agtatgtctc ttaagatgtg ttcattcttt ttcattcttt ttccttttttg ctgcttagat 166069
tggatgattt ccagtgactt gtctttgagt tcattgatat tttcttctgc ttaatctcat 166129
ttgtgggtga acctttctgt caattttttc agtttagttt aatattcctc agctctaaga 166189
tttgattgat actttcatat actttctctt tgttaaagtt ctctgttttt gcatttctct 166249
ctggacctta gtgacagtct ttataatcat tattttaaat tctctattgg gtaaattaca 166309
tctcttctat tcacttgggt caatttctga acatttattt tgctctttat ttggaatata 166369
tatttcttgt ttctttagtt tccttgactc tgtgttgttt actgcacatt agataagaca 166429
gctgcctttc ccagtcttat caaacaggac ctgtgtagaa gaaaaaatatc actagtccat 166489
ttgacaaaaa attttaatgt gcctctcaaa gctttgtttg tccaggccac tgtttctgtt 166549
```

```
attggtggct cccaggagat tgggatatgc catgtcctat caatactctg tgaactataa 166609
gatagaggcc agactttcaa aatgtagcca gaaaaatgtc aagtattaga tgtgtggtcc 166669
agttccttct atcctcatgt tgaaattggg tgcaggtgtt acttctccac tctctctgca 166729
tgaagccagg gagaggtact atggaaactg cctgtatttg tgttcaggcc acactttttg 166789
attctgggaa gatagctttg ggagtggggc cactgtttgt ctacatcttt gttatctgtg 166849
atctagagta agttaggaat gcaaagctcc accactccca agcttaggct gttaagaatt 166909
cagtcctttg ggtgggagct gtagaagttg tgacacttaa ttgtgaacaa actcttttca 166969
agaagaatag gtaggctata aaataataga agaaatgaat agagctatag aagttgtgac 167029
acttggtatg tgaacaaact ccttttagga aaaataggct ggggacaagc caagttctgc 167089
ttagtctacc tgagagctac tattagtctg tcttgttagc tccctgatgc aagctggagg 167149
ttaagctatg tagttgtcac tggatgagtg tgcagtaagc tgctagagaa aaaaaaaaaa 167209
aggagctgtg cattctagcc cctgttctcc actgctccca agagatatag ttcctggaag 167269
agtttgcatg cctgtttaaa accacctctt tgttctgtga tctagggaga cttgtatatg 167329
cctagtctct tctgctctta gagccaggag ttttgggata tagtatttct ggtaaatgct 167389
gtaaaagggc attttgtggg tgaacacact ccttccaggg agaattggga gagctgggat 167449
tattgctgag ttgagctgga ggaagtctca ggaagtgtta agctgctgct caggctgtta 167509
gagagctact ttttgcttgc ccctttaact ctcagatgcg ttagttagaa accagactgt 167569
caagtagccg ctaggggagt atgctgtaaa cctcttccag ggagaaccag gtagtggtat 167629
ttttgagtcc tgtctctgta ctaattctac taattcacag tgttaaagca cctgaaaaag 167689
tgcttgcaca cacatataaa actgccactg ttttcctgtg gtctaaataa acttgtgtat 167749
gtctaattct ctctaactcc cagagttggt gaattaagag ccaaactgtt gggcatctta 167809
taattggggt gccatatgta aggtcccaat cctctccaca gggagaatct gagtgttagt 167869
gattccagtt atatggtgaa gtacctggaa ggggtccatg ctcaagtatg cctcagattt 167929
gtctacccat ttgaagtgca tgtttgggtt tttattttgc ttttgatgtg tttttttttg 167989
tctttttttt tgagacagag tctcattctg ttgtaaaggc tagagtgcag tggcacaatc 168049
ttggctcact gcagcctctg cctccctggt tcaagtgatt ctcctgcctc agcctcccga 168109
gtagctgtga ctacagatgc gtaccaccat tcccagctaa tttttgtatt tttggtagag 168169
acagggtttc atcatgttat ccaggctggt ctcaaactcc tggactcaaa taatccacca 168229
gccttggcct cccaaagtgc tgggattaaa ggcatgagcc actgcgcccg gccatgcatg 168289
ttttctttct tgcctggtag gcaggaatct ctcaacttat ttctgacttt ctctcacagg 168349
gaattaattg agatgttcat tctgtgcatt tgtgagtatt gggagtgcca ggagcttcct 168409
attctgccat gttgctgaca tcagtctaag gaaaacagtt taaagaaagt tcatcaaaaa 168469
gtaacagtag acacatctgg gtgtcttaaa tatgaataca tttctttctt tctttctttc 168529
tttctttctt tctttctttc tttccttctt ttctttcttc ctttcc                168575
```

<210> SEQ ID NO 2
<211> LENGTH: 444
<212> TYPE: PRT
<213> ORGANISM: Homo Sapiens

<400> SEQUENCE: 2

```
Met Ser Gly Thr Lys Leu Glu Asp Ser Pro Pro Cys Arg Asn Trp Ser
 1               5                  10                  15
```

-continued

```
Ser Ala Ser Glu Leu Asn Glu Thr Gln Glu Pro Phe Leu Asn Pro Thr
            20                  25                  30

Asp Tyr Asp Asp Glu Glu Phe Leu Arg Tyr Leu Trp Arg Glu Tyr Leu
        35                  40                  45

His Pro Lys Glu Tyr Glu Trp Val Leu Ile Ala Gly Tyr Ile Ile Val
    50                  55                  60

Phe Val Val Ala Leu Ile Gly Asn Val Leu Val Cys Val Ala Val Trp
65                  70                  75                  80

Lys Asn His His Met Arg Thr Val Thr Asn Tyr Phe Ile Val Asn Leu
                85                  90                  95

Ser Leu Ala Asp Val Leu Val Thr Ile Thr Cys Leu Pro Ala Thr Leu
            100                 105                 110

Val Val Asp Ile Thr Glu Thr Trp Phe Phe Gly Gln Ser Leu Cys Lys
        115                 120                 125

Val Ile Pro Tyr Leu Gln Thr Val Ser Val Ser Val Ser Val Leu Thr
    130                 135                 140

Leu Ser Cys Ile Ala Leu Asp Arg Trp Tyr Ala Ile Cys His Pro Leu
145                 150                 155                 160

Met Phe Lys Ser Thr Ala Lys Arg Ala Arg Asn Ser Ile Val Ile Ile
                165                 170                 175

Trp Ile Val Ser Cys Ile Ile Met Ile Pro Gln Ala Ile Val Met Glu
            180                 185                 190

Cys Ser Thr Val Phe Pro Gly Leu Ala Asn Lys Thr Thr Leu Phe Thr
        195                 200                 205

Val Cys Asp Glu Arg Trp Gly Gly Glu Ile Tyr Pro Lys Met Tyr His
    210                 215                 220

Ile Cys Phe Phe Leu Val Thr Tyr Met Ala Pro Leu Cys Leu Met Val
225                 230                 235                 240

Leu Ala Tyr Leu Gln Ile Phe Arg Lys Leu Trp Cys Arg Gln Ile Pro
                245                 250                 255

Gly Thr Ser Ser Val Val Gln Arg Lys Trp Lys Pro Leu Gln Pro Val
            260                 265                 270

Ser Gln Pro Arg Gly Pro Gly Gln Pro Thr Lys Ser Arg Met Ser Ala
        275                 280                 285

Val Ala Ala Glu Ile Lys Gln Ile Arg Ala Arg Arg Lys Thr Ala Arg
    290                 295                 300

Met Leu Met Val Val Leu Leu Val Phe Ala Ile Cys Tyr Leu Pro Ile
305                 310                 315                 320

Ser Ile Leu Asn Val Leu Lys Arg Val Phe Gly Met Phe Ala His Thr
                325                 330                 335

Glu Asp Arg Glu Thr Val Tyr Ala Trp Phe Thr Phe Ser His Trp Leu
            340                 345                 350

Val Tyr Ala Asn Ser Ala Ala Asn Pro Ile Ile Tyr Asn Phe Leu Ser
        355                 360                 365

Gly Lys Phe Arg Glu Glu Phe Lys Ala Ala Phe Ser Cys Cys Cys Leu
    370                 375                 380

Gly Val His His Arg Gln Glu Asp Arg Leu Thr Arg Gly Arg Thr Ser
385                 390                 395                 400

Thr Glu Ser Arg Lys Ser Leu Thr Thr Gln Ile Ser Asn Phe Asp Asn
                405                 410                 415

Ile Ser Lys Leu Ser Glu Gln Val Val Leu Thr Ser Ile Ser Thr Leu
            420                 425                 430
```

```
Pro Ala Ala Asn Gly Ala Gly Pro Leu Gln Asn Trp
        435                 440


<210> SEQ ID NO 3
<211> LENGTH: 20
<212> TYPE: DNA
<213> ORGANISM: Artificial Sequence
<220> FEATURE:
<223> OTHER INFORMATION: nucleic acid primers

<400> SEQUENCE: 3

tactactact aggccacgcg                                                    20


<210> SEQ ID NO 4
<211> LENGTH: 21
<212> TYPE: DNA
<213> ORGANISM: Artificial Sequence
<220> FEATURE:
<223> OTHER INFORMATION: nucleic acid primers

<400> SEQUENCE: 4

acaccaggag gagaaagcta c                                                  21


<210> SEQ ID NO 5
<211> LENGTH: 22
<212> TYPE: DNA
<213> ORGANISM: Artificial Sequence
<220> FEATURE:
<223> OTHER INFORMATION: nucleic acid primers

<400> SEQUENCE: 5

atcgcctgta aagacagcaa ag                                                 22


<210> SEQ ID NO 6
<211> LENGTH: 22
<212> TYPE: DNA
<213> ORGANISM: Artificial Sequence
<220> FEATURE:
<223> OTHER INFORMATION: nucleic acid primers

<400> SEQUENCE: 6

aaagttactg agccaatgcc tc                                                 22


<210> SEQ ID NO 7
<211> LENGTH: 20
<212> TYPE: DNA
<213> ORGANISM: Artificial Sequence
<220> FEATURE:
<223> OTHER INFORMATION: nucleic acid primers

<400> SEQUENCE: 7

gagaggagct tgcagcattg                                                    20


<210> SEQ ID NO 8
<211> LENGTH: 22
<212> TYPE: DNA
<213> ORGANISM: Artificial Sequence
<220> FEATURE:
<223> OTHER INFORMATION: nucleic acid primers

<400> SEQUENCE: 8

aggaattcct cgtcgtcata gt                                                 22


<210> SEQ ID NO 9
<211> LENGTH: 21
<212> TYPE: DNA
```

-continued

<213> ORGANISM: Artificial Sequence
<220> FEATURE:
<223> OTHER INFORMATION: nucleic acid primers

<400> SEQUENCE: 9
gaagaaccac cacatgagga c 21

<210> SEQ ID NO 10
<211> LENGTH: 22
<212> TYPE: DNA
<213> ORGANISM: Artificial Sequence
<220> FEATURE:
<223> OTHER INFORMATION: nucleic acid primers

<400> SEQUENCE: 10
atcactttgc aaagggactg tc 22

<210> SEQ ID NO 11
<211> LENGTH: 22
<212> TYPE: DNA
<213> ORGANISM: Artificial Sequence
<220> FEATURE:
<223> OTHER INFORMATION: nucleic acid primers

<400> SEQUENCE: 11
gtatgcaatc tgtcaccctt tg 22

<210> SEQ ID NO 12
<211> LENGTH: 22
<212> TYPE: DNA
<213> ORGANISM: Artificial Sequence
<220> FEATURE:
<223> OTHER INFORMATION: nucleic acid primers

<400> SEQUENCE: 12
aatgcaggag acaatccaga tg 22

<210> SEQ ID NO 13
<211> LENGTH: 22
<212> TYPE: DNA
<213> ORGANISM: Artificial Sequence
<220> FEATURE:
<223> OTHER INFORMATION: nucleic acid primers

<400> SEQUENCE: 13
caggcttagc caataaaacc ac 22

<210> SEQ ID NO 14
<211> LENGTH: 22
<212> TYPE: DNA
<213> ORGANISM: Artificial Sequence
<220> FEATURE:
<223> OTHER INFORMATION: nucleic acid primers

<400> SEQUENCE: 14
gataagccaa caccatgaga ca 22

<210> SEQ ID NO 15
<211> LENGTH: 22
<212> TYPE: DNA
<213> ORGANISM: Artificial Sequence
<220> FEATURE:
<223> OTHER INFORMATION: nucleic acid primers

<400> SEQUENCE: 15
acagatccct ggaacatcat ct 22

```
<210> SEQ ID NO 16
<211> LENGTH: 22
<212> TYPE: DNA
<213> ORGANISM: Artificial Sequence
<220> FEATURE:
<223> OTHER INFORMATION: nucleic acid primers

<400> SEQUENCE: 16

ctcggatctg ctttatttca gc                                              22


<210> SEQ ID NO 17
<211> LENGTH: 22
<212> TYPE: DNA
<213> ORGANISM: Artificial Sequence
<220> FEATURE:
<223> OTHER INFORMATION: nucleic acid primers

<400> SEQUENCE: 17

ccaattagca tcctcaatgt gc                                              22


<210> SEQ ID NO 18
<211> LENGTH: 22
<212> TYPE: DNA
<213> ORGANISM: Artificial Sequence
<220> FEATURE:
<223> OTHER INFORMATION: nucleic acid primers

<400> SEQUENCE: 18

gtgtgaaaag gtaaaccagg ca                                              22


<210> SEQ ID NO 19
<211> LENGTH: 22
<212> TYPE: DNA
<213> ORGANISM: Artificial Sequence
<220> FEATURE:
<223> OTHER INFORMATION: nucleic acid primers

<400> SEQUENCE: 19

ctcagtggaa aatttcgaga gg                                              22


<210> SEQ ID NO 20
<211> LENGTH: 22
<212> TYPE: DNA
<213> ORGANISM: Artificial Sequence
<220> FEATURE:
<223> OTHER INFORMATION: nucleic acid primers

<400> SEQUENCE: 20

gttgctgatt tgagtggtca ag                                              22


<210> SEQ ID NO 21
<211> LENGTH: 22
<212> TYPE: DNA
<213> ORGANISM: Artificial Sequence
<220> FEATURE:
<223> OTHER INFORMATION: nucleic acid primers

<400> SEQUENCE: 21

ctttctgagc aagttgtgct ca                                              22


<210> SEQ ID NO 22
<211> LENGTH: 22
<212> TYPE: DNA
<213> ORGANISM: Artificial Sequence
<220> FEATURE:
```

-continued

```
<223> OTHER INFORMATION: nucleic acid primers

<400> SEQUENCE: 22

taccagtttt gaagtggtcc tg                                          22


<210> SEQ ID NO 23
<211> LENGTH: 17
<212> TYPE: DNA
<213> ORGANISM: Artificial Sequence
<220> FEATURE:
<223> OTHER INFORMATION: nucleic acid primers

<400> SEQUENCE: 23

tgtaaaacga cggccag                                                17


<210> SEQ ID NO 24
<211> LENGTH: 17
<212> TYPE: DNA
<213> ORGANISM: Artificial Sequence
<220> FEATURE:
<223> OTHER INFORMATION: nucleic acid primers

<400> SEQUENCE: 24

caggaaacag ctatgac                                                17
```

HUMAN NARCOLEPSY GENE

BACKGROUND OF THE INVENTION

Narcolepsy, a disorder which affects approximately 1 in 2,000 individuals, is characterized by daytime sleepiness, sleep fragmentation, and symptoms of abnormal rapid eye movement (REM) sleep that include cataplexy (loss of muscle tone), sleep paralysis, and hypnagogic hallucinations (Aldrich, M. S., *Neurology* 42:34–43 (1992); Siegel, J. M., *Cell* 98:409–412 (1999)). In humans, susceptibility to narcolepsy has been associated with a specific human leukocyte antigen (HLA) alleles, including DQB1*0602 (Mignot, E., *Neurology* 50:S16–22 (1998); Kadotani, H. et al., *Genome Res*. 8:427–434 (1998); Faraco, J. et al., *J Hered*. 90:129–132 (1999)); however, attempts to verify narcolepsy as an autoimmune disorder have failed (Mignot, E. et al., *Adv. Neuroimmunol*. 5:23–37 (1995); Mignot, E., *Curr. Opin. Pulm. Med*. 2:482–487 (1996)). In a canine model of narcolepsy, the disorder is transmitted as an autosomal recessive trait, canarc-1 (Foutz, A.S. et al., *Sleep* 1:413–421 91979); Baker, T. L. and Dement, W. C., Brain Mechanisms of Sleep (D. J. McGinty et al., eds., New York: Raven Press, pp. 199–233 (1985)). The possibility of linkage between canare-1 and the canine major histocompatibility complex has been excluded (Mignot, E. et al., *Proc. Natl. Acad. Sci. USA* 88:3475–3478 (1991)).

A mutation in the hypocretin (orexin) receptor 2 gene in canines has been identified in narcolepsy (Lin, L. et al., *Cell* 98:365–376 (1999)); Hypocrexins/orexins (orexin-A and -B) are neuropeptides associated with regulation of food consumption (de Lecea, L., et al., *Proc. natl. Acad. Sci. USA* 95:322–327 (1998); Sakurai, T. et al., *Cell* 92:573–585 (1998)) as well as other possible functions (Peyron, C. et al., *J Neurosci*. 18:9996–10015 (1998)). Human cDNA of receptors for orexins have been cloned (Sakurai, T. et al., *Cell* 92:573–585 (1998)), however, full human genes for the orexin receptors have not yet been identified.

Diagnosis of narcolepsy is difficult, as it is necessary to distinguish narcolepsy from other conditions such as chronic fatigue syndrome or other sleep disorders (Ambrogetti, A. and Olson, L. C., *Med. J Aust*. 160:426–429 (1994); Aldrich, M. S., *Neurology* 50:S2–7 (1998)). Methods of diagnosing narcolepsy based on specific criteria would facilitate identification of the disease, reduce the time and expense associated with diagnosis, and expedite commencement of treatment.

SUMMARY OF THE INVENTION

As described herein, a full gene for the human hypocretin (orexin) receptor 2 (HCRTR2) has been identified. The sequence of the HCRTR2 gene as described herein is shown in FIG. 1 (SEQ ID NO: 1). Accordingly, this invention pertains to an isolated nucleic acid molecule containing the HCRTR2 gene. The invention also relates to DNA constructs comprising the nucleic acid molecules described herein operatively linked to a regulatory sequence, and to recombinant host cells, such as bacterial cells, fingal cells, plant cells, insect cells and mammalian cells, comprising the nucleic acid molecules described herein operatively linked to a regulatory sequence. The invention also pertains to methods of diagnosing narcolepsy in an individual. The methods include detecting the presence of a mutation in the HCRTR2 gene. The invention additionally pertains to pharmaceutical compositions comprising the HCRTR2 nucleic acids of the invention. The invention further pertains to methods of treating narcolepsy, by administering HCRTR2 nucleic acids of the invention or compositions comprising the HCRTR2 nucleic acids. The methods of the invention allow the accurate diagnosis of narcolepsy and reduce the need for time-consuming and expensive sleep laboratory assessments.

BRIEF DESCRIPTION OF THE DRAWINGS

FIG. 1 depicts the sequence of the human orexin receptor 2 gene (SEQ ID NO:1) and the encoded receptor (SEQ ID NO:2).

The foregoing and other objects, features and advantages of the invention will be apparent from the following more particular description of preferred embodiments of the invention, as illustrated in the accompanying drawings

DETAILED DESCRIPTION OF THE INVENTION

The present invention relates to a human hypocretin (orexin) receptor 2 (HCRTR2) gene, and the relationship of the gene to narcolepsy. As described herein, Applicants have isolated the HCRTR2 gene. The gene and its products are implicated in the pathogenesis of narcolepsy, as mutations in a closely related receptor, hypocretin (orexin) receptor 2, have been associated with the presence of narcolepsy in a well-established canine model of narcolepsy (Lin, L. et al., *Cell* 98:365–376 (1999)).

NUCLEIC ACIDS OF THE INVENTION

Accordingly, the invention pertains to an isolated nucleic acid molecule containing the human HCRTR2 gene. The term, "HCRTR2 gene," refers to an isolated genomic nucleic acid molecule that encodes the human hypocretin (orexin) receptor 2. As used herein, the term, "genomic nucleic acid molecule" indicates that the nucleic acid molecule contains introns and exons as are found in genomic DNA (i.e., not cDNA). The nucleic acid molecules can be double-stranded or single-stranded; single stranded nucleic acid molecules can be either the coding (sense) strand or the non-coding (antisense) strand. The nucleic acid molecule can additionally contain a marker sequence, for example, a nucleotide sequence which encodes a polypeptide, to assist in isolation or purification of the polypeptide. Such sequences include, but are not limited to, those which encode a glutathione-S-transferase (GST) fusion protein and those which encode a hemagglutinin A (HA) peptide marker from influenza. In a preferred embodiment, the nucleic acid molecule has the sequence shown in the Figure (SEQ ID NO:1).

As used herein, an "isolated" or "substantially pure" gene or nucleic acid molecule is intended to mean a gene which is not flanked by nucleotide sequences which normally (in nature) flank the gene (as in other genomic sequences). Thus, an isolated gene can include a gene which is synthesized chemically or by recombinant means. Thus, recombinant DNA contained in a vector are included in the definition of "isolated" as used herein. Also, isolated nucleotide sequences include recombinant DNA molecules in heterologous host cells, as well as partially or substantially purified DNA molecules in solution. Such isolated nucleotide sequences are useful in the manufacture of the encoded protein, as probes for isolating homologous sequences (e.g., from other mammalian species), for gene mapping (e.g., by in situ hybridization with chromosomes), or for detecting expression of the HCRTR2 gene in tissue (e.g., human tissue), such as by Northern blot analysis.

The present invention also encompasses variations of the nucleic acid sequences of the invention. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the hypocretin (orexin) receptor 2.

Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to a designated sequences via hydrogen bonding and other chemical interactions. Such molecules include, for example, those in which peptide linkages substitute for phosphate linkages in the backbone of the molecule.

The invention also relates to fragments of the isolated nucleic acid molecules described herein. The term "fragment" is intended to encompass a portion of a nucleic acid sequence described herein which is from at least about 25 contiguous nucleotides to at least about 50 contiguous nucleotides or longer in length. One or more introns can also be present. Such fragments are useful as probes, e.g., for diagnostic methods, as described below and also as primers or probes. Particularly preferred primers and probes selectively hybridize to a nucleic acid molecule containing the HCRTR2 gene described herein.

The invention also pertains to nucleic acid molecules which hybridize under high stringency hybridization conditions, such as for selective hybridization, to a nucleotide sequence described herein (e.g., nucleic acid molecules which specifically hybridize to a nucleic acid containing the HCRTR2 gene described herein). Hybridization probes are oligonucleotides which bind in a base-specific manner to a complementary strand of nucleic acid. Suitable probes include polypeptide nucleic acids, as described in (Nielsen et al., *Science* 254, 1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1– 2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically. By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1%SDS for 15 min at 68° C. Furthermore, washes can be performed repeatedly or sequentially to obtain a desired result as known in the art. Equivalent conditions can be determined by varying one or more of the parameters given as an example, as known in the art, while maintaining a similar degree of identity or similarity between the target nucleic acid molecule and the primer or probe used.

Hybridizable nucleic acid molecules are useful as probes and primers, e.g., for diagnostic applications, as described below. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 70%, and more preferably at least about 80% identity, and even more preferably at least about 90% identity, with nucleotide sequences described herein. Particularly preferred in this instance are nucleotide sequences encoding hypocretin (orexin) receptor 2.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total# of positions×100).

The determination of percent identity between two sequences can be accomplished using a mathematical algorithm. A preferred, non-limiting example of a mathematical algorithm utilized for the comparison of two sequences is the algorithm of Karlin et al. (*Proc. Natl. Acad. Sci. USA*, 90:5873–5877 (1993)). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al. (*Nucleic Acids Res*, 25:3389–3402 (1997)). When utilizing BLAST and Gapped BLAST programs, the default parameters of the respective programs (e.g., NBLAST) can be used. See http://www.ncbi.nlm.nih.gov. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

The invention also provides expression vectors containing a nucleic acid comprising the HCRTR2 gene, operatively linked to at least one regulatory sequence. Many such vectors are commercially available, and other suitable vectors can be readily prepared by the skilled artisan. "Operatively linked" is intended to mean that the nucleic acid sequence is linked to a regulatory sequence in a manner which allows expression of the nucleic acid sequence. Regulatory sequences are art-recognized and are selected to produce a hypocretin (orexin) receptor 2. Accordingly, the term "regulatory sequence" includes promoters, enhancers, and other expression control elements such as those described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the receptor desired to be expressed. For instance, the gene of the present invention can be expressed by ligating the gene into a vector suitable for expression in either prokaryotic cells, eukaryotic cells or both (see, for example, Broach, et al., *Experimental Manipulation of Gene Expression*, ed. M. Inouye (Academic Press, 1983) p. 83*; Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Vectors can also include, for example, an autonomously replicating sequence (ARS), expression control sequences, ribosome-binding sites, RNA splice sites, polyadenylation sites, transcriptional terminator sequences, secretion signals and mRNA stabilizing sequences.

Prokaryotic and eukaryotic host cells transformed by the described vectors are also provided by this invention. For instance, cells which can be transformed with the vectors of the present invention include, but are not limited to, bacterial cells such as *E. coli* (e.g., *E. coli* K12 strains), Streptomyces, Pseudomonas, *Serratia marcescens* and *Salmonella typhimurium*, insect cells (baculovirus), including Drosophila, fungal cells, such as yeast cells, plant cells and mammalian cells, such as thymocytes, Chinese hamster ovary cells (CHO), and COS cells. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host.

The nucleic acid molecules of the present invention can be produced, for example, by replication in a suitable host cell, as described above. Alternatively, the nucleic acid molecules can also be produced by chemical synthesis.

The nucleotide sequences of the nucleic acid molecules described herein (e.g., a nucleic acid molecule comprising SEQ ID NO: 1) can be amplified by methods known in the art. For example, this can be accomplished by e.g., PCR. *See generally PCR Technology: Principles and Applications for DNA Amplification* (ed. H. A. Erlich, Freeman Press, New York, N.Y., 1992); PCR Protocols: A Guide to Methods and Applications (eds. Innis, et al., Academic Press, San Diego, Calif., 1990); Mattila et al., *Nucleic Acids Res.* 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabeled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory Manual*, (Acad. Press, 1988)). Using these or similar methods, the protein(s) and the DNA encoding the protein can be isolated, sequenced and further characterized.

METHODS OF DIAGNOSIS

The nucleic acids and the proteins described above can be used to detect, in an individual, a mutation in the HCRTR2 gene that is associated with narcolepsy. In one embodiment of the invention, diagnosis of narcolepsy is made by detecting a mutation in the HCRTR2 gene. The mutation can be the insertion or deletion of a single nucleotide, or of more than one nucleotide, resulting in a frame shift mutation; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of the gene; duplication of all or a part of the gene; transposition of all or a part of the gene; or rearrangement of all or a part of the gene. More than one such mutation may be present in a single gene. Such sequence changes cause a mutation in the receptor encoded by the HCRTR2 gene. For example, if the mutation is a frame shift mutation, the frame shift can result in a change in the encoded amino acids, and/or can result in the generation of a premature stop codon, causing generation of a truncated receptor. Alternatively, a mutation associated with narcolepsy can be a synonymous mutation in one or more nucleotides (i.e., a mutation that does not result in a change in the receptor encoded by the HCRTR2 gene, such as a mutation in an intron or an untranslated portion of the gene). Such a polymorphism may alter splicing sites, affect the stability or transport of MRNA, or otherwise affect the transcription or translation of the gene. A HCRTR2 gene that has any of the mutations described above is referred to herein as a "mutant gene." It is likely that a mutation in the HCRTR2 gene is associated with narcolepsy in humans because of the association between a mutation in the HCRTR2 gene and narcolepsy in dogs (Lin, L. et al., *Cell* 98:365–376 (1999), the entire teachings of which are incorporated herein by reference). In a preferred embodiment, the mutation in the HCRTR2 gene is to a deletion mutation, for example, a deletion that corresponds to the deletions found in the hypocretin (orexin) receptor 2 in narcoleptic dogs as described by Lin et al., supra (e.g., a deletion of one or more exons, such as a deletion of the fourth exon, that can be caused by insertion of one or more nucleotides upstream of the splice site of the exon, or a deletion of exon 6, that can be caused by a G to A transition in the splice junction consensus sequence). In another preferred embodiment, the mutation in the HCRTR2 gene is mutation that effects a "knockout" of the entire gene, such as deletion of the first exon as described by Chemelli, R. M. et al, (*Cell* 98:437–451 (1999), the entire teachings of which are incorporated herein). In a third preferred embodiment, the mutation in the HCRTR2 gene is a mutation in an intron, that affects splicing (oining of exons) during translation of the HCRTR2 gene.

In a first method of diagnosing narcolepsy, hybridization methods, such as Southern analysis, are used (see Current Protocols in Molecular Biology, Ausubel, F. et al., eds., John Wiley & Sons, including all supplements through 1999). For example, a test sample of genomic DNA, RNA, or cDNA, is obtained from an individual suspected of having (or carrying a defect for) narcolepsy (the "test individual"). The individual can be an adult, child, or fetus. The test sample can be from any source which contains genomic DNA, such as a blood sample, sample of amniotic fluid, sample of cerebrospinal fluid, or tissue sample from skin, muscle, placenta, gastrointestinal tract or other organs. A test sample of DNA from fetal cells or tissue can be obtained by appropriate methods, such as by amniocentesis or chorionic villus sampling. The DNA, RNA, or cDNA sample is then examined to determine whether a mutation in the HCRTR2 gene is present. The presence of the mutation can be indicated by hybridization of the gene in the test sample to a nucleic acid probe. A "nucleic acid probe", as used herein, can be a DNA probe or an RNA probe; the nucleic acid probe contains at least one mutation in the HCRTR2 gene. The probe can be one of the nucleic acid molecules described above (e.g., the gene, a vector comprising the gene, etc.)

To diagnose narcolepsy by hybridization, a hybridization sample is formed by contacting the test sample containing a HCRTR2 gene, with at least one nucleic acid probe. The hybridization sample is maintained under conditions which are sufficient to allow specific hybridization of the nucleic acid probe to the HCRTR2 gene. "Specific hybridization", as used herein, indicates exact hybridization (e.g., with no mismatches). Specific hybridization can be performed under high stringency conditions or moderate stringency conditions, for example, as described above. In a particularly preferred embodiment, the hybridization conditions for specific hybridization are high stringency.

Specific hybridization, if present, is then detected using standard methods. If specific hybridization occurs between the nucleic acid probe and the HCRTR2 gene in the test sample, then the HCRTR2 gene has the mutation that is present in the nucleic acid probe. More than one nucleic acid probe can also be used concurrently in this method. Specific hybridization of any one of the nucleic acid probes is indicative of a mutation in the HCRTR2 gene, and is therefore diagnostic for narcolepsy.

In another hybridization method, Northern analysis (see Current Protocols in Molecular Biology, Ausubel, F. et al., eds., John Wiley & Sons, supra) is used to identify the presence of a mutation associated with narcolepsy. For Northern analysis, a test sample of RNA is obtained from the individual by appropriate means. Specific hybridization of a nucleic acid probe, as described above, to RNA from the individual is indicative of a mutation in the HCRTR2 gene, and is therefore diagnostic for narcolepsy For representative examples of use of nucleic acid probes, see, for example, U.S. Pat. Nos. 5,288,611 and 4,851,330. Alternatively, a peptide nucleic acid (PNA) probe can be used instead of a nucleic acid probe in the hybridization methods described above. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, Nielsen, P.E. et al., *Bioconjugate Chemistry*, 1994, 5, American Chemical Society, p. 1 (1994). The PNA probe can be designed to specifically hybridize to a gene having a polymorphism associated with autoimmune disease. Hybridization of the PNA probe to the HCRTR2 gene is diagnostic for narcolepsy.

In another method of the invention, mutation analysis by restriction digestion can be used to detect mutant genes, or genes containing polymorphisms, if the mutation or polymorphism in the gene results in the creation or elimination of a restriction site. A test sample containing genomic DNA is obtained from the individual. Polymerase chain reaction (PCR) can be used to amplify the HCRTR2 gene (and, if necessary, the flanking sequences) in the test sample of genomic DNA from the test individual. RFLP analysis is conducted as described (see Current Protocols in Molecular Biology, supra). The digestion pattern of the relevant DNA fragment indicates the presence or absence of the mutation in the HCRTR2 gene, and therefore indicates the presence or absence of narcolepsy.

Sequence analysis can also be used to detect specific mutations in the HCRTR2 gene. A test sample of DNA is obtained from the test individual. PCR can be used to amplify the gene, and/or its flanking sequences. The sequence of the HCRTR2 gene, or a fragment of the gene is determined, using standard methods. The sequence of the gene (or gene fragment) is compared with the nucleic acid sequence of the gene, as described above. The presence of a mutation in the HCRTR2 gene indicates that the individual has narcolepsy.

Allele-specific oligonucleotides can also be used to detect the presence of a mutation in the HCRTR2 gene, through the use of dot-blot hybridization of amplified proteins with allele-specific oligonucleotide (ASO) probes (see, for example, Saiki, R. et al., (1986), *Nature* (London) 324:163–166). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to the HCRTR2 gene, and that contains a mutation associated with narcolepsy. An allele-specific oligonucleotide probe that is specific for particular mutation in the HCRTR2 gene can be prepared, using standard methods (see Current Protocols in Molecular Biology, supra). To identify mutations in the gene that are associated with narcolepsy, a test sample of DNA is obtained from the individual. PCR can be used to amplify all or a fragment of the HCRTR2 gene, and its flanking sequences. The DNA containing the amplified HCRTR2 gene (or fragment of the gene) is dot-blotted, using standard methods (see Current Protocols in Molecular Biology, supra), and the blot is contacted with the oligonucleotide probe. The presence of specific hybridization of the probe to the amplified HCRTR2 gene is then detected. Specific hybridization of an allele-specific oligonucleotide probe to DNA from the individual is indicative of a mutation in the HCRTR2 gene, and is therefore indicative of narcolepsy.

Other methods of nucleic acid analysis can be used to detect mutations in the HCRTR2 gene, for the diagnosis of narcolepsy. Representative methods include direct manual sequencing; automated fluorescent sequencing; single-stranded conformation polymorphism assays (SSCA); clamped denaturing gel electrophoresis (CDGE) heteoduplex analysis; chemical mismatch cleavage (CMC); RNase protection assays; use of proteins which recognize nucleotide mismatches, such as *E. coli* mutS protein; allele-specific PCR, and other methods.

PHARMACEUTICAL COMPOSITIONS

The present invention also pertains to pharmaceutical compositions comprising nucleic acids described herein, particularly nucleic acids containing the HCRTR2 gene described herein. For instance, a nucleotide or nucleic acid construct (vector) comprising a nucleotide of the present invention can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The agents are administered in a therapeutically effective amount. The amount of agents which will be therapeutically effective in the treatment of narcolepsy can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governnental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

METHODS OF THERAPY

The present invention also pertains to methods of therapy for narcolepsy, utilizing the pharmaceutical compositions comprising nucleic acids, as described herein. The therapy is designed to replace/supplement activity of the hypocretin (orexin) receptor 2 in an individual, such as by administering a nucleic acid comprising the HCRTR2 gene or a derivative or active fragment thereof. In one embodiment of the invention, a nucleic acid of the invention is used in the treatment of narcolepsy. The term, "treatment" as used herein, refers not only to ameliorating symptoms associated with the disease, but also preventing or delaying the onset of the disease, and also lessening the severity or frequency of symptoms of the disease. In this embodiment, a nucleic acid of the invention (e.g., the HCRTR2 gene (SEQ ID NO:1)) can be used, either alone or in a pharmaceutical composition as described above. For example, the HCRTR2 gene, either by itself or included within a vector, can be introduced into cells (either in vitro or in vivo) such that the cells produce native HCRTR2 receptor. If necessary, cells that have been transformed with the gene or can be introduced (or reintroduced) into an individual affected with the disease. Thus, cells which, in nature, lack native HCRTR2 expression and activity, or have mutant HCRTR2 expression and activity, can be engineered to express HCRTR2 receptors (or, for example, an active fragment of the HCRTR2 receptor). In a preferred embodiment, nucleic acid comprising the HCRTR2 gene, can be introduced into an expression vector, such as a viral vector, and the vector can be introduced into appropriate cells which lack native HCRTR2 expression in an animal. In such methods, a cell population can be engineered to inducibly or constitutively express active HCRTR2 receptor. Other gene transfer systems, including viral and nonviral transfer systems, can be used. Alternatively, nonviral gene transfer methods, such as calcium phosphate coprecipitation, mechanical techniques (e.g., microinjection); membrane fusion-mediated transfer via liposomes; or direct DNA uptake, can also be used.

The nucleic acids and/or vectors are administered in a therapeutically effective amount (i.e., an amount that is sufficient to treat the disease, such as by ameliorating symptoms associated with the disease, preventing or delaying the onset of the disease, and/or also lessening the severity or frequency of symptoms of the disease). The amount which will be therapeutically effective in the treatment of a particular disorder or condition will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or disorder, and should be decided according to the judgment of a practitioner and each patient's circumstances. Effective doses may be extrapolated from dose-response curves derived from in vitro or animal model test systems.

The following Examples are offered for the purpose of illustrating the present invention and are not to be construed to limit the scope of this invention. The teachings of all references cited herein are hereby incorporated herein by reference.

EXAMPLES

Example 1

Identification of the Human Narcolepsy Gene

A human BAC library (RPCI11 human male BAC library) was used. Twenty primers, designed from the mRNA sequence of the HCRTR2 receptor, were employed to identify clones of interest. They are set forth in Table 1.

TABLE 1

Primers Used for Hybridization

| # | Name | Primer Sequence | SEQ ID NO: |
|---|---|---|---|
| 1 | HCRTR2-1-F | TACTACTACTAGGCCACGCG | 3 |
| 2 | HCRTR2-1-R | ACACCAGGAGGAGAAAGCTAC | 4 |
| 3 | HCRTR2-2-F | ATCGCCTGTAAAGACAGCAAAG | 5 |
| 4 | HCRTR2-2-R | AAAGTTACTGAGCCAATGCCTC | 6 |
| 5 | HCRTR2-3-F | GAGAGGAGCTTGCAGCATTG | 7 |
| 6 | HCRTR2-3-R | AGGAATTCCTCGTCGTCATAGT | 8 |

TABLE 1-continued

Primers Used for Hybridization

| # | Name | Primer Sequence | SEQ ID NO: |
|---|---|---|---|
| 7 | HCRTR2-4-F | GAAGAACCACCACATGAGGAC | 9 |
| 8 | HCRTR2-4-R | ATCACTTTGCAAAGGGACTGTC | 10 |
| 9 | HCRTR2-5-F | GTATGCAATCTGTCACCCTTTG | 11 |
| 10 | HCRTR2-5-R | AATGCAGGAGACAATCCAGATG | 12 |
| 11 | HCRTR2-6-F | CAGGCTTAGCCAATAAAACCAC | 13 |
| 12 | HCRTR2-6-R | GATAAGCCAACACCATGAGACA | 14 |
| 13 | HCRTR2-7-F | ACAGATCCCTGGAACATCATCT | 15 |
| 14 | HCRTR2-7-R | CTCGGATCTGCTTTATTTCAGC | 16 |
| 15 | HCRTR2-8-F | CCAATTAGCATCCTCAATGTGC | 17 |
| 16 | HCRTR2-8-R | GTGTGAAAAGGTAAACCAGGCA | 18 |
| 17 | HCRTR2-9-F | CTCAGTGGAAAATTTCGAGAGG | 19 |
| 18 | HCRTR2-9-R | GTTGCTGATTTGAGTGGTCAAG | 20 |
| 19 | HCRTR2-10-F | CTTTCTGAGCAAGTTGTGCTCA | 21 |
| 20 | HCRTR2-10-R | CCAGTTTTGAAGTGGTCCTG | 22 |

Initial Study with Large Membranes

Four out of 5 membranes having the whole BAC library, containing a total of approximately 160,000 BAC clones representing an approximately 10-fold coverage of the human genome, were used in hybridization studies with these primers. Hybridization was performed with a pool of all 20 primers described in Table 1.

5' End Labeling for Big Membranes

Oligonucleotides were labeled at the 5' end before hybridization, using fresh (less than one month old) [$\gamma^{32}$P] ATP (6000 Ci/mmole; 10 $\mu$Ci/$\mu$l). The following protocol is adjusted for 4 membranes in 2 bottles, containing 2 membranes/30 ml of rapid hyb. Each. Briefly, a labeling mixture was made of DNA (8 pmol/$\mu$l) (10.0 $\mu$l of the primer pool), 10×buffer (12.0 $\mu$l), T4 PNK (10 u/$\mu$l) (6.0 $\mu$l), [$\gamma^{32}$P]ATP (30.0 $\mu$l, or 600 $\mu$Ci), and water (62.0 $\mu$l) for a final volume of 120 $\mu$l. 20 $\mu$l of labeling mixture was used per 10 ml rapid hybridization reaction. Incubation of the labeling mixture was for 2 hours at 37° C., followed by transfer to ice, spinning down, and mixing with the rapid hybridization solution. The membranes were prehybridized at 42° C. before the labeling mix was added. Sixty $\mu$l of the labeling mix was added to each of 2 big bottles containing 2 membranes and 30 ml of rapid hybridization solution.

Hybridization and Washing

The membranes were hybridized at 42° C. overnight. After overnight, membranes were washed with 6×SSC, 0.1% SDS at room temperature; washed with 6×SSC, 0.1% SDS at 55° C. in a shaking waterbath, repeated until the radioactivity of membranes was lower than 6 k using 1×sensitivity; and washed with 6×SSC to remove the SDS. The washed membranes were put in a cassette for overnight exposure at −80° C. with a MR single emulsion film. Positive clones were identified and gridded on small membranes.

Study of Positive Clones with Small Membranes

After growing the positively-identified clones on several small membranes (to get several copies of membranes containing the same clones), and washing the membranes, hybridization was performed using pairs of primers, instead of a total pool of primers as before. The total number of hybridizations was nine, using different primers against identical copies of membranes containing all positive clones from the first hybridization. The primer pairs are set forth in Table 2; primer numbers indicate the primers shown in Table 1.

TABLE 2

Primer Pairs Used for Hybridization

| Reaction number | Primers Used |
|---|---|
| 1 | 1 and 2 |
| 2 | 3 and 4 |
| 3 | 5 and 6 |
| 4 | 7 and 8 |
| 5 | 9 and 10 |
| 6 | 11 and 12 |
| 7 | 13 and 14 |
| 8 | 15 and 16 |
| 9 | 17 and 18 |

5' End Labelingfor Small Membranes

Oligonucleotides were labeled at the 5' end before hybridization, using fresh [$\gamma^{32}$P]ATP (5000 Ci/mmole; 10 $\mu$Ci/$\mu$l). Briefly, a labeling mixture was made of DNA (8 pmol/$\mu$l) (1.5 $\mu$l), 10×buffer (2.0 $\mu$l), T4 PNK (10 u/$\mu$l) (1.0 $\mu$l), [$\gamma^{32}$P]ATP (3.0 $\mu$l), and water (12.5 $\mu$l) for a final volume of 20 $\mu$l. Incubation of the labeling mixture was for 2.5 hours at 37° C., followed by transfer to ice, spinning down, and mixing with the rapid hybridization solution. Membranes were pre-wetted in 6×SSC, rolled in a pipette, and excess liquid drained prior to placing the membrane in the tube. Fifty ml Falcon (polypropylene) tubes were used as container for the hybridization. The membranes were prehybridized at 42° C. before 20 $\mu$l of labeling mix was added to each tube.

Hybridization and Washing

The membranes were hybridized at 42° C. overnight. After overnight, membranes were washed as described above. Four clones which were positive for primers designed using the 5' and 3' end of the MRNA were identified. Clone 403B19 was used to characterize the gene.

Sequencing ofNarcolepsy Gene in Clone 403B19

Shotgun sequencing was used to obtain the gene sequence.

Preparation of DNA Samples

BAC DNA was isolated using the Plasmix kit from TALENT-VH Bio Limited. Thirty $\mu$g of isolated DNA was fragmented by nebulization: a nebulizer (IPI Medical Products, Inc., no. 4207) was modified by removing the plastic cylinder drip ring, cutting off the outer rim of the cylinder, inverting it and placing it back into the nebulizer; the large hole in the top cover (where the mouth piece was attached) was sealed with a plastic stopper; the small hole was connected to a ¼ inch length of Tycon tubing (connected to a compressed air source). A DNA sample was prepared containing 30 $\mu$g DNA, 10×TM buffer (200 $\mu$l), sterile glycerol (1 ml), and sterile dd water (q.s.) for a total volume of 2 ml. The DNA sample was nebulized in an ice-water bath for 2 minutes and 40 seconds (pressure bar reading 0.5). The sample was then briefly centrifuged at 2500 rpm to collect the DNA; the entire unit was placed in the rotor bucked of a table top centrifuge (Beckman GPR tabletop centrifuge) fitted with pieces of Styrofoam to cushion the nebulizer. The sample was then distributed into four 1.5 ml microcentrifuge tubes and ethanol precipitated. The Dried DNA pellet was resuspended in 35 $\mu$l of 1×TM buffer prior to proceeding with fragment end-repair.

Fragment End Repair, Size Selection and Phosphorylation

The DNA was resuspended in 27 $\mu$l of 1×TM buffer. The following materials were added: 10×kinase buffer (5 $\mu$l), 10 mM rATP (5 $\mu$l), 0.25 mM dNTPs (7 $\mu$l), T4 polynucleotide kinase (1 $\mu$l (3 U/$\mu$l)), Klenow DNA polymerase (2 $\mu$l (5 U/$\mu$l)), T4 DNA polymerase (1 $\mu$l (3 U/$\mu$l)), for a total volume of 48 μl. The mixture was incubated at 37° C. for 30 minutes, and then 5 μl of agarose gel loading dye was added. The mixture was then applied to separate wells of a 1% low melting temperature agarose gel and electrophoresed for 30–60 minutes at 100–120 mA. The DNA was then eluted from each sample lane, extracted from the agarose using Ultrafree-DA columns (Millipore) and then cleaned with Microcon-100 columns (Amicon), precipitated in ethanol, and resuspended in 10 μl of 10:0.1 TE buffer.

Ligation

EcoRV-linearized, CLAP-dephosphorylated Bluescript vector was used as a cloning vector. The following reagents were combined in a microcentrifuge tube, and incubated overnight at 4° C.: DNA fragments (100–1000 ng), cloning vector (2 μl (10 ng/μl)), 10×ligation buffer (1 μl), T4 DNA ligase (NEB 202L) (1 μl (400 U/μl)), sterile dd water (q.s.), for a total of 10 μl.

Transformation of Ligated Products

The ligation products were diluted 1:5 with dd water and used to transform electrocompetent TOP 10 F cells (Invitrogen) using GenePulser II (Biorad; voltage, 2.5 W, resistance 100 ohm). Transformants were plated on LB plates with 50 Il of 4% X-GAL and 50 μl of 4% IPTG, and ampicillin. Transformants were grown overnight at 37° C., white colonies were picked, grown in a culture of 3 ml LB liquid media plus 200 μg/μl ampicillin for 16–20 hours with shaking. DNA was isolated from the liquid cultures using Autogen 740 Automatic Plasmid Isolation System.

Cycle Sequencing ofIsolated Plasmid DNA

Isolated plasmids were then sequenced using the M13 primers: M13-forward (SEQ ID NO:23) TGTAAAACGACGGCCAG; and M13-reverse (SEQ ID NO:24) CAGGAAACAGCTATGAC. For the sequencing reaction, 2.5 μl plasmid template was mixed with 4 μl Big Dye Ready reaction mix (ABI), 1 μl of 8 pM M13 primer, and 2.5 μl dd water. For cycle sequencing, 25 cycles of 96° C. for 10 seconds, 50° C. for 5 seconds, and 60 ° C. for 4 minutes were performed, followed by holding at 4° C. The cycle sequencing reaction products were cleaned by spinning through Sephadex G-50 columns. The eluted cycle sequencing products were then dissolved in 3 μl formamide/dye and 1.5 μl of sample was loaded on ABI 377 automated sequencers. The data was analyzed using Phred and Phrap, and viewed in Consed viewer.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid molecule comprising the nucleic acid of SEQ ID NO: 1.

2. A DNA construct comprising the isolated nucleic acid molecule of claim 1 operatively linked to a regulatory sequence.

3. An isolated recombinant host cell comprising the isolated nucleic acid molecule of claim 1 operatively linked to a regulatory sequence.

* * * * *